US009493781B2

(12) United States Patent
Lira et al.

(10) Patent No.: US 9,493,781 B2
(45) Date of Patent: Nov. 15, 2016

(54) SYNTHETIC *BRASSICA*-DERIVED CHLOROPLAST TRANSIT PEPTIDES

(71) Applicant: DOW AGROSCIENCES LLC, Indianapolis, IN (US)

(72) Inventors: Justin M Lira, Zionsville, IN (US); Robert Cicchillo, Zionsville, IN (US); Carla N Yerkes, Crawfordsville, IN (US); Andrew E Robinson, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 666 days.

(21) Appl. No.: 13/757,613

(22) Filed: Feb. 1, 2013

(65) Prior Publication Data

US 2013/0295638 A1 Nov. 7, 2013

Related U.S. Application Data

(60) Provisional application No. 61/625,222, filed on Apr. 17, 2012, provisional application No. 61/593,555, filed on Feb. 1, 2012.

(51) Int. Cl.

| | |
|---|---|
| ***C12N 15/82*** | (2006.01) |
| ***C07K 14/415*** | (2006.01) |
| ***C12N 9/96*** | (2006.01) |
| ***C12N 9/10*** | (2006.01) |

(52) U.S. Cl.

CPC ......... *C12N 15/8221* (2013.01); *C07K 14/415* (2013.01); *C12N 9/1092* (2013.01); *C12N 9/96* (2013.01); *C12N 15/8209* (2013.01); *C12N 15/8245* (2013.01); *C12N 15/8247* (2013.01); *C12N 15/8274* (2013.01); *C12N 15/8275* (2013.01); *C12N 15/8281* (2013.01); *C12N 15/8283* (2013.01); *C12N 15/8286* (2013.01); *C07K 2319/08* (2013.01)

(58) Field of Classification Search

None

See application file for complete search history.

(56) References Cited

U.S. PATENT DOCUMENTS

| | | | | |
|---|---|---|---|---|
| 5,510,471 | A * | 4/1996 | Lebrun | C12N 15/8275 536/23.6 |
| 5,633,448 | A | 5/1997 | Lebrun et al. | |
| 6,870,075 | B1 | 3/2005 | Beetham et al. | |
| 7,169,970 | B2 * | 1/2007 | Warner | C12N 15/8275 435/320.1 |
| 8,268,622 | B2 * | 9/2012 | Gocal | C12N 9/1092 435/468 |
| 2003/0106094 | A1 | 6/2003 | Chaudhuri et al. | |
| 2009/0029861 | A1 | 1/2009 | Feng et al. | |
| 2011/0023179 | A1 * | 1/2011 | Nuccio | C07K 14/405 800/278 |
| 2011/0321187 | A1 | 12/2011 | Malcuit et al. | |
| 2012/0042412 | A1 | 2/2012 | Albert et al. | |
| 2012/0304336 | A1 * | 11/2012 | Bourett | C12N 15/8221 800/298 |
| 2013/0295638 | A1 | 11/2013 | Lira et al. | |

FOREIGN PATENT DOCUMENTS

| | | |
|---|---|---|
| CN | 1541270 | 10/2004 |
| WO | 2007084294 | 7/2007 |
| WO | 2010012796 | 2/2010 |
| WO | 2013116758 | 8/2013 |

OTHER PUBLICATIONS

Bruce, B. 2000. Chloroplast transit peptides: structure, function and evolution. Trends in Cell Biology. 10: 440-447.*

Maniatis et al. Molecular Cloning: A Laboratory Manual, Cold Spring Harbor Laboratory, 1982; pp. 387-389.*

International Search Report and Written Opinion for International Application No. PCT/US2013/036980, mailed Aug. 23, 2013.

NCBI, Gen bank assession No. AAS80163, Dec. 23, 2003.

International Search Report and Written Opinion for PCT Application No. PCT/US2013/024433, mailed May 15, 2013.

Database EMBL [Online] Apr. 15, 2009, Bancroft I et al.: "Brassica napus GSS, clone JBnB179D17, end read, primer SACR2(reverse).", XP002749505, retrieved from EBI accession No. EM GSS:FP314951 Database accession No. FP314951.

Database EMBL [Online], Jul. 6, 2001, "39RDBRI UP 092 F06 Jan. 25, 2006 038 Brassica rapa 39RDBRT Brassica rapa eDNA 5', mRNA sequence.",, XP002749503,, retrieved from EBI accession No. EM EST: ES937178 Database accession No. ES937178, * sequence * & Gasser C S et al: "A Brassica-Napus Gene Encoding 5 Enolpyruvoylshikimate-3-Phosphate Synthase", Nucleic Acids Research, vol. 18, No. 9, 1990, p. 2821.

Database UniProt [Online], Aug. 1, 1990! "RecName: Full=3-phosphoshikimate, 1-carboxyvinyltransferase!chloroplastic; EC=2. 5.1.19; AltName: Full=5-enolpyruvylshikimate-3-phosphate, synthase; Short=EPSP synthase; Flags: Precursor;" XP002749504, retrieved from EBI accession No. UniProt:P17688 Database accession No. P17688.

* cited by examiner

*Primary Examiner* — Cathy Kingdon Worley

(74) *Attorney, Agent, or Firm* — C. Philip Poirier; Magleby Cataxinos & Greenwood

(57) ABSTRACT

This disclosure concerns compositions and methods for targeting peptides, polypeptides, and proteins to plastids of plastid-containing cells. In some embodiments, the disclosure concerns chloroplast transit peptides that may direct a polypeptide to a plastid, and nucleic acid molecules encoding the same. In some embodiments, the disclosure concerns methods for producing a transgenic plant material (e.g., a transgenic plant) comprising a chloroplast transit peptide, as well as plant materials produced by such methods, and plant commodity products produced therefrom.

25 Claims, 42 Drawing Sheets mRNA molecule comprising a *Brassica*-derived chloroplast transit peptide-encoding sequence

Plasmid map of pDAB101977

Plasmid map of pDAB101978

Plasmid map of pDAB101908

TraP8-YFP infiltrated into tobacco leaf tissue was translocated into the chloroplasts of the tobacco leaf tissue.

TraP9-YFP infiltrated into tobacco leaf tissue was translocated into the chloroplasts of the tobacco leaf tissue.

Non-targeted YFP controls that were infiltrated into tobacco leaf tissue were not incorporated into the chloroplasts of the tobacco leaf tissue.

Plasmid map of pDAB106597

TraP8-YFP transformed into maize protoplasts was translocated into the chloroplasts of the maize protoplast.

Plasmid map of pDAB105526

Plasmid map of pDAB105527

Plasmid map of pDAB109807

Plasmid map of pDAB111481

Plasmid map of pDAB111479

Plasmid map of pDAB111338

FIG. 17

Plasmid map of pDAB112710

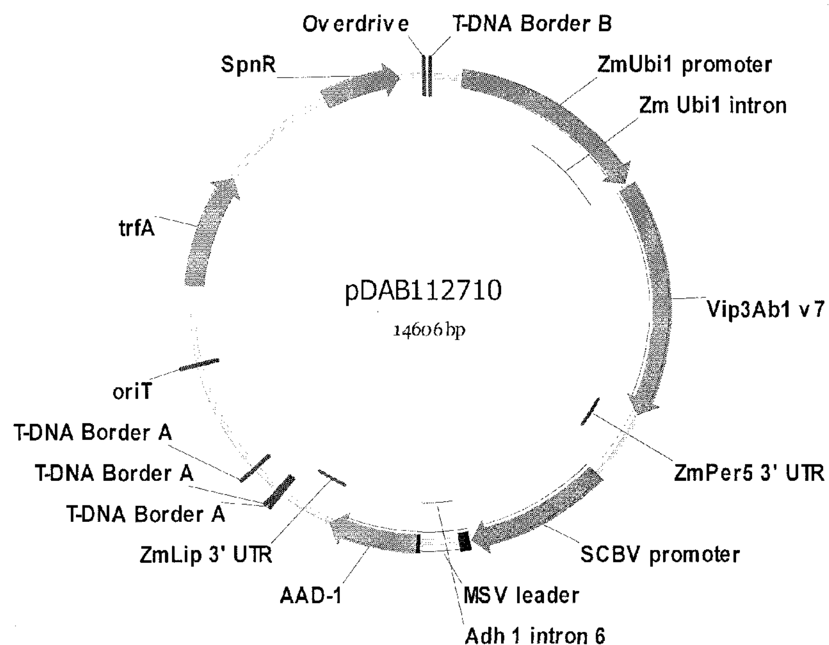

FIG. 18

**Alignment of the predicted chloroplast transit peptides for the EPSPS protein from *Brassica napus* (SEQ ID NO:1) and *Brassica rapa* (SEQ ID NO:2). The asterisk indicates where the sequences were spit and recombined to form TraP8 and Trap9.**

```
                                    1                                     *  40
Brassica napus (SEQ ID NO:1)   (1)  MAQSSRICHGVQNPCVITSNLSKSNQNKSPFSVSL-KTHQP
 Brassica rapa (SEQ ID NO:2)   (1)  MAQASRICQ---NPCVIS-NLPKSNHRKSPFSVSL-KTHQQ
                                    41                               74
Brassica napus (SEQ ID NO:1)  (41)  R-----ASSWGLKKSGTMLNGSVIRPVKVTASVS
 Brassica rapa (SEQ ID NO:2)  (37)  QRRAYQISSWGLKKS--N-NGSVIRPVK------
```

Plasmid map of pDAB107527

Plasmid map of pDAB105530

Plasmid map of pDAB105531

Plasmid map of pDAB105532

Plasmid map of pDAB105534

Plasmid map of pDAB107532

Plasmid map of pDAB107534

Plasmid map of pDAB107533

Plasmid map of pDAB102715

Plasmid map of pDAB102716

Plasmid map of pDAB102717

Plasmid map of pDAB102785

Plasmid map of pDAB102719

Plasmid map of pDAB102718

Plasmid map of pDAB107663

Plasmid map of pDAB107664

Plasmid map of pDAB107665

Plasmid map of pDAB107666

Plasmid map of pDAB109812

Plasmid map of pDAB107698

Plasmid map of pDAB108385

Plasmid map of pDAB108386

Plasmid map of pDAB108387

SYNTHETIC *BRASSICA*-DERIVED CHLOROPLAST TRANSIT PEPTIDES

CROSS-REFERENCE TO RELATED APPLICATIONS

This application claims the benefit of U.S. Provisional Patent Application Ser. No. 61/593,555 filed Feb. 1, 2012, and also to U.S. Provisional Patent Application Ser. No. 61/625,222, filed Apr. 17, 2012, the disclosure of each of which is hereby incorporated herein in its entirety by this reference.

STATEMENT ACCORDING TO 37 C.F.R. §1.821(c) or (e)—SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

TECHNICAL FIELD

This disclosure relates to compositions and methods for genetically encoding and expressing polypeptides that are targeted to plastids of plastid-containing cells. In certain embodiments, the disclosure relates to amino acid sequences that target polypeptides to chloroplasts (e.g., of higher plants), and/or nucleic acid molecules encoding the same. In certain embodiments, the disclosure relates to chimeric polypeptides comprising an amino acid sequence that controls the transit of the chimeric polypeptides to plastids, and/or nucleic acid molecules encoding the same.

BACKGROUND

Plant cells contain distinct subcellular organelles, referred to generally as "plastids." that are delimited by characteristic membrane systems and perform specialized functions within the cell. Particular plastids are responsible for photosynthesis, as well as the synthesis and storage of certain chemical compounds. All plastids are derived from proplastids that are present in the meristematic regions of the plant. Proplastids may develop into, for example: chloroplasts, etioplasts, chromoplasts, gerontoplasts, leucoplasts, amyloplasts, elaioplasts, and proteinoplasts. Plastids exist in a semi-autonomous fashion within the cell, containing their own genetic system and protein synthesis machinery, but relying upon a close cooperation with the nucleo-cytoplasmic system in their development and biosynthetic activities.

In photosynthetic leaf cells of higher plants, the most conspicuous plastids are the chloroplasts. The most essential function of chloroplasts is the performance of the light-driven reactions of photosynthesis. But, chloroplasts also carry out many other biosynthetic processes of importance to the plant cell. For example, all of the cell's fatty acids are made by enzymes located in the chloroplast stroma, using the ATP, NAOPH, and carbohydrates readily available there. Moreover, the reducing power of light-activated electrons drives the reduction of nitrite ($NO_2^-$) to ammonia ($NH_3$) in the chloroplast; this ammonia provides the plant with nitrogen required for the synthesis of amino acids and nucleotides.

The chloroplast also takes part in processes of particular importance in the agrochemical industry. For example, it is known that many herbicides act by blocking functions which are performed within the chloroplast. Recent studies have identified the specific target of several herbicides. For instance, triazine-derived herbicides inhibit photosynthesis by displacing a plastoquinone molecule from its binding site in the 32 kD polypeptide of the photosystem II. This 32 kD polypeptide is encoded in the chloroplast genome and synthesized by the organelle machinery. Mutant plants have been obtained which are resistant to triazine herbicides. These plants contain a mutant 32 kD polypeptide from which the plastoquinone can no longer be displaced by triazine herbicides. Sulfonylureas inhibit acetolactate synthase in the chloroplast. Acetolactate synthase is involved in isoleucine and valine synthesis. Glyphosate inhibits the function of 5-enol pyruvyl-3-phosphoshikimate synthase (EPSPS), which is an enzyme involved in the synthesis of aromatic amino acids. All these enzymes are encoded by the nuclear genome, but they are translocated into the chloroplast where the actual amino acid synthesis takes place.

Most chloroplast proteins are encoded in the nucleus of the plant cell, synthesized as larger precursor proteins in the cytosol, and post-translationally imported into the chloroplast. Import across the outer and inner envelope membranes into the stroma is the major means for entry of proteins destined for the stroma, the thylakoid membrane, and the thylakoid lumen. Localization of imported precursor proteins to the thylakoid membrane and thylakoid lumen is accomplished by four distinct mechanisms, including two that are homologous to bacterial protein transport systems. Thus, mechanisms for protein localization in the chloroplast are, in part, derived from the prokaryotic endosymbiont. Cline and Henry (1996), *Annu. Rev. Cell. Dev. Biol.* 12:1-26.

Precursor proteins destined for chloroplastic expression contain N-terminal extensions known as chloroplast transit peptides (CTPs). The transit peptide is instrumental for specific recognition of the chloroplast surface and in mediating the post-translational translocation of pre-proteins across the chloroplastic envelope and, thence, to the various sub-compartments within the chloroplast (e.g., stroma, thylakoid, and thylakoid membrane). These N-terminal transit peptide sequences contain all the information necessary for the import of the chloroplast protein into plastids; the transit peptide sequences are necessary and sufficient for plastid import.

Plant genes reported to have naturally-encoded transit peptide sequences at their N-terminus include the chloroplast small subunit of ribulose-1,5-bisphosphate caroxylase (RuBisCo) (de Castro Silva-Filho et al. (1996), *Plant Mol. Biol.* 30:769-80; Schnell et al. (1991), *J. Biol. Chem.* 266: 3335-42); EPSPS (see, e.g., Archer et al. (1990), *J. Bioenerg. and Biomemb.* 22:789-810, and U.S. Pat. Nos. 6,867, 293, 7,045,684, and Re. 36,449); tryptophan synthase (Zhao et al. (1995), *J. Biol. Chem.* 270:6081-7); plastocyanin (Lawrence et al. (1997), *J. Biol. Chem.* 272:20357-63); chorismate synthase (Schmidt et al. (1993), *J. Biol. Chem.* 268:27447-57); the light harvesting chlorophyll a/b binding protein (LHBP) (Lamppa et al. (1988), *J. Biol. Chem.* 263:14996-14999); and chloroplast protein of *Arabidopsis thaliana* (Lee et al. (2008), *Plant Cell* 20:1603-22). United States Patent Publication No. US 2010/0071090 provides certain chloroplast targeting peptides from *Chlamydomonas* sp.

However, the structural requirements for the information encoded by chloroplast targeting peptides remains elusive, due to their high level of sequence diversity and lack of common or consensus sequence motifs, though it is possible that there are distinct subgroups of chloroplast targeting peptides with independent structural motifs. Lee et al.

(2008), supra. Further, not all of these sequences have been useful in the heterologous expression of chloroplast-targeted proteins in higher plants.

BRIEF SUMMARY OF THE DISCLOSURE

Described herein are compositions and methods for plastid targeting of polypeptides in a plant. In some embodiments, a composition comprises a nucleic acid molecule comprising at least one nucleotide sequence encoding a synthetic *Brassica*-derived chloroplast transit peptide (e.g., a TraP8 peptide, and a TraP9 peptide) operably linked to a nucleotide sequence of interest. In particular embodiments, such nucleic acid molecules may be useful for expression and targeting of a polypeptide encoded by the nucleotide sequence of interest in a monocot or dicot plant. Further described are vectors comprising a nucleic acid molecule comprising at least one nucleotide sequence encoding a synthetic *Brassica*-derived chloroplast transit peptide operably linked to a nucleotide sequence of interest.

In some embodiments, a nucleotide sequence encoding a synthetic *Brassica*-derived CTP may be a nucleotide sequence that is derived from a reference nucleotide sequence obtained from a *Brassica* sp. gene (e.g., *B. napus, B. rapa, B. juncea*, and *B. carinata*), or a functional variant thereof. In some embodiments, a nucleotide sequence encoding a synthetic *Brassica*-derived CTP may be a chimeric nucleotide sequence comprising a partial CTP-encoding nucleotide sequence from a *Brassica* sp. gene, or a functional variant thereof. In specific embodiments, a nucleotide sequence encoding a synthetic *Brassica*-derived CTP may contain contiguous nucleotide sequences obtained from each of a reference *Brassica* sp. CTP, and a CTP from a different gene of the *Brassica* sp., a different *Brassica* sp., or a different organism (e.g., a plant, prokaryote, and lower photosynthetic eukaryote), or or functional variants of any of the foregoing. In particular embodiments, a contiguous nucleotide sequence may be obtained from an orthologous nucleotide sequence of the reference *Brassica* CTP that is obtained from a different organism's ortholog of the reference *Brassica* sp. gene (e.g., a different *Brassica* sp. genome). In these and further embodiments, a nucleotide sequence encoding a synthetic *Brassica*-derived CTP may be a chimeric nucleotide sequence comprising more than one CTP-encoding nucleotide sequence.

In some examples, a nucleotide sequence encoding a synthetic *Brassica*-derived CTP may be a chimeric nucleotide sequence comprising a partial CTP nucleotide sequence from either of *B. napus* and *B. rapa*, or functional variants thereof. In specific examples, a nucleotide sequence encoding a synthetic *Brassica*-derived CTP may contain contiguous nucleotide sequences obtained from each of *B. napus* and *B. rapa*, or functional variants thereof.

In some embodiments, a composition comprises a nucleic acid molecule comprising at least one *Brassica*-derived means for targeting a polypeptide to a chloroplast. Further described are nucleic acid molecules comprising a nucleic acid molecule comprising at least one *Brassica*-derived means for targeting a polypeptide to a chloroplast operably linked to a nucleotide sequence of interest. In particular embodiments, such nucleic acid molecules may be useful for expression and targeting of a polypeptide encoded by the nucleotide sequence of interest in a monocot or dicot plant. For the purposes of the present disclosure, a *Brassica*-derived means for targeting a polypeptide to a chloroplast refers to particular synthetic nucleotide sequences. In particular embodiments, a *Brassica*-derived means for targeting a polypeptide to a chloroplast is selected from the group consisting of the nucleotide sequences encoding the polypeptides referred to herein as TraP8 and TraP9.

Also described herein are plant materials (for example and without limitation, plants, plant tissues, and plant cells) comprising a nucleic acid molecule comprising at least one nucleotide sequence encoding a synthetic *Brassica*-derived CTP operably linked to a nucleotide sequence of interest. In some embodiments, a plant material may have such a nucleic acid molecule stably integrated in its genome. In some embodiments, a plant material may transiently express a product of a nucleic acid molecule comprising at least one nucleotide sequence encoding a synthetic *Brassica*-derived CTP operably linked to a nucleotide sequence of interest. In some embodiments, the plant material is a plant cell from which a plant cannot be regenerated.

Methods are also described for expressing a nucleotide sequence in a plastid-containing cell (e.g., a plant) in a plastid (e.g., a chloroplast) of the plastid-containing cell. In particular embodiments, a nucleic acid molecule comprising at least one nucleotide sequence encoding a synthetic *Brassica*-derived CTP operably linked to a nucleotide sequence of interest may be used to transform a plant cell, such that a precursor fusion polypeptide comprising the synthetic *Brassica*-derived CTP fused to an expression product of the nucleotide sequence of interest is produced in the cytoplasm of the plant cell, and the fusion polypeptide is then transported in vivo into a chloroplast of the plant cell. In some embodiments, the plant cell is not capable of regeneration to a plant.

Further described are methods for the production of a transgenic plant comprising a nucleic acid molecule comprising at least one nucleotide sequence encoding a synthetic *Brassica*-derived CTP operably linked to a nucleotide sequence of interest. Also described are plant commodity products (e.g., seeds) produced from such transgenic plants. In some embodiments, these transgenic plants or plant commodity products contain transgenic cells from which a plant cannot be regenerated.

The foregoing and other features will become more apparent from the following detailed description of several embodiments, which proceeds with reference to the accompanying figures.

BRIEF DESCRIPTION OF THE FIGURES

FIG. 17 illustrates a plasmid map of pDAB112710.

FIG. 18 includes an alignment of the predicted chloroplast transit peptides for the EPSPS protein from *Brassica* napes (SEQ ID NO:1) and *Brassica rapa* (SEQ ID NO:2). The asterisk indicates where the sequences were split and recombined to form TraP8 and Trap9.

SEQUENCE LISTING

Figure 1:
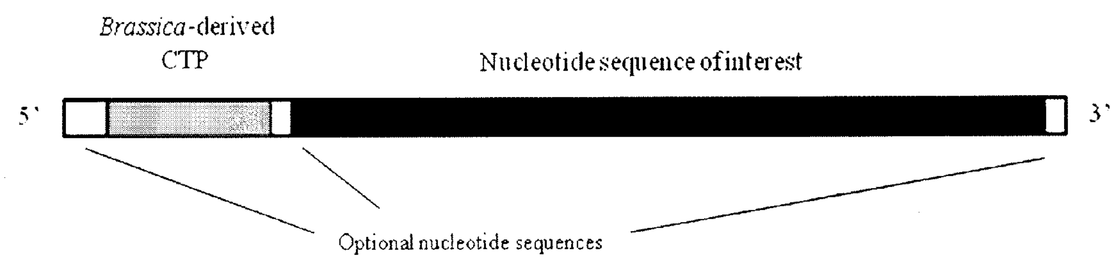
FIG. 1 illustrates an mRNA molecule that is representative of particular examples of synthetic *Brassica*-derived CTP-encoding nucleotide sequences (for example, for TraP8 and TraP9) operably linked to a nucleotide sequence of interest. In some embodiments, an mRNA molecule (such as the one shown) may be transcribed from a DNA molecule comprising an open reading frame including the synthetic *Brassica*-derived CTP-encoding sequence operably linked to the nucleotide sequence of interest. The nucleotide sequence of interest may be, in some embodiments, a sequence encoding a peptide of interest, for example and without limitation, a marker gene product or peptide to be targeted to a plastid.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 shows the amino acid sequence of a *Brassica napus* EPSPS chloroplast transit peptide.

SEQ ID NO:2 shows the amino acid sequence of a *Brassica rapa* EPSPS chloroplast transit peptide.

SEQ ID NO:3 shows the amino acid sequence of a TraP8 chimeric chloroplast transit peptide.

SEQ ID NO:4 shows the amino acid sequence of a TraP9 chimeric chloroplast transit peptide.

SEQ ID NO:5 shows a polynucleotide sequence encoding a TraP8 chimeric chloroplast transit peptide.

SEQ ID NO:6 shows a polynucleotide sequence encoding a TraP9 chimeric chloroplast transit peptide.

SEQ ID NO:7 shows a polynucleotide sequence encoding a linker sequence.

SEQ ID NO:8 shows a polynucleotide sequence encoding a TraP8 v2 chimeric chloroplast transit peptide.

SEQ ID NO:9 shows a polynucleotide sequence encoding a TraP9 v2 chimeric chloroplast transit peptide.

SEQ ID NO:10 shows a polynucleotide sequence encoding a cry2aa gene.

SEQ ID NO:11 shows a polynucleotide sequence encoding a vip3ab1v6 gene.

SEQ ID NO:12 shows a polynucleotide sequence encoding a vip3ab1v7 gene.

SEQ ID NO:13 shows a peptide having the amino acid sequence, Ser-Val-Ser-Leu.

SEQ ID NO:14 shows a polynucleotide sequence encoding the *Brassica napus* EPSPS chloroplast transit peptide of SEQ ID NO:1.

SEQ ID NO:15 shows a polynucleotide sequence encoding the *Brassica rapa* EPSPS chloroplast transit peptide of SEQ ID NO:2.

SEQ ID NO:16 shows a polynucleotide sequence encoding dgt-28 v5.

SEQ ID NO:17 shows a polynucleotide sequence encoding dgt-28 v6.

SEQ ID NO:18 shows the polynucleotide sequence of codon optimized dgt-1.

SEQ ID NO:19 shows the polynucleotide sequence of codon optimized dgt-3 v2 (G173A).

SEQ ID NO:20 shows the polynucleotide sequence of codon optimized dgt-3 v3 (G173A; P178S).

SEQ ID NO:21 shows the polynucleotide sequence of codon optimized dgt-3 v4 (T1741; P178S).

SEQ ID NO:22 shows the polynucleotide sequence of codon optimized dgt-7 v4 (T1681; P172S).

SEQ ID NO:23 shows the polynucleotide sequence of codon optimized dgt-32 v3.

SEQ ID NO:24 shows the polynucleotide sequence of codon optimized dgt-33 v3.

SEQ ID NO:25 shows the polynucleotide sequence of codon optimized dgt-31 v3.

SEQ ID NO:26 shows a polynucleotide sequence encoding transit peptide TraP4 v2.

SEQ ID NO:27 shows a polynucleotide sequence encoding transit peptide TraP5 v2.

SEQ ID NO:28 shows a polynucleotide sequence encoding transit peptide TraP8 v2.

SEQ ID NO:29 shows a polynucleotide sequence encoding transit peptide TraP9 v2.

SEQ ID NO:30 shows a polynucleotide sequence encoding transit peptide TraP12 v2.

SEQ ID NO:31 shows a polynucleotide sequence encoding transit peptide TraP13 v2.

SEQ ID NO:32 shows the polynucleotide sequence of TraP4 v2:dgt-28 v5.

SEQ ID NO:33 shows the polynucleotide sequence of TraP5 v2: dgt-28 v5.

SEQ ID NO:34 shows the polynucleotide sequence of TraP8 v2: dgt-28 v5.

SEQ ID NO:35 shows the polynucleotide sequence of TraP9 v2: dgt-28 v5.

SEQ ID NO:36 shows the polynucleotide sequence of TraP12 v2: dgt-28 v5.

SEQ ID NO:37 shows the polynucleotide sequence of TraP13 v2:dgt-28 v5.

SEQ ID NO:38 shows the polynucleotide sequence encoding transit peptide TraP14 v2.

SEQ ID NO:39 shows the polynucleotide sequence encoding transit peptide TraP23 v2.

SEQ ID NO:40 shows the polynucleotide sequence encoding transit peptide TraP24 v2.

SEQ ID NO:41 shows the polynucleotide sequence encoding transit peptide dgt-32 v3 fused to TraP14 v2.

SEQ ID NO:42 shows a polynucleotide sequence encoding transit peptide dgt-33 v3 fused to TraP24 v2.

SEQ ID NO:43 shows a polynucleotide sequence encoding transit peptide dgt-31 v3 fused to TraP23 v2.

SEQ ID NO:44 shows the oligonucleotide sequence of the DSM2A primer.

SEQ ID NO:45 shows the oligonucleotide sequence of the DSM2S primer.

SEQ ID NO:46 shows the oligonucleotide sequence of the DSM2 Cy5 probe.

SEQ ID NO:47 shows the oligonucleotide sequence of the DGT28F primer.

SEQ ID NO:48 shows the oligonucleotide sequence of the DGT28R primer.

SEQ ID NO:49 shows the oligonucleotide sequence of the TAFFY-HEX probe.

SEQ ID NO:50 shows the oligonucleotide sequence of the TAFII15-F primer.

SEQ ID NO:51 shows the oligonucleotide sequence of the TAFII15-R primer.

SEQ ID NO:52 shows the oligonucleotide sequence of the forward oligo used for dgt-28 gene expression cassette confirmation.

SEQ ID NO:53 shows the oligonucleotide sequence of the reverse oligo used for dgt-28 gene expression cassette confirmation.

SEQ ID NO:54 shows the oligonucleotide sequence of the AT26410LP primer.

SEQ ID NO:55 shows the oligonucleotide sequence of the AT26410RP primer.

SEQ ID NO:56 shows the oligonucleotide sequence of the DGT28F primer.

SEQ ID NO:57 shows the oligonucleotide sequence of the DGT28R primer.

SEQ ID NO:58 shows the oligonucleotide sequence of the GAAD1F primer.

SEQ ID NO:59 shows the oligonucleotide sequence of the GAAD1P probe.

SEQ ID NO:60 shows the oligonucleotide sequence of the GAAD1R primer.

SEQ ID NO:61 shows the oligonucleotide sequence of the IV-Probe.

SEQ ID NO:62 shows the oligonucleotide sequence of the IVF-Taq primer.

SEQ ID NO:63 shows the oligonucleotide sequence of the IVR-Taq primer.

SEQ ID NO:64 shows the oligonucleotide sequence of the zmDGT28 F primer.

SEQ ID NO:65 shows the oligonucleotide sequence of the zmDGT28 FAM probe.

SEQ ID NO:66 shows the oligonucleotide sequence of the zmDGT28 R primer.

DETAILED DESCRIPTION

I. Overview of Several Embodiments

A chloroplast transit peptide (CTP) (or plastid transit peptide) functions co-translationally or post-translationally to direct a polypeptide comprising the CTP to a plastid (e.g., a chloroplast). In some embodiments of the invention, either endogenous chloroplast proteins or heterologous proteins may be directed to a chloroplast by expression of such a protein as a larger precursor polypeptide comprising a CTP. In particular embodiments, the CTP may be derived from a nucleotide sequence obtained from a *Brassica* sp. gene, for example and without limitation, by incorporating at least one contiguous sequence from a orthologous gene obtained from a different organism, or a functional variant thereof.

In an exemplary embodiment, nucleic acid sequences, each encoding a CTP, were isolated from EPSPS gene sequences obtained from *Brassica napus* (NCBI Database Accession No. P17688) and *Brassica rapa* (NCBI Database Accession No. AAS80163). The CTP-encoding nucleic acid sequences were isolated by analyzing the EPSPS gene sequence with the ChloroP prediction server. Emanuelsson et al. (1999), *Protein Science* 8:978-84 (available at cbs.dtu.dk/services/ChloroP). The predicted protein products of the isolated CTP-encoding sequences are approximately 60-70 amino acid-long transit peptides. In this example, the native *B. napus* CTP was used as a reference sequence to design exemplary synthetic *Brassica*-derived CTPs by fusing contiguous sequences from the other CTPs at a particular position in the *B. napus* CTP. This design process illustrates the development of a novel synthetic CTP, according to some aspects, from a *Brassica* sp. nucleic acid sequence. These exemplary synthetic *Brassica*-derived CTPs are referred to throughout this disclosure as TraP8 and TraP9. These exemplary synthetic TraPs were tested for plastid-targeting function and were found to exhibit plastid targeting that was at least as favorable as that observed for the native *Brassica* sequences individually.

In a further exemplary embodiment, nucleic acid sequences, each encoding a synthetic TraP peptide of the invention, were synthesized independently and operably linked to a nucleic acid sequence encoding a yellow fluorescent protein (YFP) to produce synthetic nucleic acid molecules, each encoding a chimeric TraP:YFP fusion polypeptide. Such nucleic acid molecules, each encoding a chimeric TraP:YFP polypeptide, were each introduced into a binary vector, such that each TraP:YFP-encoding nucleic acid sequence was operably linked to an AtUbi10 promoter.

In yet a further exemplary embodiment, binary vectors comprising a TraP:YFP-encoding nucleic acid sequence operably linked to an AtUbi10 promoter each were independently, transiently transformed into tobacco (*Nicotiana benthamiana*) via *Agrobacterium*-mediated transformation. Confocal microscopy and Western blot analysis confirmed that each TraP successfully targeted YFP to tobacco chloroplasts.

In a further exemplary embodiment, nucleic acid sequences, each encoding a synthetic TraP peptide of the invention, were synthesized independently and operably linked to a nucleic acid sequence encoding an agronomically important gene sequence. The TraP sequences were fused to herbicide tolerant traits (e.g. dgt-28 and dgt-14) to produce synthetic nucleic acid molecules, each encoding a chimeric TraP:DGT-28 or TraP:DGT-14 fusion polypeptide. Such nucleic acid molecules, each encoding a chimeric TraP:DGT-28 or TraP:DGT-14 polypeptide, were each introduced into a binary vector, such that each TraP:dgt-28 or TraP:dgt-14-encoding nucleic acid sequence was operably linked to a promoter and other gene regulatory elements. The binary containing the TraP:dgt-28 or TraP:dgt-14-encoding nucleic acid sequence was used to transform varopis plant species. The transgenic plants were assayed for herbicide tolerance as a result of the expression and translocation of the DGT-28 or DGT-14 enzymes to the chloroplast.

In a further exemplary embodiment, nucleic acid sequences, each encoding a synthetic TraP peptide of the invention, were synthesized independently and operably linked to a nucleic acid sequence encoding an agronomically important gene sequence. The TraP sequences were fused to genes conferring insect tolerance traits (e.g. cry2Aa and vip3ab1) to produce synthetic nucleic acid molecules, each encoding a chimeric TraP:Cry2Aa or TraP:Vip3Ab1 fusion polypeptide. Such nucleic acid molecules, each encoding a chimeric TraP:Cry2Aa or TraP: Vip3Ab1 polypeptide, were each introduced into a binary vector, such that each TraP:Cry2Aa or TraP: Vip3Ab1-encoding nucleic acid sequence was operably linked to a promoter and other gene regulatory elements. The binary containing the TraP: Cry2Aa or TraP: Vip3Ab1-encoding nucleic acid -sequence was used to transform various plant species. The transgenic plants were bioassayed for insect resistance as a result of the expression and translocation of the Cry2Aa or Vip3Ab1 enzymes to the chloroplast.

In view of the aforementioned detailed working examples, synthetic *Brassica*-derived CTP sequences of the invention, and nucleic acids encoding the same, may be used to direct any polypeptide to a plastid in a broad range of plastid-containing cells. For example, by methods made available to those of skill in the art by the present disclosure, a chimeric polypeptide comprising a synthetic *Brassica*-derived CTP sequence fused to the N-terminus of any second peptide sequence may be introduced into (or expressed in) a plastid-containing host cell for plastid targeting of the second peptide sequence. Thus, in particular embodiments, a TraP peptide of the invention may provide increased efficiency of import and processing of a peptide for which plastid expression is desired, when compared to a native CTP.

II. Abbreviations

CTP chloroplast transit peptide

Bt *bacillus thuringiensis*

EPSPS 3-enolpyruvylshikimate-5-phosphate synthetase

YFP yellow fluorescent protein $T_i$ tumor-inducing (plasmids derived from *A. tumefaciens*)

T-DNA transfer DNA

III. Terms

In order to facilitate review of the various embodiments of the disclosure, the following explanations of specific terms are provided:

Chloroplast transit peptide: As used herein, the term "chloroplast transit peptide" (CTP) (or "plastid transit peptide") may refer to an amino acid sequence that, when present at the N-terminus of a polypeptide, directs the import of the polypeptide into a plastid of a plastid-containing cell (e.g., a plant cell, such as in a whole plant or plant cell culture). A CTP is generally necessary and sufficient to direct the import of a protein into a plastid (e.g., a primary, secondary, or tertiary plastid, such as a chloroplast) of a host cell. A putative chloroplast transit peptide may be identified by one of several available algorithms (e.g., PSORT, and ChloroP (available at cbs.dtu.dk/services/ChloroP)). ChloroP may provide particularly good prediction of CTPs. Emanuelsson et al. (1999), *Protein Science* 8:978-84. However, prediction of functional CTPs is not achieved at 100% efficiency by any existing algorithm. Therefore, it is important to verify that an identified putative CTP does indeed function as intended in, e.g., an in vitro, or in vivo methodology.

Chloroplast transit peptides may be located at the N-terminus of a polypeptide that is imported into a plastid. The CTP may facilitate co- or post-translational transport of a polypeptide comprising the CTP into the plastid. Chloroplast transit peptides typically comprise between about 40 and about 100 amino acids, and such CTPs have been observed to contain certain common characteristics. For example: CTPs contain very few, if any, negatively charged amino acids (such as aspartic acid, glutamic acid, asparagines, or glutamine); the N-terminal regions of CTPs lack charged amino acids, glycine, and proline; the central region of a CTP also is likely to contain a very high proportion of basic or hydroxylated amino acids (such as serine and threonine); and the C-terminal region of a CTP is likely to be rich in arginine, and have the ability to comprise an amphipathic beta-sheet structure. Plastid proteases may cleave the CTP from the remainder of a polypeptide comprising the CTP after importation of the polypeptide into the plastid.

Contact: As used herein, the term "contact with" or "uptake by" a cell, tissue, or organism (e.g., a plant cell; plant tissue; and plant), with regard to a nucleic acid molecule, includes internalization of the nucleic acid molecule into the organism, for example and without limitation: contacting the organism with a composition comprising the nucleic acid molecule; and soaking of organisms with a solution comprising the nucleic acid molecule.

Endogenous: As used herein, the term "endogenous" refers to substances (e.g., nucleic acid molecules and polypeptides) that originate from within a particular organism, tissue, or cell. For example, an "endogenous" polypeptide expressed in a plant cell may refer to a polypeptide that is normally expressed in cells of the same type from non-genetically engineered plants of the same species. In some examples, an endogenous gene (e.g., an EPSPS gene) from a *Brassica* sp. may be used to obtain a reference *Brassica* CTP sequence.

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation. RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, for example and without limitation: Northern blot; RT-PCR; Western blot; or in vitro; in situ; and in vivo protein activity assay(s).

Genetic material: As used herein, the term "genetic material" includes all genes, and nucleic acid molecules, such as DNA and RNA.

Heterologous: As used herein, the term "heterologous" refers to substances (e.g., nucleic acid molecules and polypeptides) that do not originate from within a particular organism, tissue, or cell. For example, a "heterologous" polypeptide expressed in a plant cell may refer to a polypeptide that is not normally expressed in cells of the same type from non-genetically engineered plants of the same species (e.g., a polypeptide that is expressed in different cells of the same organism or cells of a different organism).

Isolated: As used herein, the term "isolated" refers to molecules (e.g., nucleic acid molecules and polypeptides) that are substantially separated or purified away from other molecules of the same type (e.g., other nucleic acid molecules and other polypeptides) with which the molecule is normally associated in the cell of the organism in which the molecule naturally occurs. For example, an isolated nucleic acid molecule may be substantially separated or purified away from chromosomal DNA or extrachromosomal DNA in the cell of the organism in which the nucleic acid molecule naturally occurs. Thus, the term includes recombinant nucleic acid molecules and polypeptides that are biochemically purified such that other nucleic acid molecules, polypeptides, and cellular components are removed. The term also includes recombinant nucleic acid molecules, chemically-synthesized nucleic acid molecules, and recombinantly produced polypeptides.

The term "substantially purified," as used herein, refers to a molecule that is separated from other molecules normally associated with it in its native state. A substantially purified molecule may be the predominant species present in a composition. A substantially purified molecule may be, for example, at least 60% free, at least 75% free, or at least 90% free from other molecules besides a solvent present in a natural mixture. The term "substantially purified" does not refer to molecules present in their native state.

Nucleic acid molecule: As used herein, the term "nucleic acid molecule" refers to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. Nucleic acid molecules include dimeric (so-called in tandem) forms, and the transcription products of nucleic acid molecules. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; ESTs; and recombinant nucleotide sequences.

In some embodiments, the invention includes nucleotide sequences that may be isolated, purified, or partially purified, for example, using separation methods such as, for example, ion-exchange chromatography; by exclusion based on molecular size or by affinity; by fractionation techniques based on solubility in different solvents; and methods of genetic engineering such as amplification, cloning, and subcloning.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the team "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981), *Adv. Appl. Math.* 2:482; Needleman and Wunsch (1970), *J. Mol. Biol.* 48:443; Pearson and Lipman (1988), *Proc. Natl. Acad. Sci. U.S.A.* 85:2444; Higgins and Sharp (1988), *Gene* 73:237-44; Higgins and Sharp (1989), *CABIOS* 5:151-3; Corpet et al. (1988), *Nucleic Acids Res.* 16:10881-90; Huang et al. (1992), *Comp. Appl. Biosci.* 8:155-65; Pearson et al. (1994), *Methods Mol. Biol.* 24:307-31; Tatiana et al. (1999), *FEMS Microbiol. Lett.* 174:247-50. A detailed consideration of sequence alignment methods and homology calculations can be found in, e.g., Altschul et al. (1990), *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "specifically complementary" are terms that indicate a sufficient degree of complementarity, such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization, IRL Press, Oxford*, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under stringent conditions (e.g., the Moderate Stringency conditions set forth, supra) to the reference nucleic acid sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" (or "orthologous") refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

When determining the percentage of sequence identity between amino acid sequences, it is well-known by those of skill in the art that the identity of the amino acid in a given position provided by an alignment may differ without affecting desired properties of the polypeptides comprising the aligned sequences. In these instances, the percent sequence identity may be adjusted to account for similarity between conservatively substituted amino acids. These adjustments are well-known and commonly used by those of skill in the art. See, e.g., Myers and Miller (1988), *Computer Applications in Biosciences* 4:11-7.

Embodiments of the invention include functional variants of exemplary plastid transit peptide amino acid sequences, and nucleic acid sequences encoding the same. A functional variant of an exemplary transit peptide sequence may be, for example, a fragment of an exemplary transit peptide amino acid sequence (such as an N-terminal or C-terminal fragment), or a modified sequence of a full-length exemplary transit peptide amino acid sequence or fragment of an exemplary transit peptide amino acid sequence. An exemplary transit peptide amino acid sequence may be modified in some embodiments be introducing one or more conservative amino acid substitutions. A "conservative" amino acid substitution is one in which the amino acid residue is replaced by an amino acid residue having a similar functional side chain, similar size, and/or similar hydrophobicity. Families of amino acids that may be used to replace another amino acid of the same family in order to introduce a conservative substitution are known in the art. For example, these amino acid families include: Basic amino acids (e.g., lysine, arginine, and histidine); acidic amino acids (e.g., aspartic acid and glutamic acid); uncharged (at physiological pH) polar amino acids (e.g., glycine, asparagines, glutamine, serine, threonine, tyrosine, and cytosine); non-polar amino acids (e.g., alanine, valine, leucine, isoleucine, proline, phenylalanine, methionine, and tryptophan); beta-branched amino acids (e.g., threonine, valine, and isoleucine); and aromatic amino acids (e.g., tyrosine, phenylalanine, tryptophan, and histidine). See, e.g., Sambrook et al. (Eds.), supra; and Innis et al., *PCR Protocols: A Guide to Methods and Applications,* 1990, Academic Press, NY, USA.

Operably linked: A first nucleotide sequence is "operably linked" with a second nucleotide sequence when the first nucleotide sequence is in a functional relationship with the second nucleotide sequence. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

When used in reference to two or more amino acid sequences, the term "operably linked" means that the first amino acid sequence is in a functional relationship with at least one of the additional amino acid sequences. For instance, a transit peptide (e.g., a CTP) is operably linked to a second amino acid sequence within a polypeptide comprising both sequences if the transit peptide affects expression or trafficking of the polypeptide or second amino acid sequence.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions.

Any inducible promoter can be used in some embodiments of the invention. See Ward et al. (1993), *Plant Mol. Biol.* 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991), *Proc. Natl. Acad. Sci. USA* 88:0421).

Exemplary constitutive promoters include, but are not limited to: Promoters from plant viruses, such as the 35S promoter from CaMV; promoters from rice actin genes; ubiquitin promoters; pEMU; MAS; maize H3 histone promoter; and the ALS promoter, XbaI/NcoI fragment 5' to the *Brassica napus* ALS3 structural gene (or a nucleotide sequence similarity to said XbaI/NcoI fragment) (International PCT Publication No. WO 96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986), *Nature* 319:791-3);

lipofection (Felgner et al. (1987), *Proc. Natl. Acad. Sci. USA* 84:7413-7); microinjection (Mueller et al. (1978), *Cell* 15:579-85); *Agrobacterium*-mediated transfer (Fraley et al. (1983), *Proc. Natl. Acad. Sci. USA* 80:4803-7); direct DNA uptake; and microprojectile bombardment (Klein et al. (1987), *Nature* 327:70).

Transgene: An exogenous nucleic acid sequence. In some examples, a transgene may be a sequence that encodes a polypeptide comprising at least one synthetic *Brassica*-derived CTP. In particular examples, a transgene may encode a polypeptide comprising at least one synthetic *Brassica*-derived CTP and at least an additional peptide sequence (e.g., a peptide sequence that confers herbicide-resistance), for which plastid expression is desirable. In these and other examples, a transgene may contain regulatory sequences operably linked to a coding sequence of the transgene (e.g., a promoter). For the purposes of this disclosure, the term "transgenic" when used to refer to an organism (e.g., a plant), refers to an organism that comprises the exogenous nucleic acid sequence. In some examples, the organism comprising the exogenous nucleic acid sequence may be an organism into which the nucleic acid sequence was introduced via molecular transformation techniques. In other examples, the organism comprising the exogenous nucleic acid sequence may be an organism into which the nucleic acid sequence was introduced by, for example, introgression or cross-pollination in a plant.

Transport: As used herein, the terms "transport(s)," "target(s)," and "transfer(s)" refers to the property of certain amino acid sequences of the invention that facilitates the movement of a polypeptide comprising the amino acid sequence from the nucleus of a host cell into a plastid of the host cell. In particular embodiments, such an amino acid sequence (i.e., a synthetic *Brassica*-derived CTP sequence) may be capable of transporting about 100%, at least about 95%, at least about 90%, at least about 85%, at least about 80%, at least about 70%, at least about 60%, and/or at least about 50% of a polypeptide comprising the amino acid sequence into plastids of a host cell.

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Synthetic *Brassica*-Derived CTP-Encoding Sequence In some embodiments, this disclosure provides a nucleic acid molecule comprising at least one nucleotide sequence encoding a synthetic *Brassica*-derived CTP operably linked to a nucleotide sequence of interest. In particular embodiments, the nucleotide sequence of interest may be a nucleotide sequence that encodes a polypeptide of interest. In particular examples, a single nucleic acid molecule is provided that encodes a polypeptide wherein a TraP8 or TraP9 sequence is fused to the N-terminus of a polypeptide of interest.

A synthetic *Brassica*-derived CTP may be derived from a *Brassica* EPSPS gene. In particular examples of such embodiments, the *Brassica* EPSPS gene may be one that comprises the nucleic acid sequence set forth as SEQ ID NO:14, or a homologous nucleic acid sequence from a different EPSPS gene, or may be an ortholog of the *Brassica* EPSPS gene comprising the nucleic acid sequence set forth as SEQ ID NO:14 (for example, the *Brassica* EPSPS gene comprising the nucleic acid sequence set forth as SEQ ID NO:15).

In some embodiments, a synthetic *Brassica*-derived chloroplast transit peptide may be a chimeric *Brassica*-derived CTP. A synthetic chimeric *Brassica*-derived CTP may be derived from a reference *Brassica* CTP sequence by joining a first contiguous amino acid sequence comprised within the reference *Brassica* CTP sequence to a second contiguous amino acid sequence comprised within a different CTP sequence (e.g., a second *Brassica* CTP sequence). In particular embodiments, the different CTP sequence comprising the second contiguous amino acid sequence may be encoded by a homologous gene sequence from a genome other than that of the *Brassica* sp. from which the reference sequence was obtained (e.g., a different *Brassica* sp., a plant other than a *Brassica* sp.; a lower photosynthetic eukaryote, for example, a Chlorophyte; and a prokaryote, for example, a *Cyanobacterium* or *Agrobacterium*). Thus, a nucleotide sequence encoding a synthetic *Brassica*-derived CTP may be derived from a reference *Brassica* CTP-encoding gene sequence by fusing a nucleotide sequence that encodes a contiguous amino acid sequence of the reference *Brassica* CTP sequence with a nucleotide sequence that encodes the contiguous amino acid sequence from a different CTP sequence that is homologous to the remainder of the reference *Brassica* CTP sequence. In these and other examples, the contiguous amino acid sequence of the reference *Brassica* CTP sequence may be located at the 5' end or the 3' end of the synthetic *Brassica*-derived CTP.

In some embodiments, a synthetic chimeric *Brassica*-derived CTP may be derived from a plurality of *Brassica* CTP sequences (including a reference *Brassica* CTP sequence) by joining a contiguous amino acid sequence comprised within one *Brassica* CTP sequence to a contiguous amino acid sequence comprised within a different *Brassica* CTP sequence. In particular embodiments, the plurality of *Brassica* CTP sequences may be encoded by orthologous gene sequences in different *Brassica* species. In some examples, the plurality of *Brassica* CTP sequences may be exactly two *Brassica* CTP sequences. Thus, a nucleotide sequence encoding a synthetic chimeric *Brassica*-derived CTP may be derived from two homologous (e.g., substantially homologous) *Brassica* CTP-encoding gene sequences (e.g., orthologous gene sequences) by fusing the nucleotide sequence that encodes a contiguous amino acid sequence of one of the *Brassica* CTP sequences with the nucleotide sequence that encodes the contiguous amino acid sequence from the other of the *Brassica* CTP sequences that is homologous to the remainder of the first *Brassica* CTP sequence. TraP8 and TraP9 are illustrative examples of such a synthetic chimeric *Brassica*-derived CTP.

One of ordinary skill in the art will understand that, following the selection of a first contiguous amino acid sequence within a reference *Brassica* CTP sequence, the identification and selection of the contiguous amino acid sequence from the remainder of a homologous CTP sequence according to the foregoing derivation process is unambiguous and automatic. In some examples, the first contiguous amino acid sequence may be between about 25 and about 41 amino acids in length (e.g., 24, 25, 26, 27, 28, 29, 30, 31, 32, 33, 34, 35, 36, 37, 38, 39, 40, 41, and 42 amino acids in length). In some embodiments, the first contiguous amino acid sequence within the reference *Brassica* CTP sequence is defined by the position at the 3' end of a "SVSL" (SEQ ID NO:13) motif that is conserved within some *Brassica* EPSPS genes.

Examples of synthetic chimeric *Brassica*-derived CTP sequences according to the foregoing process are represented by SEQ ID NO:3 and SEQ ID NO:4. In view of the degeneracy of the genetic code, the genus of nucleotide sequences encoding these peptides will be immediately envisioned by one of ordinary skill in the art. Examples of such polynucleotide sequences include SEQ ID NOs: 5, 6, 8, and 9. These particular examples illustrate the structural features of synthetic chimeric *Brassica*-derived CTPs by incorporating contiguous sequences from a homologous CTP from one of several ESPSP orthologs of a *B. napus* ESPSP gene.

Some embodiments include functional variants of a synthetic *Brassica*-derived chloroplast transit peptide, and/or nucleic acids encoding the same. Such functional variants include, for example and without limitation: a synthetic *Brassica*-derived CTP-encoding sequence that is derived from a homolog and/or ortholog of one or both of the *Brassica* CTP-encoding sequences set forth as SEQ ID NOs:14 and/or SEQ ID NO:15, and/or a CTP encoded thereby; a nucleic acid that encodes a synthetic *Brassica*-derived CTP that comprises a contiguous amino acid sequence within SEQ ID NO:1 and/or SEQ ID NO:2, and/or a CTP encoded thereby; a truncated synthetic *Brassica*-derived CTP-encoding sequence that comprises a contiguous nucleic acid sequence within one of SEQ ID NOs:5, 6, 8, and 9; a truncated synthetic *Brassica*-derived CTP-encoding sequence that comprises a contiguous nucleic acid sequence that is substantially homologous to one of SEQ ID NOs: 5, 6, 8, and 9; a truncated synthetic *Brassica*-derived CTP that comprises a contiguous amino acid sequence within one of SEQ ID NOs: 3 and 4; a nucleic acid that encodes a synthetic *Brassica*-derived CTP comprising a contiguous amino acid sequence within one of SEQ ID NOs: 5, 6, 8, and 9, and/or a CTP encoded thereby; a nucleic acid that encodes a synthetic *Brassica*-derived CTP comprising a contiguous amino acid sequence within one of SEQ ID NOs: 3 and 4 that has one or more conservative amino acid substitutions, and/or a CTP encoded thereby; and a nucleic acid that encodes a synthetic *Brassica*-derived CTP comprising a contiguous amino acid sequence within one of SEQ ID NOs: 3 and 4 that has one or more non-conservative amino acid substitutions that are demonstrated to direct an operably linked peptide to a plastid in a plastid-containing cell, and/or a CTP encoded thereby.

Thus, some embodiments of the invention include a nucleic acid molecule comprising a nucleotide sequence encoding a synthetic chimeric *Brassica*-derived CTP comprising one or more conservative amino acid substitutions. Such a nucleic acid molecule may be useful, for example, in facilitating manipulation of a CTP-encoding sequence of the invention in molecular biology techniques. For example, in some embodiments, a CTP-encoding sequence of the invention may be introduced into a suitable vector for sub-cloning of the sequence into an expression vector, or a CTP-encoding sequence of the invention may be introduced into a nucleic acid molecule that facilitates the production of a further nucleic acid molecule comprising the CTP-encoding sequence operably linked to a nucleotide sequence of interest. In these and further embodiments, one or more amino acid positions in the sequence of a synthetic chimeric *Brassica*-derived CTP may be deleted. For example, the sequence of a synthetic chimeric *Brassica*-derived CTP may be modified such that the amino acid(s) at 1, 2, 3, 4, 5, 6, 7, 8, 9, 10, 11, 12, 13, 14, 15, 16, 17, 18, 19, or 20 positions in the sequence are deleted. An alignment of homologous CTP sequences may be used to provide guidance as to which amino acids may be deleted without affecting the function of the synthetic CTP.

In particular examples, a synthetic *Brassica*-derived chloroplast transit peptide is less than 80 amino acids in length. For example, a synthetic *Brassica*-derived CTP may be 79, 78, 77, 76, 75, 74, 73, 72, 71, 70, 69, 68, 67, 66, 65, 64, 63, 62, 61, 60, or fewer amino acids in length. In certain examples, a synthetic *Brassica*-derived CTP may be about 65, about 68, about 72, or about 74 amino acids in length. In these and further examples, a synthetic *Brassica*-derived CTP may comprise an amino acid sequence set forth in one of SEQ ID NOs: 3 and 4, or a functional variant of any of the foregoing. Thus, a synthetic *Brassica*-derived CTP may comprise an amino acid sequence comprising one of SEQ ID NOs: 3 and 4 or a functional variant thereof, wherein the length of the synthetic *Brassica*-derived CTP is less than 80 amino acids in length. In certain examples, a synthetic *Brassica*-derived CTP may comprise an amino acid sequence that is, e.g., at least 80%, at least 85%, at least 90%, at least 92%, at least 94%, at least 95%, at least 96%, at least 97%, at least 98%, at least 99%, or 100% identical to one of SEQ ID NOs: 3 and 4.

All of the nucleotide sequences that encode a particular synthetic *Brassica*-derived CTP, for example, the TraP8 peptide of SEQ ID NO:3 and the TraP9 peptide of SEQ ID NO:4, or functional variants of any of the foregoing including any specific deletions and/or conservative amino acid substitutions, will be recognizable by those of skill in the art in view of the present disclosure. The degeneracy of the genetic code provides a finite number of coding sequences for a particular amino acid sequence. The selection of a particular sequence to encode a synthetic *Brassica*-derived CTP is within the discretion of the practitioner. Different coding sequences may be desirable in different applications. For example, to increase expression of the synthetic *Brassica*-derived CTP in a particular host, a coding sequence may be selected that reflects the codon usage bias of the host. By way of example, a synthetic *Brassica*-derived CTP may be encoded by a nucleotide sequence set forth as one of SEQ ID NOs: 5, 6, 8, and 9.

In nucleic acid molecules provided in some embodiments of the invention, the last codon of a nucleotide sequence encoding a synthetic *Brassica*-derived CTP and the first codon of a nucleotide sequence of interest may be separated by any number of nucleotide triplets, e.g., without coding for an intron or a "STOP." In some examples, a sequence encoding the first amino acids of a mature protein normally associated with a chloroplast transit peptide in a natural precursor polypeptide may be present between the last codon of a nucleotide sequence encoding a synthetic *Brassica*-derived CTP and the first codon of a nucleotide sequence of interest. A sequence separating a nucleotide sequence encoding a synthetic *Brassica*-derived CTP and the first codon of a nucleotide sequence of interest may, for example, consist of any sequence, such that the amino acid sequence encoded is not likely to significantly alter the translation of the chimeric polypeptide and its translocation to a plastid. In these and further embodiments, the last codon of a nucleotide sequence encoding a synthetic *Brassica*-derived chloroplast transit peptide may be fused in phase-register with the first codon of the nucleotide sequence of interest directly contiguous thereto, or separated therefrom by no more than a short peptide sequence, such as that encoded by a synthetic nucleotide linker (e.g., a nucleotide linker that may have been used to achieve the fusion).

In some embodiments, it may be desirable to modify the nucleotides of a nucleotide sequence of interest and/or a synthetic *Brassica*-derived CTP-encoding sequence fused thereto in a single coding sequence, for example, to enhance expression of the coding sequence in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991), *Gene* 105:61-72. Codons may be substituted to reflect the preferred codon usage of a particular host in a process sometimes referred to as "codon optimization." Optimized coding sequences containing codons preferred by a particular prokaryotic or eukaryotic host may be prepared, for example, to increase the rate of translation or to produce recombinant RNA transcripts having desirable properties (e.g., a longer half-life, as compared with transcripts produced from a non-optimized sequence).

Any polypeptide may be targeted to a plastid of a plastid-containing cell by incorporation of a synthetic *Brassica*-derived CTP sequence. For example, a polypeptide may be linked to a synthetic *Brassica*-derived CTP sequence in some embodiments, so as to direct the polypeptide to a plastid in a cell wherein the linked polypeptide-CTP molecule is expressed. In particular embodiments, a polypeptide targeted to a plastid by incorporation of a synthetic *Brassica*-derived CTP sequence may be, for example, a polypeptide that is normally expressed in a plastid of a cell wherein the polypeptide is natively expressed. For example and without limitation, a polypeptide targeted to a plastid by incorporation of a synthetic *Brassica*-derived CTP sequence may be a polypeptide involved in herbicide resistance, virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. A polypeptide targeted to a plastid by incorporation of a synthetic *Brassica*-derived CTP sequence may alternatively be, for example and without limitation, a polypeptide involved in plant vigor or yield (including polypeptides involved in tolerance for extreme temperatures, soil conditions, light levels, water levels, and chemical environment), or a polypeptide that may be used as a marker to identify a plant comprising a trait of interest (e.g., a selectable marker gene product, a polypeptide involved in seed color, etc.).

Non-limiting examples of polypeptides involved in herbicide resistance that may be linked to a synthetic *Brassica*-derived CTP sequence in some embodiments of the invention include: acetolactase synthase (ALS), mutated ALS, and precursors of ALS (see, e.g., U.S. Pat. No. 5,013,659); EPSPS (see, e.g., U.S. Pat. Nos. 4,971,908 and 6,225,114), such as a CP4 EPSPS, a class III EPSPS, or a class IV EPSPS; enzymes that modify a physiological process that occurs in a plastid, including photosynthesis, and synthesis of fatty acids, amino acids, oils, arotenoids, terpenoids, starch, etc. Other non-limiting examples of polypeptides that may be linked to a synthetic *Brassica*-derived chloroplast transit peptide in particular embodiments include: zeaxanthin epoxidase, choline monooxygenase, ferrochelatase, omega-3 fatty acid desaturase, glutamine synthetase, starch modifying enzymes, polypeptides involved in synthesis of essential amino acids, provitamin A, hormones, Bt toxin proteins, etc. Nucleotide sequences encoding the aforementioned peptides are known in the art, and such nucleotide sequences may be operably linked to a nucleotide sequence encoding a synthetic *Brassica*-derived CTP to be expressed into a polypeptide comprising the polypeptide of interest linked to the synthetic *Brassica*-derived CTP. Furthermore, additional nucleotide sequences encoding any of the aforementioned polypeptides may be identified by those of skill in the art (for example, by cloning of genes with high homology to other genes encoding the particular polypeptide). Once such a nucleotide sequence has been identified, it is a straightforward process to design a nucleotide sequence comprising a synthetic *Brassica*-derived CTP-encoding sequence operably linked to the identified nucleotide sequence, or a sequence encoding an equivalent polypeptide.

V. Expression of Polypeptides Comprising a Synthetic *Brassica*-Derived Chloroplast Transit Peptide In some embodiments, at least one nucleic acid molecule(s) comprising a nucleotide sequence encoding a polypeptide comprising at least one synthetic *Brassica*-derived CTP, or functional equivalent thereof, may be introduced into a cell, tissue, or organism for expression of the polypeptide therein. In particular embodiments, a nucleic acid molecule may comprise a nucleotide sequence of interest operably linked to a nucleotide sequence encoding a synthetic *Brassica*-derived CTP. For example, a nucleic acid molecule may comprise a coding sequence encoding a polypeptide comprising at least one synthetic *Brassica*-derived CTP and at least an additional peptide sequence encoded by a nucleotide sequence of interest. In some embodiments, a nucleic acid molecule of the invention may be introduced into a plastid-containing host cell, tissue, or organism (e.g., a plant cell, plant tissue, and plant), such that a polypeptide may be expressed from the nucleic acid molecule in the plastid-containing host cell, tissue, or organism, wherein the expressed polypeptide comprises at least one synthetic *Brassica*-derived CTP and at least an additional peptide sequence encoded by a nucleotide sequence of interest. In certain examples, the synthetic *Brassica*-derived CTP of such an expressed polypeptide may facilitate targeting of a portion of the polypeptide comprising at least the additional peptide sequence to a plastid of the host cell, tissue, or organism.

In some embodiments, a nucleic acid molecule of the invention may be introduced into a plastid-containing cell by one of any of the methodologies known to those of skill in the art. In particular embodiments, a host cell, tissue, or organism may be contacted with a nucleic acid molecule of the invention in order to introduce the nucleic acid molecule into the cell, tissue, or organism. In particular embodiments, a cell may be transformed with a nucleic acid molecule of the invention such that the nucleic acid molecule is introduced into the cell, and the nucleic acid molecule is stably integrated into the genome of the cell. In some embodiments, a nucleic acid molecule comprising at least one nucleotide sequence encoding a synthetic *Brassica*-derived CTP operably linked to a nucleotide sequence of interest may be used for transformation of a cell, for example, a plastid-containing cell (e.g., a plant cell). In order to initiate or enhance expression, a nucleic acid molecule may comprise one or more regulatory sequences, which regulatory sequences may be operably linked to the nucleotide sequence encoding a polypeptide comprising at least one synthetic *Brassica*-derived CTP.

A nucleic acid molecule may, for example, be a vector system including, for example, a linear or a closed circular plasmid. In particular embodiments, the vector may be an expression vector. Nucleic acid sequences of the invention may, for example, be inserted into a vector, such that the nucleic acid sequence is operably linked to one or more regulatory sequences. Many vectors are available for this purpose, and selection of the particular vector may depend, for example, on the size of the nucleic acid to be inserted into the vector and the particular host cell to be transformed with the vector. A vector typically contains various components, the identity of which depend on a function of the vector (e.g., amplification of DNA and expression of DNA), and the particular host cell(s) with which the vector is compatible.

Some embodiments may include a plant transformation vector that comprises a nucleotide sequence comprising at least one of the above-described regulatory sequences operatively linked to one or more nucleotide sequence(s) encoding a polypeptide comprising at least one synthetic *Brassica*-derived CTP. The one or more nucleotide sequences may be expressed, under the control of the regulatory sequence(s), in a plant cell, tissue, or organism to produce a polypeptide comprising a synthetic *Brassica*-derived CTP that targets at least a portion of the polypeptide to a plastid of the plant cell, tissue, or organism.

In some embodiments, a regulatory sequence operably linked to a nucleotide sequence encoding a polypeptide comprising at least one synthetic *Brassica*-derived CTP, may be a promoter sequence that functions in a host cell, such as a bacterial cell wherein the nucleic acid molecule is to be amplified, or a plant cell wherein the nucleic acid molecule is to be expressed. Promoters suitable for use in nucleic acid molecules of the invention include those that are inducible, viral, synthetic, or constitutive, all of which are well known in the art. Non-limiting examples of promoters that may be useful in embodiments of the invention are provided by: U.S. Pat. Nos. 6,437,217 (maize RS81 promoter); 5,641,876 (rice actin promoter); 6,426,446 (maize RS324 promoter); 6,429,362 (maize PR-1 promoter); 6,232,526 (maize A3 promoter); 6,177,611 (constitutive maize promoters); 5,322,938, 5,352,605, 5,359,142, and 5,530,196 (35S promoter); 6,433,252 (maize L3 oleosin promoter); 6,429,357 (rice actin 2 promoter, and rice actin 2 intron); 6,294,714 (light-inducible promoters); 6,140,078 (salt-inducible promoters); 6,252,138 (pathogen-inducible promoters); 6,175,060 (phosphorous deficiency-inducible promoters); 6,388,170 (bidirectional promoters); 6,635,806 (gamma-coixin promoter); and U.S. patent application Ser. No. 09/757,089 (maize chloroplast aldolase promoter).

Additional exemplary promoters include the nopaline synthase (NOS) promoter (Ebert et al. (1987), *Proc. Natl. Acad. Sci. USA* 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987), *Plant Mol. Biol.* 9:315-24); the CaMV 35S promoter (Odell et al. (1985), *Nature* 313:810-2; the figwort mosaic virus 35S-promoter (Walker et al. (1987), *Proc. Natl. Acad. Sci. USA* 84(19):6624-8); the sucrose synthase promoter (Yang and Russell (1990), *Proc. Natl. Acad. Sci. USA* 87:4144-8); the R gene complex promoter (Chandler et al. (1989), *Plant Cell* 1:1175-83); the chlorophyll a/b binding protein gene promoter; CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982), *J. Mol. Appl. Genet.* 1:561-73; Bevan et al. (1983), *Nature* 304:184-7).

In particular embodiments, nucleic acid molecules of the invention may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used in a composition or method of the invention.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995), *Molecular Biotech.* 3(3):225-36. Non-limiting examples of 5' UTRs are provided by: GmHsp (U.S. Pat. No. 5,659,122); PhDnaK (U.S. Pat. No. 5,362,865); AtAnt1; TEV (Carrington and Freed (1990), *J. Virol.* 64:1590-7); and AGRtunos (GenBank Accession No. V00087; and Bevan et al. (1983), *Nature* 304:184-7).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3; Fraley et al. (1983), *Proc. Natl. Acad. Sci. USA* 80:4803-7). An example of the use of different 3' nontranslated regions is provided in Ingelbrecht et al., (1989), *Plant Cell* 1:671-80. Non-limiting examples of polyadenylation signals include one from a *Pisum sativum* RbcS2 gene (Ps.RbcS2-E9; Coruzzi et al. (1984), *EMBO J.* 3:1671-9) and AGRtu.nos (GenBank Accession No. E01312).

A recombinant nucleic acid molecule or vector of the present invention may comprise a selectable marker that confers a selectable phenotype on a transformed cell, such as a plant cell. Selectable markers may also be used to select for plants or plant cells that comprise recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a pat or bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987), *Plant Mol. Biol. Rep.* 5:387-405); an R-locus gene, which encodes a product that regulates the production of anthocyanin pigments (red color) in plant tissues (Dellaporta et al. (1988), "Molecular cloning of the maize R-nj allele by transposon tagging with Ac." In 18$^{th}$ *Stadler Genetics Symposium*, P. Gustafson and R. Appels, eds. (New York: Plenum), pp. 263-82); a β-lactamase gene (Sutcliffe et al. (1978), *Proc. Natl. Acad. Sci. USA* 75:3737-41); a gene which encodes an enzyme for which various chromogenic substrates are known (e.g., PADAC, a chromogenic cephalosporin); a luciferase gene (Ow et al. (1986), *Science* 234:856-9); a xylE gene that encodes a catechol dioxygenase that can convert chromogenic catechols (Zukowski et al. (1983), *Gene* 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983), *J. Gen. Microbiol.* 129:2703-14); and an α-galactosidase.

Suitable methods for transformation of host cells include any method by which DNA can be introduced into a cell, for example and without limitation: by transformation of protoplasts (see, e.g., U.S. Pat. No. 5,508,184); by desiccation/inhibition-mediated DNA uptake (see, e.g., Potrykus et al. (1985). *Mol. Gen. Genet.* 199:183-8); by electroporation (see, e.g., U.S. Pat. No. 5,384,253); by agitation with silicon carbide fibers (see, e.g., U.S. Pat. Nos. 5,302,523 and 5,464,765); by *Agrobacterium*-mediated transformation (see, e.g., U.S. Pat. Nos. 5,563,055, 5,591,616, 5,693,512, 5,824,877, 5,981,840, and 6,384,301); and by acceleration of DNA-coated particles (see, e.g., U.S. Pat. Nos. 5,015,580, 5,550,318, 5,538,880, 6,160,208, 6,399,861, and 6,403,865); etc. Through the application of techniques such as these, the cells of virtually any species may be stably transformed. In some embodiments, transforming DNA is integrated into the genome of the host cell. In the case of multicellular species, transgenic cells may be regenerated into a transgenic organism. Alternatively, the transgenic cells may not be capable of regeneration to a plant. Any of these techniques may be used to produce a transgenic plant, for example, comprising one or more nucleic acid sequences of the invention in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by terminal repeats. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a synthetic *Brassica*-derived CTP-encoding nucleic acid.

Thus, in some embodiments, a plant transformation vector may be derived from a $T_i$ plasmid of *A. tumefaciens* (See, e.g., U.S. Pat. Nos. 4,536,475, 4,693,977, 4,886,937, and 5,501,967; and European Patent EP 0 122 791) or a Ri plasmid of *A. rhizogenes*. Additional plant transformation vectors include, for example and without limitation, those described by Herrera-Estrella et al. (1983), *Nature* 303:209-13; Bevan et al. (1983), *Nature* 304:184-7; Klee et al. (1985), *Bio/Technol.* 3:637-42; and in European Patent EP 0 120 516, and those derived from any of the foregoing. Other bacteria such as *Sinorhizobium, Rhizohium*, and *Mesorhizobium* that interact with plants naturally can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one synthetic *Brassica*-derived CTP) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

By way of example, integration events may be analyzed by PCR amplification using, e.g., oligonucleotide primers specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002), *Plant J.* 32:243-53), and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In particular embodiments, copies of at least one polypeptide comprising at least one synthetic *Brassica*-derived CTP are produced in a plastid-containing cell, into which has been introduced at least one nucleic acid molecule(s) comprising a nucleotide sequence encoding the at least one polypeptide comprising at least one synthetic *Brassica*-derived CTP. Each polypeptide comprising at least one synthetic *Brassica*-derived CTP may be expressed from multiple nucleic acid sequences introduced in different transformation events, or from a single nucleic acid sequence introduced in a single transformation event. In some embodiments, a plurality of such polypeptides is expressed under the control of a single promoter. In other embodiments, a plurality of such polypeptides is expressed under the control of multiple promoters. Single polypeptides may be expressed that comprise multiple peptide sequences, each of which peptide sequences is to be targeted to a plastid.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence encoding a polypeptide comprising at least one synthetic *Brassica*-derived CTP may be introduced into a first plant line that is amenable to transformation, to produce a transgenic plant, which transgenic plant may be crossed with a second plant line to introgress the nucleotide sequence that encodes the polypeptide into the second plant line.

VI. Plant Materials Comprising a Synthetic *Brassica*-Derived Chloroplast Transit Peptide-Directed Polypeptide In some embodiments, a plant cell is provided, wherein the plant cell comprises a nucleotide sequence encoding a polypeptide comprising at least one synthetic *Brassica*-derived CTP. In particular embodiments, such a plant cell may be produced by transformation of a plant cell that is not capable of regeneration to produce a plant. In some embodiments, a plant is provided, wherein the plant comprises a plant cell comprising a nucleotide sequence encoding a polypeptide comprising at least one synthetic *Brassica*-derived CTP. In particular embodiments, such a plant may be produced by transformation of a plant tissue or plant cell, and regeneration of a whole plant. In further embodiments, such a plant may be obtained from a commercial source, or through introgression of a nucleic acid comprising a nucleotide sequence encoding a polypeptide comprising at least one synthetic *Brassica*-derived CTP into a germplasm. In particular embodiments, such a plant comprises plant cells comprising a nucleotide sequence encoding a polypeptide comprising at least one synthetic *Brassica*-derived CTP that are not capable of regeneration to produce a plant. Plant materials comprising a plant cell comprising a nucleotide sequence encoding a polypeptide comprising at least one synthetic *Brassica*-derived CTP are also provided. Such a plant material may be obtained from a plant comprising the plant cell.

A transgenic plant, nonregenerable plant cell, or plant material comprising a nucleotide sequence encoding a polypeptide comprising at least one synthetic *Brassica*-derived CTP may in some embodiments exhibit one or more of the following characteristics: expression of the polypeptide in a cell of the plant; expression of a portion of the polypeptide in a plastid of a cell of the plant; import of the polypeptide from the cytosol of a cell of the plant into a plastid of the cell; plastid-specific expression of the polypeptide in a cell of the plant; and/or localization of the polypeptide in a cell of the plant. Such a plant may additionally have one or more desirable traits other than expression of the encoded polypeptide. Such traits may include, for example: resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid molecule of the invention. Accordingly, the plant may be a dicot or monocot. Non-limiting examples of dicotyledonous plants usable in the present methods include *Arabidopsis*, alfalfa, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, *Brassica*, onion, rice, sorghum, wheat, rye, millet, sugarcane, oat, triticale, switchgrass, and turfgrass. Transgenic plants according to the invention may be used or cultivated in any manner.

Some embodiments also provide commodity products containing one or more nucleotide sequences encoding a polypeptide comprising at least one synthetic *Brassica*-derived CTP, for example, a commodity product produced from a recombinant plant or seed containing one or more of such nucleotide sequences. Commodity products containing one or more nucleotide sequences encoding a polypeptide comprising at least one synthetic *Brassica*-derived CTP include, for example and without limitation: food products, meals, oils, or crushed or whole grains or seeds of a plant comprising one or more nucleotide sequences encoding a polypeptide comprising at least one synthetic *Brassica*-derived CTP. The detection of one or more nucleotide sequences encoding a polypeptide comprising at least one synthetic *Brassica*-derived CTP in one or more commodity or commodity products is de facto evidence that the commodity or commodity product was at least in part produced from a plant comprising one or more nucleotide sequences encoding a polypeptide comprising at least one synthetic *Brassica*-derived CTP. In particular embodiments, a commodity product of the invention comprise a detectable amount of a nucleic acid sequence encoding a polypeptide comprising at least one synthetic *Brassica*-derived CTP. In some embodiments, such commodity products may be produced, for example, by obtaining transgenic plants and preparing food or feed from them.

In some embodiments, a transgenic plant, nonregenerable plant cell, or seed comprising a transgene comprising a nucleotide sequence encoding a polypeptide comprising at least one synthetic *Brassica*-derived CTP also may comprise at least one other transgenic event in its genome, including without limitation: a transgenic event from which is transcribed an iRNA molecule; a gene encoding an insecticidal protein (e.g., an *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

VII. Synthetic *Brassica*-Derived Chloroplast Transit Peptide-Mediated Localization of Gene Products to Plastids Some embodiments of the present invention provide a method for expression and/or localization of a gene product to a plastid (e.g., a chloroplast). In particular embodiments, the gene product may be a marker gene product, for example, a fluorescent molecule. Expression of the gene product as part of a polypeptide also comprising a synthetic *Brassica*-derived CTP may provide a system to evaluate the plastid-localizing capabilities of a particular synthetic *Brassica*-derived CTP sequence. In some embodiments, expression of a marker gene product as part of a synthetic *Brassica*-derived CTP-containing polypeptide is utilized to target expression of the marker gene product to a plastid of a cell wherein the polypeptide is expressed. In certain embodiments, such a marker gene product is localized in plastid(s) of the host cell. For example, the marker gene product may be expressed at higher levels in the plastid(s) than in the cytosol or other organelles of the host cell; the marker gene product may be expressed at much higher levels in the plastid(s); the marker gene product may be expressed essentially only in the plastid(s); or the marker gene product may be expressed entirely in the plastid(s), such that expression in the cytosol or non-plastid organelles cannot be detected.

In some embodiments, a polypeptide comprising a functional variant of a synthetic *Brassica*-derived CTP, wherein the polypeptide is operably linked to a marker gene product is used to evaluate the characteristics of the functional variant peptide. For example, the sequence of a synthetic *Brassica*-derived CTP may be varied, e.g., by introducing at least one conservative mutation(s) into the synthetic *Brassica*-derived CTP, and the resulting variant peptide may be linked to a marker gene product. After expression in a suitable host cell (for example, a cell wherein one or more regulatory elements in the expression construct are operable), expression of the marker gene product may be determined. By comparing the sub-cellular localization of the marker gene product between the reference synthetic *Brassica*-derived CTP-marker construct and the variant peptide-marker construct, it may be determined whether the variant peptide provides, for example, greater plastid localization, or substantially identical plastid localization. Such a variant may be considered a functional variant. By identifying functional variants of synthetic *Brassica*-derived CTP that provide greater plastic localization, the mutations in such variants may be incorporated into further variants of synthetic *Brassica*-derived CTPs. Performing multiple rounds of this evaluation process, and subsequently incorporating identified favorable mutations in a synthetic *Brassica*-derived CTP sequence, may yield an iterative process for optimization of a synthetic *Brassica*-derived CTP sequence. Such optimized synthetic *Brassica*-derived CTP sequences, and nucleotide sequences encoding the same, are considered part of the present invention, whether or not such optimized synthetic *Brassica*-derived CTP sequences may be further optimized by additional mutation.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1

Design and Production of Chimeric Chloroplast Transit Peptide (TraP) Sequences Plastids are cytoplasmic organelles found in higher plant species and are present in all plant tissues. Choloroplasts are a specific type of plastid found in green photosynthetic tissues which are responsible for essential physiological functions. For example, one such primary physiological function is the synthesis of aromatic amino acids required by the plant. Nuclear encoded enzymes are required in this biosynthetic pathway and are transported from the cytoplasm to the interior of the chloroplast. These nuclear encoded enzymes usually possess an N-terminal transit peptide that interacts with the chloroplast membrane to facilitate transport of the peptide to the stroma of the chloroplast. Bruce B. (2000) Chloroplast transit peptides: structure, function, and evolution. *Trends Cell Bio.* 10:440-447. Upon import, stromal peptidases cleave the transit peptide, leaving the mature functional protein imported within the chloroplast. Richter S, Lamppa G K. (1999) Stromal processing peptidase binds transit peptides and initiates their ATP-dependent turnover in chloroplasts. *Journ. Cell Bio.* 147:33-43. The chloroplast transit peptides are variable sequences which are highly divergent in length, composition and organization. Bruce B. (2000) Chloroplast transit peptides: structure, function, and evolution. *Trends Cell Bio.* 10:440-447. The sequence similarities of chloroplast transit peptides diverge significantly amongst homologous proteins from different plant species. The amount of divergence between chloroplast transit peptides is unexpected given that the homologous proteins obtained from different plant species typically share relatively high levels of sequence similarity when comparing the processed mature functional protein.

Novel chimeric chloroplast transit peptide sequences were designed, produced and tested in planta. The novel chimeric chloroplast transit peptides were shown to possess efficacious translocation and processing properties for the import of agronomic important proteins within the chloroplast. Initially, native 5-enolpyruvylshikimate-3-phosphate synthase (EPSPS) protein sequences from different plant species were analyzed via the ChloroP™ computer program to identify putative chloroplast transit peptide sequences (Emanuelsson O, Nielsen H, von Heijne G, (1999) ChloroP, a neural network-based method for predicting chloroplast transit peptides and their cleavage sites, *Protein Science* 8; 978-984), available at www.cbs.dtu.dk/services/ChloroP/. After the native chloroplast transit peptides were identified, a first chloroplast transit peptide sequence was aligned with a second chloroplast transit peptide sequences from a second organism. FIG. 18 illustrates the alignment of the EPSPS chloroplast transit peptide sequences of *Brassica napus* (NCBI Accession No: P17688) and *Brassica rapa* (NCBI Accession No: AAS80163). Utilizing the chloroplast transit peptide sequence alignment, novel chimeric chloroplast transit peptides were designed by combining the first half of the chloroplast transit peptide sequence from the first organism with the second half of the chloroplast transit peptide sequence from the second organism in an approximate ratio of 1:1. Exemplary sequences of the newly designed chimeric chloroplast transit peptides are TraP8 (SEQ ID NO:3) and TraP9(SEQ ID NO:4). These novel chimeric chloroplast transit peptide sequences are derived from the EPSPS proteins of *Brassica napus* [ATCC Accession No: P17688] and *Brassica rapa*[ATCC Accession No: AAS80163]. The TraP8 (SEQ ID NO:3) chimeric chloroplast transit peptide sequence comprises an N-terminus which is derived from *Brassica napus*, and the C-terminus of the chloroplast transit peptide is derived from *Brassica Rapa*. The TraP9(SEQ ID NO:4) chloroplast transit peptide sequence comprises an N-terminus which is derived from *Brassica rapa*, and the C-terminus of the chloroplast transit peptide is derived from *Brassica napus*. The chimeric chloroplast transit peptides were tested via multiple assays which included a transient in planta expression system and transgenically as a stable transformation event comprising a gene expression element fused to an agronomic important transgene sequence.

Example 2

Figure 2:
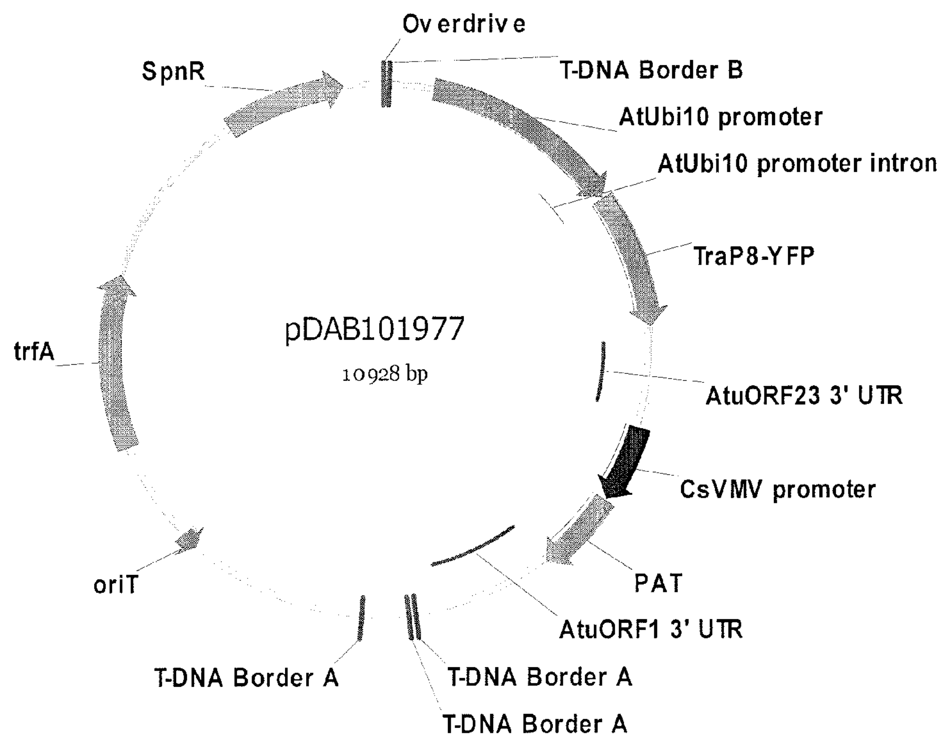
FIG. 2 illustrates a plasmid map of pDAB101977.
Figure 3:
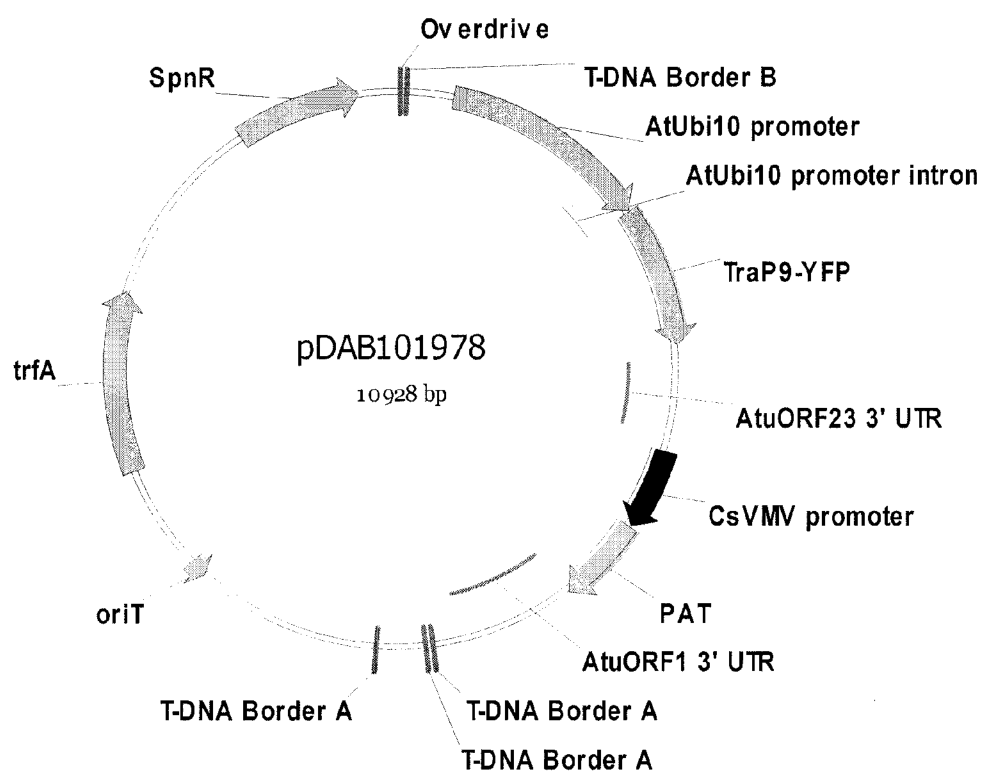
FIG. 3 illustrates a plasmid map of pDAB101978.
Figure 4:
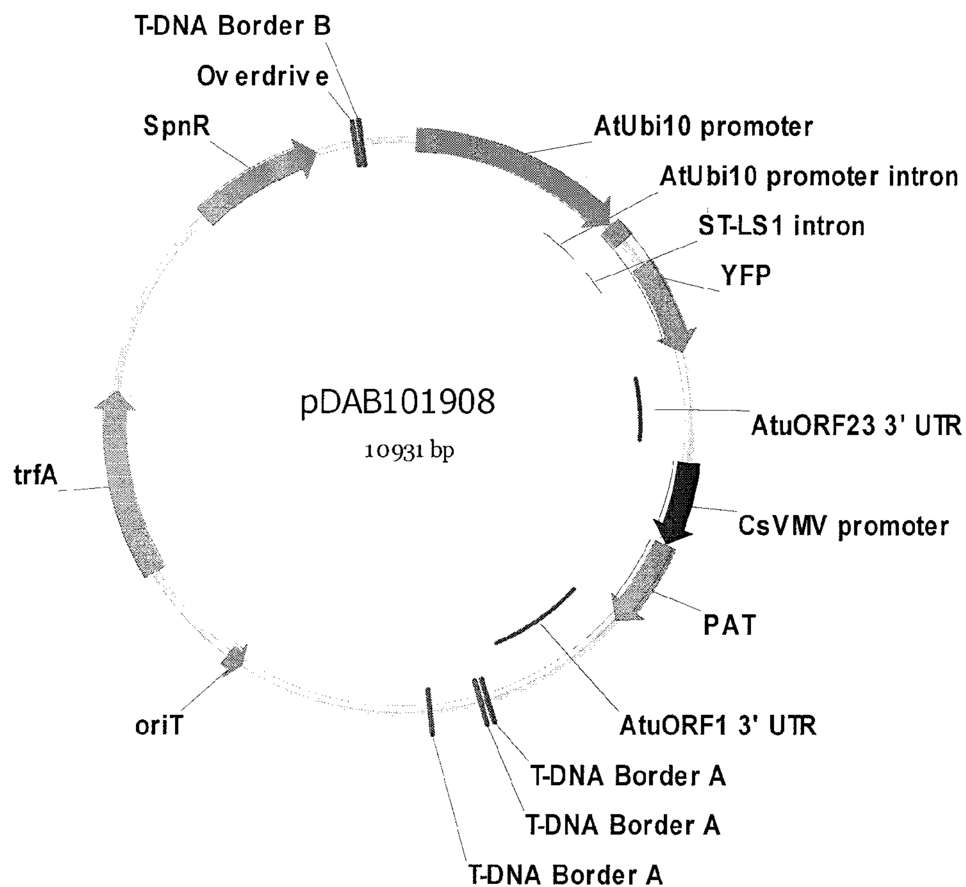
FIG. 4 illustrates a plasmid map of pDAB101908.

Transient in Planta Testing of Chimeric Chloroplast Transit Peptide (TraP) Sequences Tobacco Transient Assay:

The Trap8 and TraP9 chimeric chloroplast transit peptide sequences were initially tested via a transient in planta assay. Polynucleotide sequences which encode the Trap8 (SEQ ID NO:5) and TraP9 (SEQ ID NO:6) chimeric chloroplast transit peptide sequences were synthesized. A linker sequence (SEQ ID NO:7) was incorporated between the TraP sequence and the yfp coding sequence. The resulting constructs contained two plant transcription units (PTU). The first PTU was comprised of the *Arabidopsis thaliana* Ubiquitin 10 promoter (AtUbi10 promoter; Callis, et al., (1990) *J. Biol. Chem.,* 265: 12486-12493), TraP-yellow fluorescent protein fusion gene (TraP-YFP; US Patent App. 2007/0298412), and *Agrobacterium tumefaciens* ORF 23 3' untranslated region (AtuORF23 3'UTR; U.S. Pat. No. 5,428, 147). The second PTU was comprised of the Cassava Vein Mosaic Virus promoter (CsVMV promoter; Verdaguer et al., (1996) *Plant Molecular Biology,* 31:1129-1139), phosphinothricin acetyl transferase (PAT; Wohlleben et al., (1988) *Gene,* 70: 25-37), and *Agrobacterium tumefaciens* ORF 1 3' untranslated region (AtuORF1 3'UTR; Huang et al., (1990) *J. Bacteria,* 172:1814-1822). Construct pDAB101977 contains the TraP8 chimeric chloroplast transit peptide (FIG. 2). Construct pDAB101978 contains the TraP9 chimeric chloroplast transit peptide (FIG. 3). A control plasmid, 101908, which did not contain a chloroplast transit peptide sequence upstream of the yfp gene was built and included in the studies (FIG. 4). The constructs were confirmed via restriction enzyme digestion and sequencing. Finally, the constructs were transformed into *Agrobacterium tumefaciens* and stored as glycerol stocks.

From an *Agrobacterium* glycerol stock, a loop full of frozen culture was inoculated into 2 ml of YPD (100 μg/ml spectinomycin) in a 14 ml sterile tube. The inoculated media was incubated at 28° C. overnight with shaking at 200 rpm. The following day about 100 μl of the culture was used to inoculate 25 ml of YPD (100 μg/ml spectinomycin) in a 125 ml sterile tri-baffled flask, and incubated overnight at 28° C. overnight with shaking at 200 rpm. The following day the cultures were diluted to an $OD_{600}$ of 0.5 in sterile $ddH_20$ (pH 8.0). The diluted *Agrobacterium* strain was mixed with a second *Agrobacterium* strain containing the P19 helper protein at a ratio of 1:1. The culture were used for tobacco leaf infiltration via the method of Voinnet O, Rivas S, Mestre P, and Baulcombe D., (2003) An enhanced transient expression system in plants based on suppression of gene silencing by the p19 protein of tomato bushy stunt virus, *The Plant Journal,* 33:949-956. Infiltrated tobacco plants were placed in a Conviron™ set at 16 hr of light at 24° C. for at least three days until being assayed.

Microscopy Results:

*Agrobacterium*-infiltrated tobacco leaves were severed from the plant, and placed into a petri-dish with water to prevent dehydration. The infiltrated tobacco leaves were observed under blue light excitation with long-pass filter glasses held in place using a Dark Reader Hand Lamp™ (Clare Chemical Research Co.; Dolores, Colo.) to identify undamaged areas of the leaf that were successfully expressing the YFP reporter proteins. Specifically identified leaf areas were dissected from the leaf and mounted in water for imaging by confocal microscopy (Leica TCS-SP5 AOBS™; Buffalo Grove, Ill.). The YFP reporter protein was excited by a 514 nm laser line, using a multi-line argon-ion laser. The width of the detection slits was adjusted using a non-expressing (dark) control leaf sample to exclude background leaf autofluoresence. Chlorophyll autofluorescence was simultaneously collected in a second channel for direct comparison to the fluorescent reporter protein signal for determination of chloroplastic localization.

Figure 5:
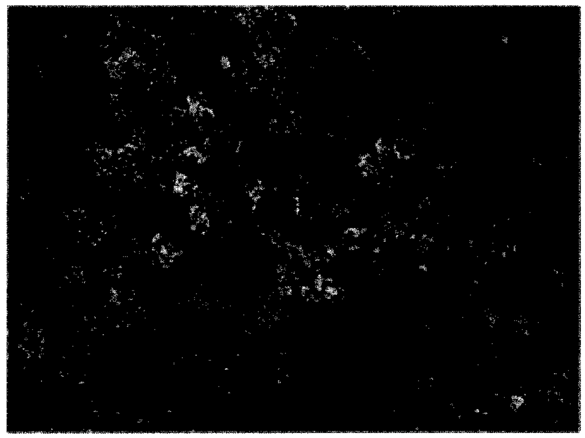
FIG. 5 includes a microscopy image showing that TraP8-YFP infiltrated into tobacco leaf tissue was translocated into the chloroplasts of the tobacco leaf tissue.
Figure 6:
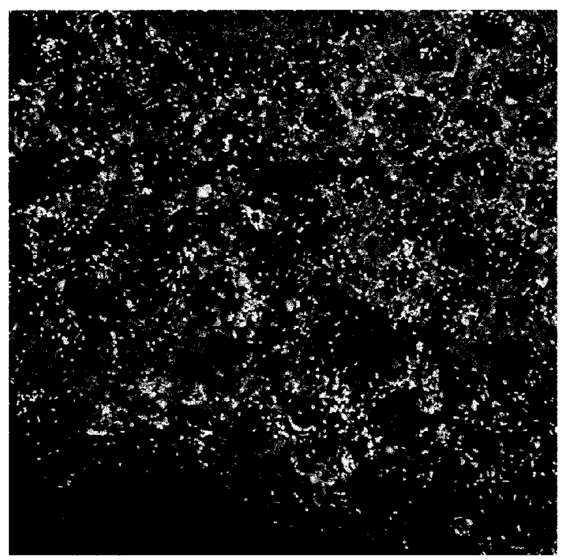
FIG. 6 includes a microscopy image showing that TraP9-YFP infiltrated into tobacco leaf tissue was translocated into the chloroplasts of the tobacco leaf tissue.
Figure 7:
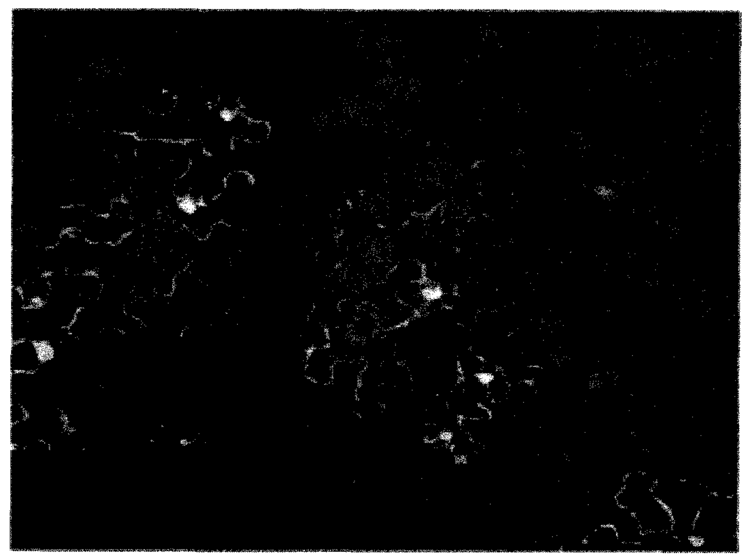
FIG. 7 includes a microscopy image showing that non-targeted YFP controls that were infiltrated into tobacco leaf tissue were not incorporated into the chloroplasts of the tobacco leaf tissue.

The microscopy imaging results indicated that the YFP fluorescent protein comprising a TraP8 or TraP9 chloroplast transit peptide accumulated within the chloroplasts located in the cytoplasm of the tobacco cells as compared to the control YFP fluorescent proteins which did not translocate into the chloroplasts of the cytoplasm of the tobacco cells (FIG. 5 and FIG. 6). These microscopy imaging results suggest that the translocation of the YFP protein into the chloroplast was a result of the TraP8 or TraP9 chloroplast transit peptide. As shown in FIG. 5 and FIG. 6 the YFP fluorescence signal is localized in the chloroplasts which also fluoresce red due to auto-fluorescence under the microscopy imaging conditions. Comparatively, FIG. 7 provides a microscopy image of tobacco leaf tissue infiltrated with the control construct pDAB101908 that does not contain a chloroplast transit peptide. The chloroplasts in this image only fluoresce red due to auto-fluorescence under the microscopy imaging conditions, and are devoid of any YFP fluorescence signal that is exhibited in the TraP infiltrated tobacco cells. Rather, the YFP fluorescence signal in the control tobacco plant cells is expressed diffusely throughout the cytoplasm of the tobacco plant cells.

Western Blot Results:

Samples of the infiltrated tobacco plants were assayed via Western blotting. Leaf punches were collected and subjected to bead-milling. About 100-200 mg of leaf material was mixed with 2 BBs (steel balls) (Daisy; Rogers, Ark.) and 500 ml of PBST for 3 minutes in a Kleco™ bead mill. The samples were then spun down in a centrifuge at 14,000×g at 4° C. The supernatant was removed and either analyzed directly via Western blot or immunoprecipitated. The immunoprecipitations were performed using the Pierce Direct IP Kit™ (Thermo Scientific; Rockford, Ill.) following the manufacturer's protocol. Approximately, 50 μg of anti-YFP was bound to the resin. The samples were incubated with the resin overnight at 4° C. Next, the samples were washed and eluted the following morning and prepped for analysis by combining equal volumes of 2×8M Urea sample buffer and then boiling the samples for 5 minutes. The boiled samples were run on a 4-12% SDS-Bis Tris gel in MOPS buffer for 40 minutes. The gel was then blotted using the Invitrogen iBlot™ (Life Technologies; Carlsbad, Calif.) following the manufacturer's protocol. The blotted membrane was blocked for 10 minutes using 5% non-fat dry milk in PBS-Tween solution. The membrane was probed with the primary antibody (monoclonal anti-GFP in rabbit) used at a 1:1000 dilution in the 5% non-fat dry milk in PBS-Tween solution for 1 hour. Next, the membrane was rinsed three times for five minutes with PBS-Tween to remove all unbound primary antibody. The membrane was probed with a secondary monoclonal anti-rabbit in goat antibody (Life Technologies) used at a 1:1000 dilution, for 60 minutes. The membrane was washed as previously described and developed by adding Themo BCIP/NBT substrate. The colormetric substrate was allowed to develop for 5-10 minutes and then the blots were rinsed with water before being dried.

The Western blot results indicated that the YFP protein was expressed in the infiltrated tobacco cells. Both, the pDAB101977 and pDAB101978 infiltrated tobacco plant leaf tissues expressed the YFP protein as indicated by the presence of a protein band which reacted to the YFP antibodies and was equivalent in size to the YFP protein band obtained from tobacco plant leaf tissue infiltrated with the YFP control construct. Moreover, these results indicated that the TraP chimeric chloroplast transit peptides were processed and cleaved from the YFP protein. The TraP8-YFP and TraP9-YFP constructs express a pre-processed protein band that is larger in molecular weight than the control YFP protein. The presence of bands on the Western blot which are equivalent in size to the control YFP indicate that the TraP8 and TraP9 chloroplast transit peptide sequences were processed, thereby reducing the size of the YFP to a molecular weight size which is equivalent to the YFP control.

Figure 8:
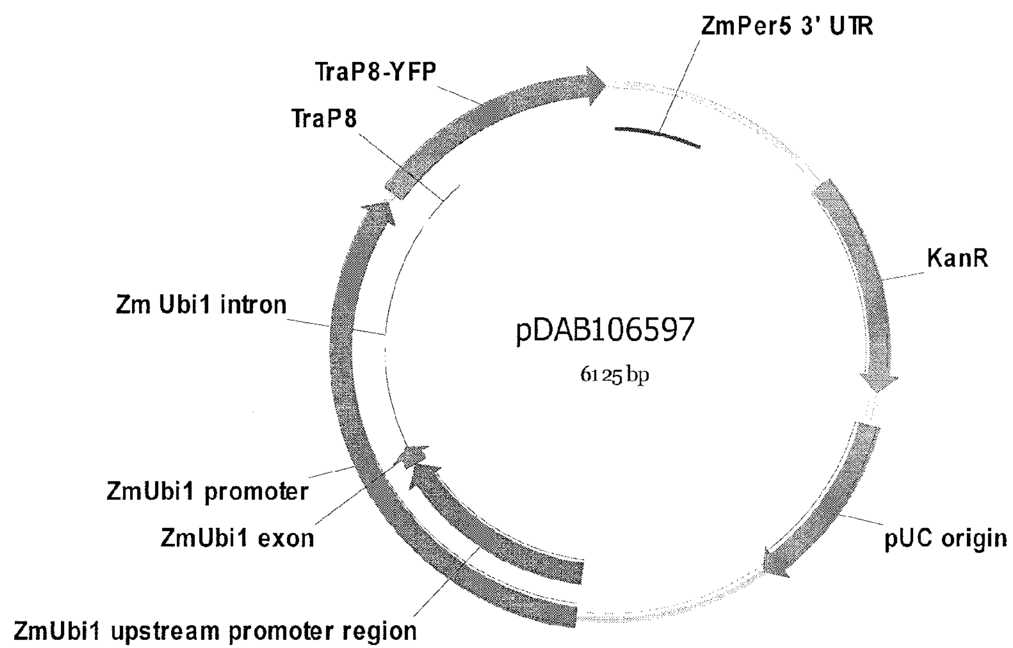
FIG. 8 illustrates a plasmid map of pDAB106597.

Maize Protoplast Transient Assay:

The Trap8 chimeric chloroplast transit peptide-encoding polynucleotide sequence (SEQ ID NO:5) and the linker-encoding polynucleotide sequence (SEQ ID NO:7) were cloned upstream of the yellow fluorescent protein gene and incorporated into construct pDAB106597 (FIG. 8) for testing via the maize protoplast transient in planta assay. The resulting constructs contained a single plant transcription unit (PTU). The PTU was comprised of the *Zea mays* Ubiquitin 1 promoter (ZmUbi1 promoter; Christensen, A., Sharrock R., and Quail P., (1992) Maize polyubiquitin genes: structure, thermal perturbation of expression and transcript splicing, and promoter activity following transfer to protoplasts by electroporation, Plant Molecular Biology, 18:675-689), TraP-yellow fluorescent protein fusion gene (TraP8-YFP; US Patent App. 2007/0298412), and *Zea mays* Peroxidase 5 3' untranslated region (ZmPer5 3'UTR; U.S. Pat. No. 6,384,207). The constructs were confirmed via restriction enzyme digestion and sequencing.

Seed of *Zea mays* var. B104 were surface sterilized by shaking vigorously in 50% Clorox (3% sodium hypochlorite), containing 2-3 drops of Tween 20, for about 20 minutes. The seeds were rinsed thoroughly with sterile distilled water. The sterile seed were plated onto ½ MS medium in Phytatrays or similar type boxes, and allowed to grow in the dark (28° C.) for 12 to 20 days. A maize protoplast transient assay was used to obtain and transfect maize protoplasts from leaves of B104-maize. This maize protoplast assay is a modification of the system described by Yoo, S.-D., Cho, Y.-H., and Sheen, J., (2007), *Arabidopsis* Mesophyll Protoplasts: A Versitile Cell System for Transient Gene Expression Analysis, *Nature Protocols,* 2:1565-1572. The solutions were prepared as described by Yoo et. al, (2007), with the exception that the mannitol concentration used for the following experiments was change to 0.6 M.

Transfection of 100 to 500 μl of protoplasts ($1-5\times10^5$) was completed by adding the protoplasts to a 2 ml microfuge tube containing about 40 μg of plasmid DNA (pDAB106597), at room temperature. The volume of DNA was preferably kept to about 10% of the protoplast volume. The protoplasts and DNA were occasionally mixed during a 5 minute incubation period. An equal volume of PEG solution was slowly added to the protoplasts and DNA, 2 drops at a time with mixing inbetween the addition of the drops of PEG solution. The tubes were allowed to incubate for about 10 minutes with occasional gentle mixing. Next, 1 ml of W5+ solution was added and mixed by inverting the tube several times. The tube(s) were centrifuged for 5 minutes at 75×g at a temperature of 4° C. Finally, the supernatant was removed and the pellet was resuspended in 1 ml of WI solution and the protoplasts were placed into a small Petri plate (35×10 mm) or into 6-well multiwell plates and incubated overnight in the dark at room temperature. Fluorescence of YFP was viewed by microscopy after 12 hours of incubation. The microscopy conditions previously described were used for the imaging.

Figure 9:
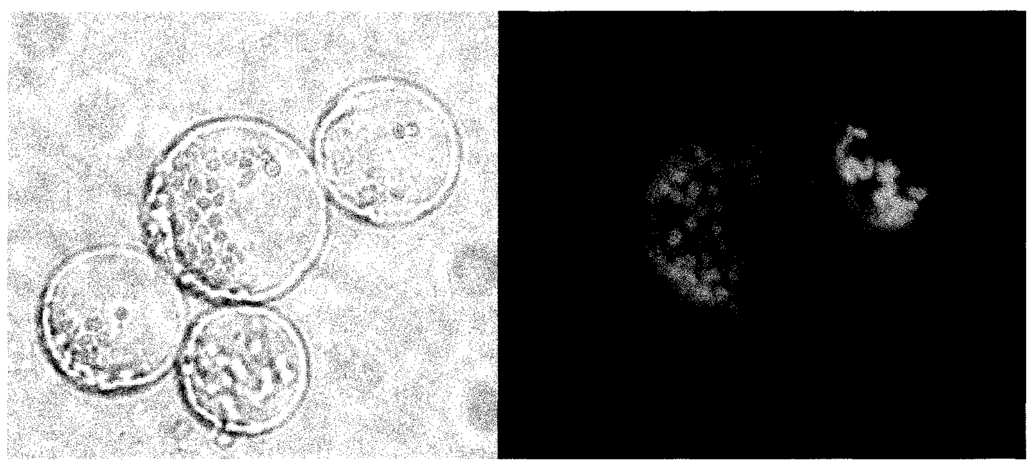
FIG. 9 includes a microscopy image of the TraP8-YFP construct transformed into maize protoplasts showing the translocation into the chloroplasts of the maize protoplast.

The microscopy imaging results indicated that the YFP fluorescent protein comprising a TraP8 chimeric chloroplast transit peptide accumulated within the chloroplasts located in the cytoplasm of the maize cells as compared to the control YFP fluorescent proteins which did not translocate into the chloroplasts of the cytoplasm of the maize cells (FIG. 9). These microscopy imaging results suggest that the translocation of the YFP protein into the chloroplast was a result of the TraP8 chimeric chloroplast transit peptide.

Example 3

Chimeric Chloroplast Transit Peptide (TraP) Sequences for Expression of Agronomically Important Transgenes in *Arabidopsis*

A single amino acid mutation (G96A) in the *Escherichia coli* 5-enolpyruvylshikimate 3-phosphate synthase enzyme (EPSP synthase) can result in glyphosate insensitivity (Padgette et al., (1991); Eschenburg et al., (2002); Priestman et al., (2005); Haghani et al., (2008)). While this mutation confers tolerance to glyphosate, it is also known to adversely affect binding of EPSP synthase with its natural substrate, phosphoenolpyruvate (PEP). The resulting change in substrate binding efficiency can render a mutated enzyme unsuitable for providing in planta tolerance to glyphosate.

The NCBI Genbank database was screened in silico for EPSP synthase protein and polynucleotide sequences that naturally contain an alanine at an analogous position within the EPSP synthase enzyme as that of the G96A mutation which was introduced into the K coli version of the enzyme (Padgette et al., (1991); Eschenburg et al., (2002); Priestman et al., (2005); Haghani et al., (2008)).

One enzyme that was identified to contain a natural alanine at this position was DGT-28 (GENBANK ACC NO: ZP_06917240.1) from *Streptomyces sviceus* ATCC29083. Further in silico data mining revealed three other unique *Streptomyces* enzymes with greater homology to DGT-28; DGT-31 (GENBANK ACC NO: YP_004922608.1); DGT-32 (GENBANK ACC NO: ZP_04696613); and DGT-33 (GENBANK ACC NO: NC_010572). Each of these enzymes contains a natural alanine at an analogous position within the EPSP synthase enzyme as that of the G96A mutation that was introduced into the *E. coli* version of the enzyme. FIG. 1.

Because EPSP synthase proteins from different organisms are of different lengths, the numbering of the mutation for the *E. coli* version of the EPSP synthase enzyme does not necessarily correspond with the numbering of the mutation for the EPSP synthase enzymes from the other organisms. These identified EPSP synthase enzymes were not previously characterized in regard to glyphosate tolerance or PEP substrate affinity. Furthermore, these EPSP synthase enzymes represent a new class of EPSP synthase enzymes and do not contain any sequence motifs that have been used to characterize previously described Class I (plant derived sequences further described in U.S. Pat. No. RE39247), II (bacterially derived sequences further described in U.S. Pat. No. RE39247), and III (bacterially derived sequences further described in International Patent Application WO 2006/110586) EPSP synthase enzymes.

The novel DGT-14, DGT-28, DGT-31, DGT-32, and DGT-33 enzymes were characterized for glyphosate tolerance and PEP substrate affinity by comparison to Class I EPSP synthase enzymes. The following Class I enzymes; DGT-1 from *Glycine max*, DGT-3 from *Brassica napus* (GENBANK ACC NO: P17688), and DGT-7 from *Triticum aestivum* (GENBANK ACC NO: EU977181) were for comparison. The Class I EPSP synthase enzymes and mutant variants thereof were synthesized and evaluated. A mutation introduced into the plant EPSP synthase enzymes consisted of the Glycine to Alanine mutation made within the EPSP synthase enzyme at a similar location as that of the G96A mutation from the *E. coli* version of the enzyme. In addition, Threonine to Isoleucine and Proline to Serine mutations were introduced within these Class I EPSP synthase enzymes at analogous positions as that of amino acid 97 (T to I) and amino acid 101 (P to S) in the EPSP synthase of *E. coli* as described in Funke et al., (2009).

DGT14:

Transgenic $T_1$ *Arabidopsis* plants containing the TraP8 and TraP9 chimeric chloroplast transit peptides fused to the dgt-14 transgene were produced using the floral dip method from Clough and Bent (1998), *Plant J.* 16:735-743. Transgenic *Arabidopsis* plants were obtained and confirmed to contain the transgene via molecular confirmation. The transgenic plants were sprayed with differing rates of glyphosate. A distribution of varying concentrations of glyphosate rates, including elevated rates, were applied in this study to determine the relative levels of resistance (105, 420, 1,680 or 3,360 g ae/ha). The typical 1× field usage rate of glyphosate is 1,120 g ae/ha. The $T_1$ *Arabidopsis* plants that were used in this study were variable in copy number for the dgt-14 transgene. The low copy dgt-14 $T_1$ *Arabidopsis* plants were identified using molecular confirmation assays, and self-pollinated and used to produce $T_2$ plants. Table 1 shows the resistance for dgt-14 transgenic plants, as compared to control plants comprising a glyphosate herbicide resistance gene, dgt-1 (as described in U.S. patent Ser. No. 12/558,351, incorporated herein by reference in its entirety), and wildtype controls.

The *Arabidopsis* $T_1$ transformants were first selected from the background of untransformed seed using a glufosinate selection scheme. Three flats, or 30,000 seed, were analyzed for each $T_1$ construct. The selected $T_1$ plants were molecularly characterized and the plants were subsequently transplanted to individual pots and sprayed with various rates of commercial glyphosate as previously described. The dose response of these plants is presented in terms of % visual injury 2 weeks after treatment (WAT). Data are presented in the tables below which show individual plants exhibiting little or no injury (<20%), moderate injury (20-40%), or severe injury (>40%). An arithmetic mean and standard deviation is presented for each construct used for *Arabidopsis* transformation. The range in individual response is also indicated in the last column for each rate and transformation. Wildtype, non-transformed *Arabidopsis* (c.v. Columbia) served as a glyphosate sensitive control.

Figure 10:
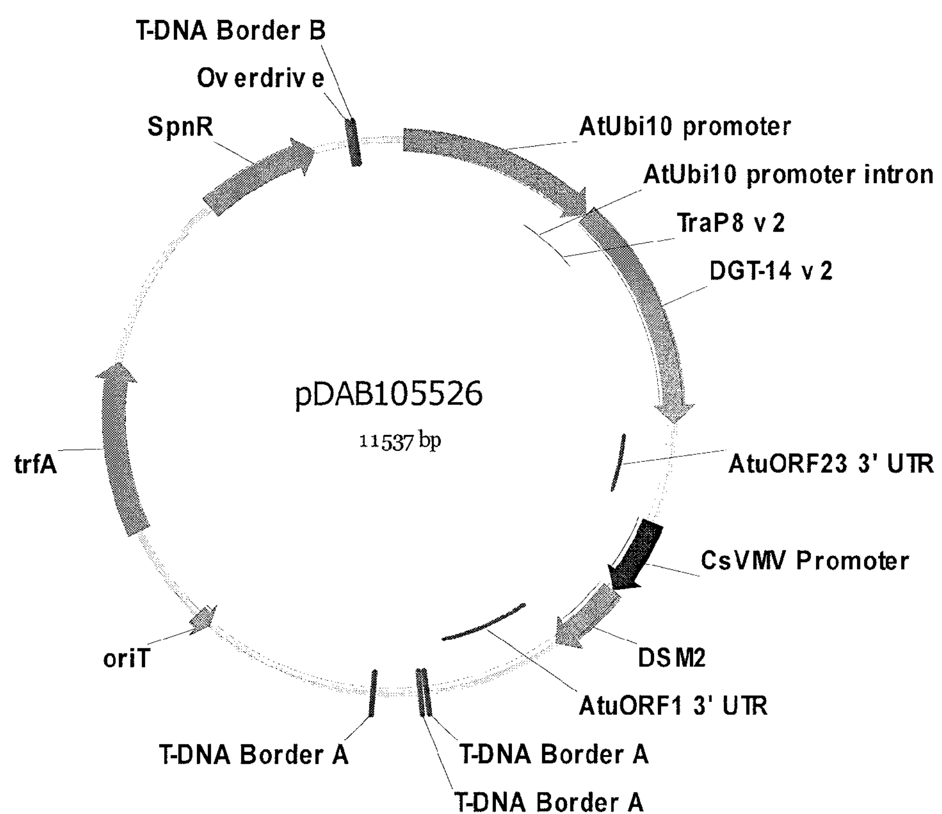
FIG. 10 illustrates a plasmid map of pDAB105526.
Figure 11:
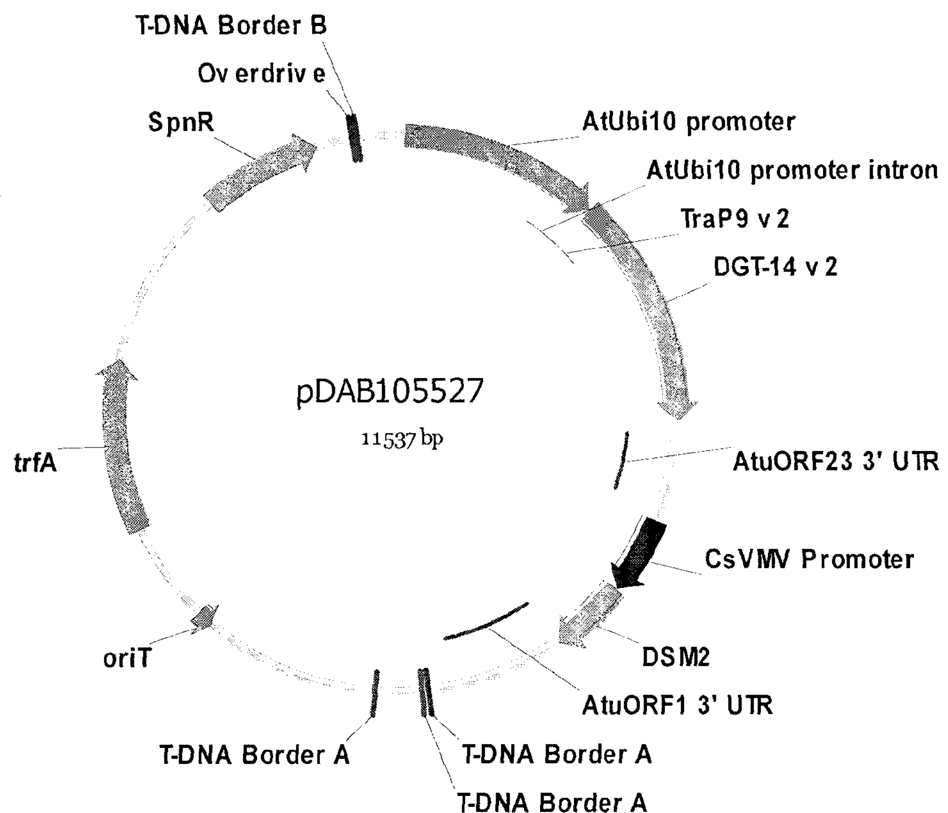
FIG. 11 illustrates a plasmid map of pDAB105527.

The level of plant response varied in the $T_1$ *Arabidopsis* plants. This variance can be attributed to the fact each plant represents an independent transformation event and thus the copy number of the gene of interest varies from plant to plant. An overall population injury average by rate is presented in Table 1 to demonstrate the tolerance provided by each of the dgt-14 constructs linked with either the TraP8 v2 or TraP9 v2 chloroplast transit peptide versus the dgt-1 and non-transformed wildtype controls for varying rates of glyphosate. The events contained dgt-14 linked with TraP8 v2 (SEQ ID NO:8) which is contained in construct pDAB105526 (FIG. 10) and TraP9 v2 (SEQ ID NO:9) which is contained in construct pDAB105527 (FIG. 11). Data from the glyphosate selection of $T_1$ plants demonstrated that when dgt-14 was linked with these chloroplast transit peptides, robust tolerance to high levels of glyphosate was provided. Comparatively, the non-transformed (or wildtype) controls did not provide tolerance to the treatment of high concentrations of glyphosate when treated with similar rates of glyphosate. In addition, there were instances when events that were shown to contain three or more copies of dgt-14 were more susceptible to elevated rates of glyphosate. These instances are demonstrated within the percent visual injury range shown in Table 1. It is likely that the presence of high copy numbers of the transgenes within the *Arabidopsis* plants result in transgene silencing or other epigenetic effects which resulted in sensitivity to glyphosate, despite the presence of the dgt-14 transgene.

TABLE 1 dgt-14 transformed $T_1$ *Arabidopsis* response to a range of glyphosate rates applied postemergence, compared to a dgt-1 ($T_2$) segregating population, and a non-transformed control. Visual % injury 2 weeks after application.

| | % Injury Range (No. Replicates) | | | % Injury Analysis | | |
|---|---|---|---|---|---|---|
| Application Rate | <20% | 20-40% | >40% | Ave | Std dev | Range (%) |
| TraP8 v2::dgt-14 (pDAB105526) | | | | | | |
| 0 g ae/ha glyphosate | 4 | 0 | 0 | 0.0 | 0.0 | 0 |
| 105 g ae/ha glyphosate | 0 | 2 | 2 | 40.0 | 14.1 | 20-50 |
| 420 g ae/ha glyphosate | 3 | 0 | 1 | 23.8 | 31.5 | 0-70 |
| 1680 g ae/ha glyphosate | 0 | 1 | 3 | 66.3 | 28.4 | 25-85 |
| 3360 g ae/ha glyphosate | 3 | 0 | 1 | 26.5 | 42.5 | 0-90 |
| TraP9 v2::dgt-14 (pDAB105527) | | | | | | |
| 0 g ae/ha glyphosate | 4 | 0 | 0 | 0.0 | 0.0 | 0 |
| 105 g ae/ha glyphosate | 2 | 1 | 1 | 23.0 | 25.7 | 0-50 |
| 420 g ae/ha glyphosate | 2 | 0 | 2 | 37.5 | 37.7 | 0-70 |
| 1680 g ae/ha glyphosate | 2 | 0 | 2 | 48.8 | 39.0 | 15-85 |
| 3360 g ae/ha glyphosate | 1 | 0 | 3 | 63.8 | 39.2 | 5-85 |
| dgt-1 (pDAB3759) | | | | | | |
| 0 g ae/ha glyphosate | 4 | 0 | 0 | 0.0 | 0.0 | 0 |
| 105 g ae/ha glyphosate | 0 | 3 | 1 | 40.0 | 14.1 | 30-60 |
| 420 g ae/ha glyphosate | 0 | 4 | 0 | 30.0 | 0.0 | 30 |
| 1680 g ae/ha glyphosate | 0 | 3 | 1 | 55.0 | 30.0 | 40-100 |
| 3360 g ae/ha glyphosate | 0 | 0 | 4 | 57.5 | 8.7 | 45-65 |
| Non-transformed control | | | | | | |
| 0 g ae/ha glyphosate | 4 | 0 | 0 | 0.0 | 0.0 | 0 |

TABLE 1-continued dgt-14 transformed $T_1$ *Arabidopsis* response to a range of glyphosate rates applied postemergence, compared to a dgt-1 ($T_2$) segregating population, and a non-transformed control. Visual % injury 2 weeks after application.

| | % Injury Range (No. Replicates) | | | % Injury Analysis | | |
|---|---|---|---|---|---|---|
| Application Rate | <20% | 20-40% | >40% | Ave | Std dev | Range (%) |
| 105 g ae/ha glyphosate | 0 | 0 | 4 | 100.0 | 0.0 | 100 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Selected $T_1$ *Arabidopsis* plants which were identified to contain low-copy numbers of transgene insertions (1-3 copies) were self-fertilized to produce a second generation for additional assessment of glyphosate tolerance. The second generation *Arabidopsis* plants ($T_2$) which contained 1-3 copies of the dgt-14 transgene fused to the TraP8 and TraP9 chimeric chloroplast transit peptides were further characterized for glyphosate tolerance and glufosinate tolerance (glufosinate resistance indicated that the PAT expression cassette was intact and did not undergo rearrangements during the selfing of the $T_1$ plants). In the $T_2$ generation hemizygous and homozygous plants were available for testing for each event and therefore were included for each rate of glyphosate tested. Hemizygous plants contain two different alleles at a locus as compared to homozygous plants which contain the same two alleles at a locus. The copy number and ploidy levels of the $T_2$ plants were confirmed using molecular analysis protocols. Likewise, glyphosate was applied using the methods and rates as previously described. The dose response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for *Arabidopsis* transformation. The range in individual response is also indicated in the last column for each rate and transformation. Wildtype, non-transformed *Arabidopsis* (cv. Columbia) served as a glyphosate sensitive control. In addition, plants comprising a glyphosate herbicide resistance gene, dgt-1 (as described in U.S. patent Ser. No. 12/558,351, incorporated herein by reference in its entirety) were included as a positive control.

In the $T_2$ generation both single copy and low-copy (two or three copy) dgt-14 events were characterized for glyphosate tolerance. An overall population injury average by rate is presented in Table 2 to demonstrate the tolerance provided by each of the dgt-14 constructs linked with a chloroplast transit peptide versus the dgt-1 and non-transformed wildtype controls for varying rates of glyphosate. The $T_2$ generation events contained dgt-14 linked with TraP8 v2 (pDAB105526) and TraP9 v2 (pDAB105527). Both of these events are highly resistant to glyphosate. The results indicated that the injury range for the $T_2$ *Arabidopsis* plants was less than 20% for all concentrations of glyphosate that were tested. Comparatively, the non-transformed (or wild-type) controls did not provide tolerance to the treatment of high concentrations of glyphosate when treated with similar rates of glyphosate. Overall, the results showed that plants containing and expressing DGT-14 fused to the TraP8 and TraP9 chimeric transit peptide proteins yielded commercial level resistance to glyphosate at levels of up to 3 times the field rate (1120 g ae/ha).

TABLE 2 dgt-14 transformed $T_2$ *Arabidopsis* response to a range of glyphosate rates applied postemergence, compared to a dgt-1 ($T_2$) segregating population, and a non-transfomied control. Visual % injury 2 weeks after application. Data represents a selected single copy line from each construct that segregated as a single locus in the heritability screen.

| Application Rate | % Injury Range (No. Replicates) <20% | 20-40% | >40% | % Injury Analysis Ave | Std dev | Range (%) |
|---|---|---|---|---|---|---|
| TraP8 v2::dgt-14 (pDAB105526) | | | | | | |
| 0 g ae/ha glyphosate | 4 | 0 | 0 | 0.0 | 0.0 | 0 |
| 420 g ae/ha glyphosate | 4 | 0 | 0 | 0.5 | 1.0 | 0-2 |
| 840 g ae/ha glyphosate | 4 | 0 | 0 | 0.0 | 0.0 | 0 |
| 1680 g ae/ha glyphosate | 4 | 0 | 0 | 2.5 | 2.9 | 0-5 |
| 3360 g ae/ha glyphosate | 4 | 0 | 0 | 5.0 | 4.8 | 0-10 |
| TraP9 v2::dgt-14 (pDAB105527) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 1.8 | 2.4 | 0-5 |
| 3360 g ae/ha glyphosate | 2 | 2 | 0 | 17.5 | 17.6 | 0-35 |
| dgt-1 (pDAB3759) | | | | | | |
| 0 g ae/ha glyphosate | 4 | 0 | 0 | 0.0 | 0.0 | 0 |
| 420 g ae/ha glyphosate | 2 | 0 | 2 | 40.0 | 40.4 | 5-75 |
| 840 g ae/ha glyphosate | 0 | 2 | 2 | 47.5 | 31.8 | 20-75 |
| 1680 g ae/ha glyphosate | 0 | 2 | 2 | 41.3 | 23.9 | 20-70 |
| 3360 g ae/ha glyphosate | 0 | 4 | 0 | 35.0 | 0.0 | 35 |
| Non-transformed control | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Randomly selected $T_2$ *Arabidopsis* plants which were identified to contain low-copy numbers of transgene insertions (1-3 copies) were self-fertilized to produce a third generation for additional assessment of glyphosate tolerance. *Arabidopsis* seed from the third generation ($T_3$) were planted and evaluated for glyphosate tolerance using the same protocols as previously described. The events tested in the $T_3$ generation contained replicates from each line that were homozygous (as determined by using a glufosinate resistance screen to identify if any of the advanced plants showed segregation of the transgenes). These Events were assayed via LC-MS-MS to confirm that the plants expressed the DGT-14 protein. The results of the $T_3$ generation for overall population injury average by rate of glyphosate is presented in Table 3 which shows the tolerance to glyphosate provided by each of the dgt-14 constructs for varying rates of glyphosate. Exemplary resistant $T_3$ Events comprised dgt-14 linked with TraP8 v2 (pDAB105526) and TraP9 v2 (pDAB105527). Both of these Events are highly resistant to glyphosate. The results indicated that the injury range for the $T_3$ *Arabidopsis* plants was less than 20% for all concentrations of glyphosate that were tested. Comparatively, the non-transformed (or wild-type) controls did not provide tolerance to the treatment of high concentrations of glyphosate when treated with similar rates of glyphosate. Overall, the results showed that plants containing and expressing DGT-14 yielded commercial level resistance to glyphosate at levels of up to 3 times the field rate (1120 g ae/ha).

TABLE 3 dgt-14 transformed $T_3$ *Arabidopsis* response to a range of glyphosate rates applied postemergence, compared to a dgt-1 ($T_2$) segregating population, and a non-transformed control. Visual % injury 2 weeks after application. Data represents a selected single copy population from each construct that segregated as a single locus in the $T_2$ heritability screen.

| Application Rate | % Injury Range (No. Replicates) <20% | 20-40% | >40% | % Injury Analysis Ave | Std dev | Range (%) |
|---|---|---|---|---|---|---|
| TraP8 v2::dgt-14 (pDAB105526) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 1.3 | 2.5 | 0-5 |
| 1680 g ae/ha glyphosate | 4 | 0 | 0 | 0.0 | 0.0 | 0 |
| 3360 g ae/ha glyphosate | 4 | 0 | 0 | 4.0 | 4.0 | 2-10 |
| TraP9 v2::dgt-14 (pDAB105527) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 0.0 | 0.0 | 0 |
| 3360 g ae/ha glyphosate | 4 | 0 | 0 | 4.3 | 1.5 | 2-5 |
| dgt-1 (pDAB3759) | | | | | | |
| 0 g ae/ha glyphosate | 4 | 0 | 0 | 0.0 | 0.0 | 0 |
| 420 g ae/ha glyphosate | 0 | 2 | 2 | 42.5 | 9.6 | 30-50 |
| 840 g ae/ha glyphosate | 0 | 4 | 0 | 40.0 | 0.0 | 40 |
| 1680 g ae/ha glyphosate | 0 | 3 | 1 | 47.5 | 15.0 | 40-70 |
| 3360 g ae/ha glyphosate | 0 | 0 | 4 | 77.5 | 17.1 | 60-100 |
| Non-transformed control | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

The data show that expression of a glyphosate-resistant enzyme (e.g., DGT-28), when targeted to the chloroplast of a plant cell by a TraP transit peptide in a fusion protein, is capable of conferring glyphosate resistance to the plant cell and plants comprised of these cells.

DGT-28, DGT-31, DGT-32, and DGT-33:

The newly-designed, dicotyledonous plant optimized dgt-28 v5 polynucleotide sequence is listed in SEQ ID NO:16. The newly-designed, monocotyledonous plant optimized dgt-28 v6 polynucleotide sequence is listed in SEQ ID NO:17; this sequence was slightly modified by including an alanine at the second amino acid position to introduce a restriction enzyme site. The resulting DNA sequences have a higher degree of codon diversity, a desirable base composition, contains strategically placed restriction enzyme recognition sites, and lacks sequences that might interfere with transcription of the gene, or translation of the product mRNA.

Synthesis of DNA fragments comprising SEQ ID NO:16 and SEQ ID NO:17 containing additional sequences, such as 6-frame stops (stop codons located in all six reading frames that are added to the 3' end of the coding sequence), and a 5' restriction site for cloning were performed by commercial suppliers (DNA2.0, Menlo Park, Calif.). The synthetic nucleic acid molecule was then cloned into expression vectors and transformed into plants or bacteria as described in the Examples below.

Similar codon optimization strategies were used to design dgt-1, dgt-3 v2 (G173A), dgt-3 v3 (G173A; P178S), dgt-3 v4 (T1741; P178S), dgt-7 v4 (T1681; P172S), dgt-32 v3, dgt-33 v3, and dgt-31 v3. The codon optimized version of these genes are listed as SEQ ID NO:18, SEQ ID NO:19, SEQ ID NO:20, SEQ ID NO:21, SEQ ID NO:22, SEQ ID NO:23, SEQ ID NO:24, and SEQ ID NO:25, respectively.

Plant Binary Vector Construction. Standard cloning methods were used in the construction of entry vectors containing a chloroplast transit peptide polynucleotide sequence joined to dgt-28 as an in-frame fusion. The entry vectors containing a transit peptide (TraP) fused to dgt-28 were assembled using the IN-FUSION™ Advantage Technology (Clontech, Mountain View, Calif.). As a result of the fusion, the first amino acid, methionine, was removed from dgt-28. Transit peptides TraP4 v2 (SEQ ID NO:26), TraP8 v2 (SEQ ID NO:27), TraP8 v2 (SEQ ID NO:28), TraP9 v2 (SEQ ID NO:29), TraP12 v2 (SEQ ID NO:30), and TraP13 v2 (SEQ ID NO:31) were each synthesized by DNA2.0 (Menlo Park, Calif.) and fused to the 5' end fragment of dgt-28, up to and including a unique AccI restriction endonuclease recognition site.

Binary plasmids which contained the various TraP and dgt-28 expression cassettes were driven by the *Arabidopsis thaliana* Ubiquitin 10 promoter (AtUbi10 v2; Callis, et al., (1990) *J. Biol. Chem.,* 265: 12486-12493) and flanked by the *Agrobacterium tumefaciens* open reading frame twenty-three 3' untranslated region (AtuORF23 3' UTR v1; U.S. Pat. No. 5,428,147).

The assembled TraP and dgt-28 expression cassettes were engineered using GATEWAY® Technology (Invitrogen, Carlsbad, Calif.) and transformed into plants via *Agrobacterium*-mediated plant transformation. Restriction endonucleases were obtained from New England BioLabs (NEB; Ipswich, Mass.) and T4 DNA Ligase (Invitrogen) was used for DNA ligation. Gateway reactions were performed using GATEWAY® LR CLONASE® enzyme mix (Invitrogen) for assembling one entry vector into a single destination vector which contained the selectable marker cassette Cassava Vein Mosaic Virus promoter (CsVMV v2; Verdaguer et al., (1996) *Plant Mol. Biol.,* 31: 1129-1139)—DSM-2 (U.S. Pat. App. No. 2007/086813)-*Agrobacterium tumefaciens* open reading frame one 3' untranslated region (AtuORF1 3' UTR v6; Huang et al., (1990) *J. Bacteriol.* 172:1814-1822). Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAquick™ Gel Extraction Kit (Qiagen) after agarose Tris-acetate gel electrophoresis.

Colonies of all assembled plasmids were initially screened by restriction digestion of miniprep DNA. Plasmid DNA of selected clones was sequenced by a commercial sequencing vendor (Eurofins™ MWG Operon, Huntsville, Ala.). Sequence data were assembled and analyzed using the SEQUENCHER™ software (Gene Codes Corp., Ann Arbor, Mich.).

Figure 19:
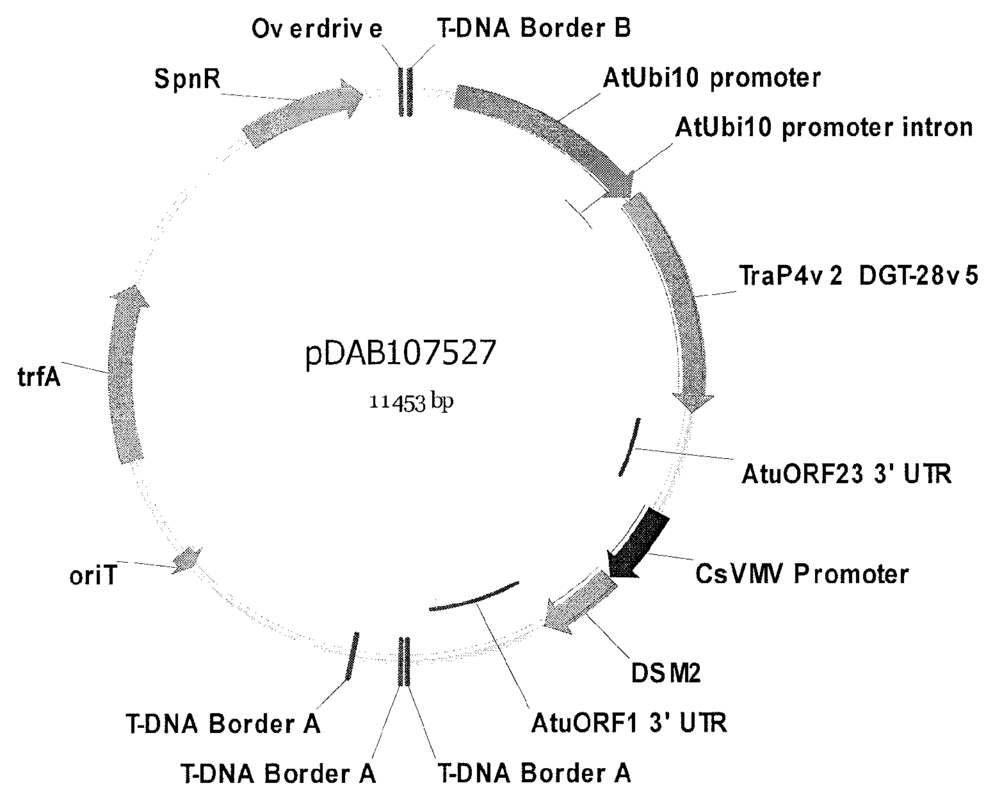
FIG. 19 illustrates a plasmid map of pDAB107527.
Figure 20:
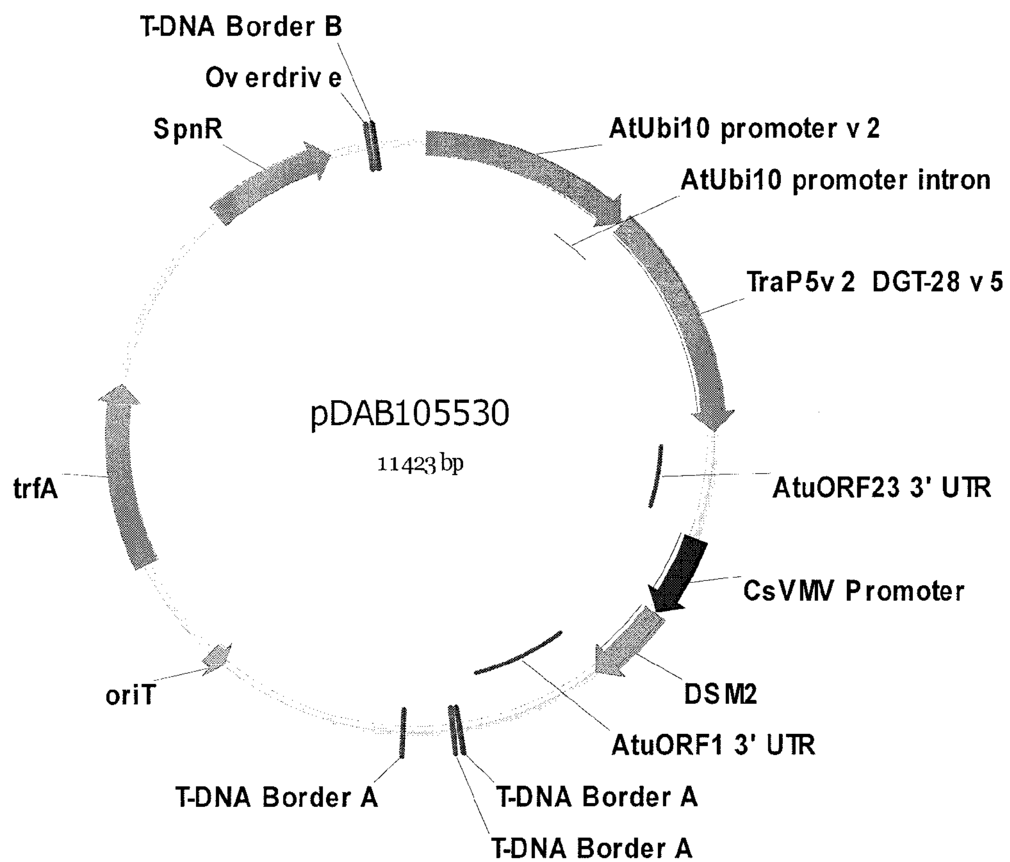
FIG. 20 illustrates a plasmid map of pDAB105530.
Figure 21:
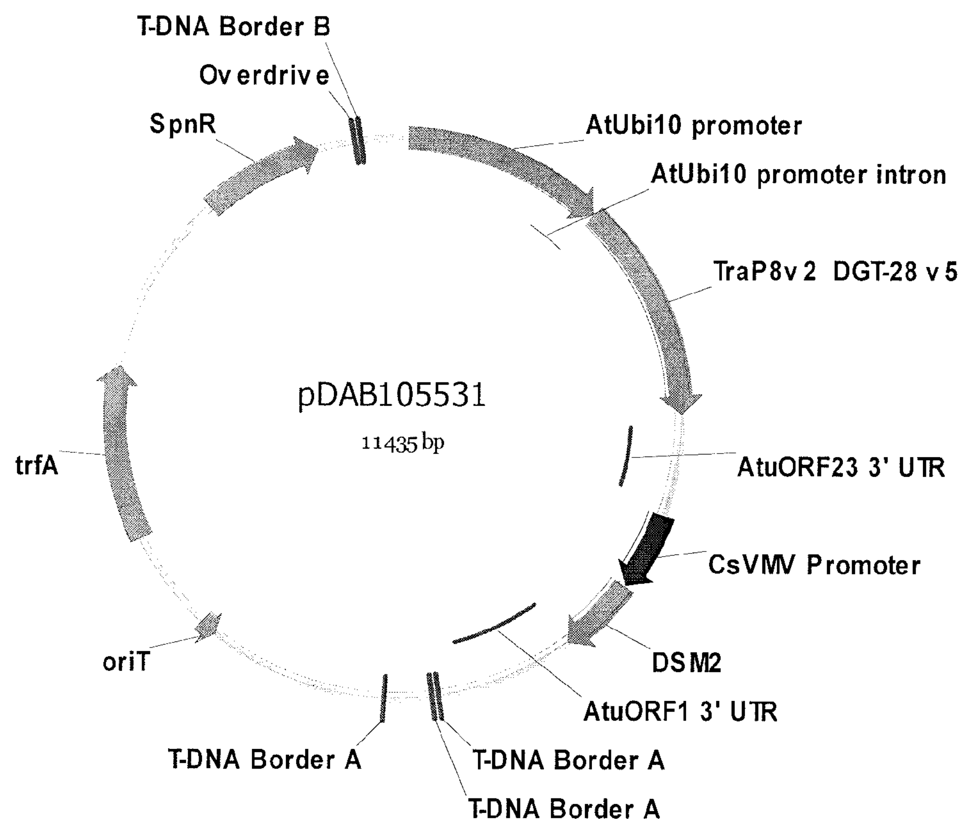
FIG. 21 illustrates a plasmid map of pDAB105531.
Figure 22:
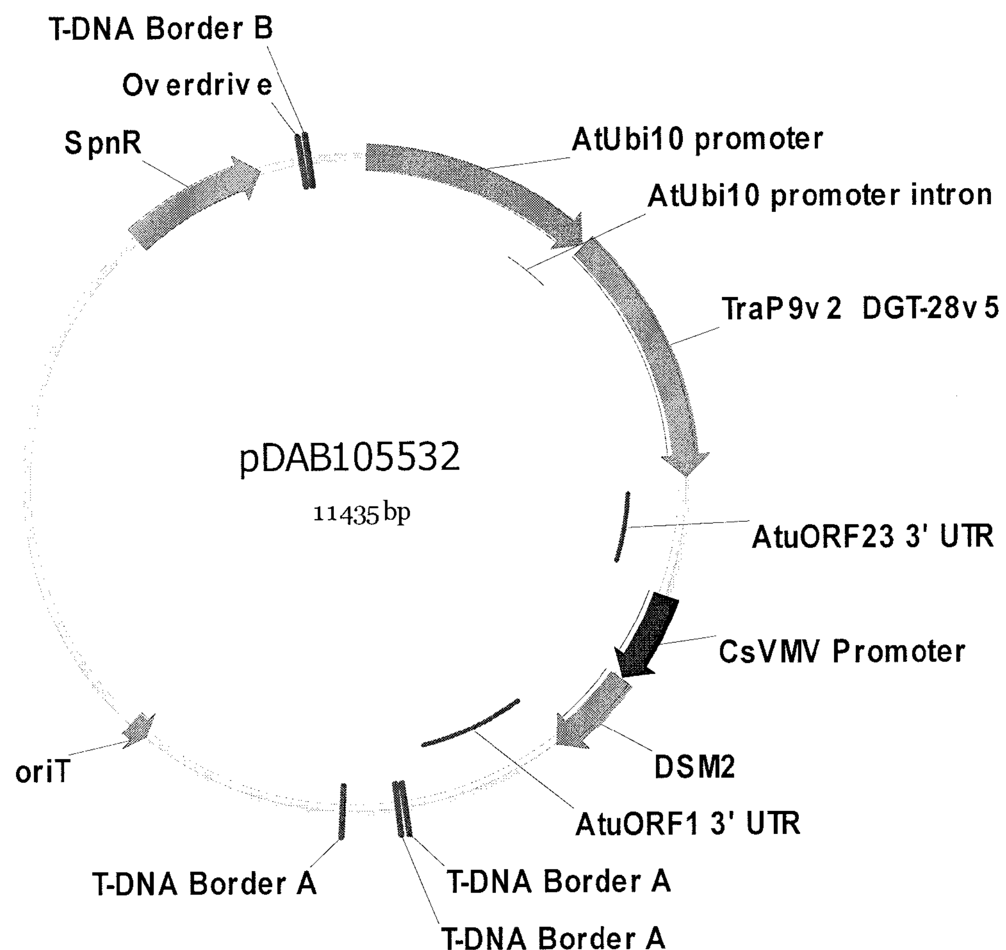
FIG. 22 illustrates a plasmid map of pDAB105532.
Figure 23:
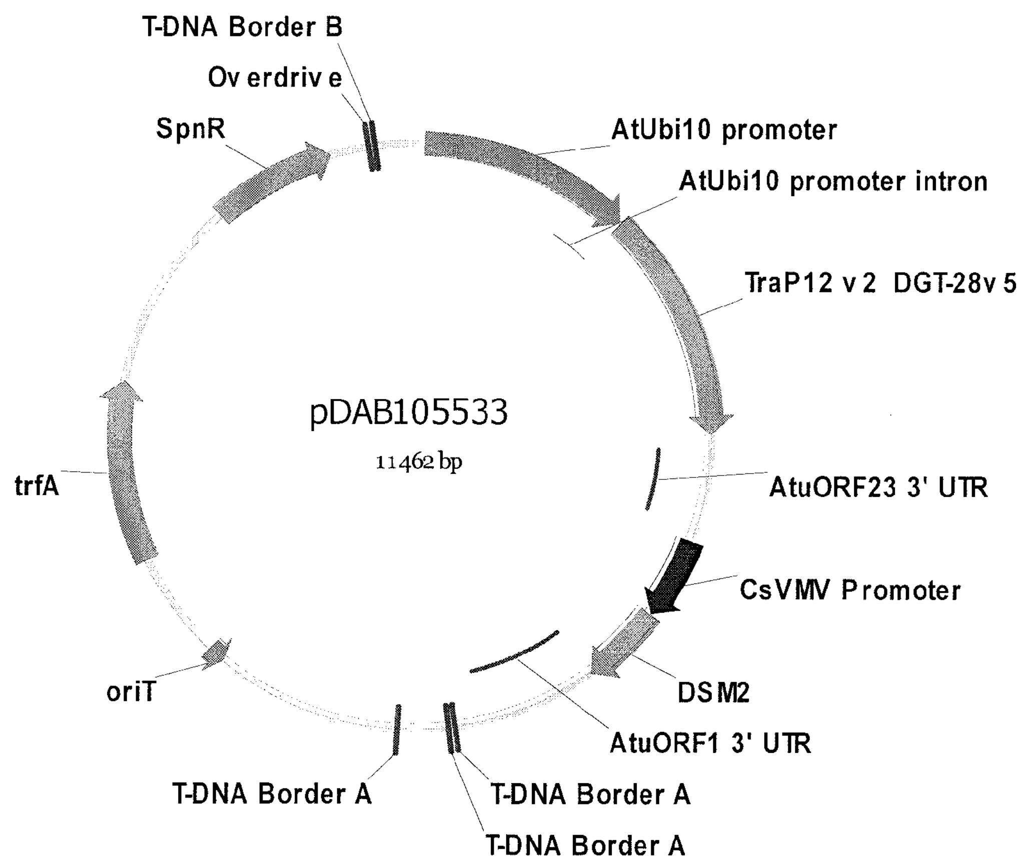
FIG. 23 illustrates a plasmid map of pDAB105533.
Figure 24:
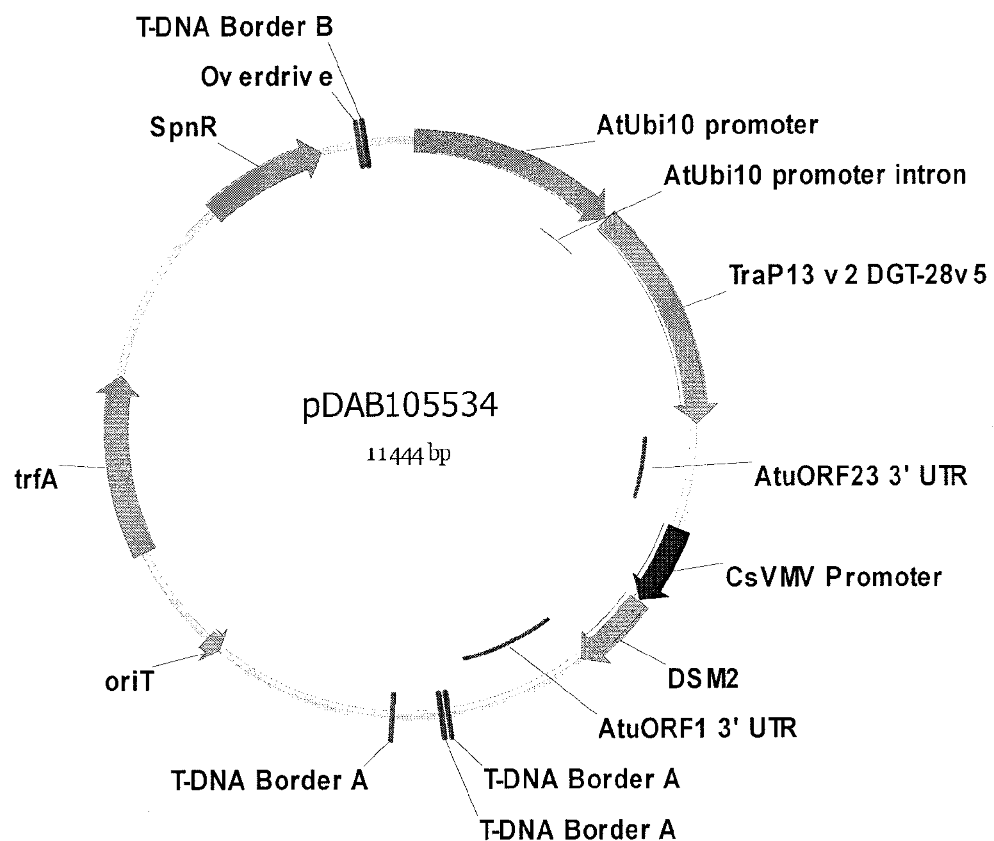
FIG. 24 illustrates a plasmid map of pDAB105534.

The following binary constructs express the various TraP: dgt-28 fusion gene sequences: pDAB107527 (FIG. 19) contains TraP4 v2:dgt-28 v5 (SEQ ID NO:32); pDAB105530 (FIG. 20) contains TraP5 v2: dgt-28 v5 (SEQ ID NO:33); pDAB105531 (FIG. 21) contains TraP8 v2: dgt-28 v5 (SEQ ID NO:34); PDAB105532 (FIG. 22) contains TraP9 v2: dgt-28 v5 (SEQ ID NO:35); pDAB105533 (FIG. 23) contains TraP12 v2: dgt-28 v5 (SEQ ID NO:36); and pDAB105534 (FIG. 24) contains TraP13 v2:dgt-28 v5 (SEQ ID NO:37). The dgt-28 v5 sequence of pDAB105534 was modified wherein the first codon (GCA) was changed to (GCT).

Additional Plant Binary Vector Construction. Cloning strategies similar to those described above were used to construct binary plasmids which contain dgt-31, dgt-32, dgt-33, dgt-1, dgt-3, and dgt-7.

Figure 25:
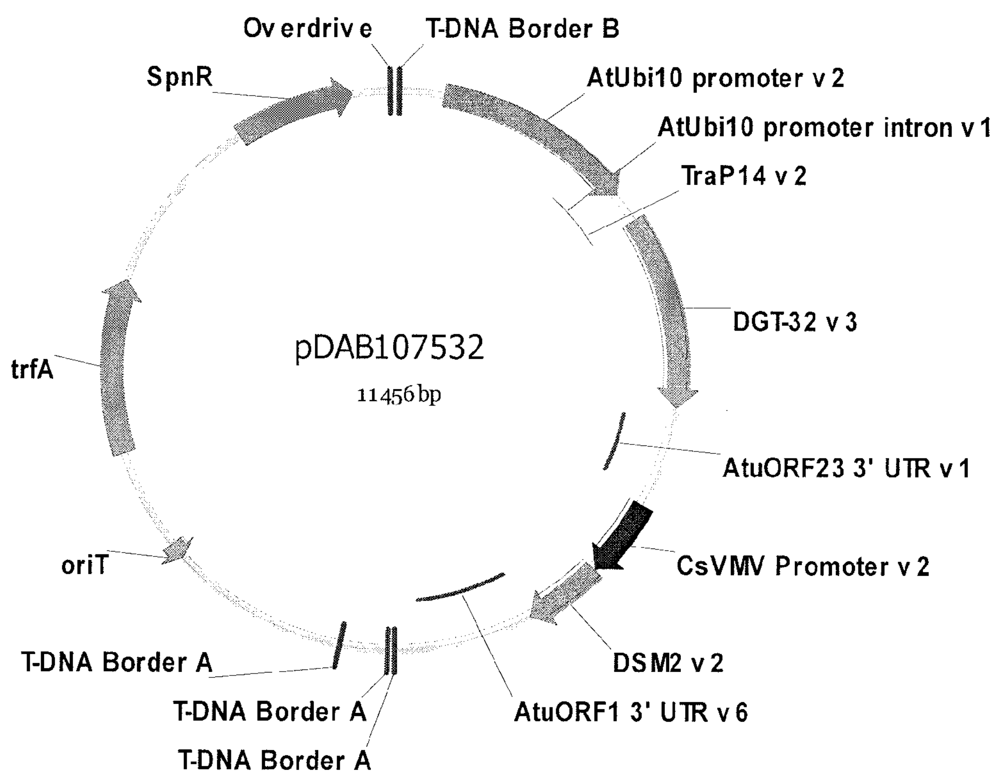
FIG. 25 illustrates a plasmid map of pDAB107532.
Figure 26:
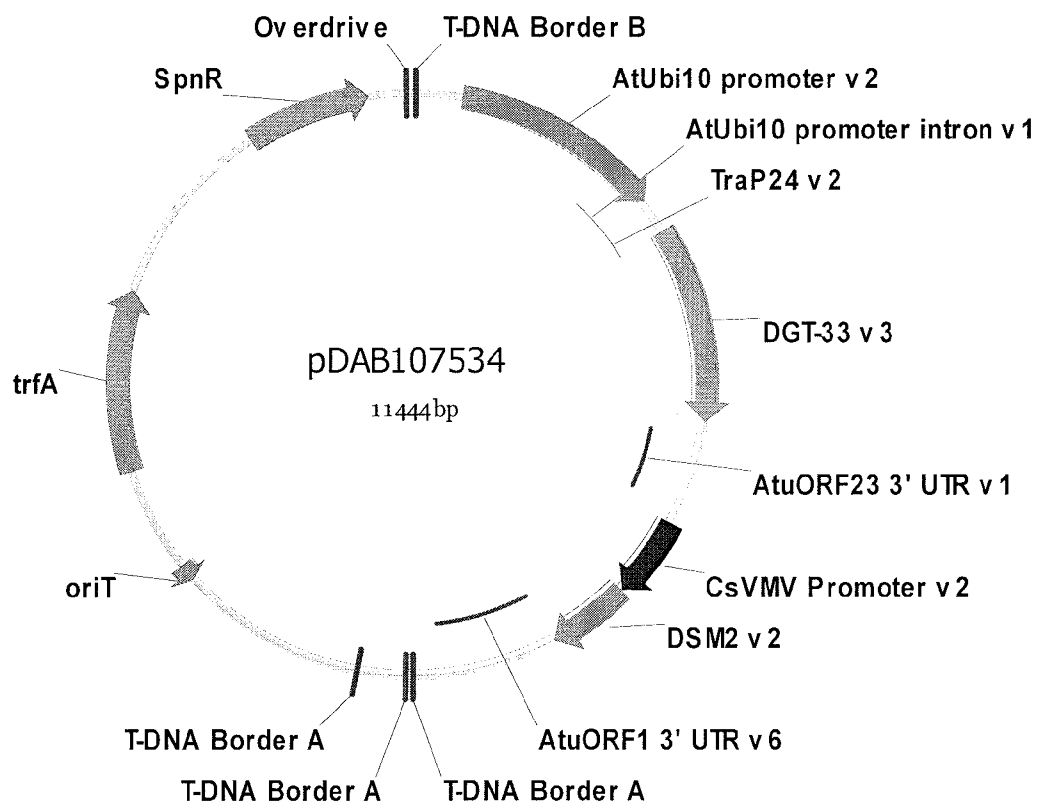
FIG. 26 illustrates a plasmid map of pDAB107534.
Figure 27:
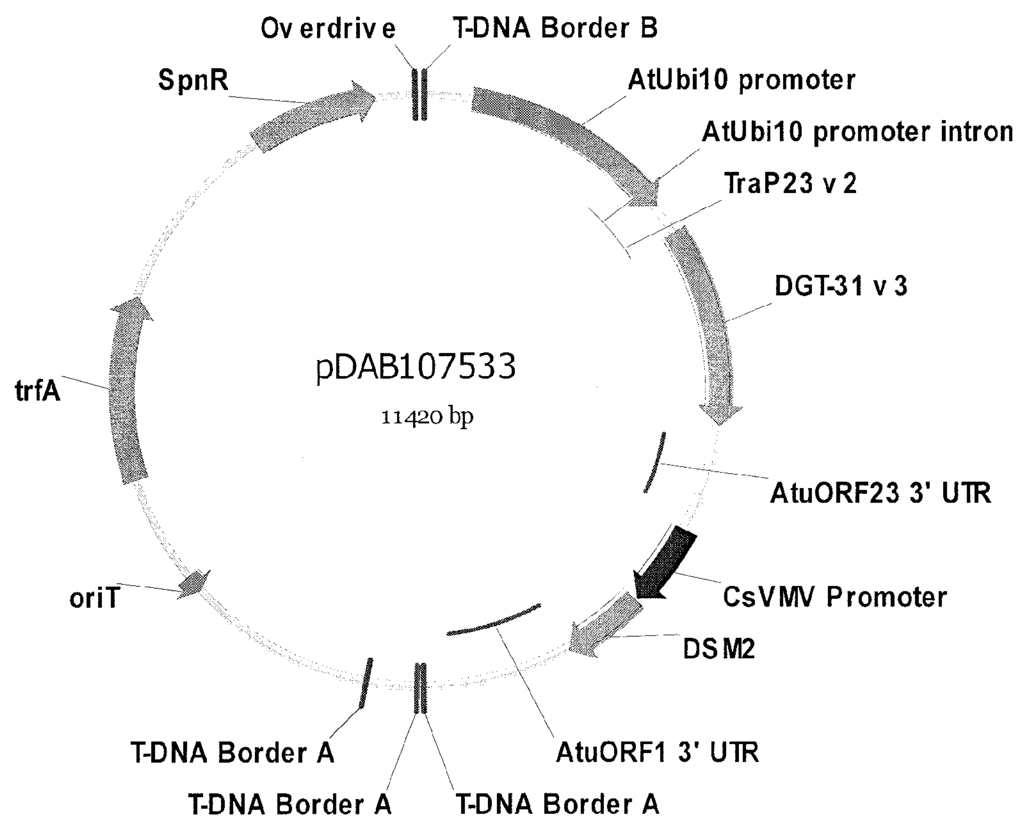
FIG. 27 illustrates a plasmid map of pDAB107533.

The microbially derived genes; dgt-31, dgt-32, and dgt-33, were fused with different chloroplast transit peptides than previously described. The following chloroplast transit peptides were used; TraP14 v2 (SEQ ID NO:38), TraP23 v2 (SEQ ID NO:39), TraP24 v2 (SEQ ID NO:40). pDAB107532 (FIG. 25) contains dgt-32 v3 fused to TraP14 v2 (SEQ ID NO:41), pDAB107534 (FIG. 26) contains dgt-33 v3 fused to TraP24 v2 (SEQ ID NO:42), and pDAB107533 (FIG. 27) contains dgt-31 v3 fused to TraP23 v2 (SEQ ID NO:43). The dgt expression cassettes were driven by the *Arabidopsis thaliana* Ubiquitin 10 promoter (AtUbi10 promoter v2) and flanked by the *Agrobacterium tumefaciens* open reading frame twenty-three 3' untranslated region (AtuORF23 3' UTR v1). A DSM-2 selectable marker cassette containing Cassava Vein Mosaic Virus promoter (CsVMV v2)—DSM-2—*Agrobacterium tumefaciens* open reading frame one 3' untranslated region (AtuORF1 3' UTR v6) was also present in the binary vector.

Additional binaries are constructed wherein dgt-31 v3, dgt-32 v3, and dgt-33 v3 are fused to the previously described chloroplast transit peptide sequences. For example, the TraP8 v2 sequence is fused to dgt-31 v3, dgt-32 v3, and dgt-33 v3, and cloned into binary vectors as described above.

Figure 28:
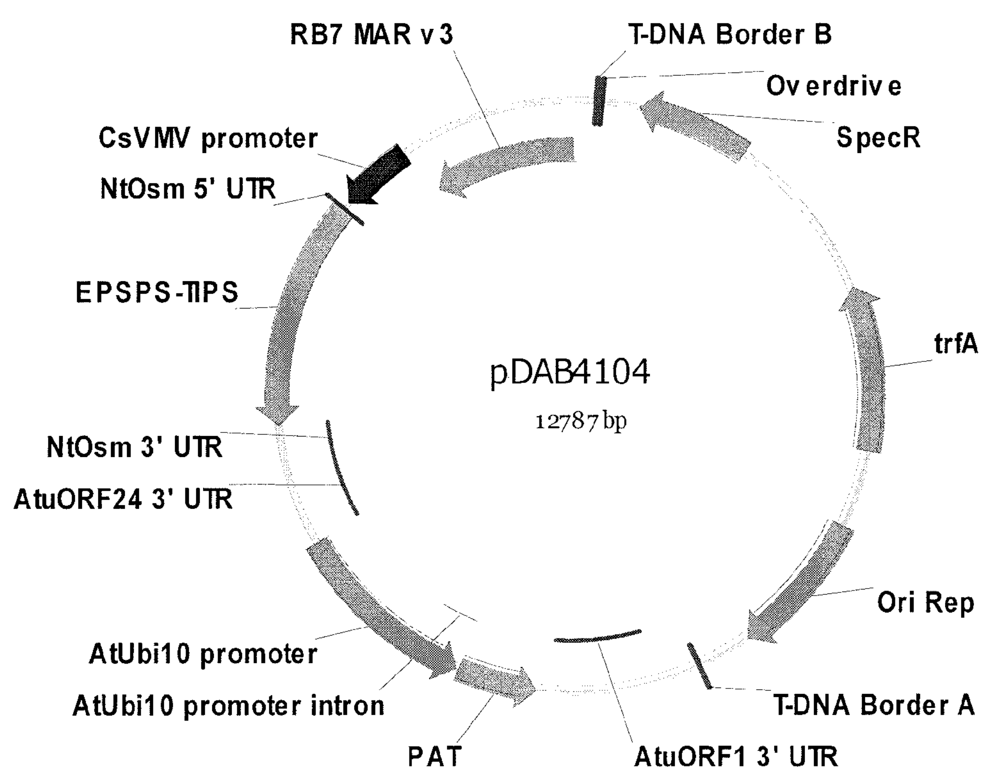
FIG. 28 illustrates a plasmid map of pDAB4104.
Figure 29:
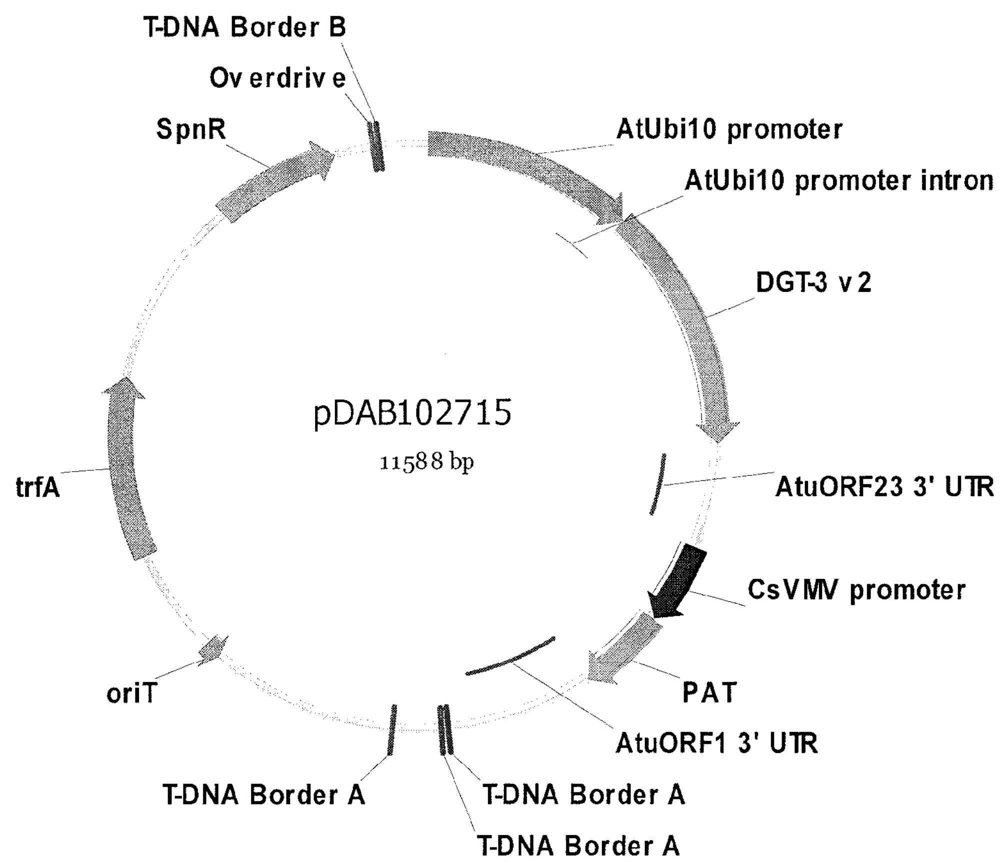
FIG. 29 illustrates a plasmid map of pDAB102715.
Figure 30:
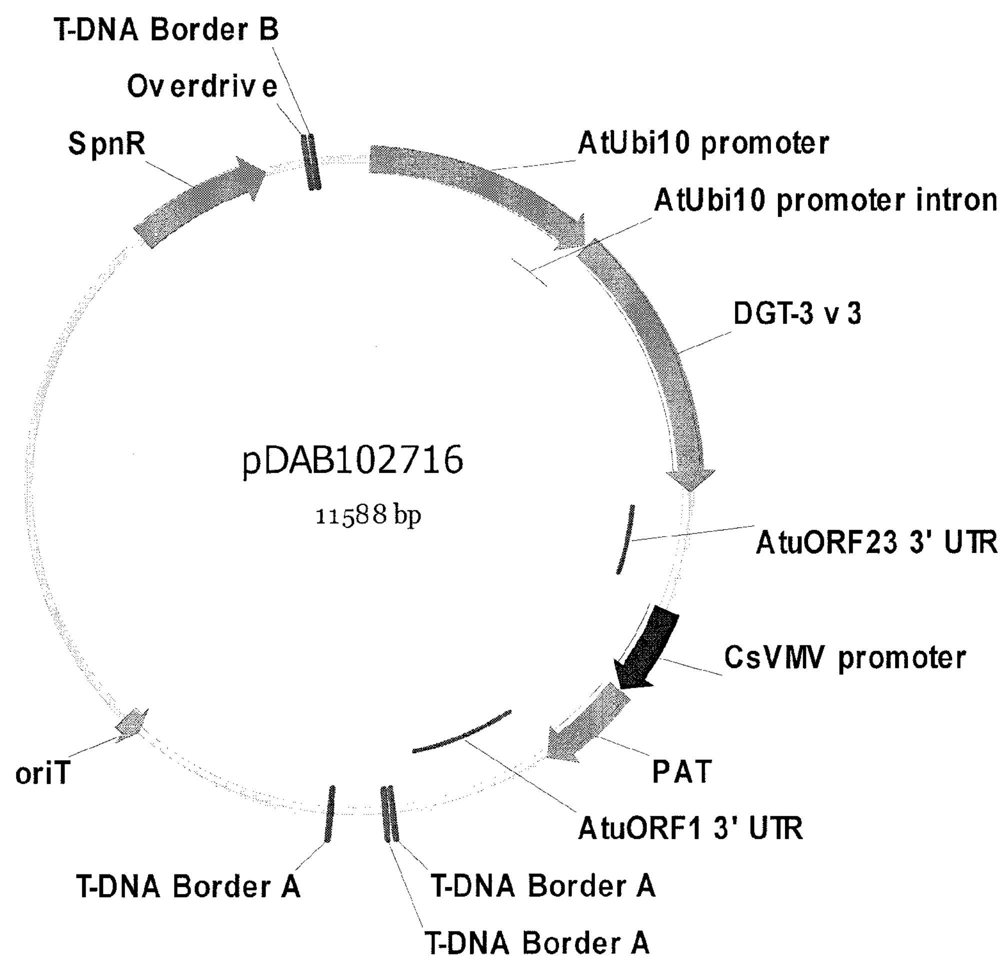
FIG. 30 illustrates a plasmid map of pDAB102716.
Figure 31:
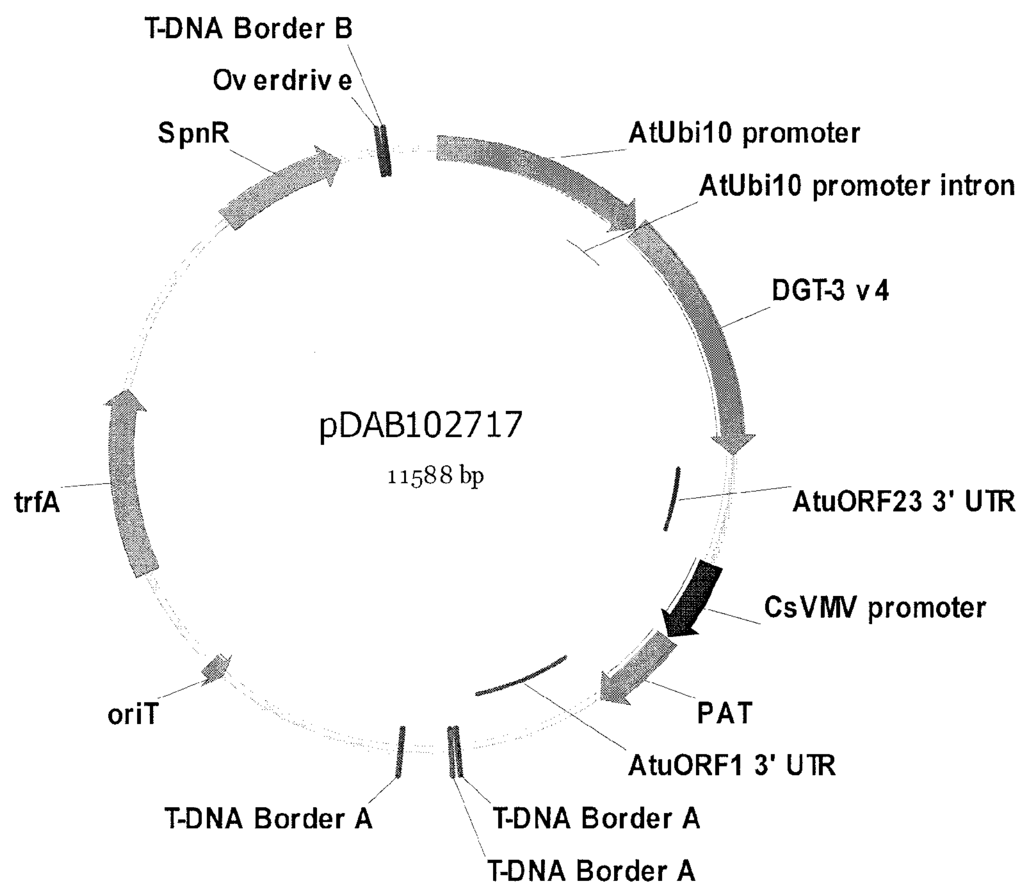
FIG. 31 illustrates a plasmid map of pDAB102717.
Figure 32:
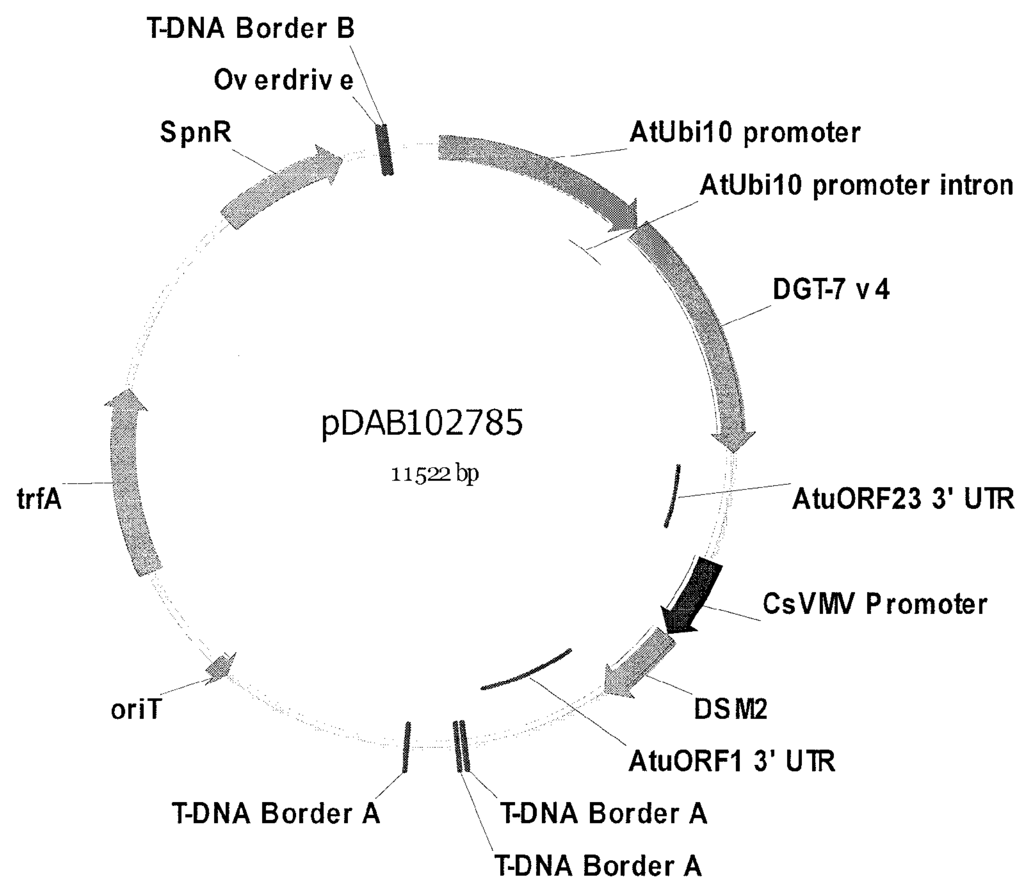
FIG. 32 illustrates a plasmid map of pDAB102785.

Binary vectors containing the Class I genes (dgt-1, dgt-3, and dgt-7) were constructed. The following binary vectors were constructed and transformed into plants: pDAB4104 (FIG. 28), which contains the dgt-1 v4 sequence as described in U.S. Patent Application Publication No. 2011/0124503, which is flanked by the *Nicotiana tabacum* Osmotin sequences as described in U.S. Patent Application Publication No. 2009/0064376; pDAB102715 (FIG. 29); pDAB102716 (FIG. 30); pDAB102717 (FIG. 31); and pDAB102785 (FIG. 32). The various TraP chloroplast transit peptides that were fused to dgt-28, dgt-31, dgt-32, and dgt-33 were not added to the Class I genes, as these plant derived sequences possess native plant chloroplast transit peptides. These vectors are described in further detail in Table 4.

TABLE 4

Description of the binary vectors which contain a Class I EPSP synthase gene (i.e., dgt-1, dgt-3, or dgt-7).

| Name | Description | EPSPS mutation |
|---|---|---|
| pDAB4104 | RB7 MAR v2 :: CsVMV promoter v2/NtOsm 5' UTR v2/dgt-1 v4/NtOsm 3' UTR v2/AtuORF24 3' UTR v2 :: AtUbi10 promoter v4/pat v3/AtuORF1 3'UTR v3 binary vector | TI PS |
| pDAB102715 | AtUbi10 promoter v2/dgt-3 v2/AtuORF23 3'UTR v1 :: CsVMV promoter v2/pat v9/AtuORF1 3'UTR v6 binary vector | GA |
| pDAB102716 | AtUbi10 promoter v2/dgt-3 v3/AtuORF23 3'UTR v1 :: CsVMV promoter v2/pat v9/AtuORF1 3'UTR v6 binary vector | GA PS |
| pDAB102717 | AtUbi10 promoter v2/dgt-3 v4/AtuORF23 3'UTR v1 :: CsVMV promoter v2/pat v9/AtuORF1 3'UTR v6 binary vector | TI PS |
| pDAB102785 | AtUbi10 promoter v2/dgt-7 v4/AtuORF23 3'UTR :: CsVMV promoter v2/DSM-2 v2/AtuORF1 3'UTR v6 binary vector | TI PS |

*Arabidopsis thaliana* Transformation. *Arabidopsis* was transformed using the floral dip method from Clough and Bent (1998). A selected *Agrobacterium* colony containing one of the binary plasmids described above was used to inoculate one or more 100 mL pre-cultures of YEP broth containing spectinomycin (100 mg/L) and kanamycin (50 mg/L). The culture was incubated overnight at 28° C. with constant agitation at 225 rpm. The cells were pelleted at approximately 5000×g for 10 minutes at room temperature, and the resulting supernatant discarded. The cell pellet was gently resuspended in 400 mL dunking media containing: 5% (w/v) sucrose, 10 μg/L 6-benzylaminopurine, and 0.04% Silwet™ L-77. Plants approximately 1 month old were dipped into the media for 5-10 minutes with gentle agitation. The plants were laid down on their sides and covered with transparent or opaque plastic bags for 2-3 hours, and then placed upright. The plants were grown at 22° C., with a 16-hour light/8-hour dark photoperiod. Approximately 4 weeks after dipping, the seeds were harvested.

Selection of Transformed Plants. Freshly harvested $T_1$ seed [containing the dgt and DSM-2 expression cassettes] was allowed to dry for 7 days at room temperature. $T_1$ seed was sown in 26.5×51-cm germination trays, each receiving a 200 mg aliquot of stratified $T_1$ seed (~10,000 seed) that had previously been suspended in 40 mL of 0.1% agarose solution and stored at 4° C. for 2 days to complete dormancy requirements and ensure synchronous seed germination.

Sunshine Mix LP5 was covered with fine vermiculite and subirrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate postemergence spray (selecting for the co-transformed DSM-2 gene).

Seven days after planting (DAP) and again 11 DAP, $T_1$ plants (cotyledon and 2-4-lf stage, respectively) were sprayed with a 0.2% solution of Liberty herbicide (200 g ai/L glufosinate, Bayer Crop Sciences, Kansas City, Mo.) at a spray volume of 10 mL/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50130% RH, 14 h light:10 dark, minimum 500 $\mu E/m^2s^1$ natural+supplemental light). Molecular confirmation analysis was completed on the surviving $T_1$ plants to confirm that the glyphosate tolerance gene had stably integrated into the genome of the plants.

Molecular Confirmation. The presence of the dgt-28 and DSM-2 transgenes within the genome of *Arabidopsis* plants that were transformed with pDAB107527, pDAB105530, pDAB105531, pDAB105532, pDAB105533, or pDAB105534 was confirmed. The presence of these polynucleotide sequences was confirmed via hydrolysis probe assays, gene expression cassette PCR (also described as plant transcription unit PCR—PTU PCR), Southern blot analysis, and Quantitative Reverse Transcription PCR analyses.

The $T_1$ *Arabidopsis* plants were initially screened via a hydrolysis probe assay, analogous to TAQMAN™, to confirm the presence of the DSM-2 and dgt-28 transgenes. Events were screened via gene expression cassette PCR to determine whether the dgt expression cassette completely integrated into the plant genomes without rearrangement. The data generated from these studies were used to determine the transgene copy number and identify select *Arabidopsis* events for self fertilization and advancement to the $T_2$ generation. The advanced $T_2$ *Arabidopsis* plants were also screened via hydrolysis probe assays to confirm the presence and to estimate the copy number of the DSM-2 and dgt genes within the plant chromosome. Finally, a Southern blot assay was used to confirm the estimated copy number on a subset of the $T_1$ *Arabidopsis plants*.

Similar assays were used to confirm the presence of the dgt-1 transgene from plants transformed with pDAB4101, the presence of the dgt-32 transgene from plants transformed with pDAB107532, the presence of the dgt-33 transgene from plants transformed with pDAB107534, the presence of the dgt-3 transgene from plants transformed with pDAB102715, the presence of the dgt-3 transgene from plants transformed with pDAB102716, the presence of the dgt-3 transgene from plants transformed with pDAB102717, and the presence of the dgt-7 transgene from plants transformed with pDAB102785.

Hydrolysis Probe Assay. Copy number was determined in the $T_1$ and $T_2$ *Arabidopsis* plants using the hydrolysis probe assay described below. Plants with varying numbers of transgenes were identified and advanced for subsequent glyphosate tolerance studies.

Tissue samples were collected in 96-well plates and lyophilized for 2 days. Tissue maceration was performed with a KLECO™ tissue pulverizer and tungsten beads (Environ Metal INC., Sweet Home, Oreg.). Following tissue maceration, the genomic DNA was isolated in high-throughput format using the Biosprint™ 96 Plant kit (Qiagen™ Germantown, Md.) according to the manufacturer's suggested protocol. Genomic DNA was quantified by QUANT-IT™ PICO GREEN DNA ASSAY KIT (Molecular Probes, Invitrogen, Carlsbad, Calif.). Quantified genomic DNA was adjusted to around 2 ng/μL for the hydrolysis probe assay using a BIOROBOT3000™ automated liquid handler (Qiagen, Germantown, Md.). Transgene copy number determination by hydrolysis probe assay was performed by real-time PCR using the LIGHTCYCLER®480 system (Roche Applied Science, Indianapolis, Ind.). Assays were designed for DSM-2, dgt-28 and the internal reference gene, TAF1115 (Genbank ID: NC 003075; Duarte et al., (201) *BMC Evol. Biol.,* 10:61).\

For amplification, LIGHTCYCLER®480 Probes Master mix (Roche Applied Science, Indianapolis, Ind.) was prepared at a 1× final concentration in a 10 μL volume multiplex reaction containing 0.1 μM of each primer for DSM-2 and dgt-28, 0.4 μM of each primer for TAF1115 and 0.2 μM of each probe.

Table 5. A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LightCycler™ software release 1.5 using the relative quant module and is based on the ΔΔCt method. For this, a sample of genomic DNA from a single copy calibrator and known 2 copy check were included in each run. The copy number results of the hydrolysis probe screen were determined for the $T_1$ and $T_2$ transgenic *Arabidopsis* plants.

TABLE 5

Primer and probe Information for hydrolysis probe assay of DSM-2, dgt-28 and internal reference gene (TAFII15).

| Primer Name | Sequence |
|---|---|
| DSM2A (SEQ ID NO: 44) | 5' AGCCACATCCCAGTAACGA 3' |
| DSM2S (SEQ ID NO: 45) | 5' CCTCCCTCTTTGACGCC 3' |
| DSM2 Cy5 probe (SEQ ID NO: 46) | 5' CAGCCCAATGAGGCATCAGC 3' |
| DGT28F (SEQ ID NO: 47) | 5' CTTCAAGGAGATTTGGGATTTGT 3' |
| DGT28R (SEQ ID NO: 48) | 5' GAGGGTCGGCATCGTAT 3' |
| UPL154 probe | Cat# 04694406001 (Roche, Indianapolis, IN) |
| TAFFY-HEX probe (SEQ ID NO: 49) | 5' AGAGAAGTTTCGACGGATTTCGGGC 3' |
| TAFII15-F (SEQ ID NO: 50) | 5' GAGGATTAGGGTTTCAACGGAG 3' |
| TAFII15-R (SEQ ID NO: 51) | 5' GAGAATTGAGCTGAGACGAGG 3' |

dgt-28 Integration Confirmation Via Southern Blot Analysis. Southern blot analysis was used to establish the integration pattern of the inserted T-strand DNA fragment and identify events which contained dgt-28. Data were generated to demonstrate the integration and integrity of the transgene inserts within the *Arabidopsis* genome. Southern blot data were used to identify simple integration of an intact copy of the T-strand DNA. Detailed Southern blot analysis was conducted using a PCR amplified probe specific to the dgt-28 gene expression cassette. The hybridization of the probe with genomic DNA that had been digested with specific restriction enzymes identified genomic DNA fragments of specific molecular weights, the patterns of which were used to identify full length, simple insertion $T_1$ transgenic events for advancement to the next generation.

Tissue samples were collected in 2 mL conical tubes (Eppendorf' M) and lyophilized for 2 days. Tissue maceration was performed with a KLECKO™ tissue pulverizer and tungsten beads. Following tissue maceration, the genomic DNA was isolated using a CTAB isolation procedure. The genomic DNA was further purified using the Qiagen™ Genomic Tips kit. Genomic DNA was quantified by Quant-IT™ Pico Green DNA assay kit (Molecular Probes, Invitrogen, Carlsbad, Calif.). Quantified genomic DNA was adjusted to 4 μg for a consistent concentration.

For each sample, 4 μg of genomic DNA was thoroughly digested with the restriction enzyme SwaI (New England Biolabs, Beverley, Mass.) and incubated at 25° C. overnight, then NsiI was added to the reaction and incubated at 37° C. for 6 hours. The digested DNA was concentrated by precipitation with Quick Precipitation Solution™ (Edge Biosystems, Gaithersburg, Md.) according to the manufacturer's suggested protocol. The genomic DNA was then resuspended in 25 μL of water at 65° C. for 1 hour. Resuspended samples were loaded onto a 0.8% agarose gel prepared in 1×TAE and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments to nylon membranes was performed by passively wicking 20×SSC solution overnight through the gel onto treated IMMOBILON™ NY+ transfer membrane (Millipore, Billerica, Mass.) by using a chromatography paper wick and paper towels. Following transfer, the membrane was briefly washed with 2×SSC, cross-linked with the STRATALINKER™ 1800 (Stratagene, LaJolla, Calif.), and vacuum baked at 80° C. for 3 hours.

Blots were incubated with pre-hybridization solution (Perfect Hyb plus, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX™ II gel extraction kit and labeled with $\alpha^{32}$P-dCTP via the Random RT Prime IT™ labeling kit (Stratagene, La Jolla, Calif.). Blots were hybridized overnight at 65° C. with denatured probe added directly to hybridization buffer to approximately 2 million counts per blot per mL. Following hybridization, blots were sequentially washed at 65° C. with 0.1×SSC/0.1% SDS for 40 minutes. Finally, the blots were exposed to storage phosphor imaging screens and imaged using a Molecular Dynamics Storm 860™ imaging system.

The Southern blot analyses completed in this study were used to determine the copy number and confirm that selected events contained the dgt-28 transgene within the genome of *Arabidopsis*.

dgt-28 Gene Expression Cassette Confirmation Via PCR Analysis. The presence of the dgt-28 gene expression cassette contained in the $T_1$ plant events was detected by an end point PCR reaction. Primers (Table 6) specific to the AtUbi10 promoter v2 and AtuORF23 3'UTR v1 regions of the dgt-28 gene expression cassette were used for detection.

TABLE 6

Oligonucleotide primers used for dgt-28 gene expression cassette confirmation.

| Primer Name | Sequence |
|---|---|
| Forward oligo (SEQ ID NO: 52) | 5' CTGCAGGTCAACGGATCAGGATAT 3' |
| Reverse oligo (SEQ ID NO: 53) | 5' TGGGCTGAATTGAAGACATGCTCC 3' |

The PCR reactions required a standard three step PCR cycling protocol to amplify the gene expression cassette. All of the PCR reactions were completed using the following PCR conditions: 94° C. for three minutes followed by 35 cycles of 94° C. for thirty seconds, 60° C. for thirty seconds, and 72° C. for three minutes. The reactions were completed using the EX-TAQ™ PCR kit (TaKaRa Biotechnology Inc. Otsu, Shiga, Japan) per manufacturer's instructions. Following the final cycle, the reaction was incubated at 72° C. for 10 minutes. TAE agarose gel electrophoresis was used to determine the PCR amplicon size. PCR amplicons of an expected size indicated the presence of a full length gene expression cassette was present in the genome of the transgenic *Arabidopsis* events.

dgt-28 Relative Transcription Confirmation Via Quantitative Reverse Transcription PCR analysis. Tissue samples of dgt-28 transgenic plants were collected in 96-well plates and frozen at 80° C. Tissue maceration was performed with a KLECO™ tissue pulverizer and tungsten beads (Environ Metal INC., Sweet Home, Oreg.). Following tissue maceration, the Total RNA was isolated in high-throughput format using the Qiagen™ Rneasy 96 kit (Qiagen™, Germantown, Md.) according to the manufacturer's suggested protocol which included the optional DnaseI treatment on the column. This step was subsequently followed by an additional DnaseI (Ambion™, Austin, Tex.) treatment of the eluted total RNA. cDNA synthesis was carried out using the total RNA as template with the High Capacity cDNA Reverse Transcription™ kit (Applied Biosystems, Austin, Tex.) following the manufacturer's suggested procedure with the addition of the oligonucleotide, TVN. Quantification of expression was completed by hydrolysis probe assay and was performed by real-time PCR using the LIGHTCYCLER® 480 system (Roche Applied Science, Indianapolis, Ind.). Assays were designed for dgt-28 and the internal reference gene "unknown protein" (Genbank Accession Number: AT4G24610) using the LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume singleplex reaction containing 0.4 μM of each primer, and 0.2 μM of each probe. Table 7.

TABLE 7

PCR primers used for quantitative reverse transcription PCR analysis of dgt-28.

| Primer Name | Sequence |
|---|---|
| AT26410LP (SEQ ID NO: 54) | 5' CGTCCACAAAGCTGAATGTG 3' |
| AT26410RP (SEQ ID NO: 55) | 5' CGAAGTCATGGAAGCCACTT3' |
| UPL146 | Cat# 04694325001 (Roche, Indianapolis, IN) |
| DGT28F (SEQ ID NO: 56) | 5' CTTCAAGGAGATTTGGGATTTGT3' |
| DGT28R (SEQ ID NO: 57) | 5' GAGGGTCGGCATCGTAT 3' |
| UPL154 probe | Cat# 04694406001 (Roche, Indianapolis, IN) |

A two-step amplification reaction was performed with an extension at 60° C. for 40 seconds with fluorescence acquisition. All samples were run in triplicate and the averaged Cycle threshold (Ct) values were used for analysis of each sample. A minus reverse transcription reaction was run for each sample to ensure that no gDNA contamination was present. Analysis of real time PCR data was performed based on the ΔΔCt method. This assay was used to determine the relative expression of dgt-28 in transgenic *Arabidopsis* events which were determined to be hemizygous and homozygous. The relative transcription levels of the dgt-28 mRNA ranged from 2.5 fold to 207.5 fold higher than the internal control. These data indicate that dgt-28 transgenic plants contained a functional dgt-28 gene expression cassette, and the plants were capable of transcribing the dgt-28 transgene.

Western Blotting Analysis. DGT-28 was detected in leaf samples obtained from transgenic *Arabidopsis thaliana* plants. Plant extracts from dgt-28 transgenic plants and DGT-28 protein standards were incubated with NUPAGE® LDS sample buffer (Invitrogen, Carlsbad, Calif.) containing DTT at 90° C. for 10 minutes and electrophoretically separated in an acrylamide precast gel. Proteins were then electro-transferred onto nitrocellulose membrane using the manufacturer's protocol. After blocking with the WESTERNBREEZE® Blocking Mix (Invitrogen) the DGT-28 protein was detected by anti-DGT-28 antiserum followed by goat anti-rabbit phosphatase. The detected protein was visualized by chemiluminescence substrate BCIP/NBT Western Analysis Reagent (KPL, Gaithersburg, Md.). Production of an intact DGT-28 protein via Western blot indicated that the dgt-28 transgenic plants which were assayed expressed the DGT-28 protein.

Transgenic $T_1$ *Arabidopsis* plants containing the dgt-28 transgene were sprayed with differing rates of glyphosate. Elevated rates were applied in this study to determine the relative levels of resistance (105, 420, 1,680 or 3,360 g ae/ha). A typical 1× usage rate of glyphosate that will control non-transformed *Arabidopsis* is 420 g ae/ha. Glyphosate formulations with the addition of ammonium sulfate were applied to the $T_1$ plants with a track sprayer calibrated at 187 L/ha. The $T_1$ *Arabidopsis* plants that were used in this study were variable copy number for the dgt-28 transgene. The low copy dgt-28 $T_1$ *Arabidopsis* plants were self-pollinated and used to produce $T_2$ plants. Table 8 shows the comparison of dgt-28 transgenic plants, drawn to a glyphosate herbicide resistance gene, dgt-1, and wildtype controls. Table 9 shows the comparison of dgt-32, and dgt-33 drawn to a glyphosate herbicide resistance gene, dgt-1, and wildtype controls. Table 10 shows the comparison of the novel bacterial EPSP synthase enzymes to the Class I EPSP synthase enzymes and the controls at a glyphosate rate of 1,680 g ae/ha.

Results of Glyphosate Selection of Transformed dgt-28 *Arabidopsis* Plants. The *Arabidopsis* $T_1$ transformants were first selected from the background of untransformed seed using a glufosinate selection scheme. Three flats or 30,000 seed were analyzed for each $T_1$ construct. The $T_1$ plants selected above were molecularly characterized and representative plants with variable copy number were subsequently transplanted to individual pots and sprayed with various rates of commercial glyphosate as previously described. The response of these plants is presented in terms of % visual injury 2 weeks after treatment (WAT). Data are presented in a table which shows individual plants exhibiting little or no injury (<20%), moderate injury (20-40%), or severe injury (>40%). An arithmetic mean and standard deviation is presented for each construct used for *Arabidopsis* transformation. The range in individual response is also indicated in the last column for each rate and transformation. Wild-type, non-transformed *Arabidopsis* (c.v. Columbia) served as a glyphosate sensitive control.

The level of plant response varied. This variance can be attributed to the fact each plant represents an independent transformation event and thus the copy number of the gene of interest varies from plant to plant. It was noted that some plants which contained the transgene were not tolerant to glyphosate; a thorough analysis to determine whether these plants expressed the transgene was not completed. It is likely that the presence of high copy numbers of the transgene within the $T_1$ *Arabidopsis* plants resulted in transgene silencing or other epigenetic effects which resulted in sensitivity to glyphosate, despite the presence of the dgt-28 transgene.

An overall population injury average by rate is presented in Table 10 for rates of glyphosate at 1,680 g ae/ha to demonstrate the significant difference between the plants transformed with dgt-3, dgt-7, dgt-28, dgt-32, and dgt-33 versus the dgt-1 and wild-type controls.

The tolerance provided by the novel bacterial EPSP synthases varied depending upon the specific enzyme. DGT-28, DGT-32, and DGT-33 unexpectedly provided significant tolerance to glyphosate. The dgt genes imparted herbicide resistance to individual $T_1$ *Arabidopsis* plants across all transit peptides tested. As such, the use of additional chloroplast transit peptides (i.e., TraP8—dgt-32 or TraP8—dgt-33) would provide protection to glyphosate with similar injury levels as reported within a given treatment.

TABLE 8 dgt-28 transformed $T_1$ *Arabidopsis* response to a range of glyphosate rates applied postemergence, compared to a dgt-1 ($T_4$) homozygous resistant population, and a non-transformed control. Visual % injury 14 days after application.

| | % Injury | | | % Injury | | |
|---|---|---|---|---|---|---|
| Averages | <20% | 20-40% | >40% | Ave | Std dev | Range (%) |
| pDAB107527: TraP4 v2 - dgt-28 v5 | | | | | | |
| 0 g ae/ha glyphosate | 4 | 0 | 0 | 0.0 | 0.0 | 0 |
| 105 g ae/ha glyphosate | 4 | 0 | 0 | 3.8 | 7.5 | 0-15 |
| 420 g ae/ha glyphosate | 2 | 1 | 1 | 28.8 | 28.1 | 0-65 |
| 1680 g ae/ha glyphosate | 0 | 2 | 2 | 55.0 | 26.8 | 35-85 |
| 3360 g ae/ha glyphosate | 0 | 2 | 2 | 43.8 | 18.0 | 30-70 |
| pDAB105530: TraP5 v2 - dgt-28 v5 | | | | | | |
| 0 g ae/ha glyphosate | 6 | 0 | 0 | 0.0 | 0.0 | 0 |
| 105 g ae/ha glyphosate | 2 | 2 | 2 | 39.3 | 37.4 | 8-100 |
| 420 g ae/ha glyphosate | 1 | 4 | 1 | 33.0 | 26.6 | 8-85 |
| 1680 g ae/ha glyphosate | 0 | 4 | 2 | 47.5 | 27.5 | 25-85 |
| 3360 g ae/ha glyphosate | 0 | 0 | 6 | 76.7 | 13.7 | 50-85 |
| pDAB105531: TraP8 v2 -- dgt-28 v5 | | | | | | |
| 0 g ae/ha glyphosate | 4 | 0 | 0 | 0.0 | 0.0 | 0 |
| 105 g ae/ha glyphosate | 3 | 1 | 0 | 10.8 | 10.4 | 0-25 |
| 420 g ae/ha glyphosate | 3 | 0 | 1 | 22.8 | 18.6 | 8-50 |
| 1680 g ae/ha glyphosate | 4 | 0 | 0 | 5.3 | 3.8 | 0-8 |
| 3360 g ae/ha glyphosate | 0 | 4 | 0 | 29.3 | 6.8 | 22-35 |
| pDAB105532: TraP9 v2 -- dgt-28 v5 | | | | | | |
| 0 g ae/ha glyphosate | 4 | 0 | 0 | 0.0 | 0.0 | 0 |
| 105 g ae/ha glyphosate | 3 | 0 | 1 | 17.5 | 28.7 | 0-60 |
| 420 g ae/ha glyphosate | 1 | 1 | 2 | 39.5 | 25.1 | 18-70 |
| 1680 g ae/ha glyphosate | 3 | 0 | 1 | 26.3 | 36.1 | 5-80 |
| 3360 g ae/ha glyphosate | 3 | 0 | 1 | 25.8 | 32.9 | 8-75 |
| pDAB105533: TraP12 v2 -- dgt-28 v5 | | | | | | |
| 0 g ae/ha glyphosate | 5 | 0 | 0 | 0.0 | 0.0 | 0 |
| 105 g ae/ha glyphosate | 4 | 1 | 0 | 10.0 | 10.0 | 0-25 |
| 420 g ae/ha glyphosate | 1 | 1 | 3 | 53.6 | 34.6 | 8-85 |
| 1680 g ae/ha glyphosate | 4 | 1 | 0 | 11.0 | 8.2 | 0-20 |
| 3360 g ae/ha glyphosate | 0 | 2 | 3 | 55.0 | 25.5 | 25-80 |
| pDAB105534: TraP13 v2 -- dgt-28 v5 | | | | | | |
| 0 g ae/ha glyphosate | 5 | 0 | 0 | 0.0 | 0.0 | 0 |
| 105 g ae/ha glyphosate | 4 | 0 | 1 | 14.0 | 20.6 | 0-50 |
| 420 g ae/ha glyphosate | 3 | 1 | 1 | 17.6 | 19.5 | 0-50 |

TABLE 8-continued dgt-28 transformed $T_1$ *Arabidopsis* response to a range of glyphosate rates applied postemergence, compared to a dgt-1 ($T_4$) homozygous resistant population, and a non-transformed control. Visual % injury 14 days after application.

| Averages | % Injury <20% | 20-40% | >40% | % Injury Ave | Std dev | Range (%) |
|---|---|---|---|---|---|---|
| 1680 g ae/ha glyphosate | 3 | 0 | 2 | 39.0 | 47.1 | 5-100 |
| 3360 g ae/ha glyphosate | 2 | 2 | 1 | 31.2 | 22.3 | 18-70 |
| pDAB4104: dgt-1 (transformed control) | | | | | | |
| 0 g ae/ha glyphosate | 5 | 0 | 0 | 0.0 | 0.0 | 0 |
| 105 g ae/ha glyphosate | 0 | 0 | 4 | 80.0 | 0.0 | 80 |
| 420 g ae/ha glyphosate | 0 | 0 | 4 | 80.0 | 0.0 | 80 |
| 1680 g ae/ha glyphosate | 0 | 0 | 4 | 80.0 | 0.0 | 80 |
| 3360 g ae/ha glyphosate | 0 | 0 | 4 | 81.3 | 2.5 | 80-85 |
| WT (non-transformed control) | | | | | | |
| 0 g ae/ha glyphosate | 5 | 0 | 0 | 0.0 | 0.0 | 0 |
| 105 g ae/ha glyphosate | 0 | 0 | 4 | 100.0 | 0.0 | 100 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

TABLE 9 dgt-32, and dgt-33 transformed $T_1$ *Arabidopsis* response to a range of glyphosate rates applied postemergence, compared to a dgt-1 ($T_4$) homozygous resistant population, and a non-transformed control. Visual % injury 14 days after application.

| Averages | % Injury <20% | 20-40% | >40% | % Injury Ave | Std dev | Range (%) |
|---|---|---|---|---|---|---|
| pDAB107532: TraP14 v2 - dgt-32 v3 | | | | | | |
| 0 g ae/ha glyphosate | 4 | 0 | 0 | 0.0 | 0.0 | 0 |
| 105 g ae/ha glyphosate | 4 | 0 | 0 | 0.0 | 0.0 | 0 |
| 420 g ae/ha glyphosate | 2 | 0 | 2 | 30.0 | 29.4 | 0-60 |
| 1680 g ae/ha glyphosate | 3 | 0 | 1 | 17.5 | 21.8 | 5-50 |
| 3360 g ae/ha glyphosate | 0 | 3 | 1 | 35.0 | 30.0 | 20-80 |
| pDAB107534: TraP24 v2 -- dgt-33 v3 | | | | | | |
| 0 g ae/ha glyphosate | 4 | 0 | 0 | 0.0 | 0.0 | 0 |
| 105 g ae/ha glyphosate | 2 | 2 | 0 | 21.3 | 14.9 | 5-40 |
| 420 g ae/ha glyphosate | 1 | 1 | 2 | 46.3 | 30.9 | 5-70 |
| 1680 g ae/ha glyphosate | 1 | 0 | 3 | 62.5 | 38.8 | 5-90 |
| 3360 g ae/ha glyphosate | 1 | 0 | 3 | 62.0 | 36.0 | 8-80 |
| pDAB4104: dgt-1 (transformed control) | | | | | | |
| 0 g ae/ha glyphosate | 4 | 0 | 0 | 0.0 | 0.0 | 0 |
| 105 g ae/ha glyphosate | 0 | 2 | 3 | 42.5 | 15.0 | 20-50 |
| 420 g ae/ha glyphosate | 0 | 1 | 2 | 38.8 | 11.1 | 25-50 |
| 1680 g ae/ha glyphosate | 0 | 0 | 4 | 79.0 | 19.4 | 50-90 |
| 3360 g ae/ha glyphosate | 0 | 0 | 4 | 50.0 | 0.0 | 50 |
| WT (non-transformed control) | | | | | | |
| 0 g ae/ha glyphosate | 4 | 0 | 0 | 0.0 | 0.0 | 0 |
| 105 g ae/ha glyphosate | 0 | 0 | 4 | 85.0 | 0.0 | 85 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

TABLE 10 dgt-28, dgt-32, dgt-33, dgt-3, and dgt-7 transformed $T_1$ *Arabidopsis* response to glyphosate applied postemergence at 1,680 g ae/ha, compared to a dgt-1 ($T_4$) homozygous resistant population, and a non-transformed control. Visual % injury 14 days after application.

| | | | % Injury <20% | 20-40% | >40% | % Injury Ave | Std dev | Range (%) |
|---|---|---|---|---|---|---|---|---|
| Bacterial Enzymes | pDAB107527 | TraP4 v2 - dgt-28 v5 | 0 | 2 | 2 | 55.0 | 26.8 | 35-85 |
| | pDAB105530 | TraP5 v2 - dgt-28 v5 | 0 | 4 | 2 | 47.5 | 27.5 | 25-85 |
| | pDAB105531 | TraP8 v2 - dgt-28 v5 | 4 | 0 | 0 | 5.3 | 3.8 | 0-8 |
| | pDAB105532 | TraP9 v2 - dgt-28 v5 | 3 | 0 | 1 | 26.3 | 36.1 | 5-80 |
| | pDAB105533 | Trap12 v2 - dgt-28 v5 | 4 | 1 | 0 | 11.0 | 8.2 | 0-20 |
| | pDAB105534 | TraP13 v2 - dgt-28 v5 | 3 | 0 | 2 | 39.0 | 47.1 | 5-100 |
| | pDAB107532 | TraP14 v2 - dgt-32 v3 | 3 | 0 | 1 | 17.5 | 21.8 | 5-50 |
| | pDAB107534 | TraP24 v2 - dgt-33 v3 | 1 | 0 | 3 | 62.5 | 38.8 | 5-90 |
| Class I Enzymes | pDAB102715 | dgt-3 v2 | 4 | 0 | 3 | 42 | 48 | 0-100 |
| | pDAB102716 | dgt-3 v3 | 2 | 0 | 1 | 14 | 23 | 0-40 |
| | pDAB102717 | dgt-3 v4 | 3 | 2 | 1 | 28 | 35 | 10-100 |

TABLE 10-continued dgt-28, dgt-32, dgt-33, dgt-3, and dgt-7 transformed $T_1$ *Arabidopsis* response to glyphosate applied postemergence at 1,680 g ae/ha, compared to a dgt-1 ($T_4$) homozygous resistant population, and a non-transformed control. Visual % injury 14 days after application.

| | | % Injury | | | % Injury | | |
|---|---|---|---|---|---|---|---|
| | | | | | | Std | Range |
| | | <20% | 20-40% | >40% | Ave | dev | (%) |
| pDAB102785 | dgt-7 v4 | 0 | 1 | 1 | 45 | 21 | 30-60 |
| pDAB4104 | dgt-1 (transformed control) | 0 | 0 | 4 | 80.0 | 0.0 | 80 |
| — | WT (non-transformed control) | 0 | 0 | 4 | 100.0 | 0.0 | 100 |

dgt-28 as a Selectable Marker. The use of dgt-28 as a selectable marker for glyphosate selection agent is tested with the *Arabidopsis* transformed plants described above. Approximately 50 $T_4$ generation *Arabidopsis* seed (homozygous for dgt-28) are spiked into approximately 5,000 wild-type (sensitive to glyphosate) seed. The seeds are germinated and plantlets are sprayed with a selecting dose of glyphosate. Several treatments of glyphosate are compared; each tray of plants receives either one or two application timings of glyphosate in one of the following treatment schemes: 7 DAP (days after planting), 11 DAP, or 7 followed by 11 DAP. Since all plants also contain a glufosinate resistance gene in the same transformation vector, dgt-28 containing plants selected with glyphosate can be directly compared to DSM-2 or pat containing plants selected with glufosinate.

Glyphosate treatments are applied with a DeVilbiss™ spray tip as previously described. Transgenic plants containing dgt-28 are identified as “resistant” or “sensitive” 17 DAP. Treatments of 26.25-1680 g ae/ha glyphosate applied 7 and 11 days after planting (DAP), show effective selection for transgenic *Arabidopsis* plants that contain dgt-28. Sensitive and resistant plants are counted and the number of glyphosate tolerant plants is found to correlate with the original number of transgenic seed containing the dgt-28 transgene which are planted. These results indicate that dgt-28 can be effectively used as an alternative selectable marker for a population of transformed *Arabidopsis*.

Heritability. Confirmed transgenic $T_1$ *Arabidopsis* events were self-pollinated to produce $T_2$ seed. These seed were progeny tested by applying Ignite™ herbicide containing glufosinate (200 g ae/ha) to 100 random $T_2$ siblings. Each individual $T_2$ plant was transplanted to 7.5-cm square pots prior to spray application (track sprayer at 187 L/ha applications rate). The $T_1$ families ($T_2$ plants) segregated in the anticipated 3 Resistant: 1 Sensitive model for a dominantly inherited single locus with Mendelian inheritance as determined by Chi square analysis (P>0.05). The percentage of $T_1$ families that segregated with the expected Mendelian inheritance are illustrated in Table 11, and demonstrate that the dgt-28 trait is passed via Mendelian inheritance to the $T_2$ generation. Seed were collected from 5 to 15 $T_2$ individuals ($T_3$ seed). Twenty-five $T_3$ siblings from each of 3-4 randomly-selected $T_2$ families were progeny tested as previously described. Data showed no segregation and thus demonstrated that dgt-28 and dgt-3 are stably integrated within the chromosome and inherited in a Mendelian fashion to at least three generations.

TABLE 11

Percentage of $T_1$ families ($T_2$ plants) segregating as single Mendelian inheritance for a progeny test of 100 plants.

| Gene of Interest | T1 Families Tested Segregating at 1 Locus (%) |
|---|---|
| dgt-3 v2 | 64% |
| dgt-3 v3 | 60% |
| dgt-3 v4 | 80% |
| dgt-7 v4 | 63% |
| TraP5 v2 - dgt-28 v5 | 100% |
| TraP8 v2 - dgt-28 v5 | 100% |
| TraP9 v2 - dgt-28 v5 | 100% |
| TraP12 v2 - dgt-28 v5 | 50% |
| TraP13 v2 - dgt-28 v5 | 75% |
| yfp Transgenic Control Plants | 100% |

$T_2$*Arabidopsis* Data. The second generation plants ($T_2$) of selected $T_1$ *Arabidopsis* events which contained low copy numbers of the dgt-28 transgene were further characterized for glyphosate tolerance. Glyphosate was applied as described previously. The response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for *Arabidopsis* transformation. The range in individual response is also indicated in the last column for each rate and transformation. Wild-type, non-transformed *Arabidopsis* (cv. Columbia) served as a glyphosate sensitive control. In the $T_2$ generation hemizygous and homozygous plants were available for testing for each event and therefore were included for each rate of glyphosate tested. Hemizygous plants contain two different alleles at a locus as compared to homozygous plants which contain the same two alleles at a locus. Variability of response to glyphosate is expected in the $T_2$ generation as a result of the difference in gene dosage for hemizygous as compared to homozygous plants. The variability in response to glyphosate is reflected in the standard deviation and range of response.

In the $T_2$ generation both single copy and multi-copy dgt-28 events were characterized for glyphosate tolerance.

Within an event, single copy plants showed similar levels of tolerance to glyphosate. Characteristic data for a single copy $T_2$ event are presented in Table 12. Events containing dgt-28 linked with TraP5 v2 did not provide robust tolerance to glyphosate as compared with the dgt-28 constructs which contained other TraP transit peptides. However, the dgt-28 TraP5 constructs did provide a low level of glyphosate tolerance as compared to the non-transformed Columbia control. There were instances when events that were shown to contain two or more copies of dgt-28 were more susceptible to elevated rates of glyphosate (data not shown). This increase in sensitivity to glyphosate is similar to the data previously described for the $T_1$ plants which also contained high copy numbers of the dgt-28 transgene. It is likely that the presence of high copy numbers of the transgene within the *Arabidopsis* plants result in transgene silencing or other epigenetic effects which resulted in sensitivity to glyphosate, despite the presence of the dgt-28 transgene.

These events contained dgt-28 linked with TraP5 v2 (pDAB105530), TraP12 v2 (pDAB105533) and TraP13 v2 (pDAB105534).

Figure 33:
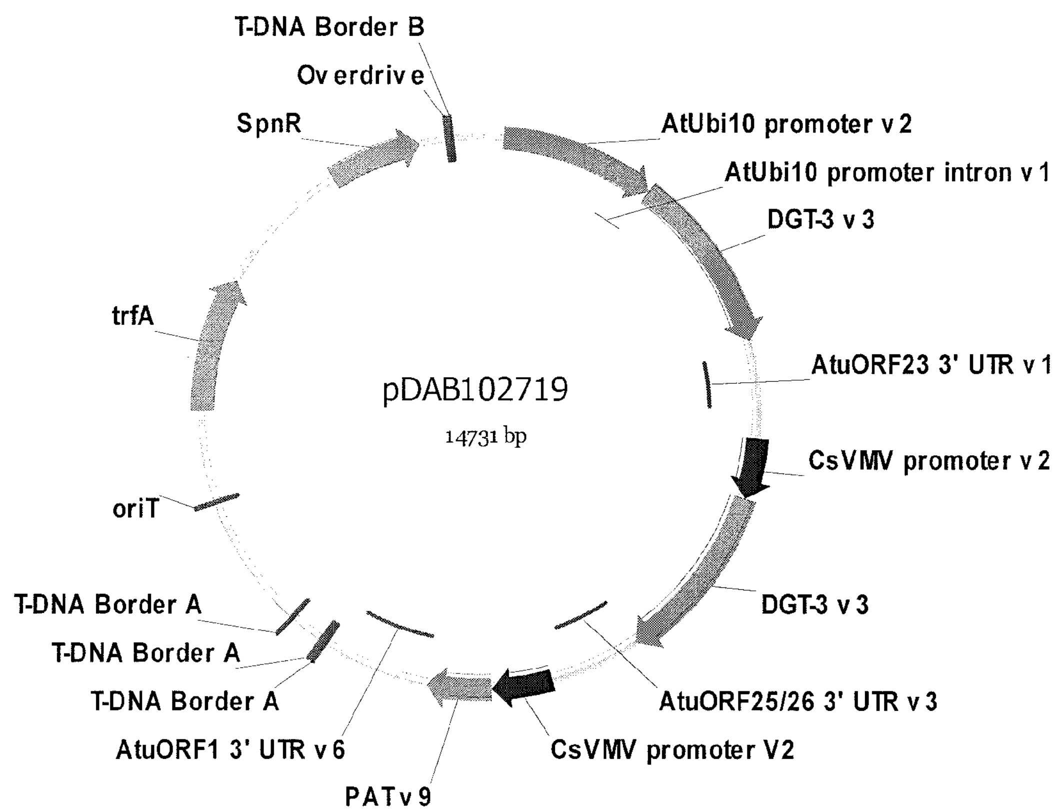
FIG. 33 illustrates a plasmid map of pDAB102719.
Figure 34:
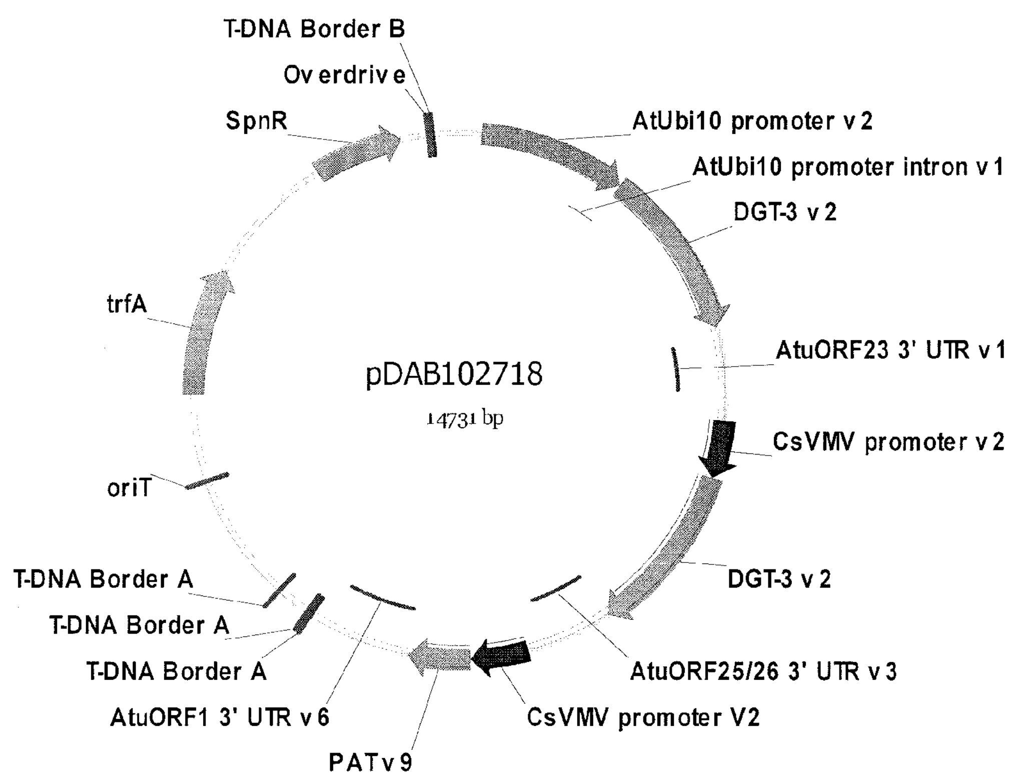
FIG. 34 illustrates a plasmid map of pDAB102718.
Figure 35:
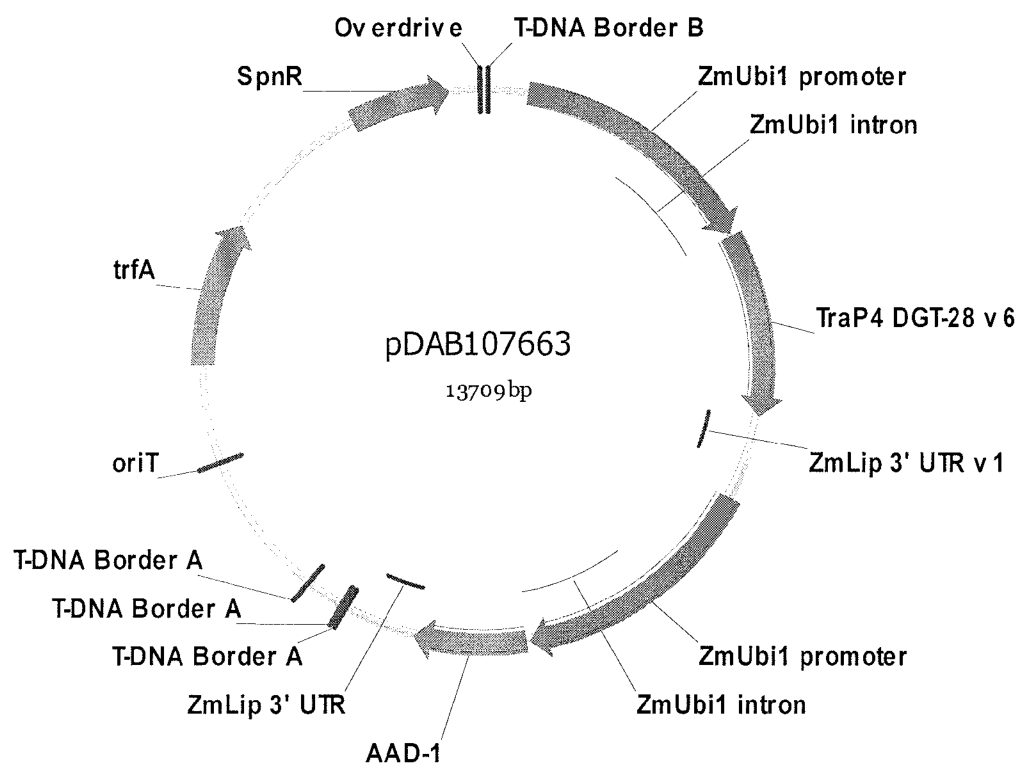
FIG. 35 illustrates a plasmid map of pDAB107663.
Figure 36:
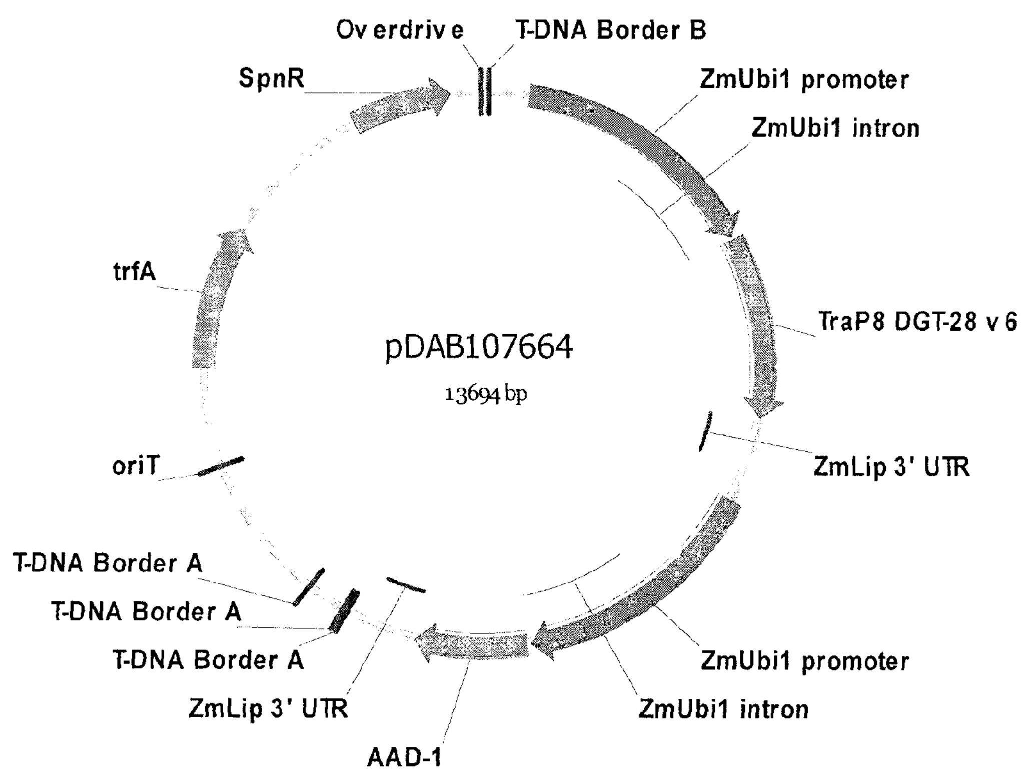
FIG. 36 illustrates a plasmid map of pDAB107664.
Figure 37:
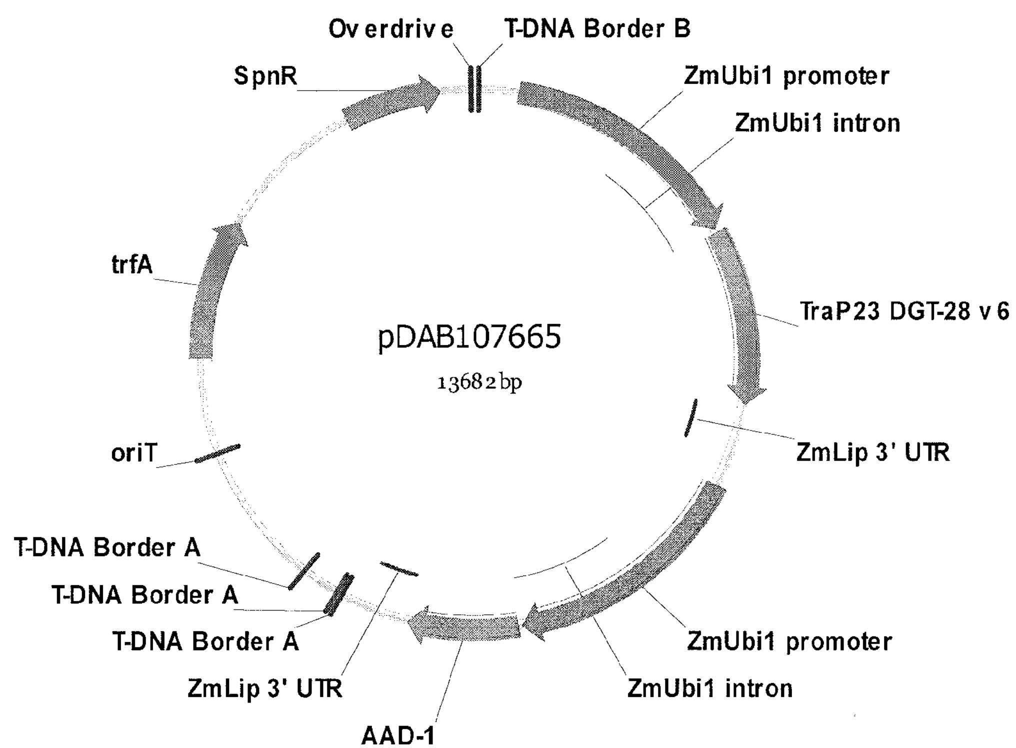
FIG. 37 illustrates a plasmid map of pDAB107665.
Figure 38:
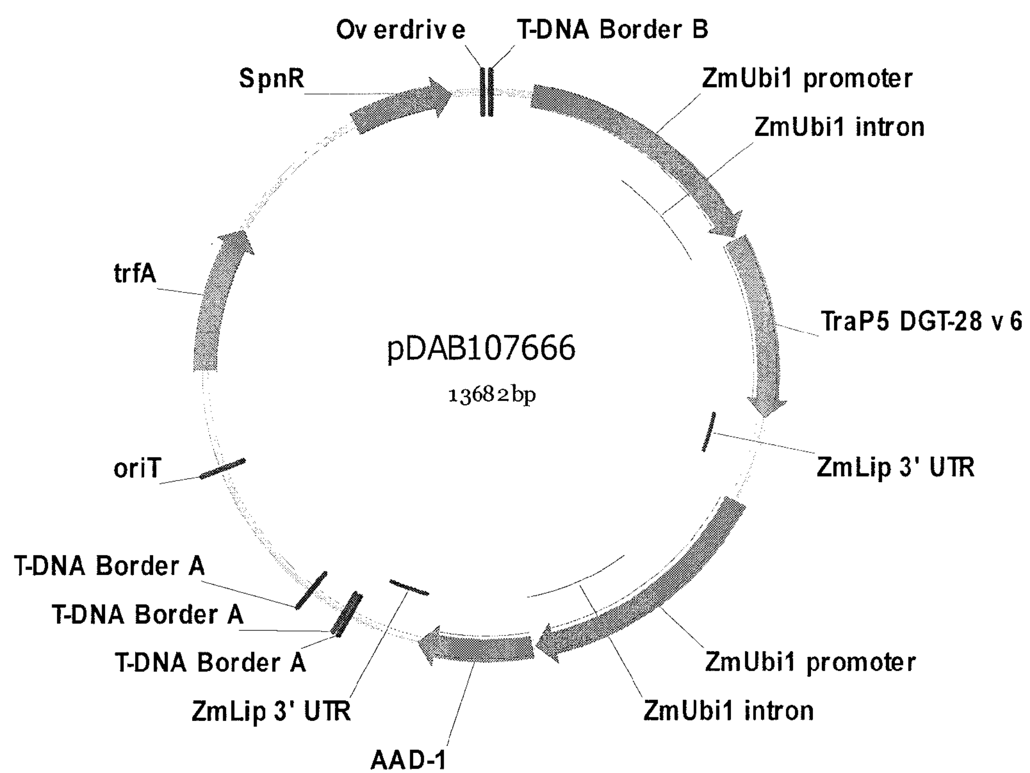
FIG. 38 illustrates a plasmid map of pDAB107666.
Figure 39:
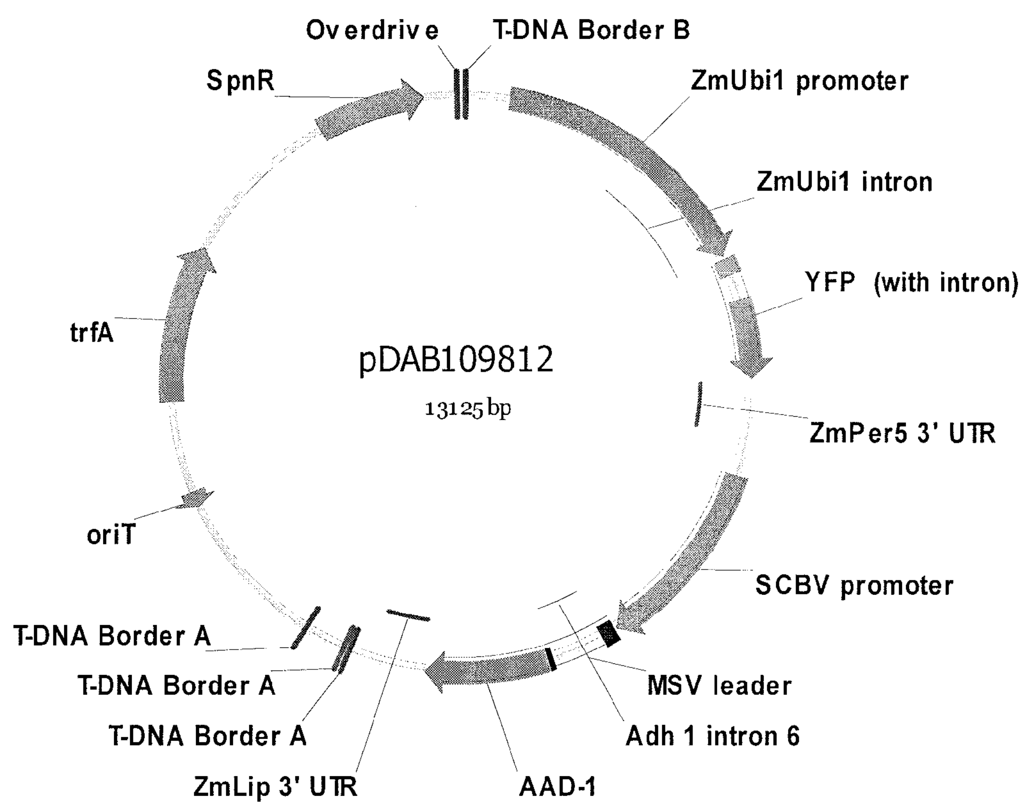
FIG. 39 illustrates a plasmid map of pDAB109812.
Figure 40:
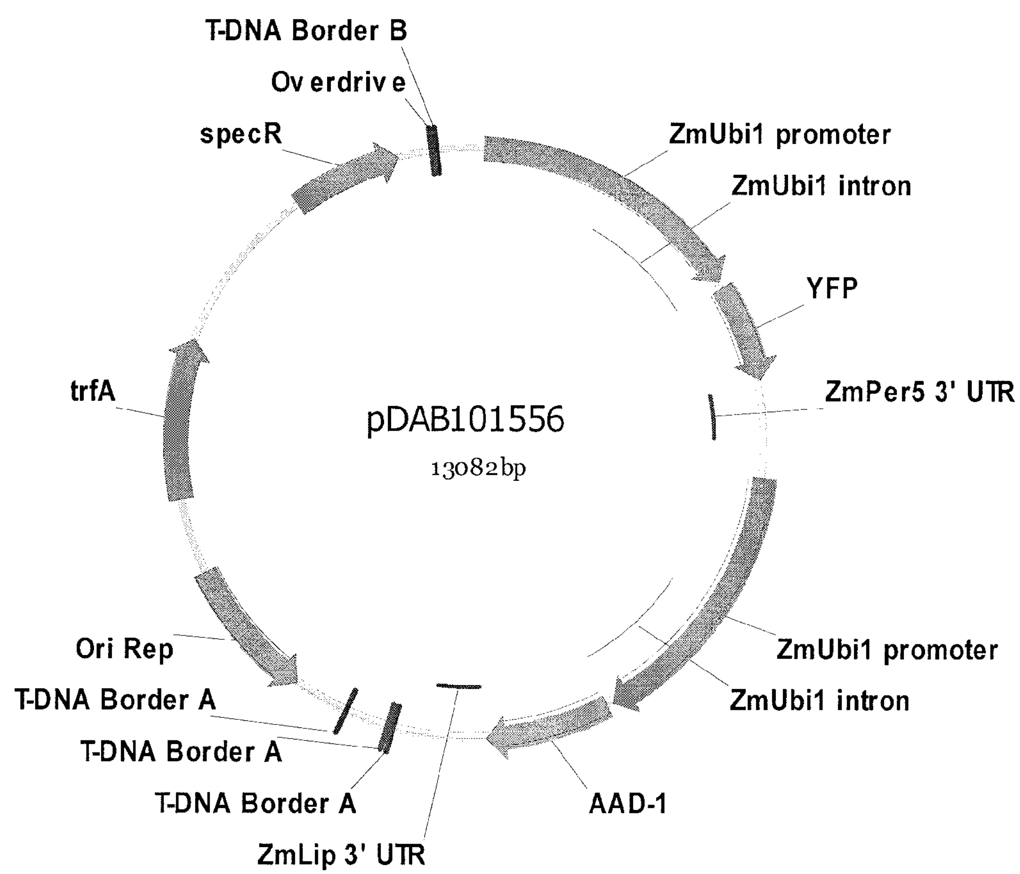
FIG. 40 illustrates a plasmid map of pDAB101556.
Figure 41:
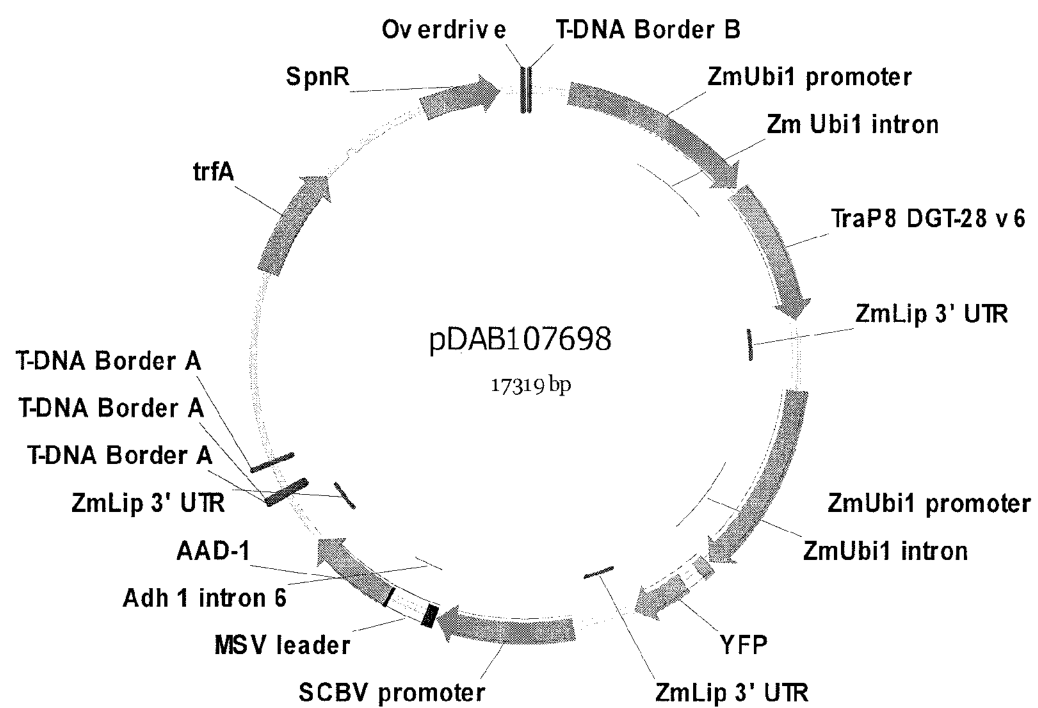
FIG. 41 illustrates a plasmid map of pDAB107698.
Figure 42:
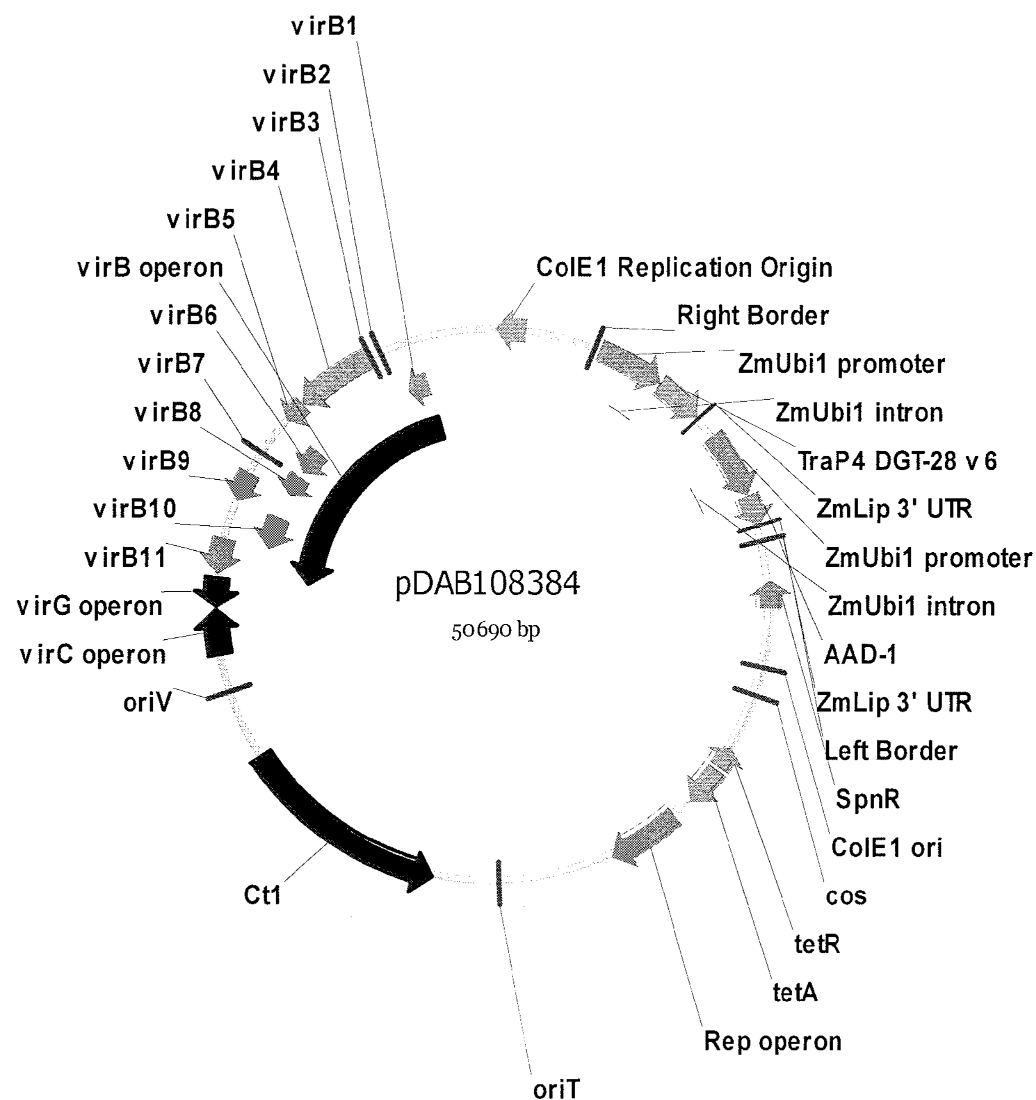
FIG. 42 illustrates a plasmid map of pDAB108384.
Figure 43:
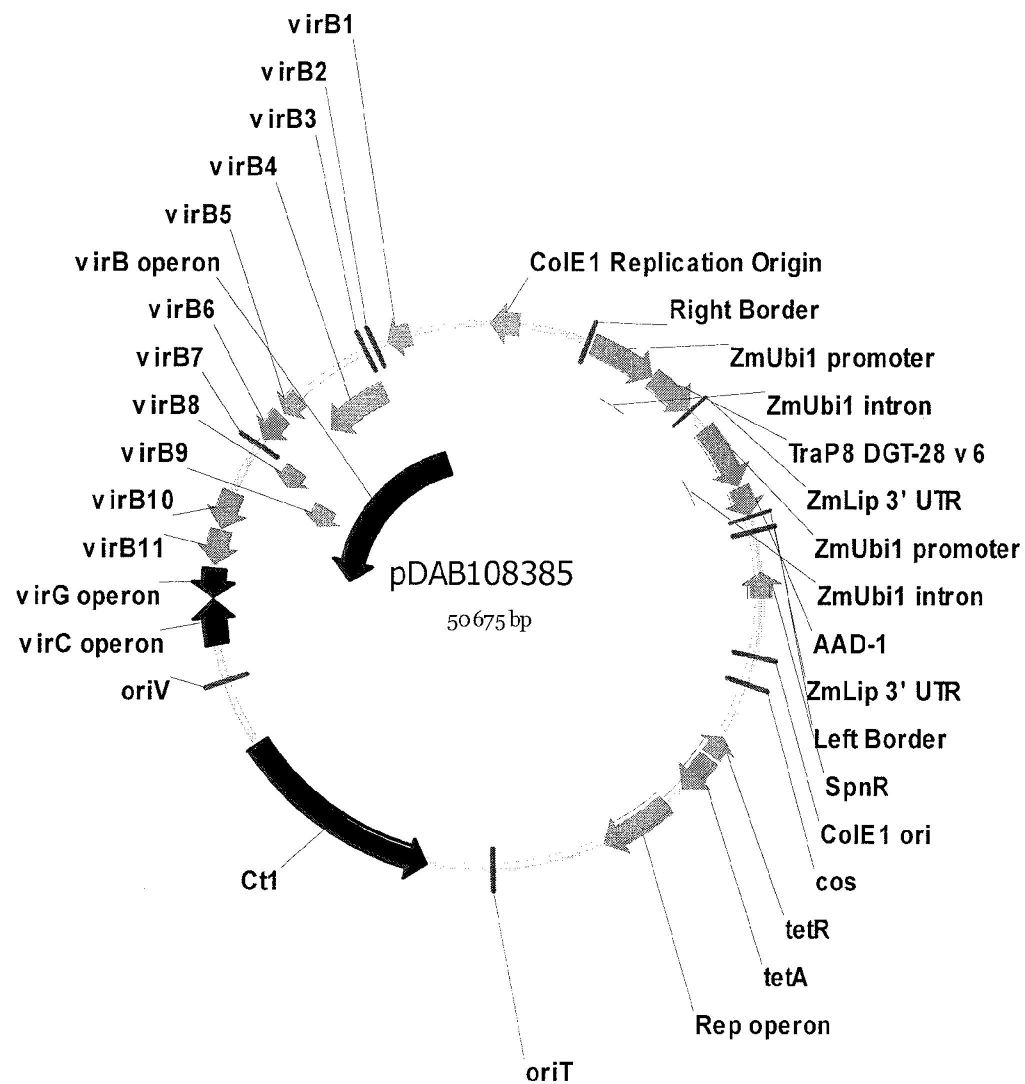
FIG. 43 illustrates a plasmid map of pDAB108385.
Figure 44:
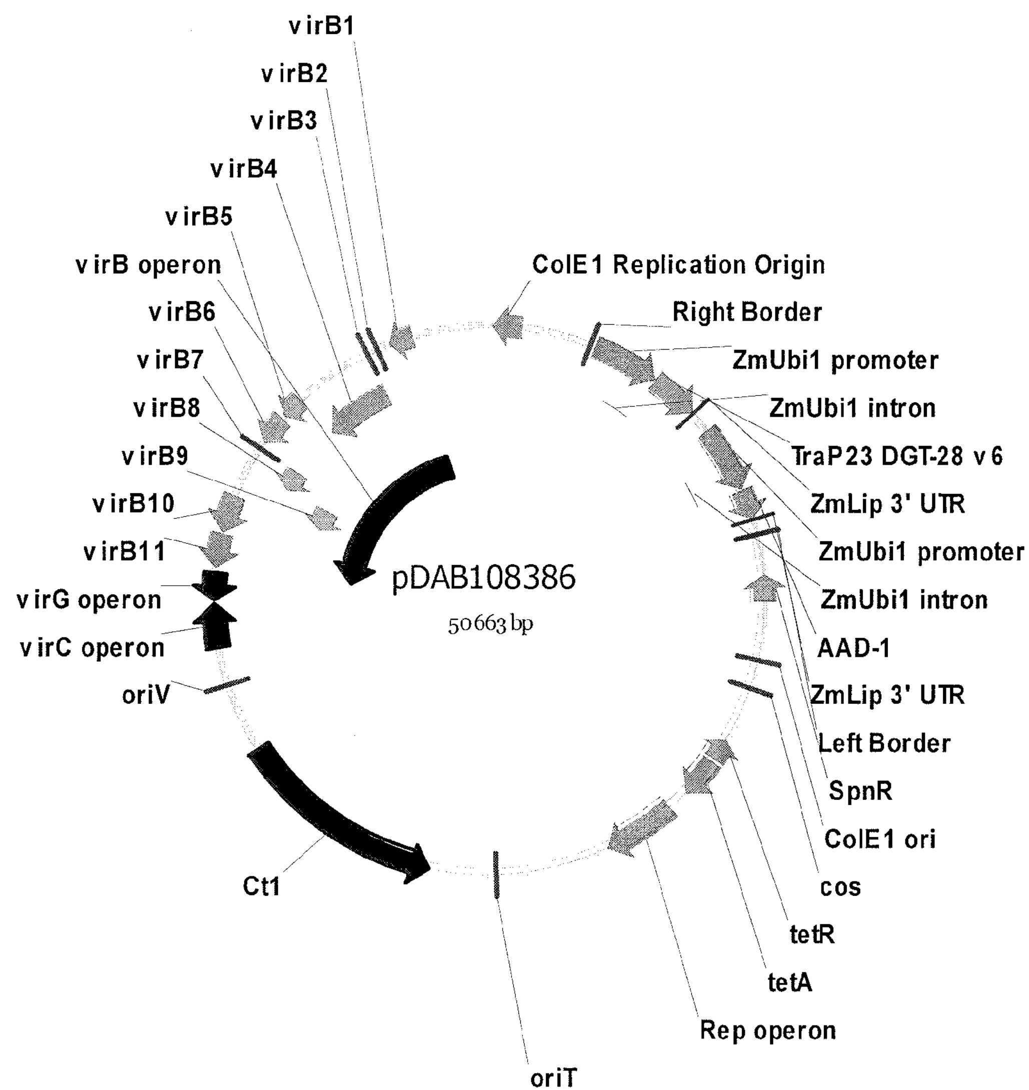
FIG. 44 illustrates a plasmid map of pDAB108386.
Figure 45:
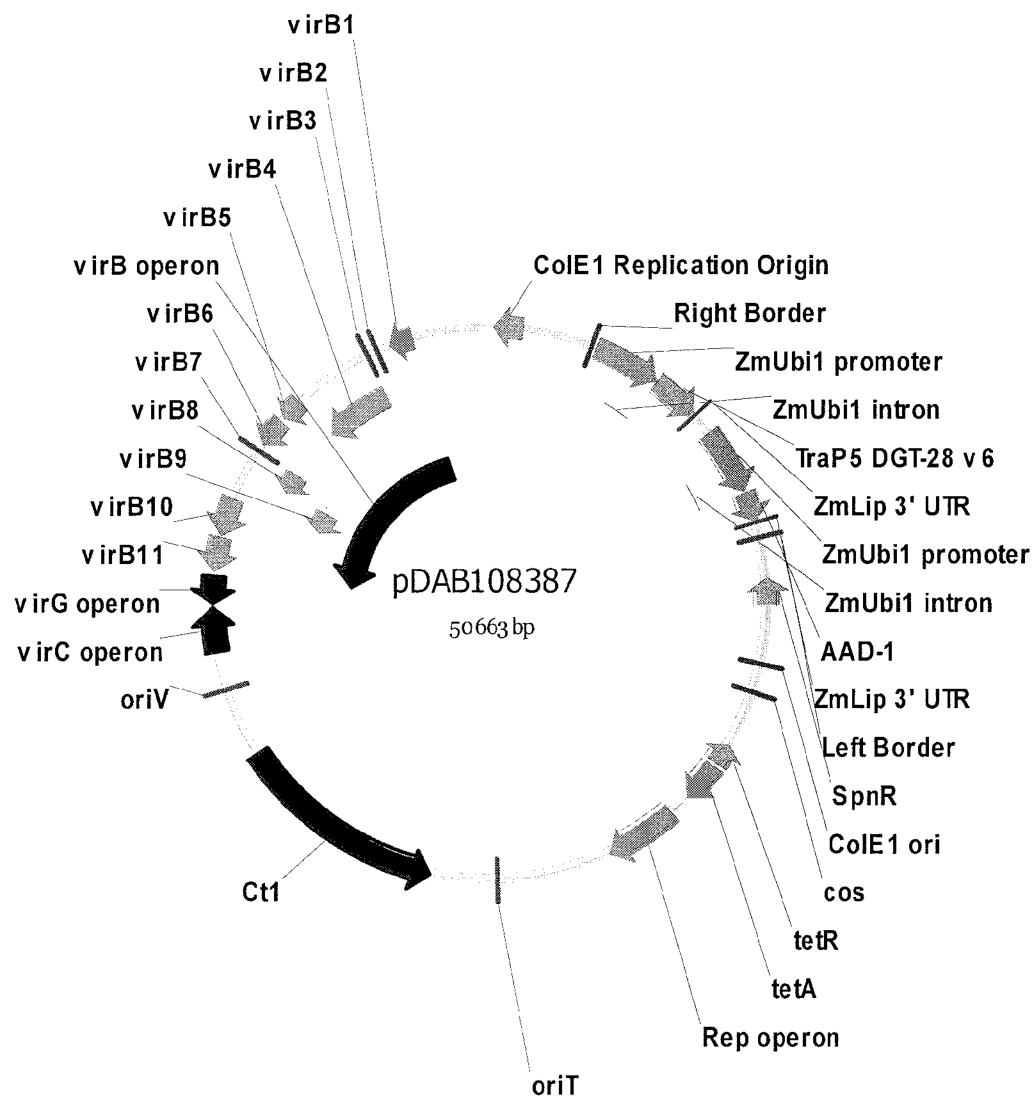
FIG. 45 illustrates a plasmid map of pDAB108387.

In addition to dgt-28, $T_2$ *Arabidopsis* events transformed with dgt-3 are presented in Table 13. As described for the dgt-28 events in Table 12, the data table contains a representative event that is characteristic of the response to glyphosate for each construct. For the dgt-3 characterization, constructs containing a single PTU (plant transformation unit) with the dgt-3 gene being driven by the AtUbi10 promoter (pDAB102716, FIG. 30 and pDAB102715, FIG. 29) were compared to constructs with the same gene containing 2 PTUs of the gene (pDAB102719, FIG. 33; pDAB102718, FIG. 34). The constructs which contained 2 PTU used the AtUbi10 promoter to drive one copy of the gene and the CsVMV promoter to drive the other copy. The use of the double PTU was incorporated to compare the dgt-3 transgenic plants with dgt-28 transgenic plants which contained two copies of the transgene. Data demonstrated that single copy $T_2$ dgt-3 events with only a single PTU were more susceptible to glyphosate than single copy dgt-28 events tested, but were more tolerant than the non-transformed control. $T_1$ families containing 2 PTUs of the dgt-3 gene provided a higher level of visual tolerance to glyphosate compared to the 1 PTU constructs. In both instances the $T_1$ families were compared to the dgt-1 and wildtype controls. $T_2$ data demonstrate that dgt-28 provides robust tolerance as single copy events.

TABLE 12

Response of selected individual $T_2$ *Arabidopsis* events containing dgt-28 to glyphosate applied postemergence at varying rates, compared to a dgt-1 ($T_4$) homozygous resistant population, and a non-transformed control. Visual % injury 14 days after application.

| | % Injury | | | % Injury | | Range |
|---|---|---|---|---|---|---|
| 1 copy | <20% | 20-40% | >40% | Ave | Std dev | (%) |
| pDAB105530: TraP5 v2 - dgt-28 v5 | | | | | | |
| 0 g ae/ha glyphosate | 4 | 0 | 0 | 0.0 | 0.0 | 0 |
| 420 g ae/ha glyphosate | 0 | 0 | 4 | 75.0 | 17.8 | 50-90 |
| 840 g ae/ha glyphosate | 0 | 0 | 4 | 80.0 | 20.0 | 50-90 |
| 1680 g ae/ha glyphosate | 0 | 0 | 4 | 75.0 | 10.8 | 60-85 |
| 3360 g ae/ha glyphosate | 0 | 0 | 4 | 76.3 | 4.8 | 70-80 |
| pDAB105531: TraP8 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 0.5 | 1.0 | 0-2 |
| 840 g ae/ha glyphosate | 4 | 0 | 0 | 1.3 | 2.5 | 0-5 |
| 1680 g ae/ha glyphosate | 4 | 0 | 0 | 7.5 | 5.0 | 5-15 |
| 3360 g ae/ha glyphosate | 4 | 0 | 0 | 7.5 | 6.5 | 0-15 |
| pDAB105532: TraP9 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 2.0 | 4.0 | 0-8 |
| 840 g ae/ha glyphosate | 4 | 0 | 0 | 9.0 | 2.0 | 8-12 |
| 1680 g ae/ha glyphosate | 4 | 0 | 0 | 7.3 | 4.6 | 2-12 |
| 3360 g ae/ha glyphosate | 4 | 0 | 0 | 11.0 | 1.2 | 10-12 |
| pDAB105533: TraP12 v2 - dgt-28 v5 | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 0.0 | 0.0 | 0 |
| 3360 g ae/ha glyphosate | 3 | 1 | 0 | 13.3 | 7.9 | 8-25 |
| pDAB105534: TraP13 v2 - dgt-28 v5 | | | | | | |
| 0 g ae/ha glyphosate | 4 | 0 | 0 | 0.0 | 0.0 | 0 |
| 420 g ae/ha glyphosate | 3 | 1 | 0 | 5.0 | 10.0 | 0-20 |
| 840 g ae/ha glyphosate | 3 | 1 | 0 | 5.0 | 10.0 | 0-20 |
| 1680 g ae/ha glyphosate | 2 | 2 | 0 | 10.0 | 11.5 | 0-20 |
| 3360 g ae/ha glyphosate | 2 | 2 | 0 | 15.0 | 12.2 | 5-30 |
| WT (non-transformed control) | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |

TABLE 12-continued

Response of selected individual $T_2$ *Arabidopsis* events containing dgt-28 to glyphosate applied postemergence at varying rates, compared to a dgt-1 ($T_4$) homozygous resistant population, and a non-transformed control. Visual % injury 14 days after application.

| 1 copy | % Injury <20% | 20-40% | >40% | % Injury Ave | Std dev | Range (%) |
|---|---|---|---|---|---|---|
| 3360 g ae/ha glyphosate | 0 | 0 | 4 | 100.0 | 0.0 | 100 |
| pDAB4104: dgt-1 (transformed control) | | | | | | |
| 0 g ae/ha glyphosate | 4 | 0 | 0 | 0.0 | 0.0 | 0 |
| 420 g ae/ha glyphosate | 0 | 4 | 0 | 37.5 | 2.9 | 35-40 |
| 840 g ae/ha glyphosate | 0 | 0 | 4 | 45.0 | 0.0 | 45 |
| 1680 g ae/ha glyphosate | 0 | 0 | 4 | 47.5 | 2.9 | 45-50 |
| 3360 g ae/ha glyphosate | 0 | 0 | 4 | 50.0 | 0.0 | 50 |

TABLE 13

Response of selected $T_2$ *Arabidopsis* events transformed with dgt-3 to glyphosate applied postemergence at varying rates. Visual % injury 14 days after application.

| 1 copy seg | % Injury <20% | 20-40% | >40% | % Injury Ave | Std dev | Range (%) |
|---|---|---|---|---|---|---|
| pDAB102716: dgt-3 v3 (1 PTU) | | | | | | |
| 0 g ae/ha glyphosate | 4 | 0 | 0 | 0 | 0 | 0 |
| 420 g ae/ha glyphosate | 1 | 1 | 2 | 39 | 25 | 15-65 |
| 840 g ae/ha glyphosate | 0 | 2 | 2 | 50 | 23 | 30-70 |
| 1680 g ae/ha glyphosate | 0 | 1 | 3 | 69 | 19 | 40-80 |
| 3360 g ae/ha glyphosate | 0 | 0 | 4 | 79 | 6 | 70-85 |
| pDAB102719: dgt-3 v3 (2 PTU) | | | | | | |
| 0 g ae/ha glyphosate | 4 | 0 | 0 | 0 | 0 | 0 |
| 420 g ae/ha glyphosate | 0 | 4 | 0 | 20 | 0 | 20 |
| 840 g ae/ha glyphosate | 0 | 3 | 1 | 38 | 5 | 35-45 |
| 1680 g ae/ha glyphosate | 3 | 1 | 0 | 15 | 7 | 10-25 |
| 3360 g ae/ha glyphosate | 2 | 2 | 0 | 21 | 8 | 15-30 |
| pDAB102715: dgt-3 v2 (1 PTU) | | | | | | |
| 0 g ae/ha glyphosate | 4 | 0 | 0 | 0 | 0 | 0 |
| 420 g ae/ha glyphosate | 2 | 2 | 0 | 26 | 16 | 10-40 |
| 840 g ae/ha glyphosate | 0 | 2 | 2 | 55 | 17 | 40-70 |
| 1680 g ae/ha glyphosate | 0 | 2 | 2 | 56 | 22 | 35-75 |

TABLE 13-continued

Response of selected $T_2$ *Arabidopsis* events transformed with dgt-3 to glyphosate applied postemergence at varying rates. Visual % injury 14 days after application.

| 1 copy seg | % Injury <20% | 20-40% | >40% | % Injury Ave | Std dev | Range (%) |
|---|---|---|---|---|---|---|
| 3360 g ae/ha glyphosate | 0 | 0 | 4 | 65 | 17 | 50-80 |
| pDAB102718: dgt-3 v2 (2 PTU) | | | | | | |
| 0 g ae/ha glyphosate | 4 | 0 | 0 | 0 | 0 | 0 |
| 420 g ae/ha glyphosate | 4 | 0 | 0 | 5 | 7 | 0-15 |
| 840 g ae/ha glyphosate | 2 | 2 | 0 | 23 | 10 | 15-35 |
| 1680 g ae/ha glyphosate | 3 | 0 | 1 | 20 | 20 | 5-50 |
| 3360 g ae/ha glyphosate | 1 | 1 | 2 | 36 | 22 | 15-60 |

$T_3$ *Arabidopsis* Data. The third generation plants ($T_3$) of selected $T_2$ *Arabidopsis* events which contained low copy numbers of the dgt-28 transgene were further characterized for glyphosate tolerance. Twenty-five plants per line were selected with glufosinate as previously described and lines from every construct tested did not segregate for the selectable marker gene. Glyphosate was applied as described previously. The response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for *Arabidopsis* transformation. The range in individual response is also indicated in the last column for each rate and transformation. Wild-type, non-transformed *Arabidopsis* (cv. Columbia) served as a glyphosate-sensitive control.

TABLE 14

Response of selected individual $T_3$ *Arabidopsis* events containing dgt-28 to glyphosate applied postemergence at varying rates, compared to a dgt-1 ($T_4$) homozygous resistant population, and a non-transformed control. Visual % injury 14 days after application.

| Application Rate | % Injury Range (No. Replicates) <20% | 20-40% | >40% | % Injury Analysis Ave | Std dev | Range (%) |
|---|---|---|---|---|---|---|
| dgt-28 (pDAB107602) | | | | | | |
| 0 g ae/ha glyphosate | 4 | 0 | 0 | 0.0 | 0.0 | 0 |
| 420 g ae/ha glyphosate | 0 | 0 | 4 | 73.8 | 2.5 | 70-75 |
| 840 g ae/ha glyphosate | 0 | 0 | 4 | 71.3 | 7.5 | 60-75 |
| 1680 g ae/ha glyphosate | 0 | 0 | 4 | 77.5 | 2.9 | 75-80 |
| 3360 g ae/ha glyphosate | 0 | 0 | 4 | 77.5 | 2.9 | 75-80 |
| TraP4::dgt-28 (pDAB107527) | | | | | | |
| 0 g ae/ha glyphosate | 4 | 0 | 0 | 0.0 | 0.0 | 0 |

TABLE 14-continued

Response of selected individual $T_3$ *Arabidopsis* events containing dgt-28 to glyphosate applied postemergence at varying rates, compared to a dgt-1 ($T_4$) homozygous resistant population, and a non-transformed control. Visual % injury 14 days after application.

| | % Injury Range (No. Replicates) | | | % Injury Analysis | | |
|---|---|---|---|---|---|---|
| Application Rate | <20% | 20-40% | >40% | Ave | Std dev | Range (%) |
| 420 g ae/ha glyphosate | 4 | 0 | 0 | 0.0 | 0.0 | 0 |
| 840 g ae/ha glyphosate | 4 | 0 | 0 | 5.0 | 0.0 | 5 |
| 1680 g ae/ha glyphosate | 4 | 0 | 0 | 10.0 | 0.0 | 10 |
| 3360 g ae/ha glyphosate | 1 | 3 | 0 | 18.8 | 2.5 | 15-20 |
| TraP5 v1::dgt-28 (pDAB102792) | | | | | | |
| 0 g ae/ha glyphosate | 4 | 0 | 0 | 0.0 | 0.0 | 0 |
| 420 g ae/ha glyphosate | 3 | 0 | 0 | 0.0 | 0.0 | 0 |
| 840 g ae/ha glyphosate | 3 | 0 | 0 | 0.0 | 0.0 | 0 |
| 1680 g ae/ha glyphosate | 3 | 0 | 0 | 6.0 | 1.7 | 5-8 |
| 3360 g ae/ha glyphosate | 2 | 0 | 0 | 6.5 | 2.1 | 5-8 |
| TraP5 v2::dgt-28 (pDAB105530) | | | | | | |
| 0 g ae/ha glyphosate | 4 | 0 | 0 | 0.0 | 0.0 | 0 |
| 420 g ae/ha glyphosate | 4 | 0 | 0 | 6.0 | 1.7 | 5-8 |
| 840 g ae/ha glyphosate | 4 | 0 | 0 | 8.0 | 0.0 | 8 |
| 1680 g ae/ha glyphosate | 4 | 0 | 0 | 14.3 | 1.5 | 12-15 |
| 3360 g ae/ha glyphosate | 1 | 3 | 0 | 18.7 | 2.5 | 15-20 |
| TraP8 v2::dgt-28 (pDAB105531) | | | | | | |
| 0 g ae/ha glyphosate | 4 | 0 | 0 | 0.0 | 0.0 | 0 |
| 420 g ae/ha glyphosate | 4 | 0 | 0 | 2.5 | 5.0 | 0-10 |
| 840 g ae/ha glyphosate | 4 | 0 | 0 | 3.3 | 3.9 | 0-8 |
| 1680 g ae/ha glyphosate | 4 | 0 | 0 | 2.5 | 2.9 | 0-5 |
| 3360 g ae/ha glyphosate | 4 | 0 | 0 | 7.3 | 6.4 | 2-15 |
| TraP9 v2::dgt-28 (pDAB105532) | | | | | | |
| 0 g ae/ha glyphosate | 4 | 0 | 0 | 0.0 | 0.0 | 0 |
| 420 g ae/ha glyphosate | 4 | 0 | 0 | 1.3 | 2.5 | 0-5 |
| 840 g ae/ha glyphosate | 4 | 0 | 0 | 1.8 | 2.4 | 0-5 |
| 1680 g ae/ha glyphosate | 4 | 0 | 0 | 0.0 | 0.0 | 0 |
| 3360 g ae/ha glyphosate | 4 | 0 | 0 | 10.0 | 4.4 | 5-15 |
| TraP12 v2::dgt-28 (pDAB105533) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 3.8 | 7.5 | 0-15 |
| 3360 g ae/ha glyphosate | 4 | 0 | 0 | 6.3 | 4.8 | 0-10 |
| TraP13 v2::dgt-28 (pDAB105534) | | | | | | |
| 0 g ae/ha glyphosate | 4 | 0 | 0 | 0.0 | 0.0 | 0 |
| 420 g ae/ha glyphosate | 2 | 2 | 0 | 10.0 | 11.5 | 0-20 |
| 840 g ae/ha glyphosate | 4 | 0 | 0 | 1.3 | 2.5 | 0-5 |
| 1680 g ae/ha glyphosate | 4 | 0 | 0 | 2.8 | 1.5 | 2-5 |
| 3360 g ae/ha glyphosate | 4 | 0 | 0 | 8.0 | 0.0 | 8 |
| TraP23::dgt-28 (pDAB107553) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 7.8 | 2.1 | 5-10 |
| 3360 g ae/ha glyphosate | 4 | 0 | 0 | 10.8 | 3.0 | 8-15 |
| WT (non-transformed control) | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Selection of transformed plants. Freshly harvested $T_1$ seed [dgt-31, dgt-32, and dgt-33 v1 gene] were allowed to dry at room temperature and shipped to Indianapolis for testing. $T_1$ seed was sown in 26.5×51-cm germination trays (T.O. Plastics Inc., Clearwater, Minn.), each receiving a 200 mg aliquots of stratified $T_1$ seed (~10,000 seed) that had previously been suspended in 40 mL of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 mL aliquot of stratified seed was sown evenly onto the vermiculite with a pipette and covered with humidity domes (KORD™ Products, Bramalea, Ontario, Canada) for 4-5 days. Domes were removed once plants had germinated prior to initial transformant selection using glufosinate postemergence spray (selecting for the co-transformed dsm-2 gene).

Six days after planting (DAP) and again 10 DAP, $T_1$ plants (cotyledon and 2-4-lf stage, respectively) were sprayed with a 0.1% solution of IGNITE™ herbicide (280 g ai/L glufosinate, Bayer Crop Sciences, Kansas City, Mo.) at a spray volume of 10 mL/tray (703 L/ha) using a DeVilbiss™ compressed air spray tip to deliver an effective rate of 200 g ae/ha glufosinate per application. Survivors (plants actively growing) were identified 4-7 days after the final spraying. Surviving plants were transplanted individually into 3-inch pots prepared with potting media (Metro Mix 360™). Plants reared in the greenhouse at least 1 day prior to tissue sampling for copy number analyses.

$T_1$ plants were sampled and copy number analysis for the dgt-31, dgt-32, and dgt-33 v1 gene were completed. $T_1$ plants were then assigned to various rates of glyphosate so that a range of copies were among each rate. For *Arabidopsis,* 26.25 g ae/ha glyphosate is an effective dose to distinguish sensitive plants from ones with meaningful levels of resistance. Elevated rates were applied to determine relative levels of resistance (105, 420, 1680, or 3360 g ae/ha). Table 15 shows the comparisons drawn to dgt-1.

All glyphosate herbicide applications were made by track sprayer in a 187 L/ha spray volume. Glyphosate used was of the commercial Durango dimethylamine salt formulation (480 g ae/L, Dow AgroSciences, LLC). Low copy $T_1$ plants that exhibited tolerance to either glufosinate or glyphosate were further accessed in the $T_2$ generation.

The first *Arabidopsis* transformations were conducted using dgt-31, dgt-32, and dgt-33 v1. $T_1$ transformants were first selected from the background of untransformed seed using a glufosinate selection scheme. Three flats or 30,000 seed were analyzed for each $T_1$ construct. Transformation frequency was calculated and results of T1 dgt-31, dgt-32, and dgt-33 constructs are listed in Table 15.

TABLE 15

Transformation frequency of T1 dgt-31, dgt-32, and dgt-33 *Arabidopsis* constructs selected with glufosinate for selection of the selectable marker gene DSM-2.

| Construct | Cassette | Transformation Frequency (%) |
|---|---|---|
| pDAB107532 | AtUbi10/TraP14 dgt-32 v1 | 0.47 |
| pDAB107533 | AtUbi10/TraP23 dgt-31 v1 | 0.36 |
| pDAB107534 | AtUbi10/TraP24 dgt-33 v1 | 0.68 |

$T_1$ plants selected above were subsequently transplanted to individual pots and sprayed with various rates of commercial glyphosate. Table 16 compares the response of dgt-31, dgt-32, and dgt-33 v1 and control genes to impart glyphosate resistance to *Arabidopsis* $T_1$ transformants. Response is presented in terms of % visual injury 2 WAT. Data are presented as a histogram of individuals exhibiting little or no injury (<20%), moderate injury (20-40%), or severe injury (>40%). An arithmetic mean and standard deviation is presented for each treatment. The range in individual response is also indicated in the last column for each rate and transformation. Wild-type non-transformed *Arabidopsis* (cv. Columbia) served as a glyphosate sensitive control. The DGT-31 (v1) gene with transit peptide TraP23 imparted slight herbicide tolerance to individual $T_1$ *Arabidopsis* plants compared to the negative control, but the gene exhibited improved tolerance with transit peptide TraP8. Both DGT-32 and DGT-33 demonstrated robust tolerance to glyphosate at the rates tested with TraP8 and with their respective differing chloroplast transit peptide (TraP 14 and TraP24 respectively). Within a given treatment, the level of plant response varied greatly, which can be attributed to the fact each plant represents an independent transformation event and thus the copy number of the gene of interest varies from plant to plant. Of important note, at each glyphosate rate tested, there were individuals that were more tolerant than others. An overall population injury average by rate is presented in Table 16 to demonstrate the significant difference between the plants transformed with dgt-31, dgt-32, and dgt-33 v1 versus the dgt-1 v1 or Wild-type controls.

TABLE 16 dgt-31, dgt-32, and dgt-33 v1 transformed $T_1$ *Arabidopsis* response to a range of glyphosate rates applied postemergence, compared to a dgt-1 (T4) homozygous resistant population, or a non-transformed control. Visual % injury 2 weeks after treatment.

| | % Injury | | | % Injury | | |
|---|---|---|---|---|---|---|
| Averages | <20% | 20-40% | >40% | Ave | Std. Dev. | Range (%) |
| TraP23 dgt-31 | | | | | | |
| 0 g ae/ha glyphosate | 4 | 0 | 0 | 0.0 | 0.0 | 0 |
| 105 g ae/ha | 0 | 0 | 4 | 81.3 | 2.5 | 80-85 |
| 420 g ae/ha | 0 | 0 | 4 | 97.3 | 4.9 | 90-100 |
| 1680 g ae/ha | 0 | 0 | 4 | 90.0 | 7.1 | 85-100 |
| 3360 g ae/ha | 0 | 0 | 4 | 91.3 | 6.3 | 85-100 |
| TraP14 dgt-32 | | | | | | |
| 0 g ae/ha glyphosate | 4 | 0 | 0 | 0.0 | 0.0 | 0 |
| 105 g ae/ha | 4 | 0 | 0 | 0.0 | 0.0 | 0 |
| 420 g ae/ha | 2 | 0 | 2 | 30.0 | 29.4 | 0-60 |
| 1680 g ae/ha | 3 | 0 | 1 | 17.5 | 21.8 | 5-50 |
| 3360 g ae/ha | 0 | 3 | 1 | 35.0 | 30.0 | 20-80 |
| TraP24 dgt-33 | | | | | | |
| 0 g ae/ha glyphosate | 4 | 0 | 0 | 0.0 | 0.0 | 0 |
| 105 g ae/ha | 2 | 2 | 0 | 21.3 | 14.9 | 5-40 |
| 420 g ae/ha | 1 | 1 | 2 | 46.3 | 30.9 | 5-70 |
| 1680 g ae/ha | 1 | 0 | 3 | 62.5 | 38.8 | 5-90 |
| 3360 g ae/ha | 1 | 0 | 3 | 62.0 | 36.0 | 8-80 |
| TraP8 dgt-31 | | | | | | |
| 0 g ae/ha glyphosate | 4 | 0 | 0 | 0.0 | 0.0 | 0.0 |
| 105 g ae/ha glyphosate | 0 | 1 | 3 | 0.0 | 43.8 | 17.0 |
| 420 g ae/ha glyphosate | 1 | 2 | 1 | 0.0 | 43.8 | 32.5 |
| 1680 g ae/ha glyphosate | 0 | 1 | 3 | 0.0 | 71.3 | 27.8 |
| 3360 g ae/ha glyphosate | 0 | 0 | 4 | 0.0 | 81.3 | 8.5 |
| | % Injury | | | % Injury | | |
| Averages | <20% | <20% | <20% | Ave. | Std. Dev. | Range (%) |
| TraP8 dgt-32 | | | | | | |
| 0 g ae/ha glyphosate | 4 | 0 | 4 | 0.0 | 0.0 | 0.0 |
| 105 g ae/ha glyphosate | 4 | 0 | 0 | 0.0 | 0.0 | 0.0 |
| 420 g ae/ha glyphosate | 4 | 0 | 0 | 0.0 | 7.5 | 5.0 |
| 1680 g ae/ha glyphosate | 3 | 1 | 0 | 0.0 | 10.8 | 9.6 |
| 3360 g ae/ha glyphosate | 4 | 0 | 0 | 0.0 | 12.8 | 3.2 |
| TraP8 dgt-33 | | | | | | |
| 0 g ae/ha glyphosate | 4 | 0 | 0 | 0.0 | 0.0 | 0.0 |
| 105 g ae/ha glyphosate | 4 | 0 | 0 | 0.0 | 0.0 | 0.0 |
| 420 g ae/ha glyphosate | 4 | 0 | 0 | 0.0 | 2.5 | 3.8 |
| 1680 g ae/ha glyphosate | 4 | 0 | 0 | 0.0 | 6.3 | 2.5 |
| 3360 g ae/ha glyphosate | 3 | 1 | 0 | 0.0 | 20.0 | 13.5 |

TABLE 16-continued dgt-31, dgt-32, and dgt-33 v1 transformed $T_1$ *Arabidopsis* response to a range of glyphosate rates applied postemergence, compared to a dgt-1 (T4) homozygous resistant population, or a non-transformed control. Visual % injury 2 weeks after treatment.

| | % Injury | | | % Injury | | |
|---|---|---|---|---|---|---|
| Averages | <20% | 20-40% | >40% | Ave | Std. Dev. | Range (%) |
| dgt-1 (transformed control) | | | | | | |
| 0 g ae/ha glyphosate | 4 | 0 | 0 | 0.0 | 0.0 | 0 |
| 105 g ae/ha | 0 | 1 | 3 | 42.5 | 15.0 | 20-50 |
| 420 g ae/ha | 0 | 2 | 2 | 38.8 | 11.1 | 25-50 |
| 1680 g ae/ha | 0 | 0 | 4 | 79.0 | 19.4 | 50-90 |
| 3360 g ae/ha | 0 | 0 | 4 | 50.0 | 0.0 | 50 |
| WT (non-transformed control) | | | | | | |
| 0 g ae/ha glyphosate | 4 | 0 | 0 | 0.0 | 0.0 | 0 |
| 105 g ae/ha | 0 | 0 | 4 | 85.0 | 0.0 | 85 |
| 420 g ae/ha | 0 | 0 | 4 | 100.0 | 0.0 | 100 |
| 1680 g ae/ha | 0 | 0 | 4 | 100.0 | 0.0 | 100 |
| 3360 g ae/ha | 0 | 0 | 4 | 100.0 | 0.0 | 100 |

Maize Transformation. Standard cloning methods, as described above, were used in the construction of binary vectors for use in *Agrobacterium tumefaciens*-mediated transformation of maize. Table 17 lists the vectors which were constructed for maize transformation. The following gene elements were used in the vectors which contained dgt-28; the *Zea mays* Ubiquitin 1 promoter (ZmUbi1; U.S. Pat. No. 5,510,474) was used to drive the dgt-28 coding sequence which is flanked by a *Zea mays* Lipase 3' untranslated region (ZmLip 3'UTR; U.S. Pat. No. 7,179,902), the selectable marker cassette consists of the *Zea mays* Ubiquitin 1 promoter which was used to drive the aad-1 coding sequence (U.S. Pat. No. 7,838,733) which is flanked by a *Zea mays* Lipase 3' untranslated region. The aad-1 coding sequence confers tolerance to the phenoxy auxin herbicides, such as, 2,4-dichlorophenoxyacetic acid (2,4-D) and to aryloxyphenoxypropionate (AOPP) herbicides.

The dgt-28 constructs were built as standard binary vectors and *Agrobacterium* superbinary system vectors (Japan Tobacco, Tokyo, JP). The standard binary vectors include; pDAB107663, pDAB107664. pDAB107665, and pDAB107665. The *Agrobacterium* superbinary system vectors include pDAB108384, pDAB108385, pDAB108386, and pDAB108387.

Additional constructs were completed which contain a yellow fluorescent protein (yfp; US Patent Application 2007/0298412) reporter gene. pDAB109812 contains a yfp reporter gene cassette which is driven by the *Zea mays* Ubiquitin 1 promoter and flanked by the *Zea mays* per 5 3' untranslated region (Zm per5 3'UTR; U.S. Pat. No. 7,179,902), the selectable marker cassette consists of the sugar cane bacilliform virus promoter (SCBV; U.S. Pat. No. 5,994,123) which is used to drive the expression of aad-1 and is flanked by the *Zea mays* Lipase 3' untranslated region. pDAB101556 contains a yfp cassette which is driven by the *Zea mays* Ubiquitin 1 promoter and flanked by the *Zea mays* per 5 3' untranslated region, the selectable marker cassette consists of the *Zea mays* Ubiquitin 1 promoter which is used to drive the expression of aad-1 and is flanked by the *Zea mays* Lipase 3' untranslated region. pDAB107698 contains a dgt-28 cassette which is driven by the *Zea mays* Ubiquitin 1 promoter and is flanked by a *Zea mays* Lipase 3' untranslated region, an yfp cassette which is driven by the *Zea mays* Ubiquitin 1 promoter and flanked by the *Zea mays* per 5 3' untranslated region, the selectable marker cassette consists of the sugar cane bacilliform virus promoter which is used to drive the expression of aad-1 and is flanked by the *Zea mays* Lipase 3' untranslated region. All three of these constructs are standard binary vectors.

TABLE 17

Maize Transformation Vectors

| Plasmid No. | FIG. No: | Description of Gene Elements |
|---|---|---|
| pDAB107663 | 35 | ZmUbi1/TraP4 dgt-28/ZmLip 3'UTR :: ZmUbi1/aad-1/ZmLip 3'UTR binary vector |
| pDAB107664 | 36 | ZmUbi1/TraP8 dgt-28/ZmLip 3'UTR :: ZmUbi1/aad-1/ZmLip 3'UTR binary vector |
| pDAB107665 | 37 | ZmUbi1/TraP23 dgt-28/ZmLip 3'UTR :: ZmUbi1/aad-1/ZmLip 3'UTR binary vector |
| pDAB107666 | 38 | ZmUbi1/TraP5 dgt-28/ZmLip 3'UTR :: ZmUbi1/aad-1/ZmLip 3'UTR binary vector |
| pDAB109812 | 39 | ZmUbi1/yfp/ZmPer5 3'UTR :: SCBV/aad-1/ZmLip 3'UTR binary vector |
| pDAB101556 | 40 | ZmUbi1/yfp/ZmPer5 3'UTR :: ZmUbi1/aad-1/ZmLip 3'UTR binary vector |
| pDAB107698 | 41 | ZmUbi1/TraP8 dgt-28/ZmLip 3'UTR :: ZmUbi1/yfp/ZmLip 3'UTR::SCBV/aad-1/ZmLip 3'UTR |
| pDAB108384 | 42 | ZmUbi1/TraP4 dgt-28/ZmLip 3'UTR:: ZmUbi1/aad-1/ZmLip 3'UTR superbinary vector |
| pDAB108385 | 43 | ZmUbi1/TraP8 dgt-28/ZmLip 3'UTR :: ZmUbi1/aad-1/ZmLip 3'UTR superbinary precursor |
| pDAB108386 | 44 | ZmUbi1/TraP23 dgt-28/ZmLip 3'UTR :: ZmUbi1/aad-1/ZmLip 3'UTR superbinary precursor |
| pDAB108387 | 45 | ZmUbi1/TraP5 dgt-28/ZmLip 3'UTR::ZmUbi1/aad-1/ZmLip 3'UTR superbinary precursor |

Ear sterilization and embryo isolation. To obtain maize immature embryos, plants of the *Zea mays* inbred line B104 were grown in the greenhouse and were self or sib-pollinated to produce ears. The ears were harvested approximately 9-12 days post-pollination. On the experimental day, ears were surface-sterilized by immersion in a 20% solution of sodium hypochlorite (5%) and shaken for 20-30 minutes, followed by three rinses in sterile water. After sterilization, immature zygotic embryos (1.5-2.4 mm) were aseptically dissected from each ear and randomly distributed into micro-centrifuge tubes containing liquid infection media (LS Basal Medium, 4.43 gm/L; N6 Vitamin Solution [1000X], 1.00 mL/L; L-proline, 700.0 mg/L; Sucrose, 68.5 gm/L; D(+) Glucose, 36.0 gm/L; 10 mg/ml of 2,4-D, 150 μL/L). For a given set of experiments, pooled embryos from three ears were used for each transformation.

*Agrobacterium* Culture Initiation:

Glycerol stocks of *Agrobacterium* containing the binary transformation vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-Cultivation. *Agrobacterium* colonies were taken from the YEP plate, suspended in 10 mL of infection medium in a 50 mL disposable tube, and the cell density was adjusted to $OD_{600}$ nm of 0.2-0.4 using a spectrophotometer. The *Agrobacterium* cultures were placed on a rotary shaker at 125 rpm, room temperature, while embryo dissection was performed. Immature zygotic embryos between 1.5-2.4 mm in size were isolated from the sterilized maize kernels and placed in 1 mL of the infection medium) and washed once in the same medium. The *Agrobacterium* suspension (2 mL) was added to each tube and the tubes were placed on a shaker platform for 10-15 minutes. The embryos were transferred onto co-cultivation media (MS Salts, 4.33 gm/L; L-proline, 700.0 mg/L; Myo-inositol, 100.0 mg/L; Casein enzymatic hydrolysate 100.0 mg/L; 30 mM Dicamba-KOH, 3.3 mg/L; Sucrose, 30.0 gm/L; Gelzan™, 3.00 gm/L; Modified MS-Vitamin [1000X], 1.00 ml/L; 8.5 mg/ml $AgNo_3$, 15.0 mg/L; DMSO, 100 μM), oriented with the scutellum facing up and incubated at 25° C., under 24-hour light at 50 μmole $m^{-2}$ $sec^{-1}$ light intensity for 3 days.

Callus Selection and Regeneration of Putative Events. Following the co-cultivation period, embryos were transferred to resting media (MS Salts, 4.33 gm/L; L-proline, 700.0 mg/L; 1,2,3,5/4,6-Hexahydroxycyclohexane, 100 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan 2.30 gm/L; Modified MS-Vitamin [1000X], 1.00 ml/L; 8.5 mg/ml AgNo3, 15.0 mg/L; Carbenicillin, 250.0 mg/L) without selective agent and incubated under 24-hour light at 50 μmole $m^{-2}$ $sec^{-1}$ light intensity and at 25° C. for 3 days.

Growth inhibition dosage response experiments suggested that glyphosate concentrations of 0.25 mM and higher were sufficient to inhibit cell growth in the untransformed B104 maize line. Embryos were transferred onto Selection 1 media containing 0.5 mM glyphosate (MS Salts, 4.33 gm/L; L-proline, 700.0 mg/L; Myo-inositol, 100.0 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000X], 1.00 ml/L; 8.5 mg/ml AgNo3, 15.0 mg/L; Carbenicillin, 250.0 mg/L) and incubated in either dark and/or under 24-hour light at 50 μmole $m^{-2}$ $sec^{-1}$ light intensity for 7-14 days at 28° C.

Proliferating embryogenic calli were transferred onto Selection 2 media containing 1.0 mM glyphosate (MS Salts, 4.33 gm/L; 1,2,3,5/4,6-Hexahydroxycyclohexane, 100 mg/L; L-proline, 700.0 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000X], 1.00 ml/L; 8.5 mg/mL AgNo3, 15.0 mg/L; Carbenicillin, 250.0 mg/L; R-Haloxyfop acid 0.1810 mg/L), and were incubated in either dark and/or under 24-hour light at 50 μmole $m^{-2}$ $sec^{-1}$ light intensity for 14 days at 28° C. This selection step allowed transgenic callus to further proliferate and differentiate. The callus selection period lasted for three to four weeks.

Proliferating, embryogenic calli were transferred onto PreReg media containing 0.5 mM glyphosate (MS Salts, 4.33 gm/L; 1,2,3,5/4,6-Hexahydroxycyclohexane, 100 mg/L; L-proline, 350.0 mg/L; MES [(2-(n-morpholino)-ethanesulfonic acid), free acid] 0.250 gm/L; Casein enzymatic hydrolysate 50.0 mg/L; NAA-NaOH 0.500 mg/L; ABA-EtOH 2.50 mg/L; BA 1.00 mg/L; Sucrose, 45.0 gm/L; Gelzan™ 2.50 gm/L; Modified MS-Vitamin [1000X], 1.00 ml/L; 8.5 mg/ml AgNo3, 1.00 mg/L; Carbenicillin, 250.0 mg/L) and cultured under 24-hour light at 50 μmole $m^{-2}$ $sec^{-1}$ light intensity for 7 days at 28° C.

Embryogenic calli with shoot-like buds were transferred onto Regeneration media containing 0.5 mM glyphosate (MS Salts, 4.33 gm/L; 1,2,3,5/4,6-Hexahydroxycyclohexane, 100.0 mg/L; Sucrose, 60.0 gm/L; Gellan Gum G434™ 3.00 gm/L; Modified MS-Vitamin [1000X], 1.00 ml/L; Carbenicillin, 125.0 mg/L) and cultured under 24-hour light at 50 μmole $m^{-2}$ $sec^{-1}$ light intensity for 7 days.

Small shoots with primary roots were transferred to rooting media (MS Salts, 4.33 gm/L; Modified MS-Vitamin [1000X], 1.00 ml/L; 1,2,3,5/4,6-Hexahydroxycyclohexane, 100 mg/L; Sucrose, 60.0 gm/L; Gellan Gum G434™ 3.00 gm/L; Carbenicillin, 250.0 mg/L) in phytotrays and were incubated under 16/8 hr. light/dark at 140-190 μmole $m^{-2}$ $sec^{-1}$ light intensity for 7 days at 27° C. Putative transgenic plantlets were analyzed for transgene copy number using the protocols described above and transferred to soil.

Molecular Confirmation of the Presence of the dgt-28 and aad-1 transgenes within Maize Plants. The presence of the dgt-28 and aad-1 polynucleotide sequences were confirmed via hydrolysis probe assays. Isolated $T_0$ Maize plants were initially screened via a hydrolysis probe assay, analogous to TAQMAN™, to confirm the presence of a aad-1 and dgt-28 transgenes. The data generated from these studies were used to determine the transgene copy number and used to select transgenic maize events for back crossing and advancement to the $T_1$ generation.

Tissue samples were collected in 96-well plates, tissue maceration was performed with a KLECO™ tissue pulverizer and stainless steel beads (Hoover Precision Products, Cumming, Ga.), in Qiagen™ RLT buffer. Following tissue maceration, the genomic DNA was isolated in high-throughput format using the Biosprint 96™ Plant kit (Qiagen, Germantown, Md.) according to the manufacturer's suggested protocol. Genomic DNA was quantified by Quant-IT™ Pico Green DNA assay kit (Molecular Probes, Invitrogen, Carlsbad, Calif.). Quantified genomic DNA was adjusted to around 2 ng/μL for the hydrolysis probe assay using a BIOROBOT3000™ automated liquid handler (Qiagen, Germantown, Md.). Transgene copy number determination by hydrolysis probe assay, analogous to TAQMAN® assay, was performed by real-time PCR using the LIGHTCYCLER®480 system (Roche Applied Science, Indianapolis, Ind.). Assays were designed for aad-1, dgt-28 and an internal reference gene Invertase (Genbank Accession No: U16123.1) using the LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume multiplex reaction containing 0.4 μM of each primer for aad-1 and dgt-28 and 0.2 μM of each probe (Table 18).

A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LightCycler® software release 1.5 using the relative quant module and is based on the ΔΔCt method. Controls included a sample of genomic DNA from a single copy calibrator and known two copy check that were included in each run. Table 19 lists the results of the hydrolysis probe assays.

TABLE 18

Primer and probe sequences used for hydrolysis probe assay of aad-1, dgt-28 and internal reference (Invertase).

| Oligonucleotide Name | Gene Detected | SEQ ID NO: | Oligo Sequence |
|---|---|---|---|
| GAAD1F | aad-1 forward primer | 58 | TGTTCGGTTCCCTCTACCAA |
| GAAD1P | aad-1 probe | 59 | CACAGAACCGTCGCTTCAGCAACA |
| GAAD1R | aad-1 reverse primer | 60 | CAACATCCATCACCTTGACTGA |
| IV-Probe | Invertase probe | 61 | CGAGCAGACCGCCGTGTACTTCTACC |
| IVF-Taq | Invertase forward primer | 62 | TGGCGGACGACGACTTGT |
| IVR-Taq | Invertase reverse primer | 63 | AAAGTTTGGAGGCTGCCGT |
| zmDGT28 F | dgt-28 forward primer | 64 | TTCAGCACCCGTCAGAAT |
| zmDGT28 FAM | dgt-28 probe | 65 | TGCCGAGAACTTGAGGAGGT |
| zmDGT28 R | dgt-28 reverse primer | 66 | TGGTCGCCATAGCTTGT |

TABLE 19

$T_0$ copy amount results for dgt-28 events. Low copy events consisted of 1-2 transgene copies, single copy numbers are listed in parenthesis. High copy events contained 3 or more transgene copies.

| Plasmid used for Transformation | # of Low Copy Events (single copy) | # of High Copy Events |
|---|---|---|
| pDAB107663 | 43 (31) | 10 |
| pDAB107664 | 30 (24) | 5 |
| pDAB107665 | 40 (27) | 10 |
| pDAB107666 | 24 (12) | 12 |
| pDAB109812 | 2 (1) | 0 |
| pDAB101556 | 25 (15) | 10 |
| pDAB107698 | 3 (1) | 2 |

Herbicide Tolerance in dgt-28 Transformed Corn. *Zea mays* dgt-28 transformation events ($T_0$) were allowed to acclimate in the greenhouse and were grown until plants had transitioned from tissue culture to greenhouse growing conditions (i.e., 2-4 new, normal looking leaves had emerged from the whorl). Plants were grown at 27° C. under 16 hour light: 8 hour dark conditions in the greenhouse. The plants were then treated with commercial formulations of DURANGO DMA™ (containing the herbicide glyphosate) with the addition of 2% w/v ammonium-sulfate. Herbicide applications were made with a track sprayer at a spray volume of 187 L/ha, 50-cm spray height. $T_0$ plants were sprayed with a range of glyphosate from 280-4480 g ae/ha glyphosate, which is capable of significant injury to untransformed corn lines. A lethal dose is defined as the rate that causes >95% injury to the B104 inbred.

The results of the $T_0$ dgt-28 corn plants demonstrated that tolerance to glyphosate was achieved at rates up to 4480 g ae/ha. A specific media type was used in the $T_0$ generation. Minimal stunting and overall plant growth of transformed plants compared to the non-transformed controls demonstrated that dgt-28 provides robust tolerance to glyphosate when linked to the TraP5, TraP8, and TraP23 chloroplast transit peptides.

Selected $T_0$ plants are selfed or backcrossed for further characterization in the next generation. 100 chosen dgt-28 lines containing the $T_1$ plants are sprayed with 140-1120 g ae/ha glufosinate or 105-1680 g ae/ha glyphosate. Both the selectable marker and glyphosate resistant gene are constructed on the same plasmid. Therefore, if one herbicide tolerant gene is selected for by spraying with an herbicide, both genes are believed to be present. At 14 DAT, resistant and sensitive plants are counted to determine the percentage of lines that segregated as a single locus, dominant Mendelian trait (3R:1S) as determined by Chi square analysis. These data demonstrate that dgt-28 is inheritable as a robust glyphosate resistance gene in a monocot species. Increased rates of glyphosate are applied to the $T_1$ or $F_1$ survivors to further characterize the tolerance and protection that is provided by the dgt-28 gene.

Post-Emergence Herbicide Tolerance in dgt-28 Transformed $T_0$ Corn. $T_0$ events of dgt-28 linked with TraP4, TraP5, TraP8 and TraP23 were generated by *Agrobacterium* transformation and were allowed to acclimate under controlled growth chamber conditions until 2-4 new, normal looking leaves had emerged from the whorl. Plants were assigned individual identification numbers and sampled for copy number analyses of both dgt-28 and aad-1. Based on copy number analyses, plants were selected for protein expression analyses. Plants were transplanted into larger pots with new growing media and grown at 27° C. under 16 hour light:8 hour dark conditions in the greenhouse. Remaining plants that were not sampled for protein expression were then treated with commercial formulations of DURANGO DMA™ (glyphosate) with the addition of 2% w/v ammonium-sulfate. Treatments were distributed so that each grouping of plants contained $T_0$ events of varying copy number. Herbicide applications were made with a track sprayer at a spray volume of 187 L/ha, 50-cm spray height. $T_0$ plants were sprayed with a range of glyphosate from 280-4480 g ae/ha glyphosate capable of significant injury to untransformed corn lines. A lethal dose is defined as the rate that causes >95% injury to the B104 inbred. B104 was the genetic background of the transformants.

Results of $T_0$ dgt-28 corn plants demonstrate that tolerance to glyphosate was achieved up to 4480 g ae/ha. Table 20. Minimal stunting and overall plant growth of transformed plants compared to the non-transformed controls demonstrated that dgt-28 provides robust protection to glyphosate when linked to TraP5, TraP8, and TraP23.

TABLE 20

Response of $T_0$ dgt-28 events of varying copy numbers to rates of glyphosate ranging from 280-4480 g ae/ha + 2.0% w/v ammonium sulfate 14 days after treatment.

| | % Injury | | | % Injury | | |
|---|---|---|---|---|---|---|
| Application Rate | <20% | 20-40% | >40% | Ave | Std. Dev. | Range (%) |
| TraP4 dgt-28 | | | | | | |
| 0 g ae/ha glyphosate | 4 | 0 | 0 | 0.0 | 0.0 | 0 |
| 280 g ae/ha | 5 | 0 | 0 | 1.0 | 2.2 | 0-5 |
| 560 g ae/ha | 6 | 0 | 0 | 2.0 | 4.0 | 0-10 |
| 1120 g ae/ha | 12 | 0 | 0 | 1.3 | 3.1 | 0-10 |
| 2240 g ae/ha | 7 | 0 | 0 | 1.7 | 4.5 | 0-12 |
| 4480 g ae/ha | 7 | 0 | 0 | 1.1 | 3.0 | 0-8 |
| TraP8 dgt-28 | | | | | | |
| 0 g ae/ha glyphosate | 6 | 0 | 0 | 0.0 | 0.0 | 0 |
| 280 g ae/ha | 5 | 1 | 0 | 6.7 | 8.8 | 0-20 |
| 560 g ae/ha | 0 | 2 | 0 | 20.0 | 0.0 | 20 |
| 1120 g ae/ha | 7 | 0 | 0 | 1.4 | 2.4 | 0-5 |
| 2240 g ae/ha | 3 | 1 | 0 | 7.5 | 15.0 | 0-30 |
| 4480 g ae/ha | 6 | 0 | 0 | 1.7 | 4.1 | 0-10 |
| TraP23 dgt-28 | | | | | | |
| 0 g ae/ha glyphosate | 6 | 0 | 0 | 0.8 | 2.0 | 0-5 |
| 280 g ae/ha | 7 | 0 | 0 | 0.0 | 0.0 | 0 |
| 560 g ae/ha | 4 | 0 | 0 | 1.3 | 2.5 | 0-5 |
| 1120 g ae/ha | 10 | 2 | 0 | 3.3 | 7.8 | 0-20 |
| 2240 g ae/ha | 6 | 0 | 0 | 1.3 | 3.3 | 0-8 |
| 4480 g ae/ha | 6 | 1 | 0 | 4.3 | 7.9 | 0-20 |
| TraP5 dgt-28 | | | | | | |
| 0 g ae/ha glyphosate | 4 | 0 | 0 | 0.0 | 0.0 | 0 |
| 280 g ae/ha | 7 | 1 | 0 | 5.0 | 14.1 | 0-40 |
| 560 g ae/ha | 8 | 0 | 0 | 0.6 | 1.8 | 0-5 |
| 1120 g ae/ha | 7 | 1 | 0 | 5.0 | 14.1 | 0-40 |
| 2240 g ae/ha | 8 | 0 | 0 | 0.0 | 0.0 | 0 |
| 4480 g ae/ha | 8 | 0 | 0 | 0.0 | 0.0 | 0 |

Protein expression analyses by standard ELISA demonstrated a mean range of DGT-28 protein from 12.6-22.5 ng/cm$^2$ across the constructs tested.

Confirmation of Glyphosate Tolerance in the $F_1$ Generation Under Greenhouse Conditions. Single copy $T_0$ plants that were not sprayed were backcrossed to the non-transformed background B104 for further characterization in the next generation. In the $T_1$ generation, glyphosate tolerance was assessed to confirm the inheritance of the dgt-28 gene. For $T_1$ plants, the herbicide ASSURE II™ (35 g ae/ha quizalofop-methyl) was applied at the V1 growth stage to select for the AAD-1 protein. Both the selectable marker and glyphosate resistant gene are constructed on the same plasmid. Therefore if one gene is selected, both genes are believed to be present. After 7 DAT, resistant and sensitive plants were counted and null plants were removed from the population. These data demonstrate that dgt-28 (v1) is heritable as a robust glyphosate resistance gene in a monocot species. Plants were sampled for characterization of DGT-28 protein by standard ELISA and RNA transcript level. Resistant plants were sprayed with 560-4480 g ae/ha glyphosate as previously described. The data demonstrate robust tolerance of dgt-28 linked with the chloroplast transit peptides TraP4, TraP5, TraP8 and TraP23 up to 4480 g ae/ha glyphosate. Table 21.

TABLE 21

Response of $F_1$ single copy dgt-28 events to rates of glyphosate ranging from 560-4480 g ae/ha + 2.0% w/v ammonium sulfate 14 days after treatment.

| | % Injury | | | % Injury | | |
|---|---|---|---|---|---|---|
| Application Rate | <20% | 20-40% | >40% | Ave | Std. Dev. | Range (%) |
| B104/TraP4::dgt-28 | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 9.0 | 1.2 | 8-10 |
| 2240 g ae/ha | 4 | 0 | 0 | 2.5 | 2.9 | 0-5 |
| 4480 g ae/ha | 4 | 0 | 0 | 0.0 | 0.0 | 0 |
| B104/TraP8::dgt-28 | | | | | | |
| 0 g ae/ha glyphosate | 4 | 0 | 0 | 0.0 | 0.0 | 0 |
| 560 g ae/ha | 4 | 0 | 0 | 1.3 | 2.5 | 0-5 |
| 1120 g ae/ha | 4 | 0 | 0 | 0.0 | 0.0 | 0 |
| 2240 g ae/ha | 4 | 0 | 0 | 5.0 | 4.1 | 0-10 |
| 4480 g ae/ha | 4 | 0 | 0 | 6.3 | 2.5 | 5-10 |
| B104/TraP23::dgt-28 | | | | | | |
| 0 g ae/ha glyphosate | 4 | 0 | 0 | 0.0 | 0.0 | 0 |
| 560 g ae/ha | 3 | 1 | 0 | 10.0 | 10.0 | 5-25 |
| 1120 g ae/ha | 2 | 2 | 0 | 18.8 | 11.8 | 10-35 |
| 2240 g ae/ha | 4 | 0 | 0 | 12.5 | 2.9 | 10-15 |
| 4480 g ae/ha | 3 | 1 | 0 | 10.0 | 7.1 | 5-20 |
| B104/TraP5::dgt-28 | | | | | | |
| 0 g ae/ha glyphosate | 4 | 0 | 0 | 0.0 | 0.0 | 0 |
| 560 g ae/ha | 4 | 0 | 0 | 8.0 | 0.0 | 8 |
| 1120 g ae/ha | 4 | 0 | 0 | 11.3 | 3.0 | 8-15 |
| 2240 g ae/ha | 4 | 0 | 0 | 12.5 | 2.9 | 10-15 |
| 4480 g ae/ha | 4 | 0 | 0 | 10.0 | 2.5 | 10-15 |
| Non-transformed B104 | | | | | | |
| 0 g ae/ha glyphosate | 4 | 0 | 0 | 0.0 | 0.0 | 0 |
| 560 g ae/ha | 0 | 0 | 4 | 100.0 | 0.0 | 100 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

Protein expression data demonstrate a range of mean DGT-28 protein from 42.2-88.2 ng/cm$^2$ across $T_1$ events and constructs tested, establishing protein expression in the $T_1$ generation.

Characterization of dgt-28 corn under field conditions. Single copy $T_1$ events were sent to a field location to create both hybrid hemizygous and inbred homozygous seed for additional characterization. Hybrid seeds were created by crossing $T_1$ events in the maize transformation line B104 to the inbred line 4XP811 generating hybrid populations segregating 1:1 (hemizygous:null) for the event. The resulting seeds were shipped to 2 separate locations. A total of five single copy events per construct were planted at each location in a randomized complete block design in triplicate. The fields were designed for glyphosate applications to occur at the V4 growth stage and a separate grouping of plants to be applied at the V8 growth stage. The 4XP811/B104 conventional hybrid was used as a negative control.

Experimental rows were treated with 184 g ae/ha ASSURE II™ (106 g ai/L quizalofop-methyl) to eliminate null segregants. All experimental entries segregated 1:1 (sensitive:resistant) (p=0.05) with respect to the ASSURE II™ application. Selected resistant plants were sampled from each event for quantification of the DGT-28 protein by standard ELISA.

Quizalofop-methyl resistant plants were treated with the commercial herbicide DURANGO DMA™ (480 g ae/I, glyphosate) with the addition of 2.5% w/v ammonium-sulfate at either the V4 or V8 growth stages. Herbicide applications were made with a boom sprayer calibrated to deliver a volume of 187 L/ha, 50-cm spray height. Plants were sprayed with a range of glyphosate from 1120-4480 g ae/ha glyphosate, capable of significant injury to untransformed corn lines. A lethal dose is defined as the rate that causes >95% injury to the 4XP811 inbred. Visual injury assessments were taken for the percentage of visual chlorosis, percentage of necrosis, percentage of growth inhibition and total visual injury at 7, 14 and 21 DAT (days after treatment). Assessments were compared to the untreated checks for each line and the negative controls.

Visual injury data for all assessment timings demonstrated robust tolerance up to 4480 g ae/ha DURANGO DMA™ at both locations and application timings. Representative events for the V4 application are presented from one location and are consistent with other events, application timings and locations. Table 22. One event from the construct containing dgt-28 linked with TraP23 (pDAB107665) was tolerant to the ASSURE II™ selection for the AAD-1 protein, but was sensitive to all rates of glyphosate applied.

TABLE 22

Response of dgt-28 events applied with a range of glyphosate from 1120-4480 g ae/ha + 2.5% w/v ammonium sulfate at the V4 growth stage.

| Application Rate | % Injury <20% | % Injury 20-40% | % Injury >40% | % Injury Ave | % Injury Std. Dev. | % Injury Range (%) |
|---|---|---|---|---|---|---|
| 4XPB11//B104/ TraP4::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/ TraP8::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/ TraP23::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |

TABLE 22-continued

Response of dgt-28 events applied with a range of glyphosate from 1120-4480 g ae/ha + 2.5% w/v ammonium sulfate at the V4 growth stage.

| Application Rate | % Injury <20% | % Injury 20-40% | % Injury >40% | % Injury Ave | % Injury Std. Dev. | % Injury Range (%) |
|---|---|---|---|---|---|---|
| 2240 g ae/ha | 4 | 0 | 0 | 0.0 | 0.0 | 0 |
| 4480 g ae/ha | 4 | 0 | 0 | 0.0 | 0.0 | 0 |
| 4XPB11//B104/ TraP5::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 0.0 | 0.0 | 0 |
| Non-transformed 4XPB11//B104 | | | | | | |
| 0 g ae/ha glyphosate | 4 | 0 | 0 | 0.0 | 0.0 | 0 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

Additional assessments were made during the reproductive growth stage for the 4480 g ae/ha glyphosate rate. Visual assessments of tassels, pollination timing and ear fill were similar to the untreated checks of each line for all constructs, application timings and locations. Quantification results for the DGT-28 protein demonstrated a range of mean protein expression from 186.4-303.0 ng/cm$^2$. Data demonstrates robust tolerance of dgt-28 transformed corn under field conditions through the reproductive growth stages up to 4480 g ae/ha glyphosate. Data also demonstrated DGT-28 protein detection and function based on spray tolerance results.

Confirmation of heritability and tolerance of dgt-28 corn in the homozygous state. Seed from the $T_1S2$ were planted under greenhouse conditions as previously described. The same five single copy lines that were characterized under field conditions were characterized in the homogeneous state. Plants were grown until the V3 growth stage and separated into three rates of glyphosate ranging from 1120-4480 g ae/ha glyphosate (DURANGO DMA™) and four replicates per treatment. Applications were made in a track sprayer as previously described and were formulated in 2.0% w/v ammonium sulfate. An application of ammonium sulfate served as an untreated check for each line. Visual assessments were taken 7 and 14 days after treatment as previously described. Data demonstrated robust tolerance up to 4480 g ae/ha glyphosate for all events tested. Table 23.

TABLE 23

Response of homozygous dgt-28 events applied with a range of glyphosate from 1120-4480 g ae/ha + 2.0% w/v ammonium sulfate.

| Application Rate | % Injury <20% | % Injury 20-40% | % Injury >40% | % Injury Ave | % Injury Std. Dev. | % Injury Range (%) |
|---|---|---|---|---|---|---|
| TraP4::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |

TABLE 23-continued

Response of homozygous dgt-28 events applied with a range of glyphosate from 1120-4480 g ae/ha + 2.0% w/v ammonium sulfate.

| Application Rate | % Injury <20% | 20-40% | >40% | % Injury Ave | Std. Dev. | Range (%) |
|---|---|---|---|---|---|---|
| 2240 g ae/ha | 4 | 0 | 0 | 3.8 | 2.5 | 0-5 |
| 4480 g ae/ha | 4 | 0 | 0 | 14.3 | 1.5 | 12-15 |
| TraP8::dgt-28 | | | | | | |
| 0 g ae/ha glyphosate | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 9.0 | 1.2 | 8-10 |
| 4480 g ae/ha | 4 | 0 | 0 | 11.3 | 2.5 | 10-15 |
| TraP23::dgt-28 | | | | | | |
| 0 g ae/ha glyphosate | 4 | 0 | 0 | 0.0 | 0.0 | 0 |
| 1120 g ae/ha | 4 | 0 | 0 | 4.5 | 3.3 | 0-8 |
| 2240 g ae/ha | 4 | 0 | 0 | 7.5 | 2.9 | 5-10 |
| 4480 g ae/ha | 4 | 0 | 0 | 15.0 | 0.0 | 15 |
| TraP5::dgt-28 | | | | | | |
| 0 g ae/ha glyphosate | 4 | 0 | 0 | 0.0 | 0.0 | 0 |
| 1120 g ae/ha | 4 | 0 | 0 | 1.3 | 2.5 | 0-5 |
| 2240 g ae/ha | 4 | 0 | 0 | 9.0 | 2.0 | 8-12 |
| 4480 g ae/ha | 4 | 0 | 0 | 15.0 | 2.4 | 12-18 |
| Non-transformed B104 | | | | | | |
| 0 g ae/ha glyphosate | 4 | 0 | 0 | 0.0 | 0.0 | 0 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

The line from pDAB107665 that was not tolerant under field conditions demonstrated no tolerance to glyphosate and therefore consistent with field observations (data not shown). With the exception of the one line previously mentioned, all replicates that were treated with glyphosate from the lines were not sensitive to glyphosate. Therefore data demonstrates heritability to a homogeneous population of dgt-28 corn in a Mendelian fashion. Expression of the DGT-28 protein by standard ELISA demonstrated a range of mean protein expression from 27.5-65.8 ng/cm$^2$ across single copy events that were tolerant to glyphosate. Data demonstrates functional protein and stability of the DGT-28 protein across generations.

Postemergence herbicide toleranceu use of glyphosate as a selectable marker. As previously described, $T_0$ transformed plants were moved from tissue culture and acclimated in the greenhouse. The events tested contained dgt-28 linked to TraP5, TraP8, and TraP23 chloroplast transit peptides. It was demonstrated that these $T_0$ plants provided robust tolerance up to 4480 g ae/ha glyphosate, and non-transformed plants were controlled with glyphosate at concentrations as low as 280 g ae/ha. These data demonstrate that dgt-28 can be utilized as a selectable marker using a concentration of glyphosate ranging from 280-4480 g ae/ha.

A number of seed from fixed lines of corn which contain the dgt-28 transgene are spiked into a number of non-transformed corn seed. The seed are planted and allowed to grow to the V1-V3 developmental stage, at which time the plantlets are sprayed with a selecting dose of glyphosate in the range of 280-4480 g ae/ha. Following 7-10 days, sensitive and resistant plants are counted, and the amount of glyphosate tolerant plants correlates with the original number of transgenic seed containing the dgt-28 transgene which are planted.

Stacking of dgt-28 Corn. The AAD-1 protein is used as the selectable marker in dgt-28 transformed corn for research purposes. The aad-1 gene can also be utilized as a herbicide tolerant trait in corn to provide robust 2,4-D tolerance up to a V8 application in a crop. Four events from the constructs pDAB107663 (TraP4::dgt-28), pDAB107664 (TraP8::dgt-28) and pDAB107666 (TraP5::dgt-28) were characterized for the tolerance of a tank mix application of glyphosate and 2,4-D. The characterization study was completed with $F_1$ seed under greenhouse conditions. Applications were made in a track sprayer as previously described at the following rates: 1120-2240 g ae/ha glyphosate (selective for the dgt-28 gene), 1120-2240 g ae/ha 2,4-D (selective for the aad-1 gene), or a tank mixture of the two herbicides at the rates described. Plants were graded at 7 and 14 DAT. Spray results for applications of the herbicides at 2240 g ae/ha are shown in Table 24.

TABLE 24

Response of $F_1$ aad-1 and dgt-28 corn sprayed with 2240 g ae/ha of 2,4-D, glyphosate and a tank mix combination of the two herbicides 14 days after treatment.

| $F_1$ Event | 2240 g ae/ha 2,4-D Mean % injury | Std. Dev. | 2240 g ae/ha glyphosate Mean % injury | Std. Dev. | 2240 g ae/ha 2,4-D + 2240 g ae/ha glyphosate Mean % injury | Std. Dev. |
|---|---|---|---|---|---|---|
| 107663[3]-012.AJ001 | 5.0 | 4.1 | 3.8 | 4.8 | 8.8 | 3.0 |
| 107663[3]-029.AJ001 | 2.5 | 5.0 | 1.3 | 2.5 | 5.0 | 5.8 |
| 107663[3]-027.AJ001 | 2.5 | 2.9 | 11.8 | 2.9 | 13.8 | 2.5 |
| 107663[3]-011.AJ001 | 3.8 | 2.5 | 11.5 | 1.0 | 12.8 | 1.5 |
| B104 | 27.5 | 17.7 | 100.0 | 0.0 | 100.0 | 0.0 |

The results confirm that dgt-28 can be successfully stacked with aad-1, thus increasing the spectrum herbicides that may be applied to the crop of interest (glyphosate+ phenoxyacetic acids for dgt-28 and aad-1, respectively). In crop production where hard to control broadleaf weeds or resistant weed biotypes exist the stack can be used as a means of weed control and protection of the crop of interest. Additional input or output traits can also be stacked with the dgt-28 gene in corn and other plants.

Soybean Transformation. Transgenic soybean (*Glycine max*) containing a stably integrated dgt-28 transgene was generated through *Agrobacterium*-mediated transformation of soybean cotyledonary node explants. A disarmed *Agrobacterium* strain carrying a binary vector containing a functional dgt-28 was used to initiate transformation.

*Agrobacterium*-mediated transformation was carried out using a modified half-cotyledonary node procedure of Zeng et al. (Zeng P., Vadnais D. A., Zhang Z., Polacco J. C., (2004), *Plant Cell Rep.,* 22(7): 478-482). Briefly, soybean seeds (cv. Maverick) were germinated on basal media and cotyledonary nodes are isolated and infected with *Agrobacterium*. Shoot initiation, shoot elongation, and rooting media are supplemented with cefotaxime, timentin and vancomycin for removal of *Agrobacterium*. Selection via a herbicide was employed to inhibit the growth of non-transformed shoots. Selected shoots are transferred to rooting medium for root development and then transferred to soil mix for acclimatization of plantlets.

Terminal leaflets of selected plantlets were treated topically (leaf paint technique) with a herbicide to screen for putative transformants. The screened plantlets were transferred to the greenhouse, allowed to acclimate and then leaf-painted with a herbicide to reconfirm tolerance. These putative transformed $T_0$ plants were sampled and molecular analyses was used to confirm the presence of the herbicidal selectable marker, and the dgt-28 transgene. $T_0$ plants were allowed to self fertilize in the greenhouse to produce $T_1$ seed.

A second soybean transformation method can be used to produce additional transgenic soybean plants. A disarmed *Agrobacterium* strain carrying a binary vector containing a functional dgt-28 is used to initiate transformation.

*Agrobacterium*-mediated transformation was carried out using a modified half-seed procedure of Paz et al., (Paz M., Martinez J., Kalvig A., Fonger T., and Wang K., (2005) *Plant Cell Rep.,* 25: 206-213). Briefly, mature soybean seeds were sterilized overnight with chlorine gas and imbibed with sterile $H_2O$ twenty hours before *Agrobacterium*-mediated plant transformation. Seeds were cut in half by a longitudinal cut along the hilum to separate the seed and remove the seed coat. The embryonic axis was excised and any axial shoots/buds were removed from the cotyledonary node. The resulting half seed explants were infected with *Agrobacterium*. Shoot initiation, shoot elongation, and rooting media were supplemented with cefotaxime, timentin and vancomycin for removal of *Agrobacterium*. Herbicidal selection was employed to inhibit the growth of non-transformed shoots. Selected shoots were transferred to rooting medium for root development and then transferred to soil mix for acclimatization of plantlets.

Putative transformed $T_0$ plants were sampled and molecular analyses was used to confirm the presence of the selectable marker and the dgt-28 transgene. Several events were identified as containing the transgenes. These $T_0$ plants were advanced for further analysis and allowed to self fertilize in the greenhouse to give rise to $T_1$ seed.

Confirmation of heritability of dgt-28 to the T1 generation. Heritability of the DGT-28 protein into $T_1$ generation was assessed in one of two ways. The first method included planting $T_1$ seed into Metro-mix media and applying 411 g ae/ha IGNITE™ 280 SL on germinated plants at the $1^{st}$ trifoliate growth stage. The second method consisted of homogenizing seed for a total of 8 replicates using a ball bearing and a genogrinder. ELISA strip tests to detect for the PAT protein were then used to detect heritable events as the selectable marker was on the same plasmid as dgt-28. For either method if a single plant was tolerant to glufosinate or was detected with the PAT ELISA strip test, the event demonstrated heritability to the $T_1$ generation.

A total of five constructs were screened for heritability as previously described. The plasmids contained dgt-28 linked with TraP4, TraP8 and TraP23 The events across constructs demonstrated 68% heritability of the PAT::DGT-28 protein to the $T_1$ generation.

Postemergence herbicide ttolerance in dgt-28 transformed $T_1$ soybean. Seeds from $T_1$ events that were determined to be heritable by the previously described screening methods were planted in Metro-mix media under greenhouse conditions. Plants were grown until the $1^{st}$ trifoliate was fully expanded and treated with 411 g ae/ha IGNITE™ 280 SL for selection of the pat gene as previously described. Resistant plants from each event were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment when enough plants existed. These plants were compared against wildtype Petite havana tobacco. All plants were sprayed with a track sprayer set at 187 L/ha. The plants were sprayed from a range of 560-4480 g ae/ha DURANGO™ dimethylamine salt (DMA). All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The $T_1$ generation is segregating, so some variable response is expected due to difference in zygosity.

TABLE 25

Spray results demonstrate at 14 DAT (days after treatment) robust tolerance up to 4480 g ae/ha glyphosate of at least one dgt-28 event per construct characterized. Representative single copy events of the constructs all provided tolerance up to 4480 g ae/ha compared to the Maverick negative control.

| Application Rate | % Injury <20% | % Injury 20-40% | % Injury >40% | % Injury Ave | % Injury Std. Dev. | % Injury Range (%) |
|---|---|---|---|---|---|---|
| pDAB107543 (TraP4::dgt-28) | | | | | | |
| 0 g ae/ha glyphosate | 4 | 0 | 0 | 0.0 | 0.0 | 0 |
| 560 g ae/ha | 0 | 4 | 0 | 33.8 | 7.5 | 25-40 |
| 1120 g ae/ha | 2 | 2 | 0 | 25.0 | 11.5 | 15-35 |
| 2240 g ae/ha | 2 | 2 | 0 | 17.5 | 2.9 | 15-20 |
| 4480 g ae/ha | 0 | 2 | 2 | 33.8 | 13.1 | 20-45 |
| pDAB107545 (TraP8::dgt-28) | | | | | | |
| 0 g ae/ha glyphosate | 4 | 0 | 0 | 0.0 | 0.0 | 0 |
| 560 g ae/ha | 4 | 0 | 0 | 1.5 | 1.0 | 0-2 |
| 1120 g ae/ha | 4 | 0 | 0 | 2.8 | 1.5 | 2-5 |
| 2240 g ae/ha | 4 | 0 | 0 | 5.0 | 2.4 | 2-8 |
| 4480 g ae/ha | 4 | 0 | 0 | 9.5 | 1.9 | 8-12 |
| pDAB107548 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 1.8 | 2.4 | 0-5 |
| 1120 g ae/ha | 4 | 0 | 0 | 2.8 | 1.5 | 2-5 |
| 2240 g ae/ha | 4 | 0 | 0 | 3.5 | 1.7 | 2-5 |
| 4480 g ae/ha | 4 | 0 | 0 | 8.8 | 3.0 | 5-12 |
| pDAB107553 (TraP23::dgt-28) | | | | | | |
| 0 g ae/ha glyphosate | 4 | 0 | 0 | 0.0 | 0.0 | 0 |
| 560 g ae/ha | 4 | 0 | 0 | 5.0 | 0.0 | 5 |
| 1120 g ae/ha | 4 | 0 | 0 | 9.0 | 1.2 | 8-10 |
| 2240 g ae/ha | 4 | 0 | 0 | 10.5 | 1.0 | 10-12 |
| 4480 g ae/ha | 4 | 0 | 0 | 16.5 | 1.7 | 15-18 |
| Maverick (neg. control) | | | | | | |
| 0 g ae/ha glyphosate | 4 | 0 | 0 | 0.0 | 0.0 | 0 |
| 560 g ae/ha | 0 | 0 | 4 | 82.5 | 12.6 | 70-100 |
| 1120 g ae/ha | 0 | 0 | 4 | 100.0 | 0.0 | 100 |
| 2240 g ae/ha | 0 | 0 | 4 | 100.0 | 0.0 | 100 |
| 4480 g ae/ha | 0 | 0 | 4 | 100.0 | 0.0 | 100 |

dgt-28 Protection against elevated glyphosate rates in the $T_2$ generation. A 45 plant progeny test was conducted on two to five $T_2$ lines of dgt-28 per construct. Homozygous lines were chosen based on zygosity analyses completed in the previous generation. The seeds were planted as previously described. Plants were then sprayed with 411 g ae/ha IGNITE 280 SL for the selection of the pat selectable marker as previously described. After 3 DAT, resistant and sensitive plants were counted.

For constructs containing TraP4 linked with dgt-28 (pDAB107543 and pDAB107548), nine out of twelve lines tested did not segregate, thereby confirming homogeneous lines in the $T_2$ generation. Lines containing TraP8 linked with dgt-28 (pDAB107545) demonstrated two out of the four lines with no segregants and demonstrating Mendelian inheritance through at least two generation of dgt-28 in soybean. Tissue samples were taken from resistant plants and the DGT-28 protein was quantified by standard ELISA methods. Data demonstrated a range of mean DGT-28 protein from 32.8-107.5 ng/cm$^2$ for non-segregating $T_2$ lines tested. Lines from the construct pDAB107553 (TraP23::dgt-28) were not previously selected with glufosinate, and the dose response of glyphosate was utilized as both to test homogenosity and tolerance to elevated rates of glyphosate. Replicates from the lines from construct pDAB107553 were tolerant to rates ranging from 560-4480 g ae/ha glyphosate, and were therefore confirmed to be a homogeneous population and heritable to at least two generations.

Rates of DURANGO DMA ranging from 560-4480 g ae/ha glyphosate were applied to 2-3 trifoliate soybean as previously described. Visual injury data 14 DAT confirmed the tolerance results that were demonstrated in the $T_1$ generation.

TABLE 26

The data demonstrate robust tolerance of the dgt-28 tobacco up to 3360 g ae/ha glyphosate through two generations, compared to the non-transformed control.

| Application Rate | % Injury <20% | % Injury 20-40% | % Injury >40% | % Injury Ave | % Injury Std. Dev. | % Injury Range (%) |
|---|---|---|---|---|---|---|
| pDAB107543 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 8.0 | 0.0 | 8 |
| 1120 g ae/ha | 4 | 0 | 0 | 14.3 | 1.5 | 12-15 |
| 2240 g ae/ha | 4 | 0 | 0 | 18.0 | 0.0 | 18 |
| 4480 g ae/ha | 0 | 4 | 0 | 24.5 | 3.3 | 20-28 |
| pDAB107545 (TraP8::dgt-28) | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 2.8 | 1.5 | 2-5 |
| 2240 g ae/ha | 4 | 0 | 0 | 5.0 | 0.0 | 5 |
| 4480 g ae/ha | 4 | 0 | 0 | 10.0 | 0.0 | 10 |
| pDAB107548 (TraP4::dgt-28) | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| 4480 g ae/ha | 4 | 0 | 0 | 10.0 | 0.0 | 10 |
| pDAB107553 (TraP23::dgt-28) | | | | | | |
| 0 g ae/ha glyphosate | 4 | 0 | 0 | — | 0.0 | 0.0 |
| 560 g ae/ha | 4 | 0 | 0 | — | 10.0 | 0.0 |
| 1120 g ae/ha | 4 | 0 | 0 | — | 10.0 | −4.4 |
| 2240 g ae/ha | 4 | 0 | 0 | — | 13.0 | −2.4 |
| 4480 g ae/ha | 3 | 1 | 0 | — | 15.5 | 4.1 |
| Maverick (neg. control) | | | | | | |
| 0 g ae/ha glyphosate | 4 | 0 | 0 | 0.0 | 0.0 | 0 |
| 560 g ae/ha | 0 | 0 | 4 | 77.5 | 15.0 | 70-100 |
| 1120 g ae/ha | 0 | 0 | 4 | 97.5 | 2.9 | 95-100 |
| 2240 g ae/ha | 0 | 0 | 4 | 100.0 | 0.0 | 100 |
| 4480 g ae/ha | 0 | 0 | 4 | 100.0 | 0.0 | 100 |

Transformation of rice with dgt-28. Transgenic rice (*Oryza sativa*) containing a stably integrated dgt-28 transgene is generated through *Agrobacterium*-mediated transformation of sterilized rice seed. A disarmed *Agrobacterium* strain carrying a binary vector containing a functional dgt-28 is used to initiate transformation.

Culture media are adjusted to pH 5.8 with 1 M KOH and solidified with 2.5 g/l Phytagel (Sigma-Aldrich, St. Louis, Mo.). Embryogenic calli are cultured in 100×20 mm petri dishes containing 30 ml semi-solid medium. Rice plantlets are grown on 50 ml medium in MAGENTA boxes. Cell suspensions are maintained in 125 ml conical flasks containing 35 mL liquid medium and rotated at 125 rpm. Induction and maintenance of embryogenic cultures occur in the dark at 25-26° C, and plant regeneration and whole-plant culture occur in illuminated room with a 16-h photoperiod (Zhang et al. 1996).

Induction and maintenance of embryogenic callus is performed on a modified NB basal medium as described previously (Li et al. 1993), wherein the media is adapted to contain 500 mg/L glutamine. Suspension cultures are initiated and maintained in SZ liquid medium (Zhang et al. 1998) with the inclusion of 30 g/L sucrose in place of maltose. Osmotic medium (NBO) consisting of NB medium with the addition of 0.256 M each of mannitol and sorbitol. Herbicide resistant callus is selected on NB medium supplemented with the appropriate herbicide selective agent for 3-4 weeks. Pre-regeneration is performed on medium (PRH50) consisting of NB medium with 2,4-dichlorophenoxyacetic acid (2,4-D), 1 mg/l α-naphthaleneacetic acid (NAA), 5 mg/l abscisic acid (ABA) and selective herbicide for 1 week. Regeneration of plantlets follow the culturing on regeneration medium (RNH50) comprising NB medium containing 2,4-D, 0.5 mg/l NAA, and selective herbicide until putatively transgenic shoots are regenerated. Shoots are transferred to rooting medium with half-strength Murashige and Skoog basal salts and Gamborg's B5 vitamins, supplemented with 1% sucrose and selective herbicide.

Mature desiccated seeds of *Oryza sativa* L. japonica cv. Taipei 309 are sterilized as described in Zhang et al. 1996. Embryogenic tissues are induced by culturing sterile mature rice seeds on NB medium in the dark. The primary callus approximately 1 mm in diameter, is removed from the scutellum and used to initiate cell suspension in SZ liquid medium. Suspensions are then maintained as described in Zhang 1996. Suspension-derived embryogenic tissues are removed from liquid culture 3-5 days after the previous subculture and placed on NBO osmotic medium to form a circle about 2.5 cm across in a petri dish and cultured for 4 h prior to bombardment. Sixteen to twenty hours after bombardment, tissues are transferred from NBO medium onto NBH50 selection medium, ensuring that the bombarded surface is facing upward, and incubated in the dark for 14-17 days. Newly formed callus is then separated from the original bombarded explants and placed nearby on the same medium. Following an additional 8-12 days, relatively compact, opaque callus is visually identified, and transferred to PRH50 pre-regeneration medium for 7 days in the dark. Growing callus, which become more compact and opaque is then subcultured onto RNH50 regeneration medium for a period of 14-21 days under a 16-h photoperiod. Regenerating shoots are transferred to MAGENTA boxes containing ½ MSH50 medium. Multiple plants regenerated from a single explant are considered siblings and are treated as one independent plant line. A plant is scored as positive for the dgt-28 gene if it produces thick, white roots and grows vigorously on ½ MSH50 medium. Once plantlets reach the top of the MAGENTA boxes, they are transferred to soil in a 6-cm pot under 100% humidity for a week, and then are moved to a growth chamber with a 14-h light period at 30° C. and in the dark at 21° C. for 2-3 weeks before transplanting into 13-cm pots in the greenhouse. Seeds are collected and dried at 37° C. for one week prior to storage at 4° C.

$T_0$ analysis of dgt-28 rice. Transplanted rice transformants obtained via an *Agrobacterium* transformation method were transplanted into media and acclimated to greenhouse conditions. All plants were sampled for PCR detection of dgt-28 and results demonstrate twenty-two PCR positive events for pDAB110827 (TraP8::dgt-28) and a minimum of sixteen PCR positive events for pDAB110828 (TraP23::dgt-28). Southern analysis for dgt-28 of the PCR positive events demonstrated simple (1-2 copy) events for both constructs. Protein expression of selected $T_0$ events demonstrated DGT-28 protein expression ranges from below levels of detection to 130 ng/cm$^2$. Selected $T_0$ events from construct pDAB110828 were treated with 2240 g ae/ha DURANGO DMA™ as previously described and assessed 7 and 14 days after treatment. Data demonstrated robust tolerance to the rate of glyphosate applied. All PCR positive plants were allowed to produced $T_1$ seed for further characterization.

Dgt-28 heritability in rice. A 100 plant progeny test was conducted on four $T_1$ lines of dgt-28 from construct pDAB110827 containing the chloroplast transit peptide TraP8. The seeds were planted into pots filled with media. All plants were then sprayed with 560 g ae/ha DURANGO DMA™ for the selection of the dgt-28 gene as previously described. After 7 DAT, resistant and sensitive plants were counted. Two out of the four lines tested for each construct segregated as a single locus, dominant Mendelian trait (3R:1S) as determined by Chi square analysis. Dgt-28 is a heritable glyphosate resistance gene in multiple species.

Postemergence herbicide tolerance in dgt-28 transformed $T_1$ rice. $T_1$ resistant plants from each event used in the progeny testing were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment. These plants were compared against wildtype kitaake rice. All plants were sprayed with a track sprayer set at 187 L/ha. The plants were sprayed from a range of 560-2240 g ae/ha DURANGO DMA™. All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The $T_1$ generation is segregating, so some variable response is expected due to difference in zygosity.

Spray results demonstrate at 7 DAT (days after treatment) minimal vegetative injury to elevated rates of glyphosate were detected (data not shown).

TABLE 27

Visual injury data at 14 DAT demonstrates less than 15% mean visual injury up to 2240 g ae/ha glyphosate.

| Application Rate | % Injury <20% | % Injury 20-40% | % Injury >40% | % Injury Ave | % Injury Std. Dev. | % Injury Range (%) |
|---|---|---|---|---|---|---|
| TraP8::dgt-28 Event 1 | | | | | | |
| 0 g ae/ha glyphosate | 4 | 0 | 0 | 0.0 | 0.0 | 0 |
| 560 g ae/ha | 4 | 0 | 0 | 0.0 | 0.0 | 0 |
| 1120 g ae/ha | 4 | 0 | 0 | 0.0 | 0.0 | 0 |
| 2240 g ae/ha | 4 | 0 | 0 | 0.0 | 0.0 | 0 |
| TraP8::dgt-28 Event 2 | | | | | | |
| 0 g ae/ha glyphosate | 4 | 0 | 0 | 0.0 | 0.0 | 0 |
| 560 g ae/ha | 4 | 0 | 0 | 3.8 | 4.8 | 0-10 |
| 1120 g ae/ha | 4 | 0 | 0 | 12.0 | 3.6 | 8-15 |
| 2240 g ae/ha | 4 | 0 | 0 | 15.0 | 6.0 | 8-20 |
| Non-transformed control | | | | | | |
| 0 g ae/ha glyphosate | 4 | 0 | 0 | 0.0 | 0.0 | 0 |
| 560 g ae/ha | 0 | 0 | 4 | 81.3 | 2.5 | 80-85 |
| 1120 g ae/ha | 0 | 0 | 4 | 95.0 | 5.8 | 90-100 |
| 2240 g ae/ha | 0 | 0 | 4 | 96.3 | 4.8 | 90-100 |

Protein detection of DGT-28 was assessed for replicates from all four $T_1$ lines tested from pDAB110827. Data demonstrated DGT-28 mean protein ranges from 20-82 ng/cm$^2$ and 21-209 ng/cm$^2$ for hemizygous and homozygous replicates respectively. These results demonstrated stable protein expression to the $T_1$ generation and tolerance of dgt-28 rice up to 2240 g ae/ha glyphosate following an application of 560 g ae/ha glyphosate used for selection.

Transformation of tobacco with dgt-28. Tobacco (cv. Petit Havana) leaf pieces were transformed using *Agrobacterium tumefaciens* containing the dgt-28 transgene. Single colonies containing the plasmid which contains the dgt-28 transgene were inoculated into 4 mL of YEP medium containing spectinomycin (50 μg/mL) and streptomycin (125 μg/mL) and incubated overnight at 28° C. on a shaker at 190 rpm. The 4 mL seed culture was subsequently used to inoculate a 25 mL culture of the same medium in a 125 mL baffled Erlenmeyer flask. This culture was incubated at 28° C. shaking at 190 rpm until it reached an $OD_{600}$ of ~1.2. Ten mL of *Agrobacterium* suspension were then placed into sterile 60×20 mm Petri™ dishes.

Freshly cut leaf pieces (0.5 cm$^2$) from plants aseptically grown on MS medium (Phytotechnology Labs, Shawnee Mission, Kans.) with 30 g/L sucrose in PhytaTrays™ (Sigma, St. Louis, Mo.) were soaked in 10 mL of overnight culture of *Agrobacterium* for a few minutes, blotted dry on sterile filter paper and then placed onto the same medium with the addition of 1 mg/L indoleacetic acid and 1 mg/L 6-benzylamino purine. Three days later, leaf pieces co-cultivated with *Agrobacterium* harboring the dgt-28 transgene were transferred to the same medium with 5 mg/L Basta™ and 250 mg/L cephotaxime.

After 3 weeks, individual $T_0$ plantlets were transferred to MS medium with 10 mg/L Basta™ and 250 mg/L cephotaxime an additional 3 weeks prior to transplanting to soil and transfer to the greenhouse. Selected $T_0$ plants (as identified using molecular analysis protocols described above) were allowed to self-pollinate and seed was collected from capsules when they were completely dried down. $T_1$ seedlings were screened for zygosity and reporter gene expression (as described below) and selected plants containing the dgt-28 transgene were identified.

Plants were moved into the greenhouse by washing the agar from the roots, transplanting into soil in 13.75 cm square pots, placing the pot into a Ziploc® bag (SC Johnson & Son, Inc.), placing tap water into the bottom of the bag, and placing in indirect light in a 30° C. greenhouse for one week. After 3-7 days, the bag was opened; the plants were fertilized and allowed to grow in the open bag until the plants were greenhouse-acclimated, at which time the bag was removed. Plants were grown under ordinary warm greenhouse conditions (27° C. day, 24° C. night, 16 hour day, minimum natural+supplemental light=1200 $\mu E/m^2s^1$).

Prior to propagation, $T_0$ plants were sampled for DNA analysis to determine the insert dgt-28 copy number by real-time PCR. Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy™ DNA isolation procedure was then followed (Qiagen, DNeasy 69109). An aliquot of the extracted DNA was then stained with Pico Green (Molecular Probes P7589) and read in the fluorometer (BioTek™) with known standards to obtain the concentration in ng/μl. A total of 100 ng of total DNA was used as template. The PCR reaction was carried out in the 9700 Geneamp™ thermocycler (Applied Biosystems), by subjecting the samples to 94° C. for 3 minutes and 35 cycles of 94° C. for 30 seconds, 64° C. for 30 seconds, and 72° C. for 1 minute and 45 seconds followed by 72° C. for 10 minutes. PCR products were analyzed by electrophoresis on a 1% agarose gel stained with EtBr and confirmed by Southern blots.

Five to nine PCR positive events with 1-3 copies of dgt-28 gene from 3 constructs containing a different chloroplast transit peptide sequence (TraP4, TraP8 and TraP23) were regenerated and moved to the greenhouse.

All PCR positive plants were sampled for quantification of the DGT-28 protein by standard ELISA. DGT-28 protein was detected in all PCR positive plants and a trend for an increase in protein concentration was noted with increasing copy number of dgt-28.

aad-12 (v1) Heritability in Tobacco. A 100 plant progeny test was conducted on five $T_1$ lines of dgt-28 per construct. Constructs contained one of the following chloroplast transit peptide sequences: TraP4, TraP8 or TraP23. The seeds were stratified, sown, and transplanted with respect much like that of the *Arabidopsis* procedure exemplified above, with the exception that null plants were not removed by in initial selection prior to transplanting. All plants were then sprayed with 280 g ae/ha IGNITE 280 SL for the selection of the pat selectable marker as previously described. After 3 DAT, resistant and sensitive plants were counted.

Four out of the five lines tested for each construct segregated as a single locus, dominant Mendelian trait (3R:1S) as determined by Chi square analysis. Dgt-28 is a heritable glyphosate resistance gene in multiple species.

Postemergence herbicide tolerance in dgt-28 transformed $T_1$ tobacco. $T_1$ resistant plants from each event used in the progeny testing were given unique identifiers and sampled for zygosity analyses of the dgt-28 gene. Zygosity data were used to assign 2 hemizygous and 2 homozygous replicates to each rate of glyphosate applied allowing for a total of 4 replicates per treatment. These plants were compared against wildtype Petite havana tobacco. All plants were sprayed with a track sprayer set at 187 L/ha. The plants were sprayed from a range of 560-4480 g ae/ha DURANGO DMA™. All applications were formulated in water with the addition of 2% w/v ammonium sulfate (AMS). Plants were evaluated at 7 and 14 days after treatment. Plants were assigned an injury rating with respect to overall visual stunting, chlorosis, and necrosis. The $T_1$ generation is segregating, so some variable response is expected due to difference in zygosity.

Spray results demonstrate at 7 DAT (days after treatment) minimal vegetative injury to elevated rates of glyphosate were detected (data not shown). Following 14 DAT, visual injury data demonstrates increased injury with single copy events of the construct containing TraP4 compared to single copy events from the constructs TraP8 and TraP23. Table 28.

TABLE 28

At a rate of 2240 g ae/ha glyphosate, an average injury of 37.5% was demonstrated with the event containing TraP4, where events containing TraP8 and TraP23 demonstrated an average injury of 9.3% and 9.5% respectively.

| Application Rate | % Injury <20% | % Injury 20-40% | % Injury >40% | % Injury Ave | % Injury Std. Dev. | % Injury Range (%) |
|---|---|---|---|---|---|---|
| TraP4::dgt-28 (pDAB107543) | | | | | | |
| 0 g ae/ha glyphosate | 4 | 0 | 0 | 0.0 | 0.0 | 0 |
| 560 g ae/ha | 2 | 2 | 0 | 18.0 | 8.1 | 10-25 |
| 1120 g ae/ha | 1 | 3 | 0 | 24.5 | 4.9 | 18-30 |
| 2240 g ae/ha | 0 | 3 | 1 | 37.5 | 6.5 | 30-45 |
| 4480 g ae/ha | 0 | 2 | 2 | 42.5 | 2.9 | 40-45 |
| TraP8::dgt-28 (pDAB107545) | | | | | | |
| 0 g ae/ha glyphosate | 4 | 0 | 0 | 0.0 | 0.0 | 0 |
| 560 g ae/ha | 4 | 0 | 0 | 3.3 | 3.9 | 0-8 |
| 1120 g ae/ha | 4 | 0 | 0 | 6.5 | 1.7 | 5-8 |
| 2240 g ae/ha | 4 | 0 | 0 | 9.3 | 3.0 | 5-12 |
| 4480 g ae/ha | 2 | 2 | 0 | 17.5 | 6.5 | 10-25 |
| TraP23::dgt-28 (pDAB107553) | | | | | | |
| 0 g ae/ha glyphosate | 4 | 0 | 0 | 0.0 | 0.0 | 0 |
| 560 g ae/ha | 4 | 0 | 0 | 10.0 | 1.6 | 8-12 |
| 1120 g ae/ha | 4 | 0 | 0 | 8.8 | 3.0 | 5-12 |
| 2240 g ae/ha | 4 | 0 | 0 | 9.5 | 4.2 | 5-15 |
| 4480 g ae/ha | 4 | 0 | 0 | 15.8 | 1.5 | 15-18 |
| Petite havana | | | | | | |
| 0 g ae/ha glyphosate | 4 | 0 | 0 | 0.0 | 0.0 | 0 |
| 560 g ae/ha | 0 | 0 | 4 | 85.0 | 4.1 | 80-90 |
| 1120 g ae/ha | 0 | 0 | 4 | 91.3 | 2.5 | 90-95 |
| 2240 g ae/ha | 0 | 0 | 4 | 94.5 | 3.3 | 90-98 |
| 4480 g ae/ha | 0 | 0 | 4 | 98.3 | 2.4 | 95-100 |

These results demonstrated tolerance of dgt-28 up to 4480 g ae/ha glyphosate, as well as differences in tolerance provided by chloroplast transit peptide sequences linked to the dgt-28 gene.

Dgt-28 protection against elevated glyphosate rates in the $T_2$ generation. A 25 plant progeny test was conducted on two to three $T_2$ lines of dgt-28 per construct. Homozygous lines were chosen based on zygosity analyses completed in the previous generation. The seeds were stratified, sown, and transplanted as previously described. All plants were then sprayed with 280 g ae/ha Ignite 280 SL for the selection of the pat selectable marker as previously described. After 3 DAT, resistant and sensitive plants were counted. All lines tested for each construct did not segregate thereby confirming homogeneous lines in the $T_2$ generation and demonstrating Mendelian inheritance through at least two generation of dgt-28 in tobacco.

Rates of DURANGO DMA™ ranging from 420-3360 g ae/ha glyphosate were applied to 2-3 leaf tobacco as previously described. Visual injury data 14 DAT confirmed the tolerance results that were demonstrated in the T1 generation. Foliar results from a two copy lines from the construct containing TraP4 demonstrated similar tolerance to that of single copy TraP8 and TraP23 lines (data not shown).

TABLE 29

Single copy lines from the construct containing TraP4 with dgt-28 demonstrated increased injury compared to lines from constructs containing TraP8 and TraP23 with dgt-28.

| Application Rate | % Injury <20% | % Injury 20-40% | % Injury >40% | % Injury Ave | % Injury Std. Dev. | % Injury Range (%) |
|---|---|---|---|---|---|---|
| TraP4::dgt-28 (pDAB107543) | | | | | | |
| 0 g ae/ha glyphosate | 4 | 0 | 0 | 0.0 | 0.0 | 0 |
| 420 g ae/ha | 0 | 4 | 0 | 23.8 | 4.8 | 20-30 |
| 840 g ae/ha | 0 | 4 | 0 | 30.0 | 4.1 | 25-35 |
| 1680 g ae/ha | 0 | 4 | 0 | 35.0 | 5.8 | 30-40 |
| 3360 g ae/ha | 0 | 4 | 0 | 31.3 | 2.5 | 30-35 |
| TraP8::dgt-28 (pDAB107545) | | | | | | |
| 0 g ae/ha glyphosate | 4 | 0 | 0 | 0.0 | 0.0 | 0 |
| 420 g ae/ha | 4 | 0 | 0 | 0.0 | 0.0 | 0 |
| 840 g ae/ha | 4 | 0 | 0 | 2.5 | 2.9 | 0-5 |
| 1680 g ae/ha | 4 | 0 | 0 | 9.3 | 3.4 | 5-12 |
| 3360 g ae/ha | 4 | 0 | 0 | 10.5 | 1.0 | 10-12 |
| TraP23::dgt-28 (pDAB107553) | | | | | | |
| 0 g ae/ha glyphosate | 4 | 0 | 0 | 0.0 | 0.0 | 0 |
| 420 g ae/ha | 4 | 0 | 0 | 0.0 | 0.0 | 0 |
| 840 g ae/ha | 4 | 0 | 0 | 6.3 | 2.5 | 5-10 |
| 1680 g ae/ha | 4 | 0 | 0 | 10.0 | 0.0 | 10 |
| 3360 g ae/ha | 3 | 1 | 0 | 13.8 | 4.8 | 10-20 |
| Petite havana | | | | | | |
| 0 g ae/ha glyphosate | 4 | 0 | 0 | 0.0 | 0.0 | 0 |
| 420 g ae/ha | 0 | 0 | 4 | 95.0 | 0.0 | 95 |
| 840 g ae/ha | 0 | 0 | 4 | 98.8 | 1.0 | 98-100 |
| 1680 g ae/ha | 0 | 0 | 4 | 99.5 | 1.0 | 98-100 |
| 3360 g ae/ha | 0 | 0 | 4 | 100 | 0.0 | 100 |

The data demonstrate robust tolerance of dgt-28 tobacco up to 3360 g ae/ha glyphosate through two generations compared to the non-transformed control.

Selected plants from each event were sampled prior to glyphosate applications for analyses of the DGT-28 protein by standard DGT-28 ELISA. Data demonstrated DGT-28 mean protein expression of the simple (1-2 copy) lines across constructs ranging from 72.8-114.5 ng/cm$^2$. Data demonstrates dgt-28 is expressing protein in the $T_2$ generation of transformed tobacco and tolerance data confirms functional DGT-28 protein.

Stacking of dgt-28 to increase herbicide spectrum in tobacco (cv. Petit Havana). Homozygous dgt-28 (pDAB107543 and pDAB107545) and aad-12 v1 (pDAB3278) plants (see PCT/US2006/042133 for the latter, which is incorporated herein by this reference in its entirety) were both reciprocally crossed and $F_1$ seed was collected. The $F_1$ seed from two reciprocal crosses of each gene were stratified and treated 6 reps of each cross were treated with 1120 g ae/ha glyphosate (selective for the dgt-28 gene), 1120 g ae/ha 2,4-D (selective for the aad-12 gene), or a tank mixture of the two herbicides at the rates described. Plants were graded at 14 DAT. Spray results are shown in Table 30.

TABLE 30

Response of $F_1$ aad-12 and dgt-28

| Application Rate | aad-12 × TraP4::dgt-28 Tolerance | aad-12 × TraP8::dgt-28 Tolerance | Petite havana Tolerance |
|---|---|---|---|
| 1120 g ae/ha 2,4-D | ++++ | ++++ | − |
| 1120 g ae/ha glyphosate | ++ | ++ | − |
| 1120 g ae/ha 2,4-D + 1120 g ae/ha glyphosate | ++ | ++ | − |

The results confirm that dgt-28 can be successfully stacked with aad-12 (v1), thus increasing the spectrum herbicides that may be applied to the crop of interest (glyphosate+phenoxyactetic acids for dgt-28 and aad-12, respectively). In crop production where hard to control broadleaf weeds or resistant weed biotypes exist the stack can be used as a means of weed control and protection of the crop of interest. Additional input or output traits could also be stacked with the dgt-28 gene.

Resistance To Glyphosate In Wheat. Production of binary vectors encoding DGT-28. Binary vectors containing DGT-28 expression and PAT selection cassettes were designed and assembled using skills and techniques commonly known in the art. Each DGT-28 expression cassette contained the promoter, 5' untranslated region and intron from the Ubiquitin (Ubi) gene from *Zea mays* (Toki et al., *Plant Physiology* 1992, 100 1503-07), followed by a coding sequence consisting of one of four transit peptides (TraP4, TraP8, TraP23 or TraP5) fused to the 5' end of a synthetic version of the 5-enolpyruvylshikimate-3-phosphate synthase gene (DGT-28), which had been codon optimized for expression in plants. The DGT-28 expression cassette terminated with a 3' untranslated region (UTR) comprising the transcriptional terminator and polyadenylation site of a lipase gene (Vp1) from *Z. mays* (Paek et al., *Mol. Cells.* 1998 30; 8(3) 336-42). The PAT selection cassette comprised of the promoter, 5' untranslated region and intron from the Actin (Act1) gene from *Oryza saliva* (McElroy et al., *The Plant Cell* 1990 2(2) 163-171), followed by a synthetic version of the phosphinothricin acetyl transferase (PAT) gene isolated from *Streptomyces viridochromogenes*, which had been codon optimized for expression in plants. The PAT gene encodes a protein that confers resistance to inhibitors of glutamine synthetase comprising phosphinothricin, glufosinate, and bialaphos (Wohlleben et al., Gene 1988, 70(1), 25-37). The selection cassette was terminated with the 3' UTR comprising the transcriptional terminator and polyadenylation sites from the 35S gene of cauliflower mosaic virus (CaMV) (Chenault et al., *Plant Physiology* 1993 101 (4), 1395-1396).

The selection cassette was synthesized by a commercial gene synthesis vendor (GeneArt, Life Technologies) and cloned into a Gateway-enabled binary vector. The DGT-28 expression cassettes were sub-cloned into pDONR221. The resulting ENTRY clone was used in a LR Clonase II (Invitrogen, Life Technologies) reaction with the Gateway-enabled binary vector encoding the phosphinothricin acetyl transferase (PAT) expression cassette. Colonies of all assembled plasmids were initially screened by restriction digestion of purified DNA using restriction endonucleases obtained from New England BioLabs (NEB; Ipswich, Mass.) and Promega (Promega Corporation, WI). Plasmid DNA preparations were performed using the QIAprep Spin Miniprep Kit (Qiagen, Hilden) or the Pure Yield Plasmid Maxiprep System (Promega Corporation, Wis.), following the instructions of the suppliers. Plasmid DNA of selected clones was sequenced using ABI Sanger Sequencing and Big Dye Terminator v3.1 cycle sequencing protocol (Applied Biosystems, Life Technologies). Sequence data were assembled and analyzed using the SEQUENCHER™ software (Gene Codes Corporation, Ann Arbor, Mich.).

The resulting four binary expression clones: pDAS000122 (TraP4-DGT28), pDAS000123 (TraP8-DGT28), pDAS000124 (TraP23-DGT28) and pDAS000125 (TraP5-DGT28) were each transformed into *Agrobacterium tumefaciens* strain EHA105.

Production of transgenic wheat events with Dgt-28 expression construct. Transgenic wheat plants expressing one of the four DGT-28 expression constructs were generated by *Agrobacterium*-mediated transformation using the donor wheat line Bobwhite MPB26RH, following a protocol similar to Wu et al., *Transgenic Research* 2008, 17:425-436. Putative T0 transgenic events were selected for phosphinothricin (PPT) tolerance, the phenotype conferred by the PAT selectable marker, and transferred to soil. The T0 plants were grown under glasshouse containment conditions and T1 seed was produced. Overall, about 45 independent T0 events were generated for each DGT-28 expression construct.

Glyphosate resistance in $T_0$ wheat dgt-28 wheat events. $T_0$ events were allowed to acclimate in the greenhouse and were grown until 2-4 new, normal looking leaves had emerged from the whorl (i.e., plants had transitioned from tissue culture to greenhouse growing conditions). Plants were grown at 25° C. under 12 hour of supplemental lighting in the greenhouse until maturity. An initial screen of glyphosate tolerance and Taqman analyses was completed on $T_1$ plants grown under the same conditions as previously described. Data allowed for determination of heritable $T_1$ events to be further characterized. Six low copy (1-2 copy) and two multi-copy $T_1$ events were replanted under greenhouse conditions and grown until the 3 leaf stage. $T_1$ plants were sprayed with a commercial formulation of glyphosate (Durango DMA™) from a range of 420-3360 g ae/ha, which are capable of significant injury to untransformed wheat lines. The addition of 2% w/v ammonium sulfate was included in the application. A lethal dose is defined as the rate that causes >75% injury to the Bob White MPB26RH non-transformed control. Herbicide was applied.

In this example, the glyphosate applications were utilized for both determining the segregation of the dgt-28 gene in the $T_1$ generation as well as demonstrating tolerance to increasing levels of glyphosate. The response of the plants is presented in terms of a scale of visual injury 21 days after treatment (DAT). Data are presented as a histogram of individuals exhibiting less than 25% visual injury (4), 25%-50% visual injury (3), 50%-75% visual injury (2) and greater than 75% injury (1). An arithmetic mean and standard deviation is presented for each construct used for wheat transformation. The scoring range of individual response is also indicated in the last column for each rate and transformation. Wild-type, non-transformed wheat (c.v. Bob White MPB26RH) served as a glyphosate sensitive control. In the $T_1$ generation hemizygous and homozygous plants were available for testing for each event and therefore were included for each rate of glyphosate tested. Hemizygous plants will contain half of the dose of the gene as homozygous plants, therefore variability of response to glyphosate may be expected in the $T_1$ generation.

The results of the $T_1$ dgt-28 wheat plants demonstrated that tolerance to glyphosate was achieved at rates up to 3360 g ae/ha with the chloroplast transit peptides TraP4, TraP5, TraP8 and TraP23. Table 31. Data are of a low copy $T_1$ event but are representative of the population for each construct.

TABLE 31

Response of low copy $T_1$ dgt-28 wheat events to glyphosate 21 days after treatment.

| Application | % Injury | | | | % Injury | | |
|---|---|---|---|---|---|---|---|
| Rate | <25% | 25-50% | 50-75% | >75% | Ave | Std. Dev. | Range (%) |
| TraP4::dgt-28 | | | | | | | |
| 420 g ae/ha | 5 | 0 | 0 | 0 | 4.00 | 0.00 | 4 |
| 840 g ae/ha | 6 | 2 | 0 | 0 | 3.75 | 0.46 | 3-4 |
| 1680 g ae/ha | 4 | 2 | 0 | 0 | 3.67 | 0.52 | 3-4 |
| 3360 g ae/ha | 4 | 2 | 0 | 0 | 3.67 | 0.52 | 3-4 |
| TraP8::dgt-28 | | | | | | | |
| 420 g ae/ha | 5 | 3 | 0 | 0 | 3.63 | 0.52 | 3-4 |
| 840 g ae/ha | 3 | 5 | 0 | 0 | 3.38 | 0.52 | 3-4 |
| 1680 g ae/ha | 4 | 3 | 0 | 0 | 3.57 | 0.53 | 3-4 |
| 3360 g ae/ha | 5 | 5 | 0 | 0 | 3.50 | 0.53 | 3-4 |
| TraP23::dgt-28 | | | | | | | |
| 420 g ae/ha | 9 | 2 | 0 | 0 | 3.82 | 0.40 | 3-4 |
| 840 g ae/ha | 8 | 1 | 0 | 0 | 3.89 | 0.33 | 3-4 |
| 1680 g ae/ha | 7 | 5 | 0 | 0 | 3.58 | 0.0 | 3-4 |
| 3360 g ae/ha | 8 | 2 | 0 | 0 | 3.80 | 4.8 | 3-4 |
| TraP5::dgt-28 | | | | | | | |
| 420 g ae/ha | 5 | 2 | 0 | 0 | 3.71 | 0.49 | 3-4 |
| 840 g ae/ha | 4 | 2 | 0 | 0 | 3.67 | 0.52 | 3-4 |
| 1680 g ae/ha | 7 | 3 | 0 | 0 | 3.70 | 0.48 | 3-4 |
| 3360 g ae/ha | 6 | 0 | 0 | 0 | 4.00 | 0.00 | 3-4 |
| Bobwhite MPB26RH | | | | | | | |
| 420 g ae/ha | 0 | 1 | 1 | 10 | 1.25 | 0.62 | 1-3 |
| 840 g ae/ha | 0 | 0 | 0 | 10 | 1.00 | 0.00 | 1 |
| 1680 g ae/ha | 0 | 0 | 0 | 12 | 1.17 | 0.58 | 1-3 |
| 3360 g ae/ha | 0 | 0 | 0 | 10 | 1.00 | 0.00 | 1 |

At 21 DAT, resistant and sensitive plants are counted to determine the percentage of lines that segregated as a single locus, dominant Mendelian trait (3R:1S) as determined by Chi square analysis. Table 32. These data demonstrate that dgt-28 is inheritable as a robust glyphosate resistance gene in a monocot species.

TABLE 32

Percentage of $T_1$ dgt-28 events by construct that demonstrated heritablity in a mendelian fashion based off of a glyphosate selection at rates ranging from 420-3360 g ae/ha.

| Construct ID | CTP:GOI | % $T_1$ events tested that segregated at a single locus | % $T_1$ events tested that segregated as 2 loci | No. $T_1$ events tested |
|---|---|---|---|---|
| pDAS000122 | TraP4::dgt-28 | 62.5% | 37.5% | 8 |
| pDAS000123 | TraP8::dgt-28 | 87.5% | 12.5% | 8 |
| pDAS000124 | TraP23::dgt-28 | 12.5% | 87.5% | 8 |
| pDAS000125 | TraP5::dgt-28 | 62.5% | 0.0% | 8 |

Example 4

Chimeric Chloroplast Transit Peptide (TraP) Sequences for Expression of Agronomically Important Transgenes in Maize Cry2Aa:

The Cry2Aa protein from *Bacillus thuringiensis* has demonstrated activity against *Helicoverpa zea* (CEW) and *Ostrinia nubilalis* (ECB). A single version of the cry2Aa gene (SEQ ID NO:10), codon biased for maize, was tested in maize. In this experiment, Cry2Aa was evaluated alone and in conjunction with the TraP8 chimeric chloroplast transit peptide in maize to determine the insect tolerance activity and to evaluate the effect the TraP8 v2 chimeric chloroplast transit peptide sequence would have on the expression of the Cry2Aa protein in maize.

Figure 12:
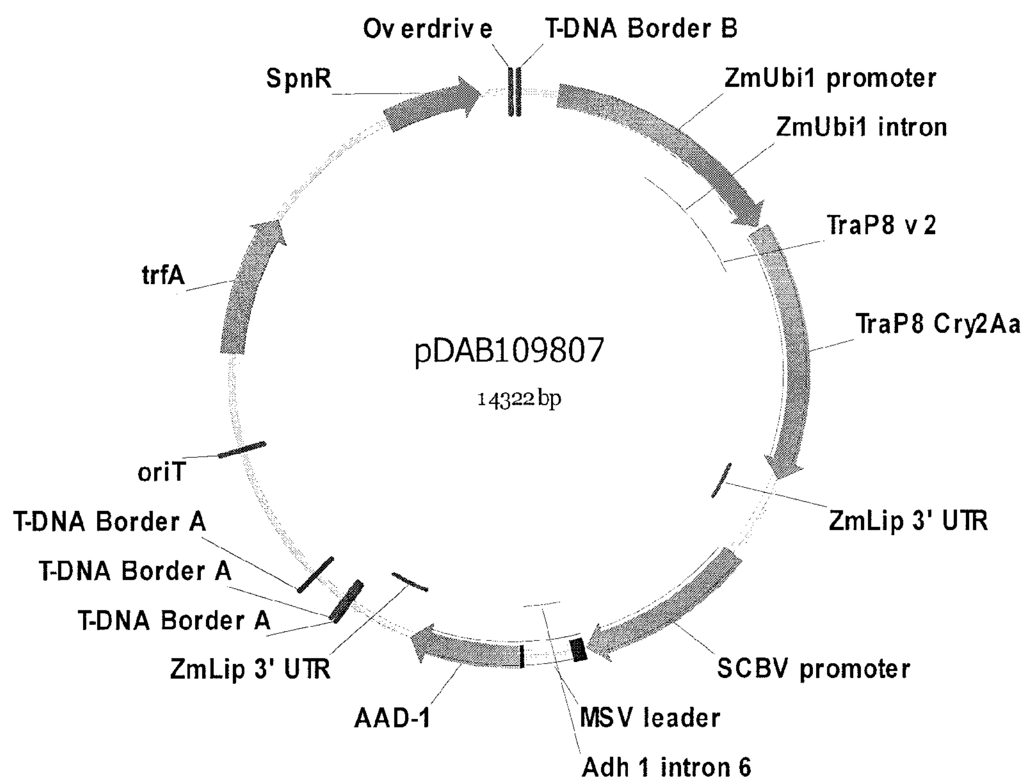
FIG. 12 illustrates a plasmid map of pDAB109807.
Figure 13:
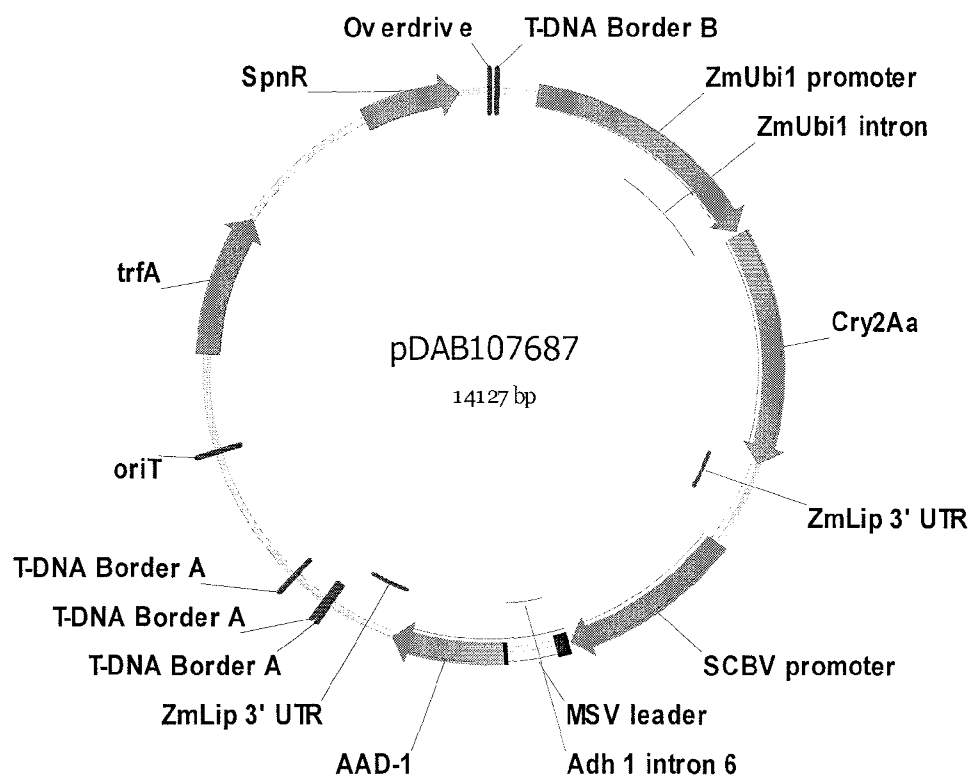
FIG. 13 illustrates a plasmid map of pDAB107687.

The pDAB109807 construct which contains the Trap8 v2 chimeric chloroplast transit peptide sequence (SEQ ID NO:8) and a GCA codon linker were cloned upstream of the cry2Aa gene and incorporated into construct pDAB109807 (FIG. 12) for insect tolerance testing in maize plants. The resulting constructs contained two plant transcription units (PTU). The first PTU comprised the *Zea mays* Ubiquitin 1 promoter (ZmUbi1 promoter; Christensen, A., Sharrock R., and Quail P., (1992) Maize polyubiquitin genes: structure, thermal perturbation of expression and transcript splicing, and promoter activity following transfer to protoplasts by electroporation, Plant Molecular Biology, 18:675-689), TraP8-cry2Aa fusion gene (TraP8 Cry2Aa), and *Zea mays* Lipase 3' untranslated region (ZmLip 3'UTR; U.S. Pat. No. 7,179,902). The constructs were confirmed via restriction enzyme digestion and sequencing. The second PTU comprised the Sugar Cane Bacilliform Virus promoter (SCBV promoter; U.S. Pat. No. 6,489,462), aad-1 herbicide tolerance gene containing a MSV leader and alcohol dehydrogenase 1 intron 6 (AAD-1; U.S. Pat. No. 7,838,733, and MSV Leader sequence; Genbank Acc. No. FJ882146.1, and the alcohol dehydrogenase intron; Genbank Acc. No. EF539368.1), and *Zea mays* Lipase 3' untranslated region (ZmLip 3'UTR). A control plasmid, pDAB107687, which did not contain a chloroplast transit peptide sequence upstream of the cry2Aa gene was built and included in the studies (FIG. 13). The plasmids were introduced into *Agrobacterium tumefaciens* for plant transformation.

Ears from *Zea mays* cultivar B104 were harvested 10-12 days post pollination. Harvested ears were de-husked and surface-sterilized by immersion in a 20% solution of commercial bleach (Ultra Clorox® Germicidal Bleach, 6.15% sodium hypochlorite) and two drops of Tween 20, for 20 minutes, followed by three rinses in sterile, deionized water inside a laminar flow hood. Immature zygotic embryos (1.8-2.2 mm long) were aseptically excised from each ear and distributed into one or more micro-centrifuge tubes containing 2.0 ml of *Agrobacterium* suspension into which 2 μl of 10% Break-Thru® S233 surfactant had been added.

Upon completion of the embryo isolation activity the tube of embryos was closed and placed on a rocker platform for 5 minutes. The contents of the tube were then poured out onto a plate of co-cultivation medium and the liquid *Agrobacterium* suspension was removed with a sterile, disposable, transfer pipette. The co-cultivation plate containing embryos was placed at the back of the laminar flow hood with the lid ajar for 30 minutes; after which time the embryos were oriented with the scutellum facing up using a microscope. The co-cultivation plate with embryos was then returned to the back of the laminar flow hood with the lid ajar for a further 15 minutes. The plate was then closed, sealed with 3M Micropore tape, and placed in an incubator at 25° C. with 24 hours/day light at approximately 60 μmol $m^{-2}$ $s^{-1}$ light intensity.

Following the co-cultivation period, embryos were transferred to Resting medium. No more than 36 embryos were moved to each plate. The plates were wrapped with 3M micropore tape and incubated at 27° C. with 24 hours/day light at approximately 50 μmol m-2 s-1 light intensity for 7-10 days. Callused embryos were then transferred onto Selection I medium. No more than 18 callused embryos were moved to each plate of Selection I. The plates were wrapped with 3M micropore tape and incubated at 27° C. with 24 hours/day light at approximately 50 μmol m-2 s-1 light intensity for 7 days. Callused embryos were then transferred to Selection II medium. No more than 12 callused embryos were moved to each plate of Selection II. The plates were wrapped with 3M micropore tape and incubated at 27° C. with 24 hours/day light at approximately 50 μmol m-2 s-1 light intensity for 14 days.

At this stage resistant calli were moved to Pre-Regeneration medium. No more than 9 calli were moved to each plate of Pre-Regeneration. The plates were wrapped with 3M micropore tape and incubated at 27° C. with 24 hours/day light at approximately 50 μmol m-2 s-1 light intensity for 7 days. Regenerating calli were then transferred to Regeneration medium in Phytatrays™ and incubated at 28° C. with 16 hours light/8 hours dark per day at approximately 150 μmol m-2 s-1 light intensity for 7-14 days or until shoots develop. No more than 5 calli were placed in each Phytatray™. Small shoots with primary roots were then isolated and transferred to Shoot/Root medium. Rooted plantlets about 6 cm or taller were transplanted into soil and moved out to a growth chamber for hardening off.

Transgenic plants were assigned unique identifiers through and transferred on a regular basis to the greenhouse. Plants were transplanted from Phytatrays™ to small pots (T. O. Plastics, 3.5-inch SVD, 700022C) filled with growing media (Premier Tech Horticulture, ProMix BX, 0581 P) and covered with humidomes to help acclimate the plants. Plants were placed in a Conviron™ growth chamber (28° C./24° C., 16-hour photoperiod. 50-70% RH, 200 mmol light intensity) until reaching V3-V4 stage. This aided in acclimating the plants to soil and harsher temperatures. Plants were then moved to the greenhouse (Light Exposure Type: Photo or Assimilation; High Light Limit: 1200 PAR; 16-hour day length; 27° C. Day/24° C. Night) and transplanted from the small pots to 5.5 inch pots. Approximately 1-2 weeks after transplanting to larger pots plants were sampled for bioassay. One plant per event was bioassayed.

Select events were identified for advancement to the next generation based on copy number of the genes, protein detection by Western blot and activity against the bioassay insects. Events that contained the Spectinomycin resistance gene were noted but not necessarily omitted from advancement. Events selected for advancement were transplanted into 5 gallon pots. Observations were taken periodically to track any abnormal phenotypes. Shoot bags were placed over the shoots prior to silk emergence to prevent cross-contamination by stray pollen. Any shoots producing silks prior to covering were noted and the shoot was removed. The second shoot was then covered and used for pollinations. Plants that produced abnormal or no shoots were recorded in the database. Silks were cut back the day prior to pollinations to provide an even brush to accept pollen and the plants were self pollinated.

Plants for T1 selection were sprayed at 7 days post sowing. They were grown in 4-inch pots of Metro 360 potting soil with 15 pots per flat. Seedling growth stage was V1-V1.5. Pots with poor germination or contain very small plants (whorl still closed) were marked so they were not included in the selection assessment. Whole flats of plants were then placed in secondary carrier trays for track sprayer application. Trays were placed two at a time in the Mandel track sprayer, calibrated to deliver a volume 187 L/ha to the target area using an 8002E flat fan nozzle (Tee Jet). A solution of 35 g ae/ha Assure II (quizalofop)+1% COC (crop oil concentrate) was formulated for the application. A volume of 15 mls./spray was used to calculate the total spray solution needed. Calculations; (35 g ae/ha)×(1 ha/187 L)×(1 L/97.7 g ae Assure II)=0.192% solution or 28.74 μl/15 ml H2O+1% v/v). After application, the plants were then allowed to dry for one hour in spray lab before returning to greenhouse. Approximately 1-2 weeks after transplanting to larger pots plants were sampled for bioassay. One plant per event was bioassayed.

All of the $T_0$ events that passed the molecular analysis screen were analyzed for Cry2Aa protein expression levels. The events from the control construct, pDAB107687, which comprised Cry2Aa without a TraP had significantly higher average expression level of Cry2Aa (15.0 ng/cm2) as compared to events from pDAB109807 (5.0 ng/cm2) which contained TraP8. Despite the reduced levels of expression of the pDAB109807 events, these events still expressed the Cry2Aa protein.

The T1 events were also analyzed were analyzed for Cry2Aa protein expression levels. The events from the control construct, pDAB107687, which comprised Cry2Aa without a TraP had significantly higher average expression level of Cry2Aa (55 and 60 ng/$cm^2$) as compared to events from pDAB109807 (about 20 to 40 ng/$cm^2$) which contained TraP8. Despite the reduced levels of expression of the pDAB109807 events, these events still expressed the Cry2Aa protein.

Transgenic plants containing single Bt genes were tested for insecticidal activity in bioassays conducted with neonate lepidopteran larvae on leaves from the transgenic plants. The lepidopteran species assayed were the European Corn Borer, *Ostrinia nubilalis* (Hübner) (ECB), and the Corn Earworm, *Helicoverpa zea* (CEW).

32-well trays (C-D International, Pitman, N.J.) were partially filled with a 2% agar solution and agar was allowed to solidify. Leaf sections approximately 1 $in^2$ were taken from each plant and placed singly into wells of the 32-well trays. One leaf piece was placed into each well, and two leaf pieces were tested per plant and per insect. Insects were mass-infested using a paintbrush, placing 10 neonate larvae into each well. Trays were sealed with perforated sticky lids which allowed ventilation during the test. Trays were placed at 28° C., 40% RH, 16 hours light: 8 hours dark for three days. After the duration of the test, a simple percent damage score was taken for each leaf piece. Damage scores for each test were averaged and used alongside protein expression analysis to conduct correlation analyses.

The results of the $T_0$ and $T_1$ bioassay indicated that the TraP8 chimeric chloroplast transit peptide sequence was functional and that the pDAB109807 events provided protection against the tested insects. In the T1 events, the plants expressing the Cry2Aa protein without a TraP (pDAB107687) had a mean leaf damage that was not significantly different than the plant expressing the Cry2Aa protein with TraP8 (pDAB109807) across all insect species tested. These results were surprising, given that the plants expressing the Cry2Aa protein without a TraP (pDAB107687) expressed higher levels of protein as compared to the plants expressing the Cry2Aa protein with TraP8 (pDAB109807).

VIP3Ab1:

The Vip3Ab1 protein from *Bacillus thuringiensis* has demonstrated activity against *Helicoverpa zea* (CEW) and Fall Armywonn (FAW) and resistant Fall Armyworm (rFAW). The vip3Ab1 v6 (SEQ ID NO:11) and vip3Ab1 v7 (SEQ ID NO:12) genes were expressed and tested for insect tolerance in maize. In this experiment, vip3Ab1 v6 and vip3Ab1 v7 were evaluated alone and in conjunction with the TraP8 chimeric chloroplast transit peptide in maize to determine the insect tolerance activity and to evaluate the effect the TraP8 v2 chimeric chloroplast transit peptide sequence would have on the expression of the Vip3Ab1 v6 and Vip3Ab1 v7 proteins in maize.

Figure 14:
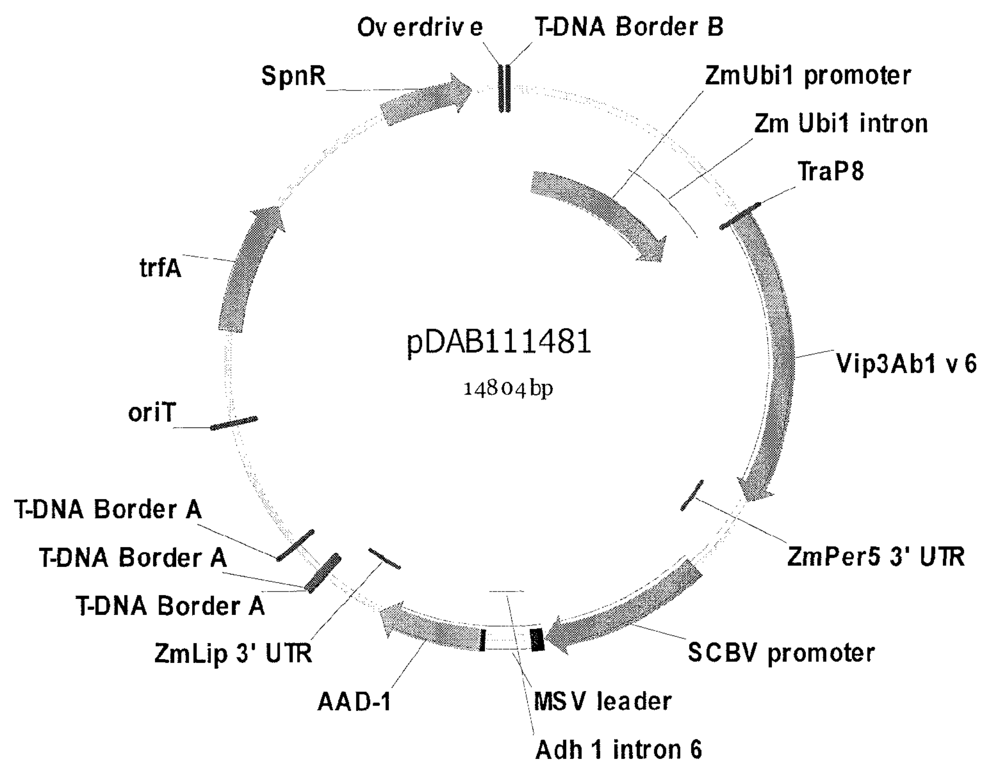
FIG. 14 illustrates a plasmid map of pDAB111481.
Figure 15:
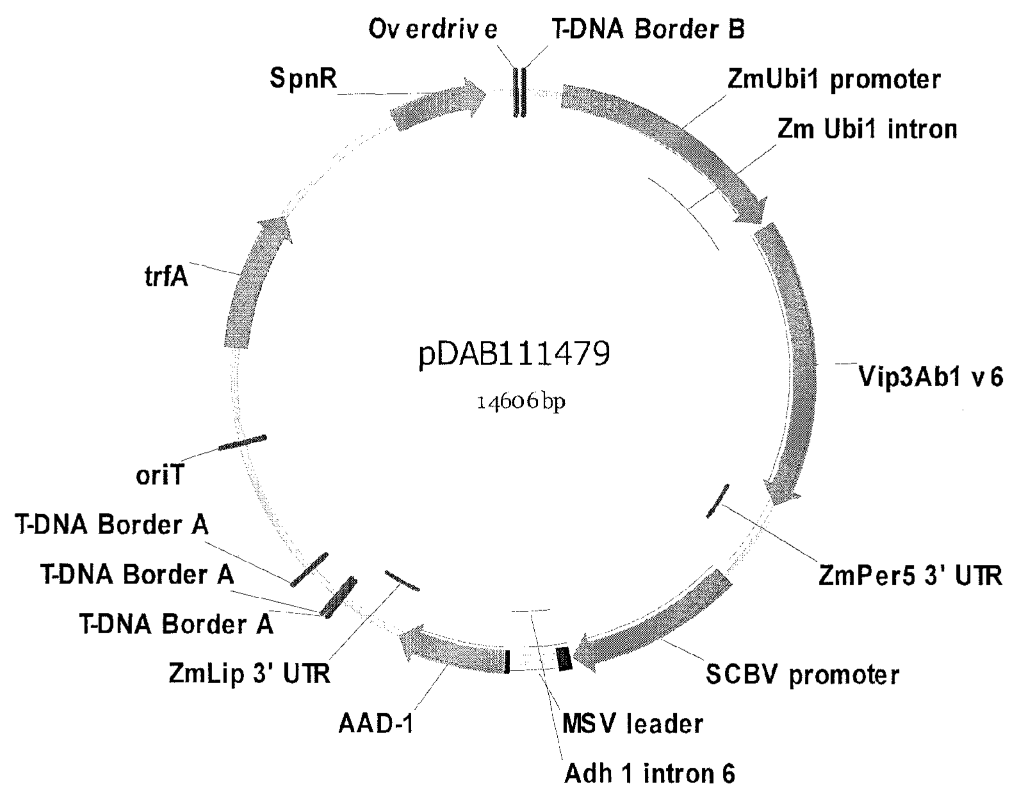
FIG. 15 illustrates a plasmid map of pDAB111479.

The pDAB111481 (FIG. 14) construct which contains the Trap8 v2 chimeric chloroplast transit peptide-encoding polynucleotide sequence (SEQ ID NO:8) and a GCA codon linker were cloned upstream of the vip3ab1 v6 gene and tested for insect tolerance in maize plants. The resulting construct contained two plant transcription units (PTU). The first PTU comprised the *Zea mays* Ubiquitin 1 promoter (ZmUbi1 promoter; Christensen, A., Sharrock R., and Quail P., (1992) Maize polyubiquitin genes: structure, thermal perturbation of expression and transcript splicing, and promoter activity following transfer to protoplasts by electroporation, *Plant Molecular Biology,* 18:675-689), TraP8-vip3ab1 v6 fusion gene (TraP8-Vip3Ablv6) and *Zea mays* Peroxidase5 3' untranslated region (ZmPer 5 3'UTR). The construct was confirmed via restriction enzyme digestion and sequencing. The second PTU comprised the Sugar Cane Bacilliform Virus promoter (SCBV promoter; U.S. Pat. No. 6,489,462), aad-1 herbicide tolerance gene containing a MSV leader and alcohol dehydrogenase 1 intron 6 (AAD-1; U.S. Pat. No. 7,838,733, and MSV Leader sequence; Genbank Ace. No. F1882146.1, and the alcohol dehydrogenase intron; Genbank Acc. No. EF539368.1), and *Zea mays* Lipase 3' untranslated region (ZmLip 3'UTR). A control plasmid, pDAB111479, which did not contain a chloroplast transit peptide sequence upstream of the vip3ab1 v6 gene was built and included in the studies (FIG. 15). The plasmids were introduced into *Agrobacterium tumefaciens* for plant transformation.

Figure 16:
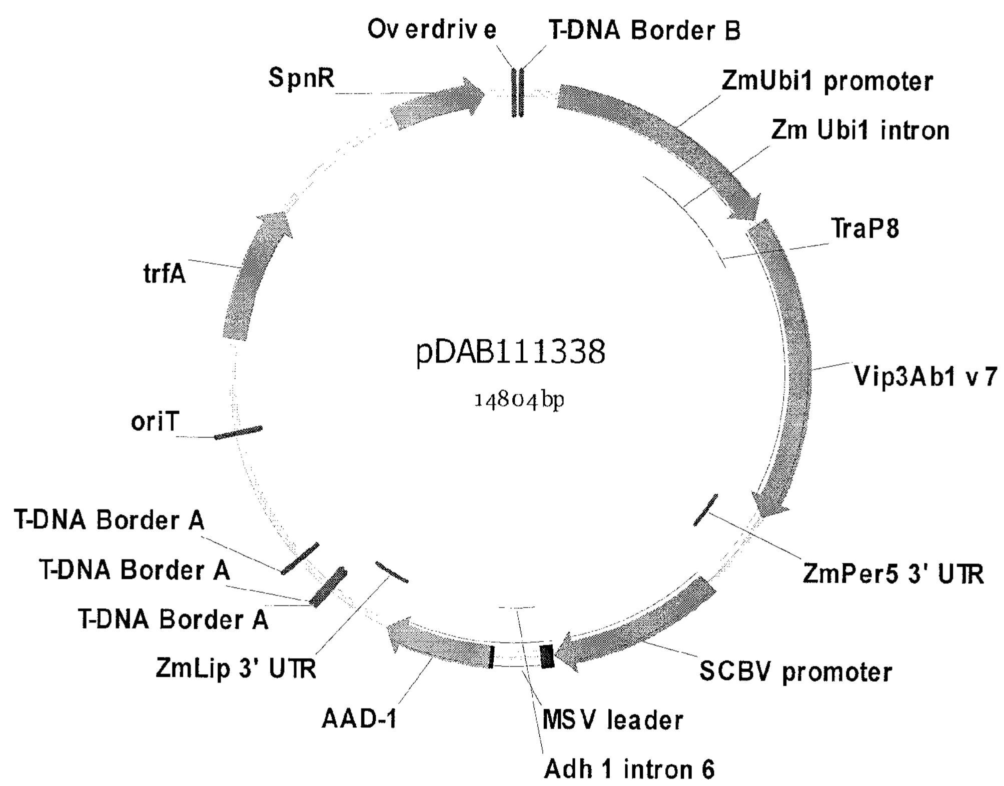
FIG. 16 illustrates a plasmid map of pDAB111338.

The pDAB111338 (FIG. 16) construct which contains the Trap8 v2 chimeric chloroplast transit peptide sequence (SEQ ID NO:8) and a GCA codon linker were cloned upstream of the vip3ab1 v7 gene and tested for insect tolerance testing in maize plants. The resulting construct contained two plant transcription units (PTU). The first PTU was comprised of the *Zea mays* Ubiquitin 1 promoter (ZmUbi1 promoter; Christensen, A., Sharrock R., and Quail P., (1992) Maize polyubiquitin genes: structure, thermal perturbation of expression and transcript splicing, and promoter activity following transfer to protoplasts by electroporation, *Plant Molecular Biology,* 18:675-689), TraP8-Vip3Ab1 v7 fusion gene (TraP8-vip3ab1 v7) and *Zea mays* Peroxidase5 3' untranslated region (ZmPer 5 3'UTR). The construct was confirmed via restriction enzyme digestion and sequencing. The second PTU was comprised of the Sugar Cane Bacilliform Virus promoter (SCBV promoter; U.S. Pat. No. 6,489,462), aad-1 herbicide tolerance gene containing a MSV leader and alcohol dehydrogenase 1 intron 6 (AAD-1; U.S. Pat. No. 7,838,733, and MSV Leader sequence; Genbank Ace. No. FJ882146.1, and the alcohol dehydrogenase intron; Genbank Acc. No. EF539368.1), and *Zea mays* Lipase 3' untranslated region (ZmLip 3'UTR). A control plasmid, pDAB112710, which did not contain a chloroplast transit peptide sequence upstream of the Vip3Ab1 v7 gene was built and included in the studies (FIG. 17). The plasmids were cloned into *Agrobacterium tumefaciens* for plant transformation.

Maize transformation, protein expression and insect bioassays were completed following the protocols previously described, and the results are shown in Table 33. The results of insect bioassays indicated that the TraP8 chimeric chloroplast transit peptide sequence was functional and that the pDAB111338 and pDAB111481 events provided protection against the insects tested in bioassay. In the tested events, the plants expressing the Vip3Ab1 protein without a TraP, (pDAB112710 and pDAB111479), had a mean leaf damage that was not significantly different than the plant expressing the Vip3Ab1 protein with TraP8 (pDAB111338 and pDAB111481). In conclusion, the Western blots and bioassays indicated that all of the tested events expressed the Vip3 Ab1 protein.

bands were in-gel digested with Trypsin (Promega; Madison, Wis.) in 25 mM ammonium bicarbonate for overnight at 37° C. The peptides were purified by a C18 ZipTip™ (Millipore, Bedford, Mass.) and eluted with 50% acetonitrile/0.1% TFA. The samples were mixed with matrix α-cyano-4-hydroxycinnamic acid in a 1:1 ratio and the mix was sported onto a MALDI sample plate and air dried.

The peptide mass spectrum was generated using a Voyager DE-PRO MALDI-TOF Mass Spectrometer™ (Applied Biosystems; Framingham, Mass.). External calibration was performed by using a Calibration Mixture 2™ (Applied Biosystems). Internal calibration was performed using the trypsin autolysis peaks at m/z 842.508, 1045.564 and 2211.108. All mass spectra were collected in the positive ion reflector model. The peptide mass fingerprint (PMF) analysis was conducted using PAWS™ (Protein Analysis WorkSheet) freeware from Proteometrics LLC by matching the PMF of the sample with theoretical PMF of target protein to verify if the sample was the target protein. The protein identification was performed by Database searching using MASCOT (MatrixScience, London, UK) against NCBI NR protein database.

TABLE 33

Results of the biochemical and bioassay results for Vip3Ab1 v6 and Vip3Ab1 v7 coding sequences that were fused to TraP8 as compared to Vip3Ab1 v6 and Vip3Ab1 v7 coding sequences that did not possess a chloroplast transit peptide sequence.

| | | Biochemical Assay Results | | | BioAssay Results | | | | | | | |
|---|---|---|---|---|---|---|---|---|---|---|---|---|
| | | | Method of analysis ELISA | | | | | | | | | |
| Plasmid | Description | Average expression | ($ng/cm_2$) LC/MS/MS ($fmole/cm_2$) | Western positive events | Events tested | Total CEW damage | CEW Mean % Leaf Damage | Total FAW damage | FAW Mean % Leaf Damage | Total FAW damage | rFAW Mean % Leaf Damage |
| pDAB111479 | Vip3Ab1 v6 No TraP | 59 | ELISA | 14/17 | 19 | 205.0 | 10.8 | 368.0 | 19.4 | 325.0 | 17.1 |
| pDAB111481 | Vip3Ab1 v6 Trap8 v2 | 239 | ELISA | 4/4 | 17 | 124.0 | 7.3 | 110.0 | 6.5 | 77.0 | 4.5 |
| pDAB112710 | Vip3Ab1 v7 No TraP | 143 | ELISA | 18/20 | 20 | 79.0 | 4.0 | 107.0 | 5.4 | 117.0 | 5.9 |
| pDAB111338 | Vip3Ab1 v7 Trap8 v2 | 180 | ELISA | 5/6 | 9 | 63.0 | 7.0 | 99.0 | 11.0 | 111.0 | 12.3 |

Example 5

In Planta Cleavage of Chimeric Chloroplast Transit Peptide (Trap) Sequences

The cleavage site of the TraP8 and TraP9 chimeric chloroplast transit peptide was determined via MALDI spectrometry and N-terminal Edman degradation sequencing. Plant material was obtained from transgenic plants which contained the TraP8-dgt14, TraP8-dgt28, TraP9-dgt14, and TraP9-dgt28 fusion genes and assayed to determine the location of cleavage of the chimeric chloroplast transit peptide occurred during translocation within the chloroplast.

MALDI Results:

The semi-purified proteins from a plant sample were separated by SDS-PAGE. The bands of protein of a size equivalent to the molecular weight of YFP were excised from the gel, de-stained and dried. Next, the dried protein N-Terminal Sequencing Via Edman Chemistry Degradation:

The N-terminal sequencing was performed on a Procise Protein Sequencer (model 494) from Applied Biosystems (Foster City, Calif.). The protein samples were separated first by SDS-PAGE, then blotted onto PVDF membrane. The protein bands were excised from the membrane and loaded into the Procise Sequencer. Eight cycles of Edman chemistry degradation were run for each sample to get five AA residues at N-terminus. A standard mix of 20 PTH-amino acids (Applied Biosystems) was run with each sample. The amino acid residues from each Edman degradation were determined based on their retention times from the C-18 column against the standards.

The results of the MALDI sequencing indicated that the DGT-28 and DGT14 proteins were expressed and that the TraP chimeric chloroplast transit peptide sequences were processed. Table 34 lists the processed sequences which were obtained by using the N-terminal Edman degradation and MALDI sequencing.

TABLE 34

Cleavage sites of TraP8 and TraP9 fused with the dgt-14 or dgt-28 coding sequences. The grey box indicates the splice site.

| Construct | Sequence | Number of Sequences with Splicing |
|---|---|---|
| TraP8-DG T14v2 | S V I R P V K A ░ / ░ A S T G G | 66/67 |
| TraP8-DG T28v1 | S V I R P V K A ░ / ░ A R G M P | 66/67 |
| TraP9-DG T14v2 | K V T A S V S A ░ / S V S A ░ A S T G G | 62/63 |
| TraP9-DG T28v1 | K V T A S V S A ░ / S V S A ░ A R G M P | — |

What is claimed is:

1. An isolated nucleic acid molecule comprising:

a synthetic polynucleotide that encodes a peptide consisting of the amino acid sequence of SEQ ID NO:3 or SEQ ID NO:4.

2. The isolated nucleic acid molecule of claim 1, further comprising a nucleotide sequence of interest operably linked to the synthetic polynucleotide, wherein the nucleotide sequence of interest encodes a polypeptide.

3. The isolated nucleic acid molecule of claim 2, further comprising an additional polynucleotide encoding a chloroplast transit peptide, wherein the additional polynucleotide is operably linked to the nucleotide sequence of interest.

4. The isolated nucleic acid molecule of claim 3, wherein the additional polynucleotide is from an organism selected from the group consisting of prokaryotes, lower photosynthetic eukaryotes, and Chlorophytes.

5. The isolated nucleic acid molecule of claim 2, wherein the synthetic polynucleotide and nucleotide sequence of interest are operably linked to one or more regulatory sequences.

6. The isolated nucleic acid molecule of claim 2, wherein the nucleic acid molecule encodes a chimeric polypeptide comprising the polypeptide encoded by the nucleotide sequence of interest and the peptide encoded by the synthetic polynucleotide.

7. The nucleic acid molecule of claim 5, wherein the molecule is a plant expression vector, and wherein the one or more regulatory sequences include a plant-operable promoter.

8. A transgenic plant material comprising the nucleic acid molecule of claim 6.

9. The transgenic plant material of claim 8, wherein the plant material is selected from the group consisting of a plant cell, a plant tissue, a plant tissue culture, a callus culture, a plant part, and a whole plant.

10. The transgenic plant material of claim 8, further comprising the chimeric polypeptide comprising the polypeptide encoded by the nucleotide sequence of interest and the peptide encoded by the synthetic polynucleotide.

11. The transgenic plant material of claim 10, wherein the polypeptide encoded by the nucleotide sequence of interest is targeted to a plastid in a cell of the plant material.

12. The transgenic plant material of claim 8, wherein the nucleic acid molecule is stably integrated into the genome of a cell from the plant material.

13. The transgenic plant material of claim 8, wherein the plant material is a whole plant.

14. The transgenic plant material of claim 8, wherein the plant material is a plant cell that is not capable of regeneration to produce a plant.

15. The transgenic plant material of claim 8, wherein the plant material is from a plant selected from the group consisting of *Arabidopsis*, alfalfa, *Brassica*, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, watermelon, corn, onion, rice, sorghum, wheat, rye, millet, sugarcane, oat, triticale, switchgrass, and turfgrass.

16. The transgenic plant material of claim 10, wherein the plant material is a plant cell that is not capable of regeneration to produce a plant.

17. A transgenic plant regenerated from the transgenic plant material of claim 10.

18. A transgenic plant commodity product produced from the plant material of claim 10, wherein the plant commodity product comprises the chimeric polypeptide.

19. The transgenic plant material of claim 10, wherein the polypeptide encoded by the nucleotide sequence of interest is involved in a process selected from the group consisting of virus resistance, bacterial pathogen resistance, insect resistance, nematode resistance, fungal resistance, plant vigor, plant yield, temperature tolerance, soil condition tolerance, low light level tolerance, low water level tolerance, high water level tolerance, chemical environment tolerance, seed color, starch modification, amino acid synthesis, photosynthesis, synthesis of fatty acids, oil synthesis, synthesis of carotenoids, synthesis of terpenoids, synthesis of starch, and herbicide resistance.

20. The transgenic plant material of claim 10, wherein the polypeptide encoded by the nucleotide sequence of interest is selected from the group consisting of zeaxanthin epoxidase, choline monooxygenase, ferrochelatase, omega-3 fatty acid desaturase, glutamine synthetase, provitamin A, hormones, and Bt toxin proteins.

21. The transgenic plant material of claim 19, wherein the polypeptide encoded by the nucleotide sequence of interest is involved in herbicide resistance.

22. The transgenic plant material of claim 10, wherein the polypeptide encoded by the nucleotide sequence of interest is selected from the group consisting of: acetolactase synthase (ALS), mutated ALS, precursors of ALS, 3-enolpyruvylshikimate-5-phosphate synthetase (EPSPS), CP4 EPSPS, and a class III EPSPS.

23. The transgenic plant material of claim 21, wherein the plant material exhibits increased herbicide resistance or herbicide tolerance when compared to a wild-type plant material of the same species.

24. An isolated nucleic acid molecule comprising a synthetic polynucleotide that encodes a peptide consisting of the amino acid sequence of SEQ ID NO:3 or SEQ ID NO:4, wherein the synthetic polynucleotide that encodes the peptide binds to a polynucleotide selected from the group consisting of SEQ ID NOs: 5, 6, 8, and 9 after:

hybridization for 16 hours in 5× saline sodium citrate (SSC) buffer at 65 ° C;

two washes for 15 minutes each in 2× SSC buffer at room temperature; and two washes for 20 minutes each in 0.5× SSC buffer at 65 ° C.

25. The isolated nucleic acid molecule of claim 24, further comprising a nucleotide sequence of interest that encodes a polvpeptide, wherein the polynucleotide of interest is operably linked to the synthetic polynucleotide that encodes the peptide, such that the nucleic acid molecule encodes a chimeric polypeptide comprising the polypeptide encoded by the nucleotide sequence of interest and the peptide encoded by the synthetic polynucleotide.

* * * * *

SEQUENCE LISTING

```
<160> NUMBER OF SEQ ID NOS: 70

<210> SEQ ID NO 1
<211> LENGTH: 69
<212> TYPE: PRT
<213> ORGANISM: Brassica napus

<400> SEQUENCE: 1

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
    50                  55                  60

Thr Ala Ser Val Ser
65


<210> SEQ ID NO 2
<211> LENGTH: 61
<212> TYPE: PRT
<213> ORGANISM: Brassica napus

<400> SEQUENCE: 2

Met Ala Gln Ala Ser Arg Ile Cys Gln Asn Pro Cys Val Ile Ser Asn
1               5                   10                  15

Leu Pro Lys Ser Asn His Arg Lys Ser Pro Phe Ser Val Ser Leu Lys
            20                  25                  30

Thr His Gln Gln Gln Arg Arg Ala Tyr Gln Ile Ser Ser Trp Gly Leu
        35                  40                  45

Lys Lys Ser Asn Asn Gly Ser Val Ile Arg Pro Val Lys
    50                  55                  60


<210> SEQ ID NO 3
<211> LENGTH: 65
<212> TYPE: PRT
<213> ORGANISM: Artificial sequence
<220> FEATURE:
<223> OTHER INFORMATION: TraP8 chimeric chloroplast transit peptide
```

```
<400> SEQUENCE: 3

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Gln Gln Arg Arg Ala Tyr Gln Ile Ser
        35                  40                  45

Ser Trp Gly Leu Lys Lys Ser Asn Asn Gly Ser Val Ile Arg Pro Val
    50                  55                  60

Lys
65


<210> SEQ ID NO 4
<211> LENGTH: 65
<212> TYPE: PRT
<213> ORGANISM: Artificial sequence
<220> FEATURE:
<223> OTHER INFORMATION: TraP9 chimeric chloroplast transit peptide

<400> SEQUENCE: 4

Met Ala Gln Ala Ser Arg Ile Cys Gln Asn Pro Cys Val Ile Ser Asn
1               5                   10                  15

Leu Pro Lys Ser Asn His Arg Lys Ser Pro Phe Ser Val Ser Leu Lys
            20                  25                  30

Thr His Gln Pro Arg Ala Ser Ser Trp Gly Leu Lys Lys Ser Gly Thr
        35                  40                  45

Met Leu Asn Gly Ser Val Ile Arg Pro Val Lys Val Thr Ala Ser Val
    50                  55                  60

Ser
65


<210> SEQ ID NO 5
<211> LENGTH: 195
<212> TYPE: DNA
<213> ORGANISM: Artificial sequence
<220> FEATURE:
<223> OTHER INFORMATION: polynucleotide encoding TraP8

<400> SEQUENCE: 5

atggctcaat cttctaggat ttgccacggt gttcaaaacc cttgcgtgat catctctaac     60

ctttccaagt ccaaccagaa caagtctcct ttcagcgttt ctcttaagac tcatcagcaa    120

cagagaaggg cttaccagat ttcttcatgg ggactcaaga agtctaacaa cggatctgtt    180

atcagacctg tgaag                                                     195


<210> SEQ ID NO 6
<211> LENGTH: 195
<212> TYPE: DNA
<213> ORGANISM: Artificial sequence
<220> FEATURE:
<223> OTHER INFORMATION: polynucleotide encoding TraP9

<400> SEQUENCE: 6

atggctcaag cttctagaat ttgccagaac ccttgcgtta tttccaacct ccctaagtct     60

aaccatagga agtctccatt ctccgtttct cttaagactc atcagcctag agcttcatct    120

tggggactta agaaatccgg aaccatgctt aacggatctg ttatcaggcc tgttaaggtt    180

accgcttctg tgtct                                                     195
```

<210> SEQ ID NO 7
<211> LENGTH: 9
<212> TYPE: DNA
<213> ORGANISM: Artificial sequence
<220> FEATURE:
<223> OTHER INFORMATION: Linker

<400> SEQUENCE: 7 gcttcttct 9

<210> SEQ ID NO 8
<211> LENGTH: 195
<212> TYPE: DNA
<213> ORGANISM: Artificial sequence
<220> FEATURE:
<223> OTHER INFORMATION: polynucleotide encoding TraP8 v2

<400> SEQUENCE: 8
atggctcaat ctagcagaat ctgccacggt gtgcagaacc catgtgtgat catttccaat 60
ctctccaaat ccaaccagaa caaatctcct ttctcagtca gcctcaagac tcaccagcag 120
cagcgtcgtg cttaccagat atctagctgg ggattgaaga agtcaaacaa cgggtccgtg 180
attcgtccgg ttaag 195

<210> SEQ ID NO 9
<211> LENGTH: 195
<212> TYPE: DNA
<213> ORGANISM: Artificial sequence
<220> FEATURE:
<223> OTHER INFORMATION: polynucleotide encoding TraP9 v2

<400> SEQUENCE: 9
atggcacaag ccagccgtat ctgccagaat ccatgtgtga tatccaatct ccccaaaagc 60
aaccaccgta agtccccttt ctctgtctca ctcaagacgc atcagcctag agcctcttca 120
tggggactta agaagtctgg caccatgctg aacggttcag tgattagacc cgtcaaggtg 180
acagcttctg tttcc 195

<210> SEQ ID NO 10
<211> LENGTH: 1902
<212> TYPE: DNA
<213> ORGANISM: Bacillus thuringiensis

<400> SEQUENCE: 10
atgaacaacg ttctcaactc tgggagaacc accatctgcg acgcgtacaa tgtggtggca 60
cacgacccat tctcatttga gcacaagagc ctggatacga tccagaaaga gtggatggaa 120
tggaaaagga cggaccattc cttgtacgtt gctccagtgg tgggcactgt gtcctcgttc 180
ctcctcaaga aagtggggtc gctgatcggg aagcggatac tctccgaact ctggggaatc 240
atctttccgt ctggctcaac aaacttgatg caagacatac tgagagagac tgagcagttc 300
ttgaatcaga ggctgaatac ggacacgctg gcgagggtga acgctgaact cattggcctc 360
caagcgaaca ttagagagtt caatcagcaa gttgataact ttctgaaccc cacacagaat 420
ccagtgcctc tgtccatcac atcatctgtg aacacaatgc agcagctgtt cttgaatagg 480
ctgccacagt ttcagattca aggctatcaa ctgcttcttc tgcctctgtt tgctcaagct 540
gcgaacatgc acctcagctt catcagagac gtgattctga acgcagatga gtggggaatc 600
agcgctgcca ctttgaggac ctacagagat tacttgagga actatacacg cgattactca 660
aactactgca tcaacaccta tcaaacagcg tttaggggac ttaacaccag actgcacgac 720

```
atgcttgagt tccggactta catgttcctc aacgtctttg agtatgtctc gatttggtcc    780

ctcttcaagt atcagagcct tatggtctcc tctggtgcta acctctacgc ctcgggttcc    840

ggaccgcagc agacccagtc attcactgcc cagaactggc cattcctcta cagccttttc    900

caagtgaaca gcaactacat cttgtctggc atctctggca caaggctctc tatcacattt    960

ccgaacattg gtggcctgcc tggctccacg acgacacaca gcctcaattc cgcacgcgtc   1020

aactactcgg gtggggtctc ctccggactc attggtgcca ctaacttgaa ccataacttc   1080

aactgttcaa cggtgctgcc acccctttca actccgtttg tcagatcgtg gcttgattct   1140

ggcactgaca gagagggagt tgccacgagc accaactggc agaccgagtc cttccagacc   1200

acactttcgc tgcgctgcgg tgccttctca gcgaggggaa actcgaacta cttcccagac   1260

tacttcatac gcaacattag cggagtcccg ttggtgatcc ggaatgagga cctcaccaga   1320

cctcttcact acaatcagat acgcaacatc gaaagcccat ctgggacacc tggaggtgca   1380

agggcatact tggttagcgt tcacaaccgg aagaacaaca tctatgctgc taatgagaat   1440

gggaccatga ttcatcttgc accggaagat tacactggct tcacgatctc acccatccat   1500

gccacccaag tgaacaacca gactcgcacg ttcatctcag agaagttcgg caaccaaggt   1560

gacagcctcc gcttcgaaca gagcaacacc acagccagat acacccttag aggcaatggc   1620

aacagctaca atctctatct gagggtgtct agcattggca attcgaccat tcgggtgacg   1680

atcaatggtc gcgtttacac ggtctccaac gtcaatacga ccactaacaa tgatggggtc   1740

aatgacaatg gtgctcgctt ctccgacatc aacatcggca acatcgtcgc ttccgacaac   1800

accaatgtta cgctggacat caatgtcacc ttgaactctg gcacaccttt cgatctgatg   1860

aacatcatgt ttgtccccac caatcttcct cccctctact ga                      1902
```

<210> SEQ ID NO 11
<211> LENGTH: 2364
<212> TYPE: DNA
<213> ORGANISM: Bacillus thuringiensis

<400> SEQUENCE: 11

```
atgaatatga ataatactaa attaaacgca agagcgctgc cttcgttcat cgactacttc     60

aacggcatct acggattcgc aactgggatc aaagacatca tgaacatgat cttcaagacg    120

gacacgggtg gaaatcttac attggatgag attctgaaga atcagcagtt gctcaacgaa    180

atctctggca aactcgacgg agttaacggg tcccttaacg acctcatagc acaaggcaat    240

cttaatacag agctgtccaa ggagattctc aagattgcga atgagcaaaa tcaagttctg    300

aacgatgtca acaacaagct ggacgccatc aacacaatgt tgcacatcta tctgcccaag    360

atcacctcta tgctctccga tgttatgaag cagaactatg cgctctcgct tcaagtcgag    420

tacttgtcaa agcaactgaa agagatttcc gacaaactgg atgttatcaa tgttaacgtg    480

ttgatcaata gcacactgac cgaaatcacc ccagcttatc aaaggattaa atacgtgaat    540

gaaaagttcg aggaattaac cttcgctacg gagacaactc tgaaagtgaa gaaagattcg    600

tcaccagccg acattctgga cgagttgacc gaattaactg aactggcgaa gtccgttaca    660

aagaatgacg ttgatggctt cgagttctat ctcaatacat tccacgatgt tatggtgggc    720

aataatctgt tcggacgctc tgctttgaaa actgcttctg aattaatcgc aaaggaaaac    780

gttaagacgt cgggttccga ggtcgggaac gtgtacaact tcttgatagt gctcacggca    840

ctgcaagcga aagcgtttct cacgctgacc acgtgcagaa agttgctggg attggctgat    900
```

```
atcgattata catccatcat gaacgagcac cttaacaaag aaaaggagga gttcagagtg    960

aacattcttc caacattgtc caacacattc tccaatccga actacgcaaa ggtgaaaggt   1020

tctgacgaag atgcaaagat gatcgtcgag gcgaaacctg ggcacgctct ggtcggcttc   1080

gagatttcca acgactcgat gacggtatta aaggtgtacg aggctaagtt gaagcaaaac   1140

tatcaagtgg acaaggactc cctttcagag gtgatctatt cagatatgga caagctgctg   1200

tgtccggatc aatctgagca aatctactac accaataata tagttttccc taacgaatac   1260

gtcattacca agattgattt cacgaagaag atgaaaaccc ttagatatga ggttactgcc   1320

aatagctacg attcatctac gggtgaaatc gatcttaaca agaagaaggt tgaatcaagc   1380

gaagccgagt atcggactct gtcagccaat aatgacggtg tgtacatgcc tcttggtgtg   1440

atttcagaga cattccttac accaattaat ggtttcggtc tgcaagctga tgaaaactcc   1500

agattaatca ctctgacgtg taagtcctac ttgagggagt tgctcctcgc cactgatctt   1560

tccaataaag aaacaaagct gattgttcca ccgatctcgt tcatctcaaa cattgtggag   1620

aacgggaacc tcgaaggcga gaatctcgaa ccgtggattg cgaacaacaa gaacgcttac   1680

gtggatcata ctggagggat caacggcacg aaggtcttgt acgtgcataa ggacggagag   1740

ttctcacagt tcgtgggtgg gaagttgaag agcaagaccg agtacgtcat ccagtacatt   1800

gtgaagggga aggcctcaat ctatctcaag gataaaaaga atgagaactc tatctacgag   1860

gaaataaata atgaccttga gggcttccaa actgtgacca agcggttcat aaccggaacg   1920

gactcttccg gaatccatct gatctttact tcccagaacg gagaaggtgc tttcggtgga   1980

aacttcatca tcagcgagat ccgcacgtca gaggagttgc ttagcccaga attgatcatg   2040

tcggacgcgt gggtgggaag ccaaggcacg tggatctctg gcaactccct caccattaat   2100

tccaacgtga atggcacgtt taggcagaat ctccctcttg agtcgtattc aacctatagc   2160

atgaacttca cggttaacgg atttgggaag gtgacggtcc gcaattctcg cgaggtgctc   2220

tttgaaaagt cgtatcctca gctctctcca aaggacatca gcgagaagtt caccaccgca   2280

gcgaataata ctggattgta tgtcgaactc tcaagatcga cttctggtgg tgcaataaac   2340

tttcgggact tctcaattaa gtga                                          2364
```

```
<210> SEQ ID NO 12
<211> LENGTH: 2364
<212> TYPE: DNA
<213> ORGANISM: Bacillus thuringiensis

<400> SEQUENCE: 12

atgaacatga ataatactaa attaaacgcg agggcgctgc cgagcttcat cgactacttc     60

aacggcatct acggcttcgc caccggcatc aaggacatca tgaacatgat cttcaagacg    120

gataccggcg gcaacctgac cctggacgag atcctgaaga accagcagct gctgaacgag    180

atcagcggca agctggacgg cgtgaacggc agcctgaacg acctgatcgc ccaaggcaac    240

ctgaatacag agctgagcaa ggagatcctg aagatcgcga acgagcagaa tcaagtgctg    300

aacgacgtga acaacaagct ggacgcgatc aacaccatgc tgcacatcta cctgcccaag    360

atcacctcca tgctgagcga cgtgatgaag cagaactacg cgctgtccct ccaagtggag    420

tacctgagca agcagctgaa ggagatcagc gacaagctgg acgtgatcaa cgtgaacgtg    480

ctgatcaact ccaccctgac cgagatcacc ccggcctacc agaggattaa atacgtgaat    540

gaaaagttcg aggaattaac cttcgccacc gagaccaccc tgaaggtgaa gaaggacagc    600

tccccggcgg acatcctgga cgagctgacc gaattaaccg agctggcgaa gtccgtgacc    660
```

```
aagaacgacg tggacggctt cgagttctac ctgaatacat tccacgacgt gatggtgggc    720

aataatctgt tcgggaggag cgccctcaag accgccagcg aattaatcgc caaggagaac    780

gtcaagacca gcggcagcga ggtgggcaac gtctacaact tcctgatcgt gctgaccgcc    840

ctccaagcga aggcgttcct gaccctgacc acctgccgca agctgctggg cctggcggac    900

atcgactata catccatcat gaacgagcac ctgaacaagg agaaggagga gttccgcgtg    960

aacatcctgc cgaccctgtc caacaccttc agcaacccga actacgccaa ggtgaagggg   1020

tccgacgagg acgcgaagat gatcgtggag gccaagccgg gccacgcgct ggtgggcttc   1080

gagatcagca acgacagcat gaccgtatta aaggtgtacg aggcgaagct gaagcagaac   1140

taccaagtgg acaaggactc cctgagcgag gtgatctaca gcgacatgga caagctgctg   1200

tgcccggacc agtccgagca aatctactac accaataata tcgtgttccc gaacgagtac   1260

gtgatcacca agatcgactt caccaagaag atgaaaaccc tgcgctacga agtgaccgcc   1320

aacagctacg actcctcaac cggcgagatc gacctgaaca agaagaaggt ggaatcaagc   1380

gaggcggagt accgcaccct gagcgcgaat aatgacggcg tgtacatgcc gctgggcgtg   1440

atctccgaga ccttcctgac cccaattaat gggttcggcc tccaagccga tgaaaactcc   1500

agattaatca ccctgacctg caagtcctac ctgagggagc tgctgctggc gaccgacctg   1560

agcaataaag agaccaagct gatcgtgccg ccgatctcct tcatctccaa catcgtggag   1620

aacggcaacc tggagggcga gaacctggag ccgtggatcg cgaacaacaa gaacgcgtac   1680

gtggatcaca cgggaggcat caacggcacc aaggtgctgt acgtccacaa ggacggcgag   1740

ttcagccagt tcgtgggcgg caagctgaag agcaagaccg agtacgtgat ccagtacatc   1800

gtgaagggca aggcctccat ctacctgaag gataaaaaga acgagaactc catctacgag   1860

gaaataaata atgacctgga gggcttccag accgtgacca agaggttcat caccggcacc   1920

gactcctccg gcatccacct gatcttcacc tctcagaacg gcgagggcgc gttcggcggc   1980

aacttcatca tcagcgagat ccgcacctcc gaggagctgc tgtccccgga gctgatcatg   2040

tccgacgcct gggtgggcag ccaaggcacc tggatctccg gcaactccct gaccattaat   2100

agcaacgtga acggcacctt ccgccagaac ctgccgctgg agagctacag cacctactcc   2160

atgaacttca ccgtgaacgg gttcggcaag gtgacggtga ggaactcccg cgaggtgctg   2220

ttcgagaagt cctacccgca gctcagcccc aaggacatct cagagaagtt caccaccgcc   2280

gccaataata ccggcctgta cgtggagctg tcaaggagca ccagcggcgg cgcaataaac   2340

ttccgcgact tctcaattaa gtga                                          2364
```

<210> SEQ ID NO 13
<211> LENGTH: 4
<212> TYPE: PRT
<213> ORGANISM: Artificial sequence
<220> FEATURE:
<223> OTHER INFORMATION: SVSL sequence

<400> SEQUENCE: 13

Ser Val Ser Leu
1

<210> SEQ ID NO 14
<211> LENGTH: 207
<212> TYPE: DNA
<213> ORGANISM: Artificial sequence
<220> FEATURE:
<223> OTHER INFORMATION: polynucleotide encoding Brassica napus EPSPS

<400> SEQUENCE: 14

```
atggcgcaat ctagcagaat ctgccatggc gtgcagaacc catgtgttat catctccaat     60
ctctccaaat ccaaccaaaa caaatcacct ttctccgtct ccttgaagac gcatcagcct    120
cgagcttctt cgtggggatt gaagaagagt ggaacgatgc taaacggttc tgtaattcgc    180
ccggttaagg taacagcttc tgtttcc                                        207
```

<210> SEQ ID NO 15
<211> LENGTH: 183
<212> TYPE: DNA
<213> ORGANISM: Artificial sequence
<220> FEATURE:
<223> OTHER INFORMATION: polynucleotide encoding Brassica rapa EPSPS

<400> SEQUENCE: 15

```
atggcgcaag ctagcagaat ctgccagaac ccatgtgtta tctccaatct ccccaaatcc     60
aaccaccgca aatcgccctt ctctgtctcg ctgaagacgc accagcagca gcgtcgagct    120
tatcagatat cttcgtgggg attgaagaag agtaacaacg gctccgtgat tcgtccggtt    180
aag                                                                  183
```

<210> SEQ ID NO 16
<211> LENGTH: 1248
<212> TYPE: DNA
<213> ORGANISM: Streptomyces sviceus

<400> SEQUENCE: 16

```
atgagaggga tgccagcctt gtctttacct ggatcaaaga gtatcacagc tagggcactc     60
tttcttgctg ctgctgctga tggggttact actttggtga ggccattgag aagtgacgac    120
acagaaggat tcgctgaggg gttagttcgt ttaggctatc gtgtagggag gacacccgat    180
acttggcaag tcgatggcag accacaagga ccagcagtgg ctgaggctga cgtctactgt    240
agagacggag caaccaccgc tagattcttg ccaaccttag cagctgctgg tcacggaaca    300
tacagatttg atgcttcacc acagatgagg agacgtcctc ttttgccctt aagcagagcc    360
ttgagggatt tgggtgtcga tcttagacac gaagaagctg aaggtcatca ccctctgact    420
gtccgtgctg ctggggttga aggaggagag gttactttgg atgctggtca gtcaagtcag    480
tatctcactg ccttgttgct ccttggtccc cttacaagac aaggactgag gataagggtt    540
actgatttgg tgtcagcacc atacgtggag attacgcttg caatgatgag ggctttcgga    600
gttgaagtgg caagggaggg agatgtgttc gttgttccac ctggtggata tcgtgcaact    660
acgtatgcta tagaacccga cgcaagtact gcttcttact tcttcgcagc tgctgctttg    720
actcctggag ctgaagtgac tgtacctggg ttaggcacgg gagcacttca aggagatttg    780
ggatttgtag atgtcttaag gagaatggga gccgaggtgt ccgtaggagc tgatgcaacc    840
actgttagag gaactggtga attgcgtggc cttacagcca acatgagaga cataagtgat    900
acgatgccga ccctcgctgc aatagcaccc tttgctagtg ctccagttag aatcgaggat    960
gttgccaaca ctcgtgtcaa agaatgtgac agacttgagg cttgtgcaga gaaccttagg   1020
aggttgggag taagggttgc aacgggtccg gactggattg agatacaccc tggtccagct   1080
actggtgctc aagtcacaag ctatggtgat cacagaattg tgatgtcatt tgcagtgact   1140
ggacttcgtg tgcctgggat cagcttcgac gaccctggct gtgttcgtaa gacttttcct   1200
gggtttcacg aggctttcgc agaattgagg cgtggcattg ggagctga                1248
```

<210> SEQ ID NO 17
<211> LENGTH: 1251
<212> TYPE: DNA
<213> ORGANISM: Streptomyces sviceus

<400> SEQUENCE: 17

```
atggcaagag ggatgccagc cttgtcgctg cctggctcaa agtcgatcac ggctagagca     60
ctctttctcg cagcagcagc cgacggagtc accacgcttg tgagaccgct gcggtcagac    120
gacaccgagg gttttgcgga aggcctcgtc agactgggct atcgggttgg gaggactccc    180
gacacgtggc aagtggacgg aaggccacaa ggtccagcag ttgccgaggc tgatgtgtat    240
tgtagagacg gtgcaacaac ggctaggttc ctccccacac tcgcagctgc tggacacggg    300
acctacagat ttgatgcctc tccccagatg aggagaaggc cactgctgcc tctttctagg    360
gctttgaggg accttggcgt tgatcttcgc cacgaggaag cggaagggca ccaccccttg    420
accgtgagag ctgctggagt cgagggaggt gaggttacac tcgatgctgg acagtcctct    480
cagtacttga cggcactgct gctgctcggt ccgctcacac gccaagggct gcggattcgc    540
gtcactgatc tggttagcgc tccgtacgtg gagattacac ttgcgatgat gagagctttt    600
ggggtcgagg ttgcacgcga aggcgacgtt ttcgtggtgc ctcctggtgg ctacagagcg    660
actacgtacg cgattgagcc agatgccagc accgcaagct acttctttgc agctgctgcg    720
ttgacacctg gagccgaggt cacagtgcct ggactcggga ccggagcgct tcaaggggat    780
ctcggcttcg tggacgtgct gcggaggatg ggtgccgagg tcagcgtggg agcagacgct    840
acgactgtta gaggcacggg tgagcttaga ggccttacag caaacatgag ggacatatcc    900
gacacgatgc cgacgcttgc tgccatcgct ccgttcgctt cagcacccgt cagaattgaa    960
gatgtggcga acactcgcgt caaagagtgc gacagacttg aagcgtgtgc cgagaacttg   1020
aggaggttgg gagtgagagt cgcaactggt ccagactgga tcgagatcca ccctggtcca   1080
gctactggag cgcaagtcac aagctatggc gaccatagga ttgttatgtc attcgcagtg   1140
accggactca gagttcctgg gatctctttc gacgaccctg gttgcgtgcg gaaaacgttc   1200
cctggcttcc acgaggcatt tgcggagctg cggagaggaa ttggttcctg a            1251
```

<210> SEQ ID NO 18
<211> LENGTH: 1599
<212> TYPE: DNA
<213> ORGANISM: Glycine max

<400> SEQUENCE: 18

```
atggctcaag tctcccgtgt tcacaatctt gctcagtcaa cccaaatctt tggacattca     60
agcaactcaa acaaactgaa gtctgtgaat tctgtctcac ttcgcccacg cctttgggga    120
gcatccaaga gtcgcatacc aatgcacaag aatgggagtt tcatgggcaa cttcaatgtt    180
gggaaaggca attctggtgt cttcaaagtt tcagcttctg ttgcagccgc agagaaaccc    240
agcacttccc ctgagattgt tcttgaaccc attaaggact tcagtggaac aatcactctg    300
cctggatcaa agagtctttc aaacagaata cttctcttgg cagctctgag tgaaggaacc    360
actgtagttg acaacctttt gtactctgaa gatattcatt acatgttggg tgctctcaga    420
actcttgggt tgagagttga agatgacaag accacaaaac aagccatagt tgaaggatgt    480
ggtgggttgt ttccaacaag caaagaatcc aaagatgaga tcaacttgtt tcttggcaat    540
gctggaattg caatgagaag cctcactgct gcagtagttg cagctggtgg gaatgcaagt    600
tatgtccttg atggtgtccc cagaatgagg gaaaggccca tcggtgacct tgtggctggc    660
```

```
ctgaaacagc ttggagcaga tgttgattgc ttcttgggca caaactgccc tccagtgaga    720

gtgaatggga agggaggttt gcctggtgga aaggtcaaac tgagtggatc agtctcttcc    780

cagtatctga ctgccttgct catggctgcc cctctggctt tgggtgatgt ggagattgaa    840

atagtggaca agttgatttc tgttccatat gtggaaatga ccctcaaact catggagagg    900

tttggagttt ctgttgaaca ttctggcaac tgggatcgtt tccttgtaca tggaggtcag    960

aagtacaaaa gccctggcaa tgcctttgtt gaaggggatg caagctctgc ttcctatctc   1020

ttggctgggg ctgccatcac tggtgggacc atcactgtga atggctgtgg cacctcatcc   1080

cttcaaggtg atgtaaagtt tgcagaggtc ttggagaaaa tgggtgccaa ggtcacctgg   1140

tctgagaaca gtgtaactgt gtctggacct cccagagact tcagtggcag aaaggttctc   1200

cgtggaattg atgtgaacat gaacaagatg ccagatgtgg ccatgaccct cgctgttgta   1260

gccctgtttg caaatggacc aactgcaatc cgtgatgttg cttcatggag ggtgaaggag   1320

acagagagga tgattgccat ttgcacagaa ctccgcaaac ttggtgcaac agttgaagag   1380

ggaccagatt actgtgtgat aaccccacct gagaagctca atgtgacagc cattgacacc   1440

tatgatgacc acagaatggc aatggctttc tcccttgctg cctgtggtga tgtgcctgtg   1500

actatcaaag accctgggtg cacaaggaag acatttccag actactttga agttttggag   1560

aggttgacaa agcactgagt agttagctta atcaccta g                          1599
```

<210> SEQ ID NO 19
<211> LENGTH: 1551
<212> TYPE: DNA
<213> ORGANISM: Brassica napus

<400> SEQUENCE: 19

```
atggctcaat cttcaaggat ttgccacggt gttcagaacc cttgtgtgat catatccaat     60

ctcagtaaga gcaatcagaa caaatcaccc ttctctgtct ccctcaaaac tcatcaacca    120

cgtgcatcta gttggggatt gaagaaaagt gggacaatgc tgaacggatc agtcattagg    180

cctgtaaagg ttacagcctc tgtgtccacg agtgaaaagg caagcgagat cgtcttacaa    240

ccgattagag aaatctctgg gcttatcaag ttgcctggct ccaaatcact ctccaatagg    300

atacttcttt tggctgcact gagtgaaggc acaactgttg tggacaactt gctcaactcc    360

gatgatatca actacatgct tgacgccttg aagaagttag gactcaatgt ggagagagat    420

agcgttaaca atcgtgctgt cgtagaagga tgtggtggca tctttcctgc atctctggat    480

tctaagagcg acatcgagct ttacttgggc aatgctgcaa cagccatgag accgttaact    540

gctgctgtta ccgcagctgg aggaaatgct agttatgtgc ttgatggtgt tccaagaatg    600

agggaaaggc caatagggga tttggtcgtc ggactgaaac agctcggtgc tgacgttgaa    660

tgtactttag gcacaaactg tcctcccgtg cgtgttaacg caaatggtgg actgcctggt    720

ggaaaggtca agttgtctgg ctccatttcc agtcaatacc ttacggcttt gctcatggct    780

gcaccacttg ccttaggtga tgtggagatt gagatcattg acaagctcat atctgttccg    840

tacgtggaaa tgacacttaa gctgatggaa agattcggag tttcagccga acattccgat    900

agctgggatc gtttctttgt aaagggtggg cagaagtaca agtctcctgg caatgcttat    960

gtggaaggtg acgcttcttc agctagttac ttcttggctg gtgcagccat aactggcgag   1020

acagttaccg tggaaggatg cggaactacc agcctccaag gtgatgtcaa gttcgcagag   1080

gtgttggaaa agatggggtg caaagtttcc tggacagaga actcagttac tgtaacggga   1140
```

```
cctagtaggg atgcttttgg gatgcgtcac cttagggcag ttgacgtgaa catgaacaag   1200

atgccagatg tcgctatgac tttagcagtt gtggcactgt ttgccgatgg tcctacaacg   1260

attagggacg tagcttcttg gagagtcaaa gaaactgaga ggatgatcgc catttgtact   1320

gagcttcgta agttgggtgc cacagttgaa gaagggtccg attactgcgt gattactcct   1380

ccagctaaag ttaagcctgc tgagattgat acctatgatg accacagaat ggctatggcc   1440

tttagcctcg ctgcatgtgc cgatgttcca gtcacgatca aggaccctgg ctgtactaga   1500

aagacatttc ccgactactt tcaagtgctt gagtcaatca cgaaacactg a            1551
```

<210> SEQ ID NO 20
<211> LENGTH: 1551
<212> TYPE: DNA
<213> ORGANISM: Brassica napus

<400> SEQUENCE: 20

```
atggctcaat cttcaaggat ttgccacggt gttcagaacc cttgtgtgat catatccaat     60

ctcagtaaga gcaatcagaa caaatcaccc ttctctgtct ccctcaaaac tcatcaacca    120

cgtgcatcta gttggggatt gaagaaaagc ggaacaatgc tgaacggatc agtcattagg    180

cctgtaaagg ttactgcatc tgtgtccacg agtgaaaagg caagcgagat cgtcttacaa    240

ccgattagag aaatctctgg gcttatcaag ttgcctggct ccaaatcact ctccaatagg    300

atacttcttt tggctgcact gagtgaaggc acaactgttg tggacaactt gctcaactcc    360

gatgatatca actacatgct tgacgccttg aagaagttag gactcaatgt ggagagagat    420

agcgttaaca atcgtgctgt cgtagaagga tgtggtggaa tctttcctgc atctctggat    480

tctaagagcg acatcgagct ttacttgggc aatgctgcaa cagccatgag atccttaact    540

gctgctgtta ccgcagctgg tggaaatgct agttatgtgc ttgatggtgt tccaagaatg    600

agggaaaggc caatagggga tttggtcgtc ggactcaaac agctcggtgc tgacgttgaa    660

tgtactttag gcacaaactg tcctcccgtg cgtgttaacg caaatggtgg actgcctggt    720

ggaaaagtca agttgtctgg ctccatttcc agtcaatacc ttacggcttt gctcatggct    780

gcaccacttg ccttaggtga tgtggagatt gagatcattg acaagctcat atctgttccg    840

tacgtggaaa tgacacttaa gctgatggaa agattcggag tttcagccga acattccgat    900

agctgggatc gtttctttgt aaagggaggg cagaagtaca agtctcctgg aaacgcatac    960

gtggaaggtg acgcttcttc agctagttac ttcttggctg gtgcagccat aactggcgag   1020

acagttaccg tggaaggatg cggaactacc agcctccaag gtgatgtcaa gttcgcagag   1080

gtgttggaaa agatggggtg caaagtttcc tggacagaga actcagttac tgtaacggga   1140

cctagtaggg atgcttttgg gatgcgtcac cttagagccg ttgacgtgaa catgaacaag   1200

atgccagatg tcgctatgac cttagctgtg gttgcactgt ttgccgatgg tcctacaacg   1260

attagggacg tagcctcttg gagagtcaaa gaaaccgaga ggatgatcgc catttgtact   1320

gagcttcgta agttgggtgc cacagttgaa gaagggtccg attactgcgt gattactcct   1380

ccagctaaag ttaagccagc agagattgat acctatgatg accacagaat ggctatggct   1440

ttcagcctcg ctgcatgtgc cgatgttcca gtcacgatca aggaccctgg ctgtactaga   1500

aagacatttc ccgactactt tcaagtgctt gagtcaatca cgaaacactg a            1551
```

<210> SEQ ID NO 21
<211> LENGTH: 1551
<212> TYPE: DNA
<213> ORGANISM: Brassica napus

<400> SEQUENCE: 21

```
atggctcaat cttcaaggat ttgccacggt gttcagaacc cttgtgtgat catatccaat     60
ctcagtaaga gcaatcagaa caaatcaccc ttctctgtct ccctgaaaac tcatcaacca    120
cgtgcatcta gttggggatt gaagaaaagt ggcacaatgc tgaacggatc agtcattagg    180
cctgtaaagg ttacagcctc tgtgtccacg agtgaaaagg caagcgagat cgtcttacaa    240
ccgattagag aaatctctgg gcttatcaag ttgcctggct ccaaatcact ctccaatagg    300
atacttcttt tggctgcact gagtgaaggg acaactgttg tggacaactt gctcaactcc    360
gatgatatca actacatgct tgacgccttg aagaagttag gactcaatgt ggagagagat    420
agcgttaaca atcgtgctgt cgtagaagga tgtggtggaa tctttcctgc atctctggat    480
tctaagagcg acatcgagct ttacttgggc aatgctggca tcgccatgag atccttaact    540
gctgctgtta ccgcagctgg tggaaatgct agttatgtgc ttgatggtgt tccaagaatg    600
agggaaaggc caatagggga tttggttgtc ggactcaaac agctcggtgc tgacgttgaa    660
tgtactttag gcacaaactg tcctcccgtg cgtgttaacg caaatggtgg actgcctggt    720
ggaaaggtca agttgtctgg ctccatttcc agtcaatacc ttacggcttt gctcatggct    780
gcaccacttg ccttaggtga tgtggagatt gagatcattg acaagctcat atctgttccg    840
tacgtggaaa tgacacttaa gctgatggaa agattcggag tttcagccga acattccgat    900
agctgggatc gtttcttcgt aaagggaggg cagaagtaca agtctcctgg gaacgcatac    960
gtggaaggtg acgcttcttc agctagttac ttcttggctg gtgcagccat aactggcgag   1020
acagttaccg tggaaggatg cggaactacc agccttcaag gtgatgtcaa gttcgcagag   1080
gtgttggaaa agatggggtg caaagtttcc tggacagaga actcagttac tgtaacggga   1140
cctagtaggg atgcttttgg aatgagacac cttagggcag ttgacgtgaa catgaacaag   1200
atgccagatg tcgctatgac tttagctgta gtggcactgt tcgcagatgg tcctacaacg   1260
ataagggacg tagcctcttg gagagtcaaa gaaaccgaga ggatgatcgc catttgtact   1320
gagcttcgta agttgggtgc cacagttgaa gaagggtccg attactgcgt gattactcct   1380
ccagctaaag ttaagccagc agagattgat acctatgatg accacagaat ggctatggcc   1440
tttagcctcg ctgcatgtgc cgatgttcca gtcacgatca aggaccctgg ctgtactaga   1500
aagacatttc ccgactactt tcaagtgctt gagtcaatca cgaaacactg a            1551
```

<210> SEQ ID NO 22
<211> LENGTH: 1533
<212> TYPE: DNA
<213> ORGANISM: Triticum aestivum

<400> SEQUENCE: 22

```
atggcaatgg ctgctgctgc tactatggct gcaagcgctt cctcttccgc tgtgagctta     60
gacagagcag ctccagcacc atctaggcgt ctgccaatgc cagcagctag accagctagg    120
agaggtgcag tccgtttgtg gggaccaagg ggagcagctg cacgtgctac aagtgtcgca    180
gcaccagcag caccgagtgg agctgaggaa gtcgtgcttc aacctatcag agagatcagc    240
ggtgccgtcc agctccctgg gtcaaagtca cttagcaaca gaatacttct tttgagcgca    300
ttgtcagagg gcacgacagt ggtggataac cttctgaact ctgaagatgt tcactacatg    360
cttgaggctt tggaggcatt aggtctttct gttgaagccg ataaggttgc taagcgtgct    420
gtggtggttg gttgcggagg gagattccca gttgagaaag atgctcaaga ggaagttaag    480
```

```
ctgtttctgg gaaatgctgg gattgcaatg aggagcttga ctgctgctgt ggttgctgct    540

ggtggaaatg ccacatacgt ccttgatgga gtgcctagaa tgagagagag accgattggg    600

gatctggtgg ttggccttca gcaacttgga gcagacgctg actgctttct tggaacaaac    660

tgtccacccg ttaggatcaa cgggaaagga ggtctccctg gtgggaaggt taagttgtct    720

ggatcaatct ctagtcagta tctgtcatca cttctcatgg ctgcacctct tgcacttgaa    780

gatgttgaga ttgaaatcat agacaaactc atatcagttc catacgtgga aatgacgctg    840

aagctgatgg agaggttcgg agtgacagca gagcactcag attcttggga taggttctac    900

atcaagggag gtcagaagta caaatcacct gggaacgctt acgtggaagg tgatgcctct    960

tctgcttcct acttcctcgc tggagcagca atcaccggag gaactgttac tgtcgaaggt   1020

tgcggaacta cttccttgca aggggacgtc aagttcgcag aagtcttaga aatgatggga   1080

gctaaagtta cttggaccga tacaagtgtt acagtgactg gtcctccacg tcaacccttt   1140

ggaaggaagc acctcaaagc cgttgatgtt aacatgaaca agatgccaga tgtcgccatg   1200

acgcttgccg ttgtggctct gttcgcagat ggtcccacag ccattagaga cgtggccagc   1260

tggagggtga aagaaactga aaggatggtc gccattagaa cagagttaac caaacttgga   1320

gctactgtgg aagagggacc cgactattgc atcattacac ctcccgagaa gctgaacata   1380

accgctattg acacttatga tgatcatcgt atggctatgg ccttttcatt agcagcttgc   1440

gctgaggtgc cagtaaccat tagagatcct gggtgtacta ggaaaacttt ccctaactac   1500

ttcgatgtcc tttcaacatt cgtgaagaat tga                                1533
```

<210> SEQ ID NO 23
<211> LENGTH: 1281
<212> TYPE: DNA
<213> ORGANISM: Streptomyces roseosporus

<400> SEQUENCE: 23

```
atgacggtga tagagatacc tgggtctaag tctgttacag ccagagcact gttcttggca     60

gctgctgccg atgggacgac tactcttctt agaccattgc gtagcgatga cactgagggc    120

ttcgcagaag gactgaggaa tctgggctat gctgtggaac aagaggctga taggtggcgt    180

gtccaaggca gaccagctgg accagcagcc acggaagcag atgtctattg cagagatggt    240

gccaccaccg ctaggttcct tccgacactg gcagcagcag ctgcttccgg aacctacaga    300

ttcgacgctt cagcacagat gcgtcgtcgt ccccttgctc cattgacaag ggcacttaca    360

gccttgggtg tggatcttag acacgaagga gcagacggac atcatccgct caccgttcgt    420

gcagctggca tcgaaggagg agaattgacg ctcgacgctg gcgagtccag ccaatacttg    480

acagcactgc tcatgctcgg acctcttaca acaaagggac ttcgcatcga agttacagaa    540

ctcgtctctg caccctacgt ggaaatcacc ctcgctatga tgagagactt tggtgtggag    600

gttgagaggg aggggaatac cttcaccgtt ccaagcccat cttcaagact taggtccaat    660

agaggtggac ccataggagg ctatagagct actacgtatg ctgtcgagcc agatgcctca    720

actgcctctt acttctttgc agctgctgcc ctcactggtc gcgaggtcac agtgcctgga    780

ttggggactg gagctttgca aggtgatttg cgtttcgtgg atgtgctgag agaaatgggt    840

gccgaggtgt ctgttggtcc ggacgccaca actgtgcgct caactggcag attgagggga    900

atcactgtga acatgagaga tatctcagac acgatgccta cactcgcagc tattgcacct    960

tatgccgatg gtccagtggt gattgaagat gttgccaaca cccgtgtgaa ggagtgtgac   1020

cgtctggagg cttgtgctga gaatctgagg gcaatgggaa tcaccgtcca tacgggtccg   1080
```

```
gataggatag aaatccatcc tggaacacct aaaccgactg ggatcgccac ccacggagat   1140

caccgcatag tcatgtcatt tgccgtcgct ggccttcgca ctcctggcct cacttacgac   1200

gaccctggct gcgtgcgtaa gaccttccct agatttcacg aggtgtttgc cgacttcgct   1260

cacgaccttg agggaaggtg a                                              1281
```

<210> SEQ ID NO 24
<211> LENGTH: 1248
<212> TYPE: DNA
<213> ORGANISM: Streptomyces griseus

<400> SEQUENCE: 24

```
atgggtgcag tgacagtcat cgacattcct ggaagcaaga gcgtgacagc aagggcactc     60

ttcttggcag cagcagccga tggaacgaca acactgcttc gtcctctgag gtcagacgac    120

acggaggggt ttgccgaggg tcttaagaat ctcggttatg ccgttgagca agaggctgac    180

cgttggaggg tcgaaggcag accggatggt ccagctgctc cggatgcaga tgtctactgc    240

cgtgatggtg caacgactgc acgctttctt ccaaccctcg tcgcagcagc agcttctgga    300

acgtatcgtt tcgacgcctc agcacagatg aggagacgtc ccttggctcc actcactagg    360

gcactgacag ctcttggcgt ggatttgaga catggtggag aggagggtca tcatccactg    420

actgtcagag ctgctggcat agaaggtggc gatgttgtcc ttgacgctgg tgaatcttct    480

cagtatctca cagcccttct tatgttgggt ccgttgactg ccaaaggtct tagaatcgaa    540

gtcactgatc tcgtgagcgc tccttacgtt gaaatcactc tggccatgat gagagatttc    600

ggagttgatg ttagcagaga aggaaacact ttcaccgtgc cgtccggagg ctatagagct    660

acagcctacg ctgtggagcc agacgcaagc acggcttctt acttctttgc agcagctgcc    720

ctcactggac gcgaggtgac ggtccctggg ctgggaattg gtgctcttca aggagacctt    780

cgttttgtgg acgtgctgcg tgatatggga gcagaggtgt ctgttggacc agatgccacg    840

acagtgcgct caactggcag actccgtggc attacagtta ctatgagaga catttcagac    900

acgatgccaa cactcgctgc tattgcacct cacgctgatg gacccgtccg tattgaggac    960

gtggcaaaca ctcgtgtcaa ggaatgtgat aggcttgagg catgtgctca aaaccttaga   1020

gctatgggaa tcacggtgca tactgggcac gattggattg agattctccc tgggactcca   1080

aagccaacgg gaatagctac gcacggagat cacagaatcg ttatgtcctt cgcagtggct   1140

ggtttgttga cccctgggct gacatacgat gatcctggct gcgtccgcaa gacttttcca   1200

aggttccacg aagttttcgc tgactttgct gcatcacccc aagcctga                 1248
```

<210> SEQ ID NO 25
<211> LENGTH: 1245
<212> TYPE: DNA
<213> ORGANISM: Artificial sequence
<220> FEATURE:
<223> OTHER INFORMATION: DGT-31 v3 nucleotide

<400> SEQUENCE: 25

```
atgactgtga ttgacatccc tggctcaaag tcagttactg ccagagcatt gttcctcgca     60

gcagctgctg atggcactac aactcttttg agacctcttc acagcgatga cacggaaggc    120

ttcactgagg gtctcactcg tttgggatac gcagtggtta gagaacccga taggtggcac    180

atagaaggac gtccctccgg tccagcagca gcagatgcag aagttcactg tagggacggt    240

gctacaactg ctcgctttct tccaaccctt gcagctgctg ctgcctccgg aacgtatcgt    300
```

```
ttcgacgcat cagctcagat gaggcgtaga cccctcgctc ccctcacgga agctcttaga    360

acacttggag tggaccttag gcatgatgga gctgaaggcc accacccctt gacaattcaa    420

gcctctggtg ttaagggtgg aggacttacg ctcgacgctg gtgagtcatc tcagtacttg    480

acagctctgc tcatgcttgg tcctctgacc gcagagggac tgagaataga agttacggag    540

cttgtctctg ctccttatgt ggagatcacc cttgcaatga tgagaggctt tggtgtggag    600

gttgttaggg aggggaatac tttcactgtg cctcctggag gttacagagc tacaacttat    660

gccatagaac cggacgcaag cacagcttcc tacttctttg cagcagcagc cctcactggg    720

agggaagtga cggtgcctgg cttgggcact ggagcacttc aaggtgatct taggttcacg    780

gaggtcctca gaaggatgga cgctgatgtt cgcacaacgt ccgactctac aacagtgcgc    840

tcagatggtc gccttgctgg gttgactgtc aacatgaggg acataagcga cacaatgcca    900

acactggcag ctatagctcc gtacgcaagc tcaccagtta ggatcgagga tgtcgcaaac    960

acccgtgtga aggaatgtga taggctggag gcttgcgctc agaatctccg ctcaatgggc   1020

atcaccgttc gcactggacc agattggatt gagatccatc ctgggactcc tagaccgacc   1080

gagatagcca cacacggtga tcatagaatc gtcatgtcat ttgccgtggc tggacttaga   1140

acccctggga tgtcttacga tgaccctggc tgcgttcgca agacttttcc tcgttttcat   1200

gaagagtttg cagccttcgt ggagcgctca tccgctggag agtga                   1245
```

```
<210> SEQ ID NO 26
<211> LENGTH: 213
<212> TYPE: DNA
<213> ORGANISM: Artificial sequence
<220> FEATURE:
<223> OTHER INFORMATION: Chloroplast Transit Peptide

<400> SEQUENCE: 26

atgcttgcta gacaaggtgg aagtctgaga gcttctcaat gcaacgctgg acttgctaga     60

agagttgaag ttggtgctct tgttgttcct agacctatct ctgttaacga cgttgttcct    120

cacgtttact ctgctccact ttctgttgct agaaggtctt gctctaagtc ctccattagg    180

tccactagaa ggcttcaaac tactgtgtgc tct                                213
```

```
<210> SEQ ID NO 27
<211> LENGTH: 186
<212> TYPE: DNA
<213> ORGANISM: Artificial sequence
<220> FEATURE:
<223> OTHER INFORMATION: Chloroplast Transit Peptide

<400> SEQUENCE: 27

atgcaactcc tgaatcagag gcaagccctg cgtcttggtc gttcatctgc ttcaaagaac     60

cagcaagttg ctccactggc ctctaggcct gcttcttcct tgagcgtcag cgcatccagc    120

gtcgcacctg cacctgcttg ctcagctcct gctggagctg gaaggcgtgc tgttgtcgtg    180

agagca                                                              186
```

```
<210> SEQ ID NO 28
<211> LENGTH: 198
<212> TYPE: DNA
<213> ORGANISM: Artificial sequence
<220> FEATURE:
<223> OTHER INFORMATION: Chloroplast Transit Peptide

<400> SEQUENCE: 28

atggctcaat ctagcagaat ctgccacggt gtgcagaacc catgtgtgat catttccaat     60
```

```
ctctccaaat ccaaccagaa caaatctcct ttctcagtca gcctcaagac tcaccagcag    120

cagcgtcgtg cttaccagat atctagctgg ggattgaaga agtcaaacaa cgggtccgtg    180

attcgtccgg ttaaggca                                                  198


<210> SEQ ID NO 29
<211> LENGTH: 198
<212> TYPE: DNA
<213> ORGANISM: Artificial sequence
<220> FEATURE:
<223> OTHER INFORMATION: Chloroplast Transit Peptide

<400> SEQUENCE: 29

atggcacaag ccagccgtat ctgccagaat ccatgtgtga tatccaatct ccccaaaagc     60

aaccaccgta agtcccccttt ctctgtctca ctcaagacgc atcagcctag agcctcttca   120

tggggactta agaagtctgg caccatgctg aacggttcag tgattagacc cgtcaaggtg    180

acagcttctg tttccgca                                                  198


<210> SEQ ID NO 30
<211> LENGTH: 225
<212> TYPE: DNA
<213> ORGANISM: Artificial sequence
<220> FEATURE:
<223> OTHER INFORMATION: Chloroplast Transit Peptide

<400> SEQUENCE: 30

atggcacaat ctagcagaat ctgccacggt gtgcagaacc catgtgtgat catttcaaat     60

ctctcaaagt ccaatcagaa caaatcacct ttctccgtct ccctcaagac acaccagcat    120

ccaagggcat acccgataag cagctcatgg ggactcaaga agagcggaat gactctgatt    180

ggctctgagc ttcgtcctct taaggttatg tcctctgttt ccgca                    225


<210> SEQ ID NO 31
<211> LENGTH: 207
<212> TYPE: DNA
<213> ORGANISM: Artificial sequence
<220> FEATURE:
<223> OTHER INFORMATION: Chloroplast Transit Peptide

<400> SEQUENCE: 31

atggcacaag ttagcagaat ctgtaatggt gtgcagaacc catctcttat ctccaatctc     60

tcaaagtcca gccaacgtaa gtctcccctc agcgtgtctc tgaaaactca gcagcccaga    120

gcttcttcat ggggtttgaa gaaatctgga acgatgctta acggctcagt cattcgtccg    180

gttaaggtga cagcctccgt ctccgct                                        207


<210> SEQ ID NO 32
<211> LENGTH: 1464
<212> TYPE: DNA
<213> ORGANISM: Artificial sequence
<220> FEATURE:
<223> OTHER INFORMATION: In-frame fusion of dgt-28 v5 and TraP4 v2

<400> SEQUENCE: 32

atgcttgcta gacaaggtgg aagtctgaga gcttctcaat gcaacgctgg acttgctaga     60

agagttgaag ttggtgctct tgttgttcct agacctatct ctgttaacga cgttgttcct    120

cacgtttact ctgctccact ttctgttgct agaaggtctt gctctaagtc ctccattagg    180

tccactagaa ggcttcaaac tactgtgtgc tctgctgcaa gagggatgcc agccttgtct    240
```

```
ttacctggat caaagagtat cacagctagg gcactctttc ttgctgctgc tgctgatggg    300
gttactactt tggtgaggcc attgagaagt gacgacacag aaggattcgc tgaggggtta    360
gttcgtttag gctatcgtgt agggaggaca cccgatactt ggcaagtcga tggcagacca    420
caaggaccag cagtggctga ggctgacgtc tactgtagag acggagcaac caccgctaga    480
ttcttgccaa ccttagcagc tgctggtcac ggaacataca gatttgatgc ttcaccacag    540
atgaggagac gtcctctttt gcccttaagc agagccttga gggatttggg tgtcgatctt    600
agacacgaag aagctgaagg tcatcaccct ctgactgtcc gtgctgctgg ggttgaagga    660
ggagaggtta ctttggatgc tggtcagtca agtcagtatc tcactgcctt gttgctcctt    720
ggtcccctta caagacaagg actgaggata agggttactg atttggtgtc agcaccatac    780
gtggagatta cgcttgcaat gatgagggct ttcggagttg aagtggcaag ggagggagat    840
gtgttcgttg ttccacctgg tggatatcgt gcaactacgt atgctataga acccgacgca    900
agtactgctt cttacttctt cgcagctgct gctttgactc ctggagctga agtgactgta    960
cctgggttag gcacgggagc acttcaagga gatttgggat ttgtagatgt cttaaggaga   1020
atgggagccg aggtgtccgt aggagctgat gcaaccactg ttagaggaac tggtgaattg   1080
cgtggcctta cagccaacat gagagacata agtgatacga tgccgaccct cgctgcaata   1140
gcaccctttg ctagtgctcc agttagaatc gaggatgttg ccaacactcg tgtcaaagaa   1200
tgtgacagac ttgaggcttg tgcagagaac cttaggaggt tgggagtaag ggttgcaacg   1260
ggtccggact ggattgagat acaccctggt ccagctactg gtgctcaagt cacaagctat   1320
ggtgatcaca gaattgtgat gtcatttgca gtgactggac ttcgtgtgcc tgggatcagc   1380
ttcgacgacc ctggctgtgt tcgtaagact tttcctgggt ttcacgaggc tttcgcagaa   1440
ttgaggcgtg gcattgggag ctga                                          1464
```

<210> SEQ ID NO 33
<211> LENGTH: 1434
<212> TYPE: DNA
<213> ORGANISM: Artificial sequence
<220> FEATURE:
<223> OTHER INFORMATION: In-frame fusion of dgt-28 v5 and TraP5 v2

<400> SEQUENCE: 33

```
atgcaactcc tgaatcagag gcaagccctg cgtcttggtc gttcatctgc ttcaaagaac     60
cagcaagttg ctccactggc ctctaggcct gcttcttcct tgagcgtcag cgcatccagc    120
gtcgcacctg cacctgcttg ctcagctcct gctggagctg gaaggcgtgc tgttgtcgtg    180
agagcagcaa gagggatgcc agccttgtct ttacctggat caaagagtat cacagctagg    240
gcactctttc ttgctgctgc tgctgatggg gttactactt tggtgaggcc attgagaagt    300
gacgacacag aaggattcgc tgaggggtta gttcgtttag gctatcgtgt agggaggaca    360
cccgatactt ggcaagtcga tggcagacca caaggaccag cagtggctga ggctgacgtc    420
tactgtagag acggagcaac caccgctaga ttcttgccaa ccttagcagc tgctggtcac    480
ggaacataca gatttgatgc ttcaccacag atgaggagac gtcctctttt gcccttaagc    540
agagccttga gggatttggg tgtcgatctt agacacgaag aagctgaagg tcatcaccct    600
ctgactgtcc gtgctgctgg ggttgaagga ggagaggtta ctttggatgc tggtcagtca    660
agtcagtatc tcactgcctt gttgctcctt ggtcccctta caagacaagg actgaggata    720
agggttactg atttggtgtc agcaccatac gtggagatta cgcttgcaat gatgagggct    780
ttcggagttg aagtggcaag ggagggagat gtgttcgttg ttccacctgg tggatatcgt    840
```

```
gcaactacgt atgctataga acccgacgca agtactgctt cttacttctt cgcagctgct    900

gctttgactc ctggagctga agtgactgta cctgggttag gcacgggagc acttcaagga    960

gatttgggat ttgtagatgt cttaaggaga atgggagccg aggtgtccgt aggagctgat   1020

gcaaccactg ttagaggaac tggtgaattg cgtggcctta cagccaacat gagagacata   1080

agtgatacga tgccgaccct cgctgcaata gcaccctttg ctagtgctcc agttagaatc   1140

gaggatgttg ccaacactcg tgtcaaagaa tgtgacagac ttgaggcttg tgcagagaac   1200

cttaggaggt tgggagtaag ggttgcaacg ggtccggact ggattgagat acaccctggt   1260

ccagctactg gtgctcaagt cacaagctat ggtgatcaca gaattgtgat gtcatttgca   1320

gtgactggac ttcgtgtgcc tgggatcagc ttcgacgacc ctggctgtgt tcgtaagact   1380

tttcctgggt ttcacgaggc tttcgcagaa ttgaggcgtg gcattgggag ctga         1434
```

```
<210> SEQ ID NO 34
<211> LENGTH: 1446
<212> TYPE: DNA
<213> ORGANISM: Artificial sequence
<220> FEATURE:
<223> OTHER INFORMATION: In-frame fusion of dgt-28 v5 and TraP8 v2

<400> SEQUENCE: 34

atggctcaat ctagcagaat ctgccacggt gtgcagaacc catgtgtgat catttccaat     60

ctctccaaat ccaaccagaa caaatctcct ttctcagtca gcctcaagac tcaccagcag    120

cagcgtcgtg cttaccagat atctagctgg ggattgaaga agtcaaacaa cgggtccgtg    180

attcgtccgg ttaaggcagc aagagggatg ccagccttgt ctttacctgg atcaaagagt    240

atcacagcta gggcactctt tcttgctgct gctgctgatg ggttactac tttggtgagg    300

ccattgagaa gtgacgacac agaaggattc gctgaggggt tagttcgttt aggctatcgt    360

gtagggagga cacccgatac ttggcaagtc gatggcagac cacaaggacc agcagtggct    420

gaggctgacg tctactgtag agacggagca accaccgcta gattcttgcc aaccttagca    480

gctgctggtc acggaacata cagatttgat gcttcaccac agatgaggag acgtcctctt    540

ttgcccttaa gcagagcctt gagggatttg ggtgtcgatc ttagacacga agaagctgaa    600

ggtcatcacc ctctgactgt ccgtgctgct ggggttgaag gaggagaggt tactttggat    660

gctggtcagt caagtcagta tctcactgcc ttgttgctcc ttggtcccct tacaagacaa    720

ggactgagga taagggttac tgatttggtg tcagcaccat acgtggagat tacgcttgca    780

atgatgaggg ctttcggagt tgaagtggca agggagggag atgtgttcgt tgttccacct    840

ggtggatatc gtgcaactac gtatgctata gaacccgacg caagtactgc ttcttacttc    900

ttcgcagctg ctgctttgac tcctggagct gaagtgactg tacctgggtt aggcacggga    960

gcacttcaag gagatttggg atttgtagat gtcttaagga gaatgggagc cgaggtgtcc   1020

gtaggagctg atgcaaccac tgttagagga actggtgaat tgcgtggcct tacagccaac   1080

atgagagaca taagtgatac gatgccgacc ctcgctgcaa tagcaccctt tgctagtgct   1140

ccagttagaa tcgaggatgt tgccaacact cgtgtcaaag aatgtgacag acttgaggct   1200

tgtgcagaga accttaggag gttgggagta agggttgcaa cgggtccgga ctggattgag   1260

atacaccctg gtccagctac tggtgctcaa gtcacaagct atggtgatca cagaattgtg   1320

atgtcatttg cagtgactgg acttcgtgtg cctgggatca gcttcgacga ccctggctgt   1380

gttcgtaaga cttttcctgg gtttcacgag gctttcgcag aattgaggcg tggcattggg   1440
```

agctga 1446

<210> SEQ ID NO 35
<211> LENGTH: 1446
<212> TYPE: DNA
<213> ORGANISM: Artificial sequence
<220> FEATURE:
<223> OTHER INFORMATION: In-frame fusion of dgt-28 v5 and TraP9 v2

<400> SEQUENCE: 35
atggcacaag ccagccgtat ctgccagaat ccatgtgtga tatccaatct ccccaaaagc 60
aaccaccgta agtccccttt ctctgtctca ctcaagacgc atcagcctag agcctcttca 120
tggggactta agaagtctgg caccatgctg aacggttcag tgattagacc cgtcaaggtg 180
acagcttctg tttccgcagc aagagggatg ccagccttgt ctttacctgg atcaaagagt 240
atcacagcta gggcactctt tcttgctgct gctgctgatg gggttactac tttggtgagg 300
ccattgagaa gtgacgacac agaaggattc gctgaggggt tagttcgttt aggctatcgt 360
gtagggagga cacccgatac ttggcaagtc gatggcagac cacaaggacc agcagtggct 420
gaggctgacg tctactgtag agacggagca accaccgcta gattcttgcc aaccttagca 480
gctgctggtc acggaacata cagatttgat gcttcaccac agatgaggag acgtcctctt 540
ttgcccttaa gcagagcctt gagggatttg ggtgtcgatc ttagacacga agaagctgaa 600
ggtcatcacc ctctgactgt ccgtgctgct ggggttgaag gaggagaggt tactttggat 660
gctggtcagt caagtcagta tctcactgcc ttgttgctcc ttggtcccct tacaagacaa 720
ggactgagga taagggttac tgatttggtg tcagcaccat acgtggagat tacgcttgca 780
atgatgaggg ctttcggagt tgaagtggca agggagggag atgtgttcgt tgttccacct 840
ggtggatatc gtgcaactac gtatgctata gaacccgacg caagtactgc ttcttacttc 900
ttcgcagctg ctgctttgac tcctggagct gaagtgactg tacctgggtt aggcacggga 960
gcacttcaag gagatttggg atttgtagat gtcttaagga gaatgggagc cgaggtgtcc 1020
gtaggagctg atgcaaccac tgttagagga actggtgaat tgcgtggcct tacagccaac 1080
atgagagaca taagtgatac gatgccgacc ctcgctgcaa tagcaccctt tgctagtgct 1140
ccagttagaa tcgaggatgt tgccaacact cgtgtcaaag aatgtgacag acttgaggct 1200
tgtgcagaga accttaggag gttgggagta agggttgcaa cgggtccgga ctggattgag 1260
atacaccctg gtccagctac tggtgctcaa gtcacaagct atggtgatca cagaattgtg 1320
atgtcatttg cagtgactgg acttcgtgtg cctgggatca gcttcgacga ccctggctgt 1380
gttcgtaaga cttttcctgg gtttcacgag gctttcgcag aattgaggcg tggcattggg 1440
agctga 1446

<210> SEQ ID NO 36
<211> LENGTH: 1473
<212> TYPE: DNA
<213> ORGANISM: Artificial sequence
<220> FEATURE:
<223> OTHER INFORMATION: In-frame fusion of dgt-28 v5 and TraP12 v2

<400> SEQUENCE: 36
atggcacaat ctagcagaat ctgccacggt gtgcagaacc catgtgtgat catttcaaat 60
ctctcaaagt ccaatcagaa caaatcacct ttctccgtct ccctcaagac acaccagcat 120
ccaagggcat acccgataag cagctcatgg ggactcaaga agagcggaat gactctgatt 180
ggctctgagc ttcgtcctct taaggttatg tcctctgttt ccgcagcaag agggatgcca 240

```
gccttgtctt tacctggatc aaagagtatc acagctaggg cactctttct tgctgctgct    300
gctgatgggg ttactacttt ggtgaggcca ttgagaagtg acgacacaga aggattcgct    360
gaggggttag ttcgtttagg ctatcgtgta gggaggacac ccgatacttg gcaagtcgat    420
ggcagaccac aaggaccagc agtggctgag gctgacgtct actgtagaga cggagcaacc    480
accgctagat tcttgccaac cttagcagct gctggtcacg gaacatacag atttgatgct    540
tcaccacaga tgaggagacg tcctcttttg cccttaagca gagccttgag ggatttgggt    600
gtcgatctta gacacgaaga agctgaaggt catcaccctc tgactgtccg tgctgctggg    660
gttgaaggag gagaggttac tttggatgct ggtcagtcaa gtcagtatct cactgccttg    720
ttgctccttg gtccccttac aagacaagga ctgaggataa gggttactga tttggtgtca    780
gcaccatacg tggagattac gcttgcaatg atgagggctt tcggagttga agtggcaagg    840
gagggagatg tgttcgttgt tccacctggt ggatatcgtg caactacgta tgctatagaa    900
cccgacgcaa gtactgcttc ttacttcttc gcagctgctg ctttgactcc tggagctgaa    960
gtgactgtac ctgggttagg cacgggagca cttcaaggag atttgggatt tgtagatgtc   1020
ttaaggagaa tgggagccga ggtgtccgta ggagctgatg caaccactgt tagaggaact   1080
ggtgaattgc gtggccttac agccaacatg agagacataa gtgatacgat gccgaccctc   1140
gctgcaatag caccctttgc tagtgctcca gttagaatcg aggatgttgc caacactcgt   1200
gtcaaagaat gtgacagact tgaggcttgt gcagagaacc ttaggaggtt gggagtaagg   1260
gttgcaacgg gtccggactg gattgagata caccctggtc cagctactgg tgctcaagtc   1320
acaagctatg gtgatcacag aattgtgatg tcatttgcag tgactggact tcgtgtgcct   1380
gggatcagct tcgacgaccc tggctgtgtt cgtaagactt ttcctgggtt tcacgaggct   1440
ttcgcagaat tgaggcgtgg cattgggagc tga                                1473
```

<210> SEQ ID NO 37
<211> LENGTH: 1455
<212> TYPE: DNA
<213> ORGANISM: Artificial sequence
<220> FEATURE:
<223> OTHER INFORMATION: In-frame fusion of dgt-28 v5 and TraP13 v2

<400> SEQUENCE: 37

```
atggcacaag ttagcagaat ctgtaatggt gtgcagaacc catctcttat ctccaatctc     60
tcaaagtcca gccaacgtaa gtctcccctc agcgtgtctc tgaaaactca gcagcccaga    120
gcttcttcat ggggtttgaa gaaatctgga acgatgctta acggctcagt cattcgtccg    180
gttaaggtga cagcctccgt ctccgctgct agagggatgc cagccttgtc tttacctgga    240
tcaaagagta tcacagctag ggcactcttt cttgctgctg ctgctgatgg ggttactact    300
ttggtgaggc cattgagaag tgacgacaca gaaggattcg ctgaggggtt agttcgttta    360
ggctatcgtg tagggaggac acccgatact tggcaagtcg atggcagacc acaaggacca    420
gcagtggctg aggctgacgt ctactgtaga gacggagcaa ccaccgctag attcttgcca    480
accttagcag ctgctggtca cggaacatac agatttgatg cttcaccaca gatgaggaga    540
cgtcctcttt tgcccttaag cagagccttg agggatttgg gtgtcgatct tagacacgaa    600
gaagctgaag gtcatcaccc tctgactgtc cgtgctgctg gggttgaagg aggagaggtt    660
actttggatg ctggtcagtc aagtcagtat ctcactgcct tgttgctcct tggtcccctt    720
acaagacaag gactgaggat aagggttact gatttggtgt cagcaccata cgtggagatt    780
```

```
acgcttgcaa tgatgagggc tttcggagtt gaagtggcaa gggagggaga tgtgttcgtt    840

gttccacctg gtggatatcg tgcaactacg tatgctatag aacccgacgc aagtactgct    900

tcttacttct tcgcagctgc tgctttgact cctggagctg aagtgactgt acctgggtta    960

ggcacgggag cacttcaagg agatttggga tttgtagatg tcttaaggag aatgggagcc   1020

gaggtgtccg taggagctga tgcaaccact gttagaggaa ctggtgaatt gcgtggcctt   1080

acagccaaca tgagagacat aagtgatacg atgccgaccc tcgctgcaat agcacccttt   1140

gctagtgctc cagttagaat cgaggatgtt gccaacactc gtgtcaaaga atgtgacaga   1200

cttgaggctt gtgcagagaa ccttaggagg ttgggagtaa gggttgcaac gggtccggac   1260

tggattgaga tacaccctgg tccagctact ggtgctcaag tcacaagcta tggtgatcac   1320

agaattgtga tgtcatttgc agtgactgga cttcgtgtgc ctgggatcag cttcgacgac   1380

cctggctgtg ttcgtaagac ttttcctggg tttcacgagg ctttcgcaga attgaggcgt   1440

ggcattggga gctga                                                    1455
```

```
<210> SEQ ID NO 38
<211> LENGTH: 186
<212> TYPE: DNA
<213> ORGANISM: Artificial sequence
<220> FEATURE:
<223> OTHER INFORMATION: Chloroplast Transit Peptide

<400> SEQUENCE: 38

atgatacttg gatctagccc aactctgcca cacgcatcac atccagccag acctggtcct     60

gccagaccga tttcagtgaa cgacgtcgtt ccccatgtct actccgctcc tctctccgtg    120

gctaggcgtt cttgtagcaa gtccagcatt aggtctacgc gtagattgca gaccacagtc    180

tgctca                                                              186
```

```
<210> SEQ ID NO 39
<211> LENGTH: 186
<212> TYPE: DNA
<213> ORGANISM: Artificial sequence
<220> FEATURE:
<223> OTHER INFORMATION: Chloroplast Transit Peptide

<400> SEQUENCE: 39

atggcacaga tcaacaagtc tgctaatggg gttaggaacg cttcactgat aagcaacttc     60

tccaataccc gtcaagccaa atcccctttc tccctctcat gcggaacaag actgaagaac    120

agcagcagag gtttgaagaa ggtggcagtt aggctcattg gctcccgtgt caaagtgtct    180

gcctca                                                              186
```

```
<210> SEQ ID NO 40
<211> LENGTH: 207
<212> TYPE: DNA
<213> ORGANISM: Artificial sequence
<220> FEATURE:
<223> OTHER INFORMATION: Chloroplast Transit Peptide

<400> SEQUENCE: 40

atgcaactgc tcaaccagag acaagccttg aggctcggga ggtcctctgc ctctaagaat     60

cagcaagtgg caccgcttgc cagccgtccc atttctgtga acgacgtcgt gccacacgtc    120

tacagcgcac ctctgtccgt tgctagacgc tcctgctcta agtcatcaat ccgcagcact    180

agaaggcttc agacgaccgt ttgttca                                       207
```

<210> SEQ ID NO 41
<211> LENGTH: 1467
<212> TYPE: DNA
<213> ORGANISM: Artificial sequence
<220> FEATURE:
<223> OTHER INFORMATION: In-frame fusion of dgt-32 v3 and TraP14 v2

<400> SEQUENCE: 41

```
atgatacttg gatctagccc aactctgcca cacgcatcac atccagccag acctggtcct     60

gccagaccga tttcagtgaa cgacgtcgtt ccccatgtct actccgctcc tctctccgtg    120

gctaggcgtt cttgtagcaa gtccagcatt aggtctacgc gtagattgca gaccacagtc    180

tgctcaatga cggtgataga gatacctggg tctaagtctg ttacagccag agcactgttc    240

ttggcagctg ctgccgatgg gacgactact cttcttagac cattgcgtag cgatgacact    300

gagggcttcg cagaaggact gaggaatctg ggctatgctg tggaacaaga ggctgatagg    360

tggcgtgtcc aaggcagacc agctggacca gcagccacgg aagcagatgt ctattgcaga    420

gatggtgcca ccaccgctag gttccttccg acactggcag cagcagctgc ttccggaacc    480

tacagattcg acgcttcagc acagatgcgt cgtcgtcccc ttgctccatt gacaagggca    540

cttacagcct tgggtgtgga tcttagacac gaaggagcag acggacatca tccgctcacc    600

gttcgtgcag ctggcatcga aggaggagaa ttgacgctcg acgctggcga gtccagccaa    660

tacttgacag cactgctcat gctcggacct cttacaacaa agggacttcg catcgaagtt    720

acagaactcg tctctgcacc ctacgtggaa atcaccctcg ctatgatgag agactttggt    780

gtggaggttg agagggaggg gaataccttc accgttccaa gcccatcttc aagacttagg    840

tccaatagag gtggacccat aggaggctat agagctacta cgtatgctgt cgagccagat    900

gcctcaactg cctcttactt ctttgcagct gctgccctca ctggtcgcga ggtcacagtg    960

cctggattgg ggactggagc tttgcaaggt gatttgcgtt tcgtggatgt gctgagagaa   1020

atgggtgccg aggtgtctgt tggtccggac gccacaactg tgcgctcaac tggcagattg   1080

aggggaatca ctgtgaacat gagagatatc tcagacacga tgcctacact cgcagctatt   1140

gcaccttatg ccgatggtcc agtggtgatt gaagatgttg ccaacacccg tgtgaaggag   1200

tgtgaccgtc tggaggcttg tgctgagaat ctgagggcaa tgggaatcac cgtccatacg   1260

ggtccggata ggatagaaat ccatcctgga acacctaaac cgactgggat cgccacccac   1320

ggagatcacc gcatagtcat gtcatttgcc gtcgctggcc ttcgcactcc tggcctcact   1380

tacgacgacc ctggctgcgt gcgtaagacc ttccctagat ttcacgaggt gtttgccgac   1440

ttcgctcacg accttgaggg aaggtga                                       1467
```

<210> SEQ ID NO 42
<211> LENGTH: 1455
<212> TYPE: DNA
<213> ORGANISM: Artificial sequence
<220> FEATURE:
<223> OTHER INFORMATION: in-frame fusion of dgt-33 v3 and TraP24 v2

<400> SEQUENCE: 42

```
atgcaactgc tcaaccagag acaagccttg aggctcggga ggtcctctgc ctctaagaat     60

cagcaagtgg caccgcttgc cagccgtccc atttctgtga acgacgtcgt gccacacgtc    120

tacagcgcac ctctgtccgt tgctagacgc tcctgctcta agtcatcaat ccgcagcact    180

agaaggcttc agacgaccgt ttgttcaatg ggtgcagtga cagtcatcga cattcctgga    240

agcaagagcg tgacagcaag ggcactcttc ttggcagcag cagccgatgg aacgacaaca    300
```

```
ctgcttcgtc ctctgaggtc agacgacacg gaggggtttg ccgagggtct taagaatctc    360

ggttatgccg ttgagcaaga ggctgaccgt tggagggtcg aaggcagacc ggatggtcca    420

gctgctccgg atgcagatgt ctactgccgt gatggtgcaa cgactgcacg ctttcttcca    480

accctcgtcg cagcagcagc ttctggaacg tatcgtttcg acgcctcagc acagatgagg    540

agacgtccct tggctccact cactagggca ctgacagctc ttggcgtgga tttgagacat    600

ggtggagagg agggtcatca tccactgact gtcagagctg ctggcataga aggtggcgat    660

gttgtccttg acgctggtga atcttctcag tatctcacag cccttcttat gttgggtccg    720

ttgactgcca aaggtcttag aatcgaagtc actgatctcg tgagcgctcc ttacgttgaa    780

atcactctgg ccatgatgag agatttcgga gttgatgtta gcagagaagg aaacactttc    840

accgtgccgt ccggaggcta tagagctaca gcctacgctg tggagccaga cgcaagcacg    900

gcttcttact tctttgcagc agctgccctc actggacgcg aggtgacggt ccctgggctg    960

ggaattggtg ctcttcaagg agaccttcgt tttgtggacg tgctgcgtga tatgggagca   1020

gaggtgtctg ttggaccaga tgccacgaca gtgcgctcaa ctggcagact ccgtggcatt   1080

acagttacta tgagagacat ttcagacacg atgccaacac tcgctgctat tgcacctcac   1140

gctgatggac ccgtccgtat tgaggacgtg gcaaacactc gtgtcaagga atgtgatagg   1200

cttgaggcat gtgctcaaaa ccttagagct atgggaatca cggtgcatac tgggcacgat   1260

tggattgaga ttctccctgg gactccaaag ccaacgggaa tagctacgca cggagatcac   1320

agaatcgtta tgtccttcgc agtggctggt ttgttgaccc ctgggctgac atacgatgat   1380

cctggctgcg tccgcaagac ttttccaagg ttccacgaag ttttcgctga ctttgctgca   1440

tcaccccaag cctga                                                    1455
```

<210> SEQ ID NO 43
<211> LENGTH: 1431
<212> TYPE: DNA
<213> ORGANISM: Artificial sequence
<220> FEATURE:
<223> OTHER INFORMATION: DGT-31 and TRAP23 construct

<400> SEQUENCE: 43

```
atggcacaga tcaacaagtc tgctaatggg gttaggaacg cttcactgat aagcaacttc     60

tccaataccc gtcaagccaa atccccttc tccctctcat gcggaacaag actgaagaac    120

agcagcagag gtttgaagaa ggtggcagtt aggctcattg gctcccgtgt caaagtgtct    180

gcctcaatga ctgtgattga catccctggc tcaaagtcag ttactgccag agcattgttc    240

ctcgcagcag ctgctgatgg cactacaact cttttgagac ctcttcacag cgatgacacg    300

gaaggcttca ctgagggtct cactcgtttg ggatacgcag tggttagaga acccgatagg    360

tggcacatag aaggacgtcc ctccggtcca gcagcagcag atgcagaagt tcactgtagg    420

gacggtgcta caactgctcg ctttcttcca acccttgcag ctgctgctgc ctccggaacg    480

tatcgtttcg acgcatcagc tcagatgagg cgtagacccc tcgctcccct cacggaagct    540

cttagaacac ttggagtgga ccttaggcat gatggagctg aaggccacca ccccttgaca    600

attcaagcct ctggtgttaa gggtggagga cttacgctcg acgctggtga gtcatctcag    660

tacttgacag ctctgctcat gcttggtcct ctgaccgcag agggactgag aatagaagtt    720

acggagcttg tctctgctcc ttatgtggag atcacccttg caatgatgag aggctttggt    780

gtggaggttg ttagggaggg gaatactttc actgtgcctc ctggaggtta cagagctaca    840

acttatgcca tagaaccgga cgcaagcaca gcttcctact tctttgcagc agcagccctc    900
```

```
actgggaggg aagtgacggt gcctggcttg ggcactggag cacttcaagg tgatcttagg    960

ttcacggagg tcctcagaag gatggacgct gatgttcgca caacgtccga ctctacaaca   1020

gtgcgctcag atggtcgcct tgctgggttg actgtcaaca tgagggacat aagcgacaca   1080

atgccaacac tggcagctat agctccgtac gcaagctcac cagttaggat cgaggatgtc   1140

gcaaacaccc gtgtgaagga atgtgatagg ctggaggctt gcgctcagaa tctccgctca   1200

atgggcatca ccgttcgcac tggaccagat tggattgaga tccatcctgg gactcctaga   1260

ccgaccgaga tagccacaca cggtgatcat agaatcgtca tgtcatttgc cgtggctgga   1320

cttagaaccc ctgggatgtc ttacgatgac cctggctgcg ttcgcaagac ttttcctcgt   1380

tttcatgaag agtttgcagc cttcgtggag cgctcatccg ctggagagtg a            1431
```

<210> SEQ ID NO 44
<211> LENGTH: 19
<212> TYPE: DNA
<213> ORGANISM: Artificial sequence
<220> FEATURE:
<223> OTHER INFORMATION: Oligonucleotide primer sequence

<400> SEQUENCE: 44

```
agccacatcc cagtaacga                                                  19
```

<210> SEQ ID NO 45
<211> LENGTH: 17
<212> TYPE: DNA
<213> ORGANISM: Artificial sequence
<220> FEATURE:
<223> OTHER INFORMATION: Oligonucleotide primer sequence

<400> SEQUENCE: 45

```
cctccctctt tgacgcc                                                    17
```

<210> SEQ ID NO 46
<211> LENGTH: 20
<212> TYPE: DNA
<213> ORGANISM: Artificial sequence
<220> FEATURE:
<223> OTHER INFORMATION: Oligonucleotide probe sequence

<400> SEQUENCE: 46

```
cagcccaatg aggcatcagc                                                 20
```

<210> SEQ ID NO 47
<211> LENGTH: 23
<212> TYPE: DNA
<213> ORGANISM: Artificial sequence
<220> FEATURE:
<223> OTHER INFORMATION: Oligonucleotide primer sequence

<400> SEQUENCE: 47

```
cttcaaggag atttgggatt tgt                                             23
```

<210> SEQ ID NO 48
<211> LENGTH: 17
<212> TYPE: DNA
<213> ORGANISM: Artificial sequence
<220> FEATURE:
<223> OTHER INFORMATION: Oligonucleotide primer sequence

<400> SEQUENCE: 48

```
gagggtcggc atcgtat                                                    17
```

<210> SEQ ID NO 49
<211> LENGTH: 25
<212> TYPE: DNA
<213> ORGANISM: Artificial sequence
<220> FEATURE:
<223> OTHER INFORMATION: Oligonucleotide probe sequence

<400> SEQUENCE: 49
agagaagttt cgacggattt cgggc 25

<210> SEQ ID NO 50
<211> LENGTH: 22
<212> TYPE: DNA
<213> ORGANISM: Artificial sequence
<220> FEATURE:
<223> OTHER INFORMATION: Oligonucleotide primer sequence

<400> SEQUENCE: 50
gaggattagg gtttcaacgg ag 22

<210> SEQ ID NO 51
<211> LENGTH: 21
<212> TYPE: DNA
<213> ORGANISM: Artificial sequence
<220> FEATURE:
<223> OTHER INFORMATION: Oligonucleotide primer sequence

<400> SEQUENCE: 51
gagaattgag ctgagacgag g 21

<210> SEQ ID NO 52
<211> LENGTH: 24
<212> TYPE: DNA
<213> ORGANISM: Artificial sequence
<220> FEATURE:
<223> OTHER INFORMATION: Oligonucleotide primer sequence

<400> SEQUENCE: 52
ctgcaggtca acggatcagg atat 24

<210> SEQ ID NO 53
<211> LENGTH: 24
<212> TYPE: DNA
<213> ORGANISM: Artificial sequence
<220> FEATURE:
<223> OTHER INFORMATION: Oligonucleotide primer sequence

<400> SEQUENCE: 53
tgggctgaat tgaagacatg ctcc 24

<210> SEQ ID NO 54
<211> LENGTH: 20
<212> TYPE: DNA
<213> ORGANISM: Artificial sequence
<220> FEATURE:
<223> OTHER INFORMATION: Oligonucleotide primer sequence

<400> SEQUENCE: 54
cgtccacaaa gctgaatgtg 20

<210> SEQ ID NO 55
<211> LENGTH: 20
<212> TYPE: DNA
<213> ORGANISM: Artificial sequence
<220> FEATURE:
<223> OTHER INFORMATION: Oligonucleotide primer sequence

<400> SEQUENCE: 55
cgaagtcatg gaagccactt 20

<210> SEQ ID NO 56
<211> LENGTH: 23
<212> TYPE: DNA
<213> ORGANISM: Artificial sequence
<220> FEATURE:
<223> OTHER INFORMATION: Oligonucleotide primer sequence

<400> SEQUENCE: 56
cttcaaggag atttgggatt tgt 23

<210> SEQ ID NO 57
<211> LENGTH: 17
<212> TYPE: DNA
<213> ORGANISM: Artificial sequence
<220> FEATURE:
<223> OTHER INFORMATION: Oligonucleotide primer sequence

<400> SEQUENCE: 57
gagggtcggc atcgtat 17

<210> SEQ ID NO 58
<211> LENGTH: 20
<212> TYPE: DNA
<213> ORGANISM: Artificial sequence
<220> FEATURE:
<223> OTHER INFORMATION: Oligonucleotide primer sequence

<400> SEQUENCE: 58
tgttcggttc cctctaccaa 20

<210> SEQ ID NO 59
<211> LENGTH: 24
<212> TYPE: DNA
<213> ORGANISM: Artificial sequence
<220> FEATURE:
<223> OTHER INFORMATION: Oligonucleotide probe sequence

<400> SEQUENCE: 59
cacagaaccg tcgcttcagc aaca 24

<210> SEQ ID NO 60
<211> LENGTH: 22
<212> TYPE: DNA
<213> ORGANISM: Artificial sequence
<220> FEATURE:
<223> OTHER INFORMATION: Oligonucleotide primer sequence

<400> SEQUENCE: 60
caacatccat caccttgact ga 22

<210> SEQ ID NO 61
<211> LENGTH: 26
<212> TYPE: DNA
<213> ORGANISM: Artificial sequence
<220> FEATURE:
<223> OTHER INFORMATION: Oligonucleotide probe sequence

<400> SEQUENCE: 61
cgagcagacc gccgtgtact tctacc 26

<210> SEQ ID NO 62

<211> LENGTH: 18
<212> TYPE: DNA
<213> ORGANISM: Artificial sequence
<220> FEATURE:
<223> OTHER INFORMATION: Oligonucleotide primer sequence

<400> SEQUENCE: 62
tggcggacga cgacttgt 18

<210> SEQ ID NO 63
<211> LENGTH: 19
<212> TYPE: DNA
<213> ORGANISM: Artificial sequence
<220> FEATURE:
<223> OTHER INFORMATION: Oligonucleotide primer sequence

<400> SEQUENCE: 63
aaagtttgga ggctgccgt 19

<210> SEQ ID NO 64
<211> LENGTH: 18
<212> TYPE: DNA
<213> ORGANISM: Artificial sequence
<220> FEATURE:
<223> OTHER INFORMATION: Oligonucleotide primer sequence

<400> SEQUENCE: 64
ttcagcaccc gtcagaat 18

<210> SEQ ID NO 65
<211> LENGTH: 20
<212> TYPE: DNA
<213> ORGANISM: Artificial sequence
<220> FEATURE:
<223> OTHER INFORMATION: Oligonucleotide probe sequence

<400> SEQUENCE: 65
tgccgagaac ttgaggaggt 20

<210> SEQ ID NO 66
<211> LENGTH: 17
<212> TYPE: DNA
<213> ORGANISM: Artificial sequence
<220> FEATURE:
<223> OTHER INFORMATION: oligonucleotide primer sequence

<400> SEQUENCE: 66
tggtcgccat agcttgt 17

<210> SEQ ID NO 67
<211> LENGTH: 13
<212> TYPE: PRT
<213> ORGANISM: Artificial
<220> FEATURE:
<223> OTHER INFORMATION: TraP8-DGT14v2 Cleavage site
<220> FEATURE:
<221> NAME/KEY: MISC_FEATURE
<222> LOCATION: (8)..(9)
<223> OTHER INFORMATION: splice site

<400> SEQUENCE: 67

Ser Val Ile Arg Pro Val Lys Ala Ala Ser Thr Gly Gly
1 5 10

<210> SEQ ID NO 68
<211> LENGTH: 13
<212> TYPE: PRT

```
<213> ORGANISM: Artificial
<220> FEATURE:
<223> OTHER INFORMATION: TraP8-DGT28v1 Cleavage site
<220> FEATURE:
<221> NAME/KEY: MISC_FEATURE
<222> LOCATION: (8)..(9)
<223> OTHER INFORMATION: splice site

<400> SEQUENCE: 68

Ser Val Ile Arg Pro Val Lys Ala Ala Arg Gly Met Pro
1               5                   10


<210> SEQ ID NO 69
<211> LENGTH: 13
<212> TYPE: PRT
<213> ORGANISM: Artificial
<220> FEATURE:
<223> OTHER INFORMATION: TraP9-DGT14v2 Cleavage site
<220> FEATURE:
<221> NAME/KEY: MISC_FEATURE
<223> OTHER INFORMATION: splice site

<400> SEQUENCE: 69

Lys Val Thr Ala Ser Val Ser Ala Ala Ser Thr Gly Gly
1               5                   10


<210> SEQ ID NO 70
<211> LENGTH: 13
<212> TYPE: PRT
<213> ORGANISM: Artificial
<220> FEATURE:
<223> OTHER INFORMATION: TraP9-DGT28v1 Cleavage site
<220> FEATURE:
<221> NAME/KEY: MISC_FEATURE
<222> LOCATION: (8)..(9)
<223> OTHER INFORMATION: splice site

<400> SEQUENCE: 70

Lys Val Thr Ala Ser Val Ser Ala Ala Arg Gly Met Pro
1               5                   10
```